(12) United States Patent
Sato et al.

(10) Patent No.: US 10,294,500 B2
(45) Date of Patent: *May 21, 2019

(54) METHOD FOR PRODUCING METHACRYLIC ACID AND/OR ESTER THEREOF

(71) Applicant: Mitsubishi Chemical Corporation, Tokyo (JP)

(72) Inventors: Eiji Sato, Kanagawa (JP); Michiko Yamazaki, Kanagawa (JP); Eiji Nakajima, Kanagawa (JP); Fujio Yu, Kanagawa (JP); Toshio Fujita, Kanagawa (JP); Wataru Mizunashi, Kanagawa (JP)

(73) Assignee: Mitsubishi Chemical Corporation, Tokyo (JP)

(*) Notice: Subject to any disclaimer, the term of this patent is extended or adjusted under 35 U.S.C. 154(b) by 252 days.

This patent is subject to a terminal disclaimer.

(21) Appl. No.: 14/419,575

(22) PCT Filed: Sep. 10, 2013

(86) PCT No.: PCT/JP2013/005359
§ 371 (c)(1),
(2) Date: Feb. 4, 2015

(87) PCT Pub. No.: WO2014/038216
PCT Pub. Date: Mar. 13, 2014

(65) Prior Publication Data
US 2015/0191756 A1    Jul. 9, 2015

(30) Foreign Application Priority Data

Sep. 10, 2012 (JP) ................ 2012-198840
Sep. 10, 2012 (JP) ................ 2012-198841
Jan. 31, 2013 (JP) ................ 2013-016947
Jul. 30, 2013 (JP) ................ 2013-157306
Aug. 1, 2013 (JP) ................ 2013-160300
Aug. 1, 2013 (JP) ................ 2013-160301
Aug. 20, 2013 (JP) ................ 2013-170404

(51) Int. Cl.
| | |
|---|---|
| *C12P 7/62* | (2006.01) |
| *C12N 9/10* | (2006.01) |
| *C12N 9/00* | (2006.01) |
| *C07C 57/04* | (2006.01) |
| *C07C 69/54* | (2006.01) |
| *C12P 7/40* | (2006.01) |
| *C12N 9/02* | (2006.01) |

(52) U.S. Cl.
CPC ............ *C12P 7/62* (2013.01); *C07C 57/04* (2013.01); *C07C 69/54* (2013.01); *C12N 9/001* (2013.01); *C12N 9/1029* (2013.01); *C12P 7/40* (2013.01); *C12Y 103/99* (2013.01); *C12Y 103/99003* (2013.01); *C12Y 203/01084* (2013.01)

(58) Field of Classification Search
None
See application file for complete search history.

(56) References Cited

U.S. PATENT DOCUMENTS

| | | | |
|---|---|---|---|
| 8,241,877 B2 * | 8/2012 | Burgard | C12P 7/40 435/136 |
| 8,501,455 B2 | 8/2013 | Gokarn et al. | |
| 2003/0148480 A1 | 8/2003 | DiCosimo et al. | |
| 2004/0076982 A1 | 4/2004 | Gokarn et al. | |
| 2007/0184524 A1 | 8/2007 | Gokarn et al. | |
| 2008/0076167 A1 | 3/2008 | Gokarn et al. | |
| 2009/0053783 A1 | 2/2009 | Gokarn et al. | |
| 2009/0130729 A1 * | 5/2009 | Symes | C12P 7/62 435/135 |
| 2009/0275096 A1 | 11/2009 | Burgard et al. | |
| 2010/0035314 A1 | 2/2010 | Mueller et al. | |
| 2011/0165640 A1 | 7/2011 | Mueller et al. | |
| 2012/0077236 A1 | 3/2012 | Gokarn et al. | |
| 2012/0276604 A1 | 11/2012 | Burgard et al. | |
| 2012/0276605 A1 | 11/2012 | Burgard et al. | |
| 2013/0065279 A1 * | 3/2013 | Burk | C12P 19/32 435/88 |

FOREIGN PATENT DOCUMENTS

| | | |
|---|---|---|
| CA | 2688292 A1 | 12/2008 |
| EP | 0187680 A2 | 7/1986 |
| EP | 0502476 A2 | 9/1992 |
| EP | 2868648 A1 | 5/2015 |
| JP | 54-046887 | 4/1979 |
| JP | 61-162191 A | 7/1986 |

(Continued)

OTHER PUBLICATIONS

Office Action dated Jun. 28, 2016 in Japanese Patent Application No. 2013-546110.
Edwige J. F. Souleyre, et al., "An alcohol acyl transferase from apple (cv. Royal Gala), MpAAT1, produces esters involved in apple fruit flavor", FEBS Journal, vol. 272, No. 12, 2005, pp. 3132-3144.

(Continued)

*Primary Examiner* — Suzanne M Noakes
(74) *Attorney, Agent, or Firm* — Oblon, McClelland, Maier & Neustadt, L.L.P.

(57) ABSTRACT

To provide a method for directly and efficiently producing methacrylic acid in a single step from renewable raw materials and/or biomass arising from the utilization of the renewable raw materials. Further provided is a method for producing methacrylic acid using microbes having the ability to produce methacrylic acid, from renewable raw materials and/or biomass arising from the utilization of the renewable raw materials, as a carbon source and/or energy source. The method for producing methacrylic acid enables methacrylic acid to be safely and easily produced from biomass, without using petroleum-derived raw materials, by utilizing microbes having the ability to produce methacrylic acid.

5 Claims, 7 Drawing Sheets
Specification includes a Sequence Listing.

(56) References Cited

FOREIGN PATENT DOCUMENTS

| | | |
|---|---|---|
| JP | 62-014788 | 1/1987 |
| JP | 01-132392 | 5/1989 |
| JP | 5-64589 | 3/1993 |
| JP | 10-337185 A | 12/1998 |
| JP | 11-243957 A | 9/1999 |
| JP | 2004-514431 A | 5/2004 |
| JP | 2005-516622 A | 6/2005 |
| JP | 2007-54011 A | 3/2007 |
| JP | 2009-538118 | 11/2009 |
| JP | 2010-528597 A | 8/2010 |
| JP | 2011-519561 A | 7/2011 |
| JP | 2011/200133 A | 10/2011 |
| WO | 00/32789 A1 | 6/2000 |
| WO | 2002/42418 A2 | 5/2002 |
| WO | 2003/066872 A1 | 8/2003 |
| WO | 2007/039415 A1 | 4/2007 |
| WO | 2007/110394 A2 | 10/2007 |
| WO | 2008/145737 A1 | 12/2008 |
| WO | 2009/135074 A2 | 11/2009 |
| WO | 2011/031897 A1 | 3/2011 |
| WO | 2012/135789 A2 | 10/2012 |
| WO | 2013/044076 A1 | 3/2013 |
| WO | WO 2014/071289 A1 | 5/2014 |

OTHER PUBLICATIONS

J. Michael Shaw, et al., "Phosphatidylmonoglucosyl Diacylglycerol of Pseudomonas diminuta ATCC 11568", Journal of Biological Chemistry, vol. 252, No. 12, 1977, pp. 4395-4401.

Takashi Yamada, et al., "Biodegradation of 2,4,6-Tribromophenol by Ochrobactrum sp. Strain TB01", Biosci Biotechnol Biochem, vol. 72, No. 5, 2008, p. 1264-p. 1271.

Database Uniprot [online], Accession No. Q91513, <http://www.uniprot.org/uniprot/ Q9I5I3.txt?version=72>, uploaded on May 29, 2013, [retrieved on Jun. 20, 2016].

Database Uniprot [online], Accession No. G7EWV0, <http://www.uniprot.org/uniprot/G7EWV0.txt?version=7>, up loaded on Apr. 3, 2013, [retrieved on Jun. 20, 2016].

Database Uniprot [online], Accession No. C1A227, <http: //www.uniprot.org/uniprot/C1A227.txt?version=31>, up loaded on Jul. 24, 2013, [retrieved on Jun. 20, 2016].

Database Uniprot [online], Accession No. J2J0W5, <http://www.uniprot.org/uniprot/J2J0W5.txt?version=5>, up loaded on Apr. 3, 2013, [retrieved on Jun. 20, 2016].

Partial Supplementary Search Report dated Jul. 23, 2015 in European Patent Application No. 13835104.4, filed Sep. 10, 2013.

Natalia Korotkova, et al., "Glyoxylate Regeneration Pathway in the Methylotroph Methylobacterium extorquens AM1", Journal of Bacteriology, vol. 184, No. 6, Mar. 1, 2002, pp. 1750-1758.

International Search Report dated Dec. 10, 2013 in PCT/JP2013/005359 filed Sep. 10, 2013.

Toru Nagasawa, et al., "Production of acrylic acid and methacrylic acid using Rhodococcus rhodochrous J1 nitrilase," Applied Microbiology and Biotechnology, vol. 34, 1990, pp. 322-324.

Ana G. Perez, et al., "Partial Purification and Some Properties of Alcohol Acyltransferase from Strawberry Fruits," Journal of Agricultural and Food Chemistry, vol. 41, 1993, pp. 1462-1466.

Database UniProt [online], Accession No. I1DTM1, Definition: Isobutyryl-CoA dehydrogenase, mitochondrial, http://www.uniprot.org/uniprot/I1DTM1, Jun. 13, 2012 uploaded [retrieved Nov. 27, 2013], pp. 1-3.

Database UniProt [online], Accession No. G2UBR1, Definition: Probable acyl-CoA dehydrogenase, http://www.uniprot.org/uniprot/G2UBR1, Nov. 16, 2011 uploaded [retrieved Nov. 27, 2013], pp. 1-3.

Database UniProt [online], Accession No. C3JI12, Definition: Isobutyryl-CoA dehydrogenase, http://www.uniprot.org/uniprot/C3J112, Jun. 16, 2009 uploaded [retrieved on Nov. 27, 2013], pp. 1-3.

Database UniProt [online], Accession No. M2XPW5, Definition: Acyl-CoA dehydrogenase, http://www.uniprot.org/uniprot/M2XPW5, May 1, 2013 uploaded [retrieved Nov. 27, 2013], pp. 1-3.

Sang-Hyun Pyo, et al., "A new route for the synthesis of methacrylic acid from 2-methyl-1,3-propanediol by integrating biotransformation and catalytic dehydration," Green Chemistry, vol. 14, 2012, pp. 1942-1948.

Mark R. Smith, et al., "The Utilization of 3-Mercapto-2-Methylpropionate as Sulphur Source by a Phototropic Bacterium," Bioorganic & Medicinal Chemistry, vol. 2, No. 7, 1994, pp. 589-593.

Jerry Vockley, et al., "Mammalian Branched-Chain Acyl-CoA Dehydrogenases: Molecular Cloning and Characterization of Recombinant Enzymes," Methods in Enzymology, vol. 324, 2000, pp. 241-258.

Lori A. Maggio-Hall, et al., "A Single Acyl-CoA Dehydrogenase Is Required for Catabolism of Isoleucine, Valine and Short-Chain Fatty Acids in Aspergillus nidulans," Fungal Genet Biology, vol. 45(3), Mar. 2008, pp. 180-189.

Ying-Xin Zhang, et al., "Genes encoding acyl-CoA dehydrogenase (AcdH) homologues from Streptomyces coelicolor and Streptomyces avermitilis provide insights into the metabolism of small branched-chain fatty acids and macrolide antibiotic production," Microbiology, vol. 145, 1999, pp. 2323-2334.

Linda K. Massey, et al., "Branched-Chain Amino Acid Catabolism in Bacteria," Bacteriological Reviews, vol. 40, No. 1., Mar. 1976, pp. 42-54.

Zuzana Swigonova, et al., "Acyl-CoA Dehydrogenases: Dynamic History of Protein Family Evolution," J. Mol. Evol., vol. 69, 2009, pp. 176-193.

Kathryn L. Hester, et al., "Purification of Pseudomonas putida Branched-Chain Keto Acid Dehydrogenase E1 Component," Methods in Enzymology, vol. 324, 2000, pp. 129-138.

Naoki Kato, "Progress and Prospect of Bio-process by Metabolic Engineering," Bio Industry, vol. 29, No. 5, 2012, pp. 17-21.

U.S. Office Action, U.S. Appl. No. 14/405,593, dated Mar. 8, 2018, 19 pages.

Cristian Balbontin, et al., "VpAAT1, a Gene Encoding an Alcohol Acyltransferase, Is involved in Ester Biosynthesis during Ripening of mountain Papaya Fruit", J. Agric. Food Chem. 2010, 58, 5114-5121.

Luis Morales-Quintana, et al., "Molecular docking simulation analysis of alcohol acyltransferases from two related fruit species explains their different substrate selectivities" Molecular Simulation, 38, 11, 912-921.

Office Action dated May 15, 2018 in Chinese Patent Application No. 201380047196.3 with English translation.

Office Action dated Aug. 27, 2018 in Indian Patent Application No. 595/CHENP/2015 (with English translation), 7 pages.

Extended European Search Report dated Oct. 8, 2018 in Patent Application No. 18175984.6, 8 pages.

Office Action dated Oct. 11 2018 in European Patent Application No. 13 835 104.4, 4 pages.

U.S. Office Action as received in related U.S. Appl. No. 14/405,593 dated Dec. 14, 2018.

\* cited by examiner 2-oxoisovaleric acid    isobutyryl-CoA    methacrylyl-CoA    methacrylic acid ester

METHOD FOR PRODUCING METHACRYLIC ACID AND/OR ESTER THEREOF

TECHNICAL FIELD

The present invention relates to a method for producing methacrylic acid and/or an ester thereof. More specifically, it relates to a method for producing methacrylic acid using microbes having the ability to produce methacrylic acid, the microbes, methacrylic acid obtained by the production method, and the like.

BACKGROUND ART

Methacrylic acid is useful as a raw material for paint or resin modifying agent, and its esters are an industrially significantly important compound as a raw material for acrylic resin.

As a method for chemical production of methacrylic acid derivatives, the ACH method intermediated by acetone cyanhydrin using cyanide and acetone as a raw material, the C4 oxidation using isobutylene or tert-butanol as a raw material, and the like are practically used. Those chemical production methods rely on fossil fuels and also require a large amount of energy.

Recently, from the viewpoint of preventing global warming and environmental protection, use of renewable biogenous resources (renewable raw materials) as a carbon source to be a substitute of fossil fuels of the related art receives attention. For example, a method for producing 2-hydroxyisobutyric acid and 3-hydroxyisobutyric acid, which are a precursor of methacrylic acid, from a natural product such as sugar using microbes existing in nature has been suggested (see, Patent Documents 1 and 2 and Non-Patent Document 1). However, those methods still rely on a chemical method in terms of the process for producing methacrylic acid by dehydration of a precursor.

Further, although a method for producing methacrylic acid from glucose using a recombinant microbe introduced with plural enzyme genes, which is not exist in nature, has been suggested, it is a mere suggestion of simple combination between known enzyme reactions and imaginary enzyme reactions deduced therefrom, and has not been practically proved (see, Patent Documents 3 to 5).

Meanwhile, as a naturally occurring microbe, a photosynthetic microbe having the ability to produce methacrylic acid is known (Non-Patent Document 2). However, the photosynthetic microbe only converts 3-mercaptoisobutyric acid, which is a special compound not existing in nature, to methacrylic acid.

Further, in Patent Document 6, a method for producing an acrylic acid ester according to an action of a hydrolase in the presence of Acryloyl-CoA and an alcohol is disclosed. It is suggested in the same literature that a methacrylic acid ester can be also similarly produced. However, considering diversity and substrate specificity of an enzyme, it only demonstrates that an acrylic acid ester can be produced with few limited hydrolases, and it remains uncertain whether or not a methacrylic acid ester having a different structure can be also similarly produced by the hydrolase. Further, it remains completely uncertain whether or not production can be made with a different kind of enzyme having a different reaction mechanism. Further, when an ester is synthesized with the hydrolase described in Patent Document 6, it is expected that an ester produced is basically dissociated due to hydrolysis activity, and thus it is difficult to be considered as an effective production method.

Meanwhile, alcohol acyl transferase (hereinbelow, "ATT") is known as an enzyme for synthesis of fruity flavor. In Patent Document 7, a method for producing various esters as fruit flavor by identifying the gene of the same enzyme, which is contained in specific fruits, is suggested. However, the possibility of synthesizing a methacrylic acid ester with the enzyme is not described and remains completely uncertain.

As described above, although several suggestions or discussions have been made, there is no example showing actual production of methacrylic acid derivatives using microbes, and thus an effective production method needs to be established.

CITATION LIST

Patent Document

Patent Document 1: WO 2007/110394 A
Patent Document 2: WO 2008/145737 A
Patent Document 3: WO 2009/135074 A
Patent Document 4: WO 2011/031897 A
Patent Document 5: WO 2012/135789 A
Patent Document 6: WO 2007/039415 A
Patent Document 7: WO 00/32789 A
Patent Document 8: JP 2011-519561 A
Patent Document 9: JP 2011-200133 A
Patent Document 10: JP 5-64589 A
Patent Document 11: JP 10-337185 A

Non-Patent Document

Non-Patent Document 1: Green Chemistry, 2012, 14, 1942-1948
Non-Patent Document 2: Bioorganic & Medicinal Chemistry, 1994, 7, 589-593
Non-Patent Document 3: Methods in Enzymology, 2000, 324, 241-258
Non-Patent Document 4: Fungal Genet. Biol., 2008, 45, 180-189
Non-Patent Document 5: Microbiology, 1999, 145, 2323-2334
Non-Patent Document 6: Bacteriol. Review, 1976, 40, 42-54 (1976)
Non-Patent Document 7: J. Mol. Evol., 2009, 69, 176-193
Non-Patent Document 8: Methods in Enzymology, 2000, 324, 129-138

DISCLOSURE OF THE INVENTION

Problem to be Solved by the Invention

According to a chemical production method of the related art, for example, the ACH method, an oxidation treatment of acetone cyanhydrin with an acid is required so that a waste acid is generated in a large amount. Further, as separation or purification is required for each step, there is a problem of having high energy consumption. For such reasons, a method for directly and efficiently producing methacrylic acid in a single step using microbes capable of producing methacrylic acid from renewable raw materials and/or biomass arising from the utilization of the renewable raw materials, as a carbon source and/or energy source, is needed.

Means for Solving Problem

To solve the problems described above, inventors of the invention conducted extensive searches for microbes having the ability to produce methacrylic acid derivatives, and as a result, found that methacrylic acid can be produced with many microbes.

Further, as described below, the inventors found that the microbes having the ability to produce methacrylic acid derivatives are a group of microbes having a certain specific function and a constant common property, and they also succeeded in finding a method for searching them.

First, the inventors of the invention tried to produce methacrylic acid derivatives, which are an intermediate of the valine metabolism pathway, from 2-oxoisovaleric acid based on a microbial reaction by producing recombinant *E. coli* which has been introduced with a gene of the valine metabolism pathway (branched chain keto acid dehydrogenase (hereinbelow, "BCKAD") and isobutyryl-CoA dehydrogenase (hereinbelow, "ACD")). However, production of the methacrylic acid derivatives as a target product was not observed while production of isobutyric acid was observed. Further, when a cell extract is prepared from the recombinant and the in vitro activity of BCKAD and ACD is measured after adding a cofactor or the like, coactivity was observed. Based on such results, it was determined that the BCKAD reaction, but not the ACD reaction, has occurred under in vivo conditions.

In mammals, it is known that the dehydrogenase reaction known as metabolism of branched amino acid or β-oxidation of fatty acid occurs in a mitochondria and liberated electrons are transferred to a respiratory chain via an electron transferring flavoprotein. In other words, it was assumed that the main reaction does not occur only by adding foreign ACD to a microbe which does not have the same function as them. The ACD reaction actually did not occur in the recombinant *E. coli* as described above.

To solve this new problem, the inventors of the invention conducted extensive searches for the microbes having the ability to produce methacrylic acid derivatives by microbes, and found that the problem can be solved using microbes capable of producing methacrylic acid and microbes capable of metabolizing isobutyryl-CoA as a substrate of ACD. Examples of the microbes capable of metabolizing isobutyryl-CoA include valine assimilating viable microbes and isobutyric acid assimilating viable microbes. Those microbes can be obtained from nature by growing them with use of valine as a sole carbon source and/or a nitrogen source or isobutyric acid as a sole carbon source.

The inventors of the invention further found that, by adding the action of AAT to the microbes having the ability to produce methacrylic acid, a methacrylic acid ester can be produced in the presence of an alcohol.

In addition, the inventors of the invention intensively studied the enzymes involved with methacrylic acid synthesis, which are derived from the aforementioned microbes, and genes which encode the enzymes. As a result, they found that there was an enzyme useful for production of methacrylic acid derivatives and succeeded in characterizing the enzyme protein. They also found that, according to combination of those enzyme proteins, synthesis of methacrylic acid derivatives can be achieved. Accordingly, the invention was completed. Specifically, the invention is as described below.

(1) A method for producing methacrylic acid and/or an ester thereof using microbes having the ability to produce methacrylic acid.

(2) The production method of (1), in which methacrylic acid and/or an ester thereof is accumulated at 0.04 ppm or more.

(3) The production method of (1) or (2), in which methacrylic acid and/or an ester thereof is produced using the microbes having the ability to produce methacrylic acid from renewable raw materials and/or biomass arising from the utilization of the renewable raw materials as a carbon source and/or energy source.

(4) The production method of any one of (1) to (3), in which the microbes having the ability to produce methacrylic acid are microbes capable of producing methacrylic acid from organic matters containing isobutyric acid or valine.

(5) The production method of any one of (1) to (4), in which the microbes having the ability to produce methacrylic acid are microbes having 16S rRNA gene which consists of a nucleotide sequence showing an identity of 81% or more to any one of nucleotide sequences described in SEQ ID NOS. 1 to 41.

(6) The production method of any one of (1) to (4), in which the microbes having the ability to produce methacrylic acid are microbes having LSUrRNA gene which consists of a nucleotide sequence showing an identity of 81% or more to any one of nucleotide sequences described in SEQ ID NOS. 42 to 49.

(7) The production method of any one of (1) to (6), in which the microbes having the ability to produce methacrylic acid are microbes belonging to the genus *Pseudomonas*, the genus *Bacillus*, the genus *Sphingobacterium*, the genus *Comamonas*, the genus *Brevundimonas*, the genus *Sphingomonas*, the genus *Ochrobactrum*, the genus *Pedobacter*, the genus *Paenibacillus*, the genus *Achromobacter*, the genus *Acinetobacter*, the genus *Shewanella*, the genus *Listonella*, the genus *Agrobacterium*, the genus *Mesorhizobium*, the genus *Rhizobium*, the genus *Paracoccus*, the genus *Xanthobacter*, the genus *Streptomyces*, the genus *Geobacillus*, the genus *Rhodococcus*, the genus *Saccharomyces*, the genus *Candida*, or the genus *Aspergillus*.

(8) The production method of any one of (1) to (7), in which a methacrylic acid ester is produced by having an alcohol or a phenol to act on methacrylyl-CoA in the presence of AAT.

(9) The production method of (8), in which AAT is derived from a plant.

(10) The microbes having the ability to produce methacrylic acid of (7).

(11) An enzyme involved with synthesis of methacrylic acid, which is derived from the microbes of (10).

(12) A gene encoding the enzyme of (11).

(13) Methacrylic acid and/or an ester thereof produced by microbes having the ability to produce methacrylic acid from renewable raw materials and/or biomass arising from the utilization of the renewable raw materials as a carbon source and/or energy source.

(14) Culture product of microbes containing the microbes having the ability to produce methacrylic acid and methacrylic acid and/or an ester thereof.

(15) The enzyme of (11) which consists of a protein selected from the group consisting of the following (a) to (c):

(a) a protein which consists of an amino acid sequence represented by SEQ ID NO. 50 or 52

(b) a protein which consists an amino acid sequence showing an identity of 45% or more to a protein consisting of an amino acid sequence represented by SEQ ID NO. 50 or 52 and which has the ACD activity, and (c) a protein which consists of an amino acid sequence with deletion, substitution, or addition of one or several amino acids in an amino acid sequence represented by SEQ ID NO. 50 or 52 and which has the ACD activity.

(16) A method for producing methacrylic acid and/or an ester thereof including using the enzyme of (15).

(17) The production method of any one of (1) to (7), in which the microbes having the ability to produce methacrylic acid are microbes belonging to the genus *Sphingobacterium*, the genus *Comamonas*, the genus *Brevundimonas*, the genus *Sphingomonas*, the genus *Ochrobactrum*, the genus *Pedobacter*, the genus *Paenibacillus*, the genus *Achromobacter*, the genus *Acinetobacter*, the genus *Shewanella*, the genus *Listonella*, the genus *Agrobacterium*, the genus *Mesorhizobium*, the genus *Paracoccus*, the genus *Xanthobacter*, the genus *Geobacillus*, the genus *Rhodococcus*, or the genus *Candida*.

The inventors of the invention also found that the AAT has an activity of synthesizing a methacrylic acid ester. Specifically, the invention is as follows according to another aspect.

(1A) A method for producing a methacrylic acid ester including a step of synthesizing a methacrylic acid ester by having an alcohol or a phenol to act on methacrylyl-CoA in the presence of AAT.

(2A) The production method for producing a methacrylic acid ester of (1A), in which the methacrylic acid ester is accumulated at 0.001 mM or more.

(3A) The production method for producing a methacrylic acid ester of (1A) or (2A), in which it further has a step of producing methacrylyl-CoA from isobutyryl-CoA or 3-hydroxyisobutyryl-CoA.

(4A) The production method for producing a methacrylic acid ester of (3A), in which the isobutyryl-CoA is produced from 2-oxoisovaleric acid.

(5A) The production method for producing a methacrylic acid ester of any one of (1A) to (4A), in which AAT is derived from a plant.

(6A) The production method for producing a methacrylic acid ester of (5A), in which the plant belongs to an order selected from the group consisting of the order Zingiberales, the order Rosales, the order Ericales, the order Cucurbitales, the order Brassicales, and the order Laurales.

(7A) The production method for producing a methacrylic acid ester of (5A), in which the plant belongs to a family selected from the group consisting of the family Musa, the family Rosales, the family Ericales, the family *Actinidia*, the family Cucurbitales, the family *Carica*, and the family Laurales.

(8A) The production method for producing a methacrylic acid ester of (5A), in which the plant belongs to genus selected from the group consisting of the genus *Musa*, the genus *Fragaria*, the genus *Malus*, the genus *Armeniaca*, the genus *Pyrus*, the genus *Vaccinium*, the genus *Actinidia*, the genus *Cucumis*, the genus *Carica*, and the genus *Persea*.

(9A) The production method for producing a methacrylic acid ester of (5A), in which the plant is any one selected from the group consisting of banana, strawberry, apple, Japanese apricot, pear, blueberry, kiwi, melon, papaya, and avocado.

(10A) The production method for producing a methacrylic acid ester of any one of (1A) to (9A), in which a genetically modified microbe with a gene introduced to express AAT is used.

(11A) The production method for producing a methacrylic acid ester of (5A), in which the plant is any one selected from plants belonging to the genus *Musaceae*, the genus *Malus*, the genus *Purunus*, the genus *Pyrus*, the genus *Vaccinium hirtum*, the genus Bower *actinidia*, the genus *Cucumis*, the genus *Carica*, or the genus *Persea*.

(12A) The production method for producing a methacrylic acid ester of (5A), in which the plant is any one selected from plants belonging to the genus *Musaceae*, the genus *Malus*, the genus *Pyrus*, the genus Bower *actinidia*, the genus *Cucumis*, the genus *Carica*, or the genus *Persea*.

(13A) The production method for producing a methacrylic acid ester of (5A), in which the plant is any one selected from the group consisting of banana, apple, Japanese apricot, pear, blueberry, kiwi, melon, papaya, and avocado.

(14A) The production method for producing a methacrylic acid ester of (5A), in which the plant is any one selected from the group consisting of banana, apple, pear, kiwi, melon, papaya, and avocado.

The inventors of the invention also found that a specific protein which is derived from a microbe and has a function of ACD has an ability of converting isobutyryl-CoA to methacrylyl-CoA at high efficiency. It is also found that 1) according to combination with BCKAD as an enzyme for producing isobutyryl-CoA, methacrylyl-CoA is synthesized from 2-oxoisovaleric acid, 2) according to combination with AAT, a methacrylic acid ester is synthesized from isobutyryl-CoA, and 3) according to combination with an enzyme having an activity of hydrolyzing methacrylyl-CoA, methacrylic acid is synthesized from isobutyryl-CoA. Specifically, the invention is as follows according to still another aspect.

(1B) A transformant which is introduced with ACD gene selected from the group consisting of the following (a) to (d):

(a) a gene encoding a protein consisting of an amino acid sequence represented by SEQ ID NO. 50 or 52

(b) a gene consisting of a nucleotide sequence represented by SEQ ID NO. 51 or 53

(c) a gene encoding a protein which consists of an amino acid sequence showing an identity of 45% or more to a protein consisting of an amino acid sequence represented by SEQ ID NO. 50 or 52 and which has the ACD activity, and (d) a gene encoding a protein which consists of an amino acid sequence with deletion, substitution, or addition of one or several amino acids in an amino acid sequence represented by SEQ ID NO. 50 or 52 and which has the ACD activity.

(2B) The transformant of (1B), which is introduced with BCKAD complex gene in addition to ACD gene.

(3B) The transformant of (2B), in which the BCKAD complex gene is a gene selected from the group consisting of the following (e) to (h):

(e) a gene encoding four polypeptides having an amino acid sequence represented by SEQ ID NOS. 54, 56, 58 and 60

(f) a gene consisting of a nucleotide sequence represented by SEQ ID NOS. 55, 57, 59 and 61

(g) a gene encoding a protein which hybridizes under a stringent condition to a complementary strand of a gene encoding four polypeptides having an amino acid sequence represented by SEQ ID NOS. 54, 56, 58 and 60 and which has the BCKAD activity, and (h) a gene encoding a protein which consists of an amino acid sequence with deletion, substitution, or addition of one or several amino acids in an amino acid sequence represented by SEQ ID NOS. 54, 56, 58 and 60 and which has the BCKAD activity.

(4B) The transformant of (2B), in which the BCKAD complex gene is a gene selected from the group consisting of the following (i) to (l):

(i) a gene encoding four polypeptides having an amino acid sequence represented by SEQ ID NOS. 62, 64, 66 and 68

(j) a gene consisting of a nucleotide sequence represented by SEQ ID NOS. 63, 65, 67 and 69

(k) a gene encoding a protein which hybridizes under a stringent condition to a complementary strand of a gene encoding four polypeptides having an amino acid sequence represented by SEQ ID NOS. 62, 64, 66 and 68 and which has the BCKAD activity, and (1) a gene encoding a protein which consists of an amino acid sequence with deletion, substitution, or addition of one or several amino acids in an amino acid sequence represented by SEQ ID NOS. 62, 64, 66 and 68 and which has the BCKAD activity.

(5B) The transformant of (2B), in which the BCKAD complex gene is a gene selected from the group consisting of the following (m) to (p):

(m) a gene encoding three polypeptides having an amino acid sequence represented by SEQ ID NOS. 70, 72 and 74

(n) a gene consisting of a nucleotide sequence represented by SEQ ID NOS. 71, 73 and 75

(o) a gene encoding a protein which hybridizes under a stringent condition to a complementary strand of a gene encoding three polypeptides having an amino acid sequence represented by SEQ ID NOS. 70, 72 and 74 and which has the BCKAD activity, and (p) a gene encoding a protein which consists of an amino acid sequence with deletion, substitution, or addition of one or several amino acids in an amino acid sequence represented by SEQ ID NOS. 70, 72 and 74 and which has the BCKAD activity.

(6B) The transformant of any one of (1B) to (5B), in which the transformant is genetically introduced into a host which has a pathway of metabolizing glucose to 2-oxoisovaleric acid.

(7B) The transformant of any one of (1B) to (6B), in which a gene of enzyme having the AAT activity is additionally introduced.

(8B) The transformant of any one of (1B) to (7B), in which a gene of an enzyme having an activity of hydrolyzing methacrylyl-CoA is additionally introduced.

(9B) A method for producing methacrylyl-CoA including expressing a protein having the ACD activity using the transformant of (1B) and using the protein.

(10B) A method for producing methacrylyl-CoA including expressing a protein having the ACD activity and 2-oxoisovalerate dehydrogenase activity using the transformant of any one of (2B) to (5B) and using the protein.

(11B) A method for producing methacrylyl-CoA including expressing a protein having the ACD activity and 2-oxoisovalerate dehydrogenase activity by introducing the ACD gene selected from the group consisting of (a) to (d) of (1B) to a host and introducing the BCKAD complex gene which is selected from (e) to (h), (i) to (l), and (m) to (p) of (3B) to (5B) to the same host or a different host and using the protein.

Hereinbelow, the terminology of the invention is explained.

The "methacrylic acid" (IUPAC name: 2-methyl-2-propenoic acid) means a compound with a chemical formula $CH_2=C(CH_3)COOH$, and it encompasses any salt or ionized form thereof. Examples of the salt of methacrylic acid include a sodium salt, a potassium salt, a calcium salt, and a magnesium salt.

The "methacrylic acid ester" means a compound represented by Formula 1. In Formula 1, R represents a linear or branched hydrocarbon group with 1 to 20 carbon atoms. The hydrocarbon group can be either a saturated or unsaturated noncyclic type, or a saturated or unsaturated cyclic type. Preferably, it is a linear or branched and unsubstituted alkyl group, an aralkyl group, or an aryl group having 1 to 10 carbon atoms. Examples of the particularly preferred include an alkyl group with 1 to 8 carbon atoms such as a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a n-hexyl group, an isohexyl group, a 2-hexyl group, a dimethylbutyl group, an ethylbutyl group, a heptyl group, an octyl group, or a 2-ethylhexyl group, a benzyl group, and a phenyl group.

$$CH_2=C(CH_3)COO-R \quad \text{(Formula 1)}$$

The "methacrylic acid derivatives" is a general name of the compounds containing a methacryloyl group ($CH_2=CCH_3COO-$) in addition to the aforementioned methacrylic acid and methacrylic acid ester. Examples of the compound containing a methacryloyl group include methacrylyl-CoA.

The "ability to produce methacrylic acid" means ability for producing methacrylic acid using renewable raw materials as a carbon source and/or energy source. The "produce" means both the synthesis and decomposition of methacrylic acid in a living body (that is, balance), and it is not limited to the synthesis.

The "renewable raw materials" indicate natural resources, for example, resources derived from an animal, a plant, or a microbe, in which the resources can be reconstructed by a process of the nature at a rate which is faster than the rate consumed by human beings or the like. The resources should be self-renewable at a rate which is the same as the rate of the consumption. For example, a plant material has an advantage that it can be cultivated without consuming it to cause a significant decrease in natural sources.

The "biomass" means general resources that can be utilized as an organic energy source derived from a living organism. Examples of the biomass include a plant material, an animal material, and a biodegradable waste.

The "carbon source" means an organic compound which can be assimilated by a microbe and used for producing a new cell.

The "energy source" is a general name of the compounds for producing an energy molecule (ATP), which is required for a carbon source to get assimilated into a cell constitutional component via a metabolism intermediate. When an energy source required for metabolism to produce ATP, that is, a catabolism process, is needed for an oxidation reaction of various compounds in microbes, those compounds become the "energy source."

The "utilization of the renewable raw materials" means a method for general utilization of the renewable raw materials for obtaining fuel components and various organic substances from the renewable raw materials, which includes at least one processing step like gasification, liquidification, saccharification, enzyme treatment, fermentation, distillation of fermentation product, hydrolysis, dehydration, concentration, and drying.

The "microbes" indicate, according to general definition, prokaryotes like bacteria of any type, arcahea, and cyanobacteria, eukaryotes like yeast, mold, acrasis, and protozoa, and viruses. It further includes undifferentiated cells of an animal or a plant, and also a tissue culture product. As described herein, the "microbes" specifically means the microbes having the ability to produce methacrylic acid. Further, with regard to those having the ability to produce methacrylic acid, it is also used as a concept which includes a culture product, a medium (a culture product from which microbial cells are removed), microbial cells (including both cultured microbial cells or washed microbial cells), a processed product of microbial cells in which the microbial cells are disrupted or lysed, and a composition having an activity of producing methacrylic acid which is obtained by purifying and processing of the medium and/or cells (crude enzyme solution and purified enzyme).

The "derived strainstrain" means a strainstrain which is derived from a certain microbe strainstrain either naturally, or by a chemical or physical treatment. In the invention, it specifically means a strain which is derived from a microbe strain having the ability to produce methacrylic acid and maintains the ability to produce methacrylic acid from renewable raw material as a carbon source and/or energy source.

The "contact" means an exposure treatment of the microbes and materials (renewable raw materials) for a certain period of time. Specifically, it indicates that microbes are added to an aqueous medium containing renewable raw materials followed by suspension mixing. At that time, it is acceptable to have proliferation of the microbes.

The "aqueous medium" means water, an aqueous solution having water as a main component, and gel (agar), and those having undissolved liquid and solid dispersed therein are also included.

The "vapor phase" means the portion taken by gas or water vapor in a culture tank (a vessel for culturing microbes) or a reaction tank (a vessel for performing the reaction), excluding the portion taken by the liquid (medium or the like).

The "culture" means a process proliferating cells of microbes or a multicellular organisms in an artificial environment.

The "culture product" means those obtained by culture of microbial cells, a broth, a cell-free extract, or cell membranes. The cell-free extract can be obtained by, after physically disrupting microbial cells after culture with a homogenizer or the like with addition of a sodium phosphate buffer solution followed by centrifuge (15,000 rpm, 10 min, 4° C.), collecting the supernatant from which non-disrupted microbes or cell membranes are removed, The "esterification" indicates the reaction for producing an ester from an alcohol and a fatty acid based on dehydration. Further, it also includes the reaction for producing a new ester based on an alcohol exchange reaction with another alcohol or a partial ester of a polyhydric alcohol.

Effect of the Invention

According to the invention, a method for directly and efficiently producing methacrylic acid in a single step from renewable raw materials and/or biomass arising from the utilization of the renewable raw materials, as a carbon source and/or energy source, is provided.

EMBODIMENTS FOR CARRYING OUT THE INVENTION

Figure 1:
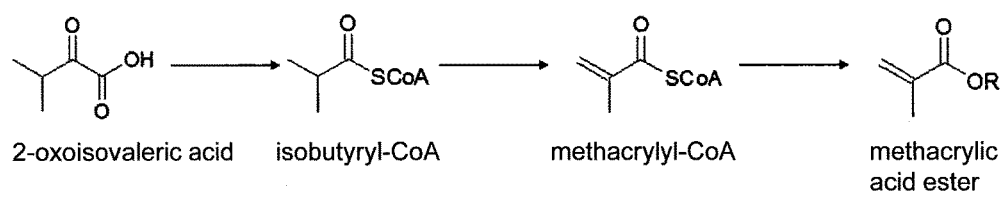
FIG. 1 is a drawing illustrating the step for producing a methacrylic acid ester from 2-oxoisovaleric acid.

Hereinbelow, preferred embodiments for carrying out the invention are explained. Meanwhile, the embodiments that are explained hereinbelow are to illustrate an example of the representative embodiment of the invention, and by no means the scope of the invention is construed narrowly by them.

1. Method for Producing Methacrylic Acid and/or Ester Thereof

According to the method for producing methacrylic acid and/or an ester thereof of the invention (hereinbelow, also simply referred to as the "production method for methacrylic acid"), methacrylic acid is produced using microbes having the ability to produce methacrylic acid from renewable raw materials and/or biomass arising from the utilization of the renewable raw materials, as a carbon source and/or energy source. Specifically, according to a step of contacting the microbes having the ability to produce methacrylic acid with renewable raw materials and/or biomass, methacrylic acid is produced. More specifically, by culturing the microbes in an aqueous medium containing the renewable raw materials and/or biomass, methacrylic acid is obtained in the aqueous medium.

(1) Microbes

With regard to the microbes that are used for production method for methacrylic acid according to the invention, they are not particularly limited as long as they are the microbes having the ability to produce methacrylic acid. As for the microbes, the microbes as follows can be used, for example. The microbes can be used either singly or as a combination of two or more types that are selected from the following microbes.

[Preferred Order of Prokaryotes]

Specific examples of the prokaryotes that are suitable for the invention include microbes belonging to Rhodospirillales, Rhodobacterales, Sphingomonadales, Caulobacterales, Rhizobiales, Parvularculales, Burkholderiales, Hydrogenophilales, Neisseriales, Nitrosomonadales, Rhodocyclales, Chromatiales, Acidithiobacillales, Xanthomonadales, Thiotrichales, Oceanospirillales, Pseudomonadales, Alteromonadales, Vibrionales, Aeromonadales, Salinisphaerales, Legionellales, Desulfobacterales, Desulfarculales, Desulfuromonadales, Syntrophobacterales, Bdellovibrionales, Myxococcales, Acidobacteriales, Actinomycetales, Bifidobacteriales, Rubrobacterales, Solirubrobacterales, Bacillales, Lactobacillales, Clostridiales, Thermoanaerobacterales, Natranaerobiales, Sphingobacteriales, Bacteroidales, Cytophagales, Flavobacteriales, Deinococcales, Thermales, Gemmatimonadales, Fusobacteriales, Chloroflexales, Herpetosiphonales, Thermomicrobiales, Thermotogales, Deferribacterales, Sulfolobales, Desulfurococcales, Thermoproteales, Acidilobales, Halobacteriales, Thermoplasmatales, or Archaeoglobales.

Among them, preferred microbes are the microbes belonging to Rhodospirillales, Rhodobacterales, Sphingomonadales, Caulobacterales, Rhizobiales, Parvularculales, Burkholderiales, Hydrogenophilales, Neisseriales, Nitrosomonadales, Rhodocyclales, Chromatiales, Xanthomonadales, Thiotrichales, Oceanospirillales, Pseudomonadales, Alteromonadales, Vibrionales, Aeromonadales, Salinisphaerales, Legionellales, Desulfobacterales, Desulfarculales, Desulfuromonadales, Syntrophobacterales, Bdellovibrionales, Myxococcales, Acidobacteriales, Actinomycetales, Rubrobacterales, Solirubrobacterales, Bacillales, Lactobacillales, Clostridiales, Thermoanaerobacterales, Natranaerobiales, Sphingobacteriales, Bacteroidales, Cytophagales, Flavobacteriales, Deinococcales, Thermales, Gemmatimonadales, Fusobacteriales, Chloroflexales, Herpetosiphonales, Thermomicrobiales, Thermotogales, Deferribacterales, Sulfolobales, Desulfurococcales, Thermoproteales, Acidilobales, Halobacteriales, Thermoplasmatales, or Archaeoglobales.

Further, examples of the particularly preferred microbes which allow experimental confirmation of the production of methacrylic acid derivatives include the microbes belonging to Rhodobacterales, Sphingomonadales, Caulobacterales, Rhizobiales, Burkholderiales, Pseudomonadales, Alteromonadales, Vibrionales, Actinomycetales, Bacillales, or Sphingobacteriales.

[Preferred Family of Prokaryotes]

Examples may include, as those belonging to Rhodospirillales, Rhodospirillaceae and Acetobacteraceae, as those belonging to Rhodobacterales, Rhodobacteraceae and Hyphomonadaceae, as those belonging to Sphingomonadales, Sphingomonadaceae and Erythrobacteraceae, as those belonging to Caulobacterales, Caulobacteraceae, as those belonging to Rhizobiales, Rhizobiaceae, Xanthobacteraceae, Brucellaceae, Phyllobacteriaceae, Aurantimonadaceae, Bradyrhizobiaceae, Methylobacteriaceae, Hyphomicrobiaceae, Rhodobiaceae and Methylocystaceae, as those belonging to Parvularculales, Parvularculaceae, as those belonging to Burkholderiales, Burkholderiaceae, Alcaligenaceae, Comamonadaceae and Oxalobacteraceae, as those belonging to Hydrogenophilales, Hydrogenophilaceae, as those belonging to Neisseriales, Neisseriaceae, as those belonging to Nitrosomonadales, Nitrosomonadaceae, as those belonging to Rhodocyclales, Rhodocyclaceae, as those belonging to Chromatiales, Chromatiaceae and Ectothiorhodospiraceae, as those belonging to Acidithiobacillales, Acidithiobacillaceae, as those belonging to Xanthomonadales, Xanthomonadaceae, as those belonging to Thiotrichales, Francisellaceae and Piscirickettsiaceae, as those belonging to Oceanospirillales, Oceanospirillaceae, Hahellaceae, Halomonadaceae and Alcanivoracaceae, as those belonging to Pseudomonadales, Pseudomonadaceae and Moraxellaceae, as those belonging to Alteromonadales, Alteromonadaceae, Shewanellaceae, Ferrimonadaceae, Idiomarinaceae, Colwelliaceae and Pseudoalteromonadaceae, as those belonging to Vibrionales, Vibrionaceae, as those belonging to Aeromonadales, Aeromonadaceae, as those belonging to Salinisphaerales, Salinisphaeraceae, as those belonging to Legionellales, Legionellaceae and Coxiellaceae, as those belonging to Desulfobacterales, Desulfobulbaceae, as those belonging to Desulfarculales, Desulfarculaceae, as those belonging to Desulfuromonadales, Geobacteraceae, as those belonging to Syntrophobacterales, Syntrophobacteraceae and Syntrophaceae, as those belonging to Bdellovibrionales, Bdellovibrionaceae and Bacteriovoracaceae, as those belonging to Myxococcales, Cystobacteraceae, Myxococcaceae, Polyangiaceae and Kofleriaceae, as those belonging to Acidobacteriales, Acidobacteriaceae, as those belonging to Acidimicrobiales, Acidimicrobiaceae, as those belonging to Actinomycetales, Streptosporangiaceae, Nocardiopsaceae, Thermomonosporaceae, Pseudonocardiaceae, Actinosynnemataceae, Micromonosporaceae, Actinopolysporaceae, Propionibacteriaceae, Nocardioidaceae, Corynebacteriaceae, Nocardiaceae, Gordoniaceae, Dietziaceae, Mycobacteriaceae, Tsukamurellaceae, Segniliparaceae, Microbacteriaceae, Micrococcaceae, Dermabacteraceae, Dermatophilaceae, Brevibacteriaceae, Cellulomonadaceae, Intrasporangiaceae, Jonesiaceae, Rarobacteraceae, Frankiaceae, Acidothermaceae, Nakamurellaceae, Cryptosporangiaceae, Geodermatophilaceae, Glycomycetaceae, Actinomycetaceae, Streptomycetaceae, Catenulisporaceae and Kineosporiaceae, as those belonging to Bifidobacteriales, Bifidobacteriaceae, as those belonging to Rubrobacterales, Rubrobacteraceae, as those belonging to Solirubrobacterales, Conexibacteraceae, as those belonging to Bacillales, Bacillaceae, Alicyclobacillaceae, Paenibacillaceae, Planococcaceae, Sporolactobacillaceae and Thermoactinomycetaceae, as those belonging to Lactobacillales, Lactobacillaceae, Leuconostocaceae, Aerococcaceae, Carnobacteriaceae and Streptococcaceae, as those belonging to Clostridiales, Clostridiaceae, Syntrophomonadaceae, Eubacteriaceae, Peptococcaceae, Peptostreptococcaceae, Lachnospiraceae and Oscillospiraceae, as those belonging to Thermoanaerobacterales, Thermoanaerobacteraceae, as those belonging to Natranaerobiales, Natranaerobiaceae, as those belonging to Sphingobacteriales, Sphingobacteriaceae and Saprospiraceae, as those belonging to Bacteroidales, Bacteroidaceae, Marinilabiliaceae, Prevotellaceae and Porphyromonadaceae, as those belonging to Cytophagales, Cytophagaceae and Flammeovirgaceae, as those belonging to Flavobacteriales, Flavobacteriaceae, as those belonging to Deinococcales, Deinococcaceae, as those belonging to Thermales, Thermaceae, as those belonging to Gemmatimonadales, Gemmatimonadaceae, as those belonging to Fusobacteriales, Fusobacteriaceae, as those belonging to Chloroflexales, Chloroflexaceae, as those belonging to Herpetosiphonales, Herpetosiphonaceae, as those belonging to Thermomicrobiales, Thermomicrobiaceae, as those belonging to Thermotogales, Thermotogaceae, as those belonging to Deferribacterales, Deferribacteraceae, as those belonging to Sulfolobales, Sulfolobaceae, as those belonging to Desulfurococcales, Desulfurococcaceae, as those belonging to Thermoproteales, Thermoproteaceae, as those belonging to Acidilobales, Acidilobaceae, as those belonging to Halobacteriales, Halobacteriaceae, as those belonging to Thermoplasmatales, Thermoplasmataceae, Picrophilaceae and Ferroplasmaceae, and as those belonging to Archaeoglobales, Archaeoglobaceae.

Among them, preferred microbes are the microbes belonging to Rhodospirillaceae, Acetobacteraceae, Rhodobacteraceae, Hyphomonadaceae, Sphingomonadaceae, Erythrobacteraceae, Caulobacteraceae, Rhizobiaceae, Xanthobacteraceae, Brucellaceae, Phyllobacteriaceae, Aurantimonadaceae, Bradyrhizobiaceae, Methylobacteriaceae, Hyphomicrobiaceae, Rhodobiaceae, Methylocystaceae, Parvularculaceae, Burkholderiaceae, Alcaligenaceae, Comamonadaceae, Oxalobacteraceae, Neisseriaceae, Nitrosomonadaceae, Rhodocyclaceae, Chromatiaceae, Ectothiorhodospiraceae, Xanthomonadaceae, Francisellaceae, Piscirickettsiaceae, Oceanospirillaceae, Hahellaceae, Halomonadaceae, Alcanivoracaceae, Pseudomonadaceae, Moraxellaceae, Alteromonadaceae, Shewanellaceae, Ferrimonadaceae, Idiomarinaceae, Colwelliaceae, Pseudoalteromonadaceae, Vibrionaceae, Aeromonadaceae, Salinisphaeraceae, Legionellaceae, Coxiellaceae, Desulfobulbaceae, Desulfarculaceae, Geobacteraceae, Syntrophobacteraceae, Syntrophaceae, Bdellovibrionaceae, Bacteriovoracaceae, Cystobacteraceae, Myxococcaceae, Polyangiaceae, Kofleriaceae, Acidobacteriaceae, Acidimicrobiaceae, Streptosporangiaceae, Nocardiopsaceae, Thermomonosporaceae, Pseudonocardiaceae, Actinosynnemataceae, Micromonosporaceae, Nocardioidaceae, Corynebacteriaceae, Nocardiaceae, Gordoniaceae, Dietziaceae, Mycobacteriaceae, Tsukamurellaceae Segniliparaceae, Microbacteriaceae, Micrococcaceae, Dermabacteraceae, Cellulomonadaceae, Intrasporangiaceae, Frankiaceae, Acidothermaceae, Nakamurellaceae, Geodermatophilaceae, Glycomycetaceae, Streptomycetaceae, Catenulisporaceae, Rubrobacteraceae, Conexibacteraceae, Bacillaceae, Alicyclobacillaceae, Paenibacillaceae, Lactobacillaceae, Carnobacteriaceae Clostridiaceae, Syntrophomonadaceae, Eubacteriaceae, Peptococcaceae, Lachnospiraceae, Oscillospiraceae, Thermoanaerobacteraceae, Natranaerobiaceae, Sphingobacteriaceae, Saprospiraceae, Porphyromonadaceae, Cytophagaceae, Flavobacteriaceae, Deinococcaceae, Thermaceae, Gemmatimonadaceae, Fusobacteriaceae, Chloroflexaceae, Herpetosiphonaceae, Thermomicrobiaceae, Thermotogaceae, Deferribacteraceae, Sulfolobaceae, Desulfurococcaceae, Thermoproteaceae, Acidilobaceae, Halobacteriaceae, Thermoplasmataceae, Picrophilaceae, Ferroplasmaceae, or Archaeoglobaceae.

Further, examples of the particularly preferred microbes which allow experimental confirmation of the production of methacrylic acid derivatives include the microbes belonging to Rhodobacteraceae, Sphingomonadaceae, Caulobacteraceae, Rhizobiaceae, Xanthobacteraceae, Brucellaceae, Phyllobacteriaceae, Alcaligenaceae, Comamonadaceae, Pseudomonadaceae, Moraxellaceae, Shewanellaceae, Vibrionaceae, Nocardiaceae, Streptomycetaceae, Bacillaceae, Paenibacillaceae or Sphingobacteriaceae.

[Preferred Genus of Prokaryotes]

Examples may include, as those belonging to Rhodospirillaceae, the genus *Magnetospirillum*, the genus *Rhodospirillum*, the genus *Azospirillum* and the genus *Tistrella*, as those belonging to Acetobacteraceae, the genus *Acetobacter*, the genus *Acidiphilium* and the genus *Gluconacetobacter*, as those belonging to Rhodobacteraceae, the genus *Rhodobacter*, the genus *Paracoccus*, the genus *Ruegeria*, the genus *Jannaschia*, the genus *Roseobacter*, the genus *Dinoroseobacter*, the genus *Pseudovibrio*, the genus *Phaeobacter*, the genus *Octadecabacter* and the genus *Ahrensia*, as those belonging to Hyphomonadaceae, the genus *Hyphomonas*, the genus *Maricaulis*, the genus *Hirschia*, as those belonging to Sphingomonadaceae, the genus *Sphingomonas*, the genus *Novosphingobium*, the genus *Sphingopyxis*, the genus *Sphingobium*, the genus *Lutibacterium* and the genus *Zymomonas*, as those belonging to Erythrobacteraceae, the genus *Erythrobacter*, as those belonging to Caulobacteraceae, the genus *Brevundimonas*, the genus *Caulobacter*, the genus *Phenylobacterium* and the genus *Asticcacaulis*, as those belonging to Rhizobiaceae, the genus *Agrobacterium*, the genus *Rhizobim* and the genus *Sinorhizobium*, as those belonging to Xanthobacteraceae, the genus *Xanthobacter* and the genus *Azorhizobium*, as those belonging to Brucellaceae, the genus *Brucella* and the genus *Ochrobactrum*, as those belonging to Phyllobacteriaceae, the genus *Mesorhizobium* and the genus *Chelativorans*, as those belonging to Aurantimonadaceae, the genus *Aurantimonas*, as those belonging to Bradyrhizobiaceae, the genus *Bradyrhizobium*, the genus *Agromonas*, the genus *Rhodopseudomonas* and the genus *Nitrobacter*, as those belonging to Methylobacteriaceae, the genus *Methylobacterium*, as those belonging to Hyphomicrobiaceae, the genus *Hyphomicrobium*, the genus *Rhodomicrobium* and the genus *Pelagibacterium*, as those belonging to Rhodobiaceae, the genus *Parvibaculum*, as those belonging to Methylocystaceae, the genus *Methylocystis*, as those belonging to Parvularculaceae, the genus *Parvularcula*, as those belonging to Burkholderiaceae, the genus *Burkholderia*, the genus *Ralstonia*, the genus *Cupriavidus* and the genus *Polynucleobacter*, as those belonging to Alcaligenaceae, the genus *Achromobacter*, the genus *Alcaligenes*, the genus *Bordetella*, the genus *Taylorella*, the genus *Pusillimonas* and the genus *Oligella*, as those belonging to Comamonadaceae, the genus *Comamonas*, the genus *Alicycliphilus*, the genus *Delftia*, the genus *Ramlibacter*, the genus *Rhodoferax*, the genus *Variovorax*, the genus *Polaromonas*, the genus *Acidovorax* and the genus *Verminephrobacter*, as those belonging to Oxalobacteraceae, the genus *Herminiimonas*, the genus *Herbaspirillum* and the genus *Collimonas*, as those belonging to Hydrogenophilaceae, the genus *Hydrogenophilus* and the genus *Thiobacillus*, as those belonging to Neisseriaceae, the genus *Chromobacterium*, the genus *Laribacter* and the genus *Pseudogulbenkianonas* those belonging to Nitrosomonadaceae, the genus *Nitrosomonas* and the genus *Nitrosospira*, as those belonging to Rhodocyclaceae, the genus *Aromatoleum*, the genus *Azoarcus*, the genus *Dechloromonas*, the genus *Thauera* and the genus *Azospira* (*Dechlorosoma*), as those belonging to Chromatiaceae, the genus *Rheinheimera*, the genus *Thiosphaera* and the genus *Nitrosococcus*, as those belonging to Ectothiorhodospiraceae, the genus *Halorhodospira*, as those belonging to Acidithiobacillaceae, the genus *Acidithiobacillus*, as those belonging to Xanthomonas, the genus *Xanthomonas*, the genus *Stenotrophomonas*, the genus *Pseudoxanthomonas* and the genus *Rhodanobacter*, as those belonging to Francisellaceae, the genus *Francisella*, as those belonging to Piscirickettsiaceae, the genus *Cycloclasticus*, as those belonging to Oceanospirillaceae, the genus *Oceanospirillum* and the genus *Marinospirillum*, as those belonging to Hahellaceae, the genus *Hahella*, as those belonging to Halomonadaceae, the genus *Halomonas*, as those belonging to Alcanivoraceae, the genus *Alcanivorax* and the genus *Kangiella*, as those belonging to Pseudomonadaceae, the genus *Pseudomonas* and the genus *Azotobacter*, as those belonging to Moraxellaceae, the genus *Acinetobacter* and the genus *Psychrobacter*, as those belonging to Alteromonadaceae, the genus *Alishewanella*, the genus *Alteromonas*, the genus *Glaciecola*, the genus *Marinobacter*, the genus *Marinobacterium* and as those belonging to Saccharophagus, the genus Shewanellaceae, the genus *Shewanella*, as those belonging to Ferrimonadaceae, the genus *Ferrimonas*, as those belonging to Idiomarinaceae, the genus *Idiomarina*, as those belonging to Colwelliaceae, the genus *Colwellia*, as those belonging to Pseudoalteromonadaceae, the genus *Pseudoalteromonas*, as those belonging to Vibrionaceae, the genus *Listonella*, the genus *Vibrio* and the genus *Photobacterium*, as those belonging to Aeromonadaceae, the genus *Aeromonas* and the genus *Oceanimonas*, as those belonging to Salinisphaeraceae, the genus *Salinisphaera*, as those belonging to Legionellaceae, the genus *Legionella*, as those belonging to Coxiellaceae, the genus *Coxiella*, as those belonging to Desulfobulbaceae, the genus *Desulfococcus*, the genus *Desulfobacterium* and the genus *Desulfatibacillum*, as those belonging to Desulfarculaceae, the genus *Desulfobulbus* and the genus *Desulfarculus*, as those belonging to Geobacteraceae, the genus *Geobacter*, as those belonging to Syntrophobacteraceae, the genus *Syntrophobacter*, as those belonging to Syntrophaceae, the genus *Syntrophus* and the genus *Desulfomonile*, as those belonging to Bdellovibrionaceae, the genus *Bdellovibrio*, as those belonging to Bacteriovoracaceae, the genus *Bacteriovorax*, as those belonging to Cystobacteraceae, the genus *Stigmatella*, as those belonging to Myxococcaceae, the genus *Myxococcus* and the genus *Anaeromyxobacter*, as those belonging to Polyangiaceae, the genus *Sorangium*, as those belonging to Kofleriaceae, the genus *Haliangium*, as those belonging to Acidobacteriaceae, the genus *Acidobacterium* and the genus *Granulicella*, as those belonging to Acidimicrobiaceae, the genus *Ilumatobacter*, as those belonging to Streptosporangiaceae, the genus *Streptosporangium*, the genus *Acrocarpospora*, the genus *Herbidospora*, the genus *Microbispora*, the genus *Nonomuraea*, the genus *Planobispora* and the genus *Planomonospora*, as those belonging to Nocardiopsaceae, the genus *Nocardiopsis* and the genus *Thermobifida*, as those belonging to Thermomonosporaceae, the genus *Actinocorallia*, the genus *Actinomadura* and the genus *Thermomonospora*, as those belonging to Pseudonocardiaceae, the genus *Pseudonocardia*, the genus *Actinoalloteichus*, the genus *Amycolatopsis*, the genus *Kibdelosporangium*, the genus *Saccharomonospora*, the genus *Saccharopolyspora*, the genus *Saccharothrix*, the genus *Streptoalloteichus*, the genus *Thermobispora* and the genus *Thermocrispum*, as those belonging to Actinosynnemataceae, the genus *Actinokineospora* and the genus *Actinosynnema*, as those belonging to Micromonosporaceae, the genus *Micromonospora*, the genus *Actinoplanes*, the genus *Catellatospora*, the genus *Couchioplanes*, the genus *Dactylosporangium*, the genus *Pilimelia*, the genus *Salinispora* and the genus *Verrucosispora*, the genus Actinopolysporaceae, the genus *Actinopolyspora*, as those belonging to Propionibacteriaceae, the genus *Propionibacterium* and the genus *Luteococcus*, as those belonging to Nocardioidaceae, the genus *Nocardioides*, the genus *Aeromicrobium*, the genus *Kribbella* and the genus *Pimelobacter*, as those belonging to Corynebacteriaceae, the genus *Corynebacterium*, the genus Nocardiaceae, the genus *Nocardia* and the genus *Rhodococcus*, as those belonging to Gordoniaceae, the genus *Gordonia*, as those belonging to Dietziaceae, the genus *Dietzia*, as those belonging to Mycobacteriaceae, the genus *Mycobacterium* and the genus *Amycolicicoccus*, as those belonging to Tsukamurellaceae, the genus *Tsukamurella*, as those belonging to Segniliparaceae, the genus *Segniliparus*, as those belonging to Microbacteriaceae, the genus *Microbacterium*, the genus *Agromyces*, the genus *Clavibacter*, the genus *Curtobacterium* and the genus *Rathayibacter*, as those belonging to Micrococcaceae, the genus *Micrococcus*, the genus *Arthrobacter*, the genus *Citricoccus*, the genus *Renibacterium*, the genus *Kocuria* and the genus *Rothia*, as those belonging to Dermabacteraceae, the genus *Brachybacterium*, the genus *Dermacoccus*, the genus *Demetria* and the genus *Kytococcus*, as those belonging to Dermatophilaceae, the genus *Dermatophilus*, as those belonging to Brevibacteriaceae, the genus *Brevibacterium*, as those belonging to Cellulomonadaceae, the genus *Cellulomonas* and the genus *Oerskovia*, as those belonging to Intrasporangiaceae, the genus *Intrasporangium*, the genus *Janibacter*, the genus *Terrabacter* and the genus *Serinicoccus*, as those belonging to Jonesiaceae, the genus *Jonesia*, as those belonging to Rarobacteraceae, the genus *Rarobacter*, the genus Frankiaceae, the genus *Frankia*, the genus *Acidothermaceae*, the genus *Acidothermus*, as those belonging to Nakamurellaceae, the genus *Nakamurella*, as those belonging to Cryptosporangiaceae, the genus *Cryptosporangium*, as those belonging to Geodermatophilaceae, the genus *Geodermatophilus*, as those belonging to Glycomycetaceae, the genus *Glycomyces* and the genus *Stackebrandtia*, as those belonging to Actinomycetaceae, the genus *Arcanobacterium*, as those belonging to Streptomycetaceae, the genus *Streptomyces* and the genus *Kitasatospora*, as those belonging to Catenulisporaceae, the genus *Catenulispora*, as those belonging to Kineosporiaceae, the genus *Kineosporia* and the genus *Kineococcus*, as those belonging to Bifidobacteriaceae, the genus *Bifidobacterium*, as those belonging to Rubrobacteraceae, the genus *Rubrobacter*, as those belonging to Conexibacteraceae, the genus *Conexibacter*, as those belonging to Bacillaceae, the genus *Bacillus*, the genus *Geobacillus*, the genus *Oceanobacillus*, the genus *Lysinibacillus* and the genus *Halobacillus*, as those belonging to Alicyclobacillaceae, the genus *Alicyclobacillus* and the genus *Kyrpidia*, as those belonging to Paenibacillaceae, the genus *Paenibacillus* and the genus *Brevibacillus*, as those belonging to Planococcaceae, the genus *Planococcus* and the genus *Kurthia*, as those belonging to Sporolactobacillaceae, the genus *Sporolactobacillus*, as those belonging to Thermoactinomycetaceae, the genus *Thermoactinomyces*, as those belonging to Lactobacillaceae, the genus *Lactobacillus* and the genus *Pediococcus*, as those belonging to Leuconostocaceae, the genus *Leuconostoc* and the genus *Weissella*, as those belonging to Aerococcaceae, the genus *Aerococcus* and the genus *Globicatella*, as those belonging to Carnobacteriaceae, the genus *Alloiococcus* and the genus *Carnobacterium*, as those belonging to Streptococcaceae, the genus *Streptococcus*, as those belonging to Clostridiaceae, the genus *Clostridium* and the genus *Alkaliphilus*, as those belonging to Syntrophomonadaceae, the genus *Syntrophomonas* and the genus *Syntrophothermus*, as those belonging to Eubacteriaceae, the genus *Eubacterium*, as those belonging to Peptococcaceae, the genus *Peptococcus*, the genus *Desulfitobacterium*, the genus *Desulfotomaculum* and the genus *Pelotomaculum*, as those belonging to Peptostreptococcaceae, the genus *Peptostreptococcus*, the genus *Lachnospiraceae*, the genus *Butyrivibrio* and the genus *Roseburia*, as those belonging to Oscillospiraceae, the genus *Oscillibacter*, as those belonging to Thermoanaerobacteraceae, the genus *Thermoanaerobacter* and the genus *Carboxydothermus*, as those belonging to Natranaerobiaceae, the genus *Natranaerobius*, as those belonging to Sphingobacteriaceae, the genus *Sphingobacterium*, the genus *Pedobacter* and the genus *Mucilaginibacter*, as those belonging to Saprospiraceae, the genus *Haliscomenobacter*, as those belonging to Bacteroidaceae, the genus *Bacteroides*, as those belonging to Marinilabiliaceae, the genus *Marinilabilia*, as those belonging to Prevotellaceae, the genus *Prevotella*, as those belonging to Porphyromonadaceae, the genus *Porphyromonas* and the genus *Odoribacter*, as those belonging to Cytophagaceae, the genus *Flexibacter*, the genus *Spirosoma* and the genus *Runella*, as those belonging to Flammeovirgaceae, the genus *Flammeovirga*, as those belonging to Flavobacteriaceae, the genus *Flavobacterium*, the genus *Chryseobacterium* and the genus *Maribacter*, as those belonging to Deinococcaceae, the genus *Deinococcus*, as those belonging to Thermaceae, the genus *Thermus*, the genus *Meiothermus*, the genus *Oceanithermus* and the genus *Marinithermus*, as those belonging to Gemmatimonadaceae, the genus *Gemmatimonas*, as those belonging to Fusobacteriaceae, the genus *Fusobacterium* and the genus *Ilyobacter*, as those belonging to Chloroflexaceae, the genus *Roseiflexus*, as those belonging to Herpetosiphonaceae, the genus *Herpetosiphon*, as those belonging to Thermomicrobiaceae, the genus *Thermomicrobium*, as those belonging to Thermotogaceae, the genus *Thermotoga*, the genus *Thermosipho* and the genus *Fervidobacterium*, as those belonging to Deferribacteraceae, the genus *Deferribacter*, the genus *Calditerrivibrio* and the genus *Flexistipes*, the genus *Sulfolobaceae*, the genus *Metallosphaera* and the genus *Acidianus*, as those belonging to Desulfurococcaceae, the genus *Aeropyrum*, as those belonging to Thermoproteaceae, the genus *Pyrobaculum*, the genus *Caldivirga* and the genus *Vulcanisaeta*, as those belonging to Acidilobaceae, the genus *Acidilobus*, as those belonging to Halobacteriaceae, the genus *Halobacterium*, the genus *Halococcus*, the genus *Haloarcula*, the genus *Haloquadratum*, the genus *Natronomonas*, the genus *Halorubrum*, the genus *Haloterrigena*, the genus *Natrialba*, the genus *Halalkalicoccus* and the genus *Halogeometricum*, as those belonging to Thermoplasmataceae, the genus *Thermoplasma*, as those belonging to Picrophilaceae, the genus *Picrophilus*, as those belonging to Ferroplasmaceae, the genus *Ferroplasma*, and as those belonging to Archaeoglobaceae, the genus *Archaeoglobus* and the genus *Ferroglobus*. Further, examples of the microbes having no determined order in terms of classification include the genus *Polymorphum*, the genus *Micavibrio*, the genus *Simiduia*, the genus *Leptothrix*, the genus *Thiomonas*, the genus *Rubrivivax*, and the genus *Methylibium*, examples of the microbes belonging to Bacillales but no determined family in terms of classification include the genus *Exiguobacterium*, examples of the microbes belonging to Clostridiales but no determined family in terms of classification include the genus Clostridiales.

Among them, preferred microbes are the microbes which have been demonstrated to have an enzyme for the metabolism pathway of branched amino acids, that is, microbes belonging to the genus *Magnetospirillum*, the genus *Rhodospirillum*, the genus *Azospirillum*, the genus *Tistrella*, the genus *Acidiphilium*, the genus *Rhodobacter*, the genus *Paracoccus*, the genus *Ruegeria*, the genus *Jannaschia*, the genus *Roseobacter*, the genus *Dinoroseobacter*, the genus *Pseudovibrio*, the genus *Phaeobacter*, the genus *Octadecabacter*, the genus *Hyphomonas*, the genus *Maricaulis*, the genus *Hirschia*, the genus *Sphingomonas*, the genus *Novosphingobium*, the genus *Sphingopyxis*, the genus *Sphingobium*, the genus *Erythrobacter*, the genus *Brevundimonas*, the genus *Caulobacter*, the genus *Phenylobacterium*, the genus *Asticcacaulis*, the genus *Agrobacterium*, the genus *Rhizobium*, the genus *Sinorhizobium*, the genus *Xanthobacter*, the genus *Azorhizobium*, the genus *Brucella*, the genus *Ochrobactrum*, the genus *Mesorhizobium*, the genus *Chelativorans*, the genus *Aurantimonas*, the genus *Bradyrhizobium*, the genus *Agromonas*, the genus *Rhodopseudomonas*, the genus *Nitrobacter*, the genus *Methylobacterium*, the genus *Rhodomicrobium*, the genus *Pelagibacterium*, the genus *Parvibaculum*, the genus *Methylocystis*, the genus *Parvularcula*, the genus *Burkholderia*, the genus *Ralstonia*, the genus *Cupriavidus*, the genus *Polynucleobacter*, the genus *Achromobacter*, the genus *Bordetella*, the genus *Taylorella*, the genus *Pusillimonas*, the genus *Comamonas*, the genus *Alicycliphilus*, the genus *Delftia*, the genus *Ramlibacter*, the genus *Rhodoferax*, the genus *Variovorax*, the genus *Polaromonas*, the genus *Acidovorax*, the genus *Verminephrobacter*, the genus *Herminiimonas*, the genus *Herbaspirillum*, the genus *Collimonas*, the genus *Chromobacterium*, the genus *Laribacter*, the genus *Pseudogulbenkiania*, the genus *Nitrosomonas*, the genus *Nitrosospira*, the genus *Aromatoleum*, the genus *Azoarcus*, the genus *Dechloromonas*, the genus *Thauera*, the genus *Azospira* (*Dechlorosoma*), the genus *Rheinheimera*, the genus *Nitrosococcus*, the genus *Halorhodospira*, the genus *Xanthomonas*, the genus *Stenotrophomonas*, the genus *Pseudoxanthomonas*, the genus *Rhodanobacter*, the genus *Francisella*, the genus *Cycloclasticus*, the genus *Oceanospirillum*, the genus *Hahella*, the genus *Halomonas*, the genus *Alcanivorax*, the genus *Kangiella*, the genus *Pseudomonas*, the genus *Azotobacter*, the genus *Acinetobacter*, the genus *Psychrobacter*, the genus *Alishewanella*, the genus *Alteromonas*, the genus *Glaciecola*, the genus *Marinobacter*, the genus *Marinobacterium*, the genus *Saccharophagus*, the genus *Shewanella*, the genus *Ferrimonas*, the genus *Idiomarina*, the genus *Colwellia*, the genus *Pseudoalteromonas*, the genus *Listonella*, the genus *Vibrio*, the genus *Photobacterium*, the genus *Aeromonas*, the genus *Oceanimonas*, the genus *Salinisphaera*, the genus *Legionella*, the genus *Coxiella*, the genus *Desulfococcus*, the genus *Desulfobacterium*, the genus *Desulfatibacillum*, the genus *Desulfobulbus*, the genus *Desulfarculus*, the genus *Geobacter*, the genus *Syntrophobacter*, the genus *Syntrophus*, the genus *Desulfomonile*, the genus *Bdellovibrio*, the genus *Bacteriovorax*, the genus *Stigmatella*, the genus *Myxococcus*, the genus *Anaeromyxobacter*, the genus *Sorangium*, the genus *Haliangium*, the genus *Acidobacterium*, the genus *Granulicella*, the genus *Ilumatobacter*, the genus *Streptosporangium*, the genus *Nocardiopsis*, the genus *Thermobifida*, the genus *Thermomonospora*, the genus *Pseudonocardia*, the genus *Amycolatopsis*, the genus *Saccharomonospora*, the genus *Saccharopolyspora*, the genus *Thermobispora*, the genus *Actinosynnema*, the genus *Micromonospora*, the genus *Salinispora*, the genus *Verrucosispora*, the genus *Nocardioides*, the genus *Kribbella*, the genus *Corynebacterium*, the genus *Nocardia*, the genus *Rhodococcus*, the genus *Gordonia*, the genus *Dietzia*, the genus *Mycobacterium*, the genus *Amycolicicoccus*, the genus *Tsukamurella*, the genus *Segniliparus*, the genus *Microbacterium*, the genus *Micrococcus*, the genus *Arthrobacter*, the genus *Citricoccus*, the genus *Renibacterium*, the genus *Kocuria*, the genus *Kytococcus*, the genus *Cellulomonas*, the genus *Intrasporangium*, the genus *Serinicoccus*, the genus *Frankia*, the genus *Acidothermus*, the genus *Nakamurella*, the genus *Geodermatophilus*, the genus *Stackebrandtia*, the genus *Streptomyces*, the genus *Catenulispora*, the genus *Rubrobacter*, the genus *Conexibacter*, the genus *Bacillus*, the genus *Geobacillus*, the genus *Oceanobacillus*, the genus *Lysinibacillus*, the genus *Halobacillus*, the genus *Alicyclobacillus*, the genus *Kyrpidia*, the genus *Paenibacillus*, the genus *Lactobacillus*, the genus *Carnobacterium*, the genus *Clostridium*, the genus *Alkaliphilus*, the genus *Syntrophomonas*, the genus *Syntrophothermus*, the genus *Eubacterium*, the genus *Desulfitobacterium*, the genus *Desulfotomaculum*, the genus *Pelotomaculum*, the genus *Butyrivibrio*, the genus *Roseburia*, the genus *Oscillibacter*, the genus *Thermoanaerobacter*, the genus *Carboxydothermus*, the genus *Natranaerobius*, the genus *Sphingobacterium*, the genus *Pedobacter*, the genus *Haliscomenobacter*, the genus *Porphyromonas*, the genus *Odoribacter*, the genus *Spirosoma*, the genus *Runella*, the genus *Maribacter*, the genus *Deinococcus*, the genus *Thermus*, the genus *Meiothermus*, the genus *Oceanithermus*, the genus *Marinithermus*, the genus *Gemmatimonas*, the genus *Fusobacterium*, the genus *Ilyobacter*, the genus *Roseiflexus*, the genus *Herpetosiphon*, the genus *Thermomicrobium*, the genus *Thermotoga*, the genus *Thermosipho*, the genus *Fervidobacterium*, the genus *Deferribacter*, the genus *Calditerrivibrio*, the genus *Flexistipes*, the genus *Metallosphaera*, the genus

*Aeropyrum*, the genus *Pyrobaculum*, the genus *Caldivirga*, the genus *Vulcanisaeta*, the genus *Acidilobus*, the genus *Haloarcula*, the genus *Haloquadratum*, the genus *Natronomonas*, the genus *Halorubrum*, the genus *Haloterrigena*, the genus *Natrialba*, the genus *Halalkalicoccus*, the genus *Halogeometricum*, the genus *Thermoplasma*, the genus *Picrophilus*, the genus *Ferroplasma*, the genus *Archaeoglobus*, the genus *Ferroglobus*, the genus *Polymorphum*, the genus *Micavibrio*, the genus *Simiduia*, the genus *Leptothrix*, the genus *Thiomonas*, the genus *Rubrivivax*, the genus *Methylibium*, the genus *Exiguobacteriumm*, or the genus *Anaerococcus*.

Further, examples of the particularly preferred microbes which allow experimental confirmation of the production of methacrylic acid derivatives include the microbes belonging to the genus *Paracoccus*, the genus *Sphingomonas*, the genus *Brevundimonas*, the genus *Agrobacterium*, the genus *Rhizobium*, the genus *Xanthobacter*, the genus *Ochrobactrum*, the genus *Mesorhizobium*, the genus *Achromobacter*, the genus *Comamonas*, the genus *Pseudomonas*, the genus *Acinetobacter*, the genus *Shewanella*, the genus *Listonella*, the genus *Rhodococcus*, the genus *Streptomyces*, the genus *Bacillus*, the genus *Geobacillus*, the genus *Paenibacillus*, the genus *Sphingobacterium*, or the genus *Pedobacter*.

[Preferred Species of Prokaryotes]
[Genus *Pseudomonas*]

Examples of the microbes that are classified as the genus *Pseudomonas* include *Pseudomonas aeruginosa, Pseudomonas agarici, Pseudomonas alcaligenes, Pseudomonas amygdale, Pseudomonas anguiliseptica, Pseudomonas antimicrobica, Pseudomonas aspleni, Pseudomonas aurantiaca, Pseudomonas aureofaciens, Pseudomonas avellanae, Pseudomonas azotoformans, Pseudomonas balearica, Pseudomonas beijerinsckii, Pseudomonas beteli, Pseudomonas boreopolis, Pseudomonas carboxyhydrogena, Pseudomonas caricapapayae, Pseudomonas cichorii, Pseudomonas cissicola, Pseudomonas citronellolis, Pseudomonas coronafaciens, Pseudomonas corrugate, Pseudomonas doudoroffii, Pseudomonas echinoids, Pseudomonas elongate, Pseudomonas ficuserectae, Pseudomonas flavescens, Pseudomonas flectens, Pseudomonas fluorescens, Pseudomonas fragi, Pseudomonas fulva, Pseudomonas fuscovaginae, Pseudomonas gelidicola, Pseudomonas geniculata, Pseudomonas glathei, Pseudomonas halophila, Pseudomonas hibiscicola, Pseudomonas huttiensis, Pseudomonas iners, Pseudomonas lancelota, Pseudomonas lemoignei, Pseudomonas lundensis, Pseudomonas luteola, Pseudomonas marginalis, Pseudomonas meliae, Pseudomonas mendocina, Pseudomonas mucidolens, Pseudomonas monteilli, Pseudomonas nautica, Pseudomonas nitroreducens, Pseudomonas oleovorans, Pseudomonas oryzihabitans, Pseudomonas pertucinogena, Pseudomonas phenazinium, Pseudomonas pictorum, Pseudomonas pseudoalcaligenes, Pseudomonas putida, Pseudomonas pyrrocinia, Pseudomonas resinovorans, Pseudomonas rhodesiae, Pseudomonas saccharophila, Pseudomonas savastanoi, Pseudomonas spinosa, Pseudomonas stanieri, Pseudomonas straminae, Pseudomonas stutzeri, Pseudomonas synxantha, Pseudomonas syringae, Pseudomonas syzygii, Pseudomonas taetrolens, Pseudomonas tolaasii, Pseudomonas veronii, Pseudomonas viridiflava, Pseudomonas vulgaris*, and *Pseudomonas wisconsinensis*.

[Genus *Bacillus*]

Examples of the microbes that are classified as the genus *Bacillus* include *Bacillus cereus, Bacillus subtilis, Bacillus thuringiensis, Bacillus acidiceler, Bacillus acidicola, Bacillus aeolius, Bacillus aerius, Bacillus aerophilus, Bacillus agaradhaerens, Bacillus akibai, Bacillus alcalophilus, Bacillus algicola, Bacillus alkalidiazotrophicus, Bacillus alkalitelluris, Bacillus altitudinis, Bacillus alveayuensis, Bacillus amyloliquefaciens, Bacillus anthracis, Bacillus aquimaris, Bacillus arenosi, Bacillus arseniciselenatis, Bacillus arsenicus, Bacillus arvi, Bacillus asahii, Bacillus atrophaeus, Bacillus aurantiacus, Bacillus axarquiensis, Bacillus azotoformans, Bacillus badius, Bacillus barbaricus, Bacillus bataviensis, Bacillus benzoevorans, Bacillus bogoriensis, Bacillus boroniphilus, Bacillus butanolivorans, Bacillus carboniphilus, Bacillus cecembensis, Bacillus cellulosilyticus, Bacillus chagannorensis, Bacillus cibi, Bacillus circulans, Bacillus clarkii, Bacillus clausii, Bacillus coagulans, Bacillus coahuilensis, Bacillus cohnii, Bacillus decisifrondis, Bacillusdecolorationis, Bacillus drentensis, Bacillus edaphicus, Bacillus endophyticus, Bacillus farraginis, Bacillus fastidiosus, Bacillus firmus, Bacillus flexus, Bacillus foraminis, Bacillus fordii, Bacillus fortis, Bacillus fumarioli, Bacillus funiculus, Bacillus galactosidilyticus, Bacillus gelatini, Bacillus gibsonii, Bacillus halmapalus, Bacillus halodurans, Bacillus halophilus, Bacillus hemicellulosilyticus, Bacillus herbersteinensis, Bacillus horikoshii, Bacillus horti, Bacillus humi, Bacillus hwajinpoensis, Bacillus idriensis, Bacillus indicus, Bacillus infantis, Bacillus infernus, Bacillus insolitus, Bacillus isabeliae, Bacillus jeotgali, Bacillus koreensis, Bacillus krulwichiae, Bacillus lehensis, Bacillus lentus, Bacillus licheniformis, Bacillus litoralis, Bacillus luciferensis, Bacillus macauensis, Bacillus macyae, Bacillus malacitensis, Bacillus mannanilyticus, Bacillus marinus, Bacillus marisflavi, Bacillus massiliensis, Bacillus megaterium, Bacillus methanolicus, Bacillus mojavensis, Bacillus mucilaginosus, Bacillus muralis, Bacillus murimartini, Bacillus mycoides, Bacillus nealsonii, Bacillus niabensis, Bacillus niacini, Bacillus novalis, Bacillus odysseyi, Bacillus okhensis, Bacillus okuhidensis, Bacillusoleronius, Bacillus oshimensis, Bacillus pallidus, Bacillus panaciterrae, Bacillus patagoniensis, Bacillus plakortidis, Bacillus pocheonensis, Bacillus polygoni, Bacillus pseudalcaliphilus, Bacillus pseudofirmus, Bacillus pseudomycoides, Bacillus psychrodurans, Bacillus psychrosaccharolyticus, Bacillus psychrotolerans, Bacillus pumilus, Bacillus pycnus, Bacillus qingdaonensis, Bacillus ruris, Bacillus safensis, Bacillus salarius, Bacillus saliphilus, Bacillus schlegelii, Bacillus selenatarsenatis, Bacillus selenitireducens, Bacillus seohaeanensis, Bacillus shackletonii, Bacillus silvestris, Bacillus simplex, Bacillus siralis, Bacillus smithii, Bacillus soli, Bacillus sonorensis, Bacillus sphaericus, Bacillus sporothermodurans, Bacillus stratosphericus, Bacillus subterraneus, Bacillus taeanensis, Bacillus tequilensis, Bacillus thermantarcticus, Bacillus thermoamylovorans, Bacillus thermocloacae, Bacillus thioparans, Bacillus tusciae, Bacillus vallismortis, Bacillus vedderi, Bacillus velezensis, Bacillus vietnamensis, Bacillus vireti, Bacillus wakoensis*, and *Bacillus weihenstephanensis*.

[Genus *Sphingobacterium*]

Examples of the microbes that are classified as the genus *Sphingobacterium* include *Sphingobacterium multivorum, Sphingobacterium spiritivorum, Sphingobacterium alimentarium, Sphingobacterium anhuiense, Sphingobacterium antarcticum, Sphingobacterium bambusae, Sphingobacterium canadense, Sphingobacterium composti, Sphingobacterium daejeonense, Sphingobacterium faecium, Sphingobacterium heparinum, Sphingobacterium kitahiroshimense, Sphingobacterium lactis, Sphingobacterium mizutaii, Sphingobacterium nematocida, Sphingobacterium piscium,*

*Sphingobacterium shayense*, *Sphingobacterium siyangense*, *Sphingobacterium thalpophilum*, and *Sphingobacterium wenxiniae*.

[Genus *Comamonas*]

Examples of the microbes that are classified as the genus *Comamonas* include *Comamonas acidovorans*, *Comamonas aquatica*, *Comamonas badia*, *Comamonas composti*, *Comamonas denitrificans*, *Comamonas granuli*, *Comamonas kerstersii*, *Comamonas koreensis*, *Comamonas nitrativorans*, *Comamonas odontotermites*, *Comamonas terrae*, *Comamonas terrigena*, *Comamonas testosteroni*, *Comamonas thiooxydans*, and *Comamonas zonglianii*.

[Genus *Brevundimonas*]

Examples of the microbes that are classified as the genus *Brevundimonas* include *Brevundimonas alba*, *Brevundimonas aurantiaca*, *Brevundimonas bacteroides*, *Brevundimonas basaltis*, *Brevundimonas bullata*, *Brevundimonas diminuta*, *Brevundimonas intermedia*, *Brevundimonas kwangchunensis*, *Brevundimonas lenta*, *Brevundimonas mediterranea*, *Brevundimonas nasdae*, *Brevundimonas olei*, *Brevundimonas subvibrioides*, *Brevundimonas terrae*, *Brevundimonas vancanneytii*, *Brevundimonas variabilis*, *Brevundimonas vesicularis*, and *Brevundimonas viscosa*.

[Genus *Sphingomonas*]

Examples of the microbes that are classified as the genus *Sphingomonas* include *Sphingomonas abaci*, *Sphingomonas adhaesiva*, *Sphingomonas aerolata*, *Sphingomonas aquatilis*, *Sphingomonas asaccharolytica*, *Sphingomonas astaxanthinifaciens*, *Sphingomonas aurantiaca*, *Sphingomonas azotifigens*, *Sphingomonas azotofornans*, *Sphingomonas capsulata*, *Sphingomonas changbaiensis*, *Sphingomonas chlorophenolica*, *Sphingomonas cynarae*, *Sphingomonas desiccabilis*, *Sphingomonas dokdonensis*, *Sphingomonas echinoides*, *Sphingomonas endophytica*, *Sphingomonas faeni*, *Sphingomonas fennica*, *Sphingomonas ginsenosidimutans*, *Sphingomonas haloaromaticamans*, *Sphingomonas herbicidovorans*, *Sphingomonas humi*, *Sphingomonas insulae*, *Sphingomonas japonica*, *Sphingomonas jaspsi*, *Sphingomonas jejuensis*, *Sphingomonas koreensis*, *Sphingomonas macrogoltabidus*, *Sphingomonas mali*, *Sphingomonas melonis*, *Sphingomonas molluscorum*, *Sphingomonas mucosissima*, *Sphingomonas natatoria*, *Sphingomonas oligophenolica*, *Sphingomonas panni*, *Sphingomonas parapaucimobilis*, *Sphingomonas paucimobilis*, *Sphingomonas phyllosphaerae*, *Sphingomonas pituitosa*, *Sphingomonas polyaromaticivorans*, *Sphingomonas pruni*, *Sphingomonas rosa*, *Sphingomonas roseiflava*, *Sphingomonas rubra*, *Sphingomonas sanguinis*, *Sphingomonas soli*, *Sphingomonas suberifaciens*, *Sphingomonas subterranea*, *Sphingomonas terrae*, *Sphingomonas trueperi*, *Sphingomonas ursincola*, *Sphingomonas wittichii*, *Sphingomonas yabuuchiae*, *Sphingomonas yanoikuyae*, and *Sphingomonas yunnanensis*.

[Genus *Ochrobactrum*]

Examples of the microbes that are classified as the genus *Ochrobactrum* include *Ochrobactrum anthropi*, *Ochrobactrum cytisi*, *Ochrobactrum daejeonense*, *Ochrobactrum gallinifaecis*, *Ochrobactrum grignonense*, *Ochrobactrum haemophilum*, *Ochrobactrum intermedium*, *Ochrobactrum lupini*, *Ochrobactrum oryzae*, *Ochrobactrum pseudintermedium*, *Ochrobactrum pseudogrignonense*, *Ochrobactrum thiophenivorans*, and *Ochrobactrum tritici*.

[Genus *Pedobacter*]

Examples of the microbes that are classified as the genus *Pedobacter* include *Pedobacter africanus*, *Pedobacter agri*, *Pedobacter alluvius*, *Pedobacter aquatilis*, *Pedobacter borealis*, *Pedobacter caeni*, *Pedobacter composti*, *Pedobacter cryoconitis*, *Pedobacter daechungensis*, *Pedobacter duraquae*, *Pedobacter ginsengisoli*, *Pedobacter hartonius*, *Pedobacter heparinus*, *Pedobacter himalayensis*, *Pedobacter j eongneungensis*, *Pedobacter koreensis*, *Pedobacter lentus*, *Pedobacter metabolipauper*, *Pedobacter nyackensis*, *Pedobacter panaciterrae*, *Pedobacter piscium*, *Pedobacter roseus*, *Pedobacter saltans*, *Pedobacter steynii*, *Pedobacter suwonensis*, and *Pedobacter terricola*.

[Genus *Paenibacillus*]

Examples of the microbes that are classified as the genus *Paenibacillus* include *Paenibacillus aestuarii*, *Paenibacillus alginolyticus*, *Paenibacillus algorifonticola*, *Paenibacillus alvei*, *Paenibacillus amylolyticus*, *Paenibacillus apiarius*, *Paenibacillus assamensis*, *Paenibacillus azoreducens*, *Paenibacillus azotofixans*, *Paenibacillus barcinonensis*, *Paenibacillus barengoltzii*, *Paenibacillus campinasensis*, *Paenibacillus cellulosilyticus*, *Paenibacillus chibensis*, *Paenibacillus chitinolyticus*, *Paenibacillus chondroitinus*, *Paenibacillus curdlanolyticus*, *Paenibacillus daejeonensis*, *Paenibacillus durus*, *Paenibacillus ehimensis*, *Paenibacillus elgii*, *Paenibacillus filicis*, *Paenibacillus frigoriresistens*, *Paenibacillus gansuensis*, *Paenibacillus ginsengihumi*, *Paenibacillus glucanolyticus*, *Paenibacillus glycanilyticus*, *Paenibacillus graminis*, *Paenibacillus hodogayensis*, *Paenibacillus hordei*, *Paenibacillus humicus*, *Paenibacillus illinoisensis*, *Paenibacillus jamilae*, *Paenibacillus kobensis*, *Paenibacillus koleovorans*, *Paenibacillus konsidensis*, *Paenibacillus kribbensis*, *Paenibacillus larvae* subsp. *larvae*, *Paenibacillus larvae* subsp. *pulvifaciens*, *Paenibacillus lautus*, *Paenibacillus macerans*, *Paenibacillus macquariensis* subsp. *defensor*, *Paenibacillus mendelii*, *Paenibacillus motobuensis*, *Paenibacillus naphthalenovorans*, *Paenibacillus nematophilus*, *Paenibacillus oceanisediminis*, *Paenibacillus odorifer*, *Paenibacillus pabuli*, *Paenibacillus pasadenensis*, *Paenibacillus peoriae*, *Paenibacillus phoenicis*, *Paenibacillus pini*, *Paenibacillus pinihumi*, *Paenibacillus polymyxa*, *Paenibacillus pueri*, *Paenibacillus rigui*, *Paenibacillus stellifer*, *Paenibacillus taiwanensis*, *Paenibacillus terrae*, *Paenibacillus terrigena*, *Paenibacillus thermophilus*, *Paenibacillus thiaminolyticus*, *Paenibacillus tundrae*, *Paenibacillus validus*, *Paenibacillusvulneris*, *Paenibacillus wooponensis*, and *Paenibacillus xylaniclasticus*.

[Genus *Acgromobacter*]

Examples of the microbes that are classified as the genus *Acgromobacter* include *Achromobacter arsenitoxydans*, *Achromobacter cholinophagum*, *Achromobacter cycloclastes*, *Achromobacter denitrificans*, *Achromobacter fischeri*, *Achromobacter hartlebii*, *Achromobacter immobilis*, *Achromobacter insolitus*, *Achromobacter lactolyticus*, *Achromobacter lyticus*, *Achromobacter methanolophila*, *Achromobacter pestifer*, *Achromobacter piechaudii*, *Achromobacter ruhlandii*, *Achromobacter spanios*, *Achromobacter viscosus*, *Achromobacter xerosis*, *Achromobacter xylosoxidans*, *Achromobacter xylosoxidans* subsp. *denitrificans*, and *Achromobacter xylosoxidans* subsp. *xylosoxidans*.

[Genus *Acinetobacter*]

Examples of the microbes that are classified as the genus *Acinetobacter* include *Acinetobacter baumannii*, *Acinetobacter aylyi*, *Acinetobacter beijerinckii*, *Acinetobacter bereziniae*, *Acinetobacter boubetii*, *Acinetobacter calcoaceticus*, *Acinetobacter gerneri*, *Acinetobacter grimontii*, *Acinetobacter guilouiae*, *Acinetobacter gyllenbergii*, *Acinetobacter haemolyticus*, *Acinetobacter johnsonii*, *Acinetobacter junii*, *Acinetobacter kyonggiensis*, *Acinetobacter lwoffii*, *Acinetobacter oleivorans*, *Acinetobacter parvus*, *Acinetobacter psychrotolerans*, *Acinetobacter radioresist-* ens, *Acinetobacter schindleri, Acinetobacter soli, Acinetobacter tandoii, Acinetobacter tartarogenes, Acinetobacter tjernbergiae, Acinetobacter towneri, Acinetobacterursingii,* and *Acinetobacter venetianus.*

[Genus *Shewanella*]

Examples of the microbes that are classified as the genus *Shewanella* include *Shewanella piezotolerans, Shewanella abyssi, Shewanella affinis, Shewanella algae, Shewanella algidipiscicola, Shewanella amazonensis, Shewanella aquimarina, Shewanella arctica, Shewanella atlantica, Shewanella baltica, Shewanella basaltis, Shewanella benthica, Shewanella candadensis, Shewanella chilikensis, Shewanella colwelliana, Shewanella corallii, Shewanella decolorationis, Shewanella denitrificans, Shewanella donghaensis, Shewanella fidelis, Shewanella fodinae, Shewanella frigidimarina, Shewanella gaetbuli, Shewanella gelidimarina, Shewanella glacialipiscicola, Shewanella gopherii, Shewanella hafniensis, Shewanella halifaxensis, Shewanella haliotis, Shewanella hanedai, Shewanella japonica, Shewanella kaireitica, Shewanella ivingstonensis, Shewanella loihica, Shewanella marina, Shewanella marinintestina, Shewanella marisflavi, Shewanella morhuae, Shewanella olleyana, Shewanella oneidensis, Shewanella pacifica, Shewanella pealeana, Shewanella pneumatophori, Shewanella profunda, Shewanella putrefaciens, Shewanella sairae, Shewanella schlegeliana, Shewanella sediminis, Shewanella surugensis, Shewanella vesiculosa, Shewanella violacea, Shewanella waksmanii, Shewanella woodyi,* and *Shewanella xiamenensis.*

[Genus *Listonella*]

Examples of the microbes that are classified as the genus *Listonella* include *Listonella anguillara, Listonella anguillarum,* and *Listonella pelagia.*

[Genus *Agrobacterium*]

Examples of the microbes that are classified as the genus *Agrobacterium* include *Agrobacterium agile, Agrobacterium aureum, Agrobacterium azotophilum, Agrobacterium gypsophilae, Agrobacterium luteum, Agrobacterium pseudotsugae, Agrobacterium rhizogenes, Agrobacterium ferrugineum, Agrobacterium sanguineum, Agrobacterium tumefaciens, Agrobacterium viscosum,* and *Agrobacterium vitis.*

[Genus *Mesorhizobium*]

Examples of the microbes that are classified as the genus *Mesorhizobium* include *Mesorhizobium albiziae, Mesorhizobium amorphae, Mesorhizobium australicum, Mesorhizobium caraganae, Mesorhizobium chacoense, Mesorhizobium ciceri, Mesorhizobium gobiense, Mesorhizobium loti, Mesorhizobium mediterraneum, Mesorhizobium metallidurans, Mesorhizobium opportunistum, Mesorhizobium plurifarium, Mesorhizobium huakuii, Mesorhizobium septentrionale, Mesorhizobium shangrilense, Mesorhizobium tarimense, Mesorhizobium temperatum, Mesorhizobium thiogangeticum,* and *Mesorhizobium tianshanense.*

[Genus *Rhizobium*]

Examples of the microbes that are classified as the genus *Rhizobium* include *Rhizobium alamii, Rhizobium alkalisoli, Rhizobium cellulosilyticum, Rhizobium daejeonense, Rhizobium endophyticum, Rhizobium etli, Rhizobium fabae, Rhizobium gallicum, Rhizobium giardinii, Rhizobium grahamii, Rhizobium hainanense, Rhizobium huautlense, Rhizobium galegae, Rhizobium indica, Rhizobium indicus, Rhizobium indigoferae, Rhizobium larrymoorei, Rhizobium leguminosarum, Rhizobium leucaenae, Rhizobium loessense, Rhizobium lupini, Rhizobium lusitanum, Rhizobium mesosinicum, Rhizobium miluonense, Rhizobium mongol-*ense, *Rhizobium multihospitium, Rhizobium nagarjuna nagarensis, Rhizobium oryzae, Rhizobium phaseoli, Rhizobium pisi, Rhizobium pusense, Rhizobium radiobacter, Rhizobium rhizogenes, Rhizobium rubi, Rhizobium selenitireducens, Rhizobium soli, Rhizobium sullae, Rhizobium tibeticum, Rhizobium trifolii, Rhizobium tropici, Rhizobium tuxtlense, Rhizobium undicola, Rhizobium validum,* and *Rhizobium vitis.*

[Genus *Paracoccus*]

Examples of the microbes that are classified as the genus *Paracoccus* include *Paracoccus aestuarii, Paracoccus alcaliphilus, Paracoccus alkenifer, Paracoccus aminophilus, Paracoccus aminovorans, Paracoccus beibuensis, Paracoccus bengalensis, Paracoccus chinensis, Paracoccus denitrificans, Paracoccus halophilus, Paracoccus homiensis, Paracoccus kocurii, Paracoccus caeni, Paracoccus kondratievae, Paracoccus koreensis, Paracoccus marinus, Paracoccus methylutens, Paracoccus oceanense, Paracoccus pantotrophus, Paracoccus seriniphilus, Paracoccus solventivorans, Paracoccus sulfuroxidans, Paracoccus thiocyanatus, Paracoccus versutus, Paracoccus yeei,* and *Paracoccus zeaxanthinifaciens.*

[Genus *Xanthobacter*]

Examples of the microbes that are classified as the genus *Xanthobacter* include *Xanthobacter agilis, Xanthobacter aminoxidans, Xanthobacter autotrophicus, Xanthobacter flavus, Xanthobacter tagetidis,* and *Xanthobacter viscosus.*

[Genus *Streptomyces*]

Examples of the microbes that are classified as the genus *Streptomyces* include *Streptomyces abikoensis, Streptomyces aburaviensis, Streptomyces aburaviensis* subsp. *tuftformis, Streptomyces achromogenes, Streptomyces achromogenes* subsp. *achromogenes, Streptomyces achromogenes* subsp. *rubradiris, Streptomyces achromogenes* subsp. *streptozoticus, Streptomyces achromogenes* subsp. *tomaymyceticus, Streptomyces acidiscabies, Streptomyces acidoresistans, Streptomyces acrimycini, Streptomyces actuosus, Streptomyces aculeolatus, Streptomyces adephospholyticus, Streptomyces afghaniensis, Streptomyces africanus, Streptomyces agglomeratus, Streptomyces ahygroscopicus, Streptomyces akiyoshiensis, Streptomyces alanosinicus, Streptomyces albaduncus, Streptomyces albiaxialis, Streptomyces albidochromogenes, Streptomyces albidoflavus, Streptomyces albidus, Streptomyces albireticuli, Streptomyces albochromogenes, Streptomyces albocinerescens, Streptomyces albofaciens, Streptomyces alboflavus, Streptomyces albogriseolus, Streptomyces albohelvatus, Streptomyces albolongus, Streptomyces alboniger, Streptomyces albospinus, Streptomyces albosporeus, Streptomyces albosporeus* subsp. *labilomyceticus, Streptomyces albovinaceus, Streptomyces alboviridis, Streptomyces albulus, Streptomyces albus, Streptomyces albus* subsp. *albus, Streptomyces albus* subsp. *coleimyceticus, Streptomyces albus* subsp. *pathocidicus, Streptomyces alcalophilus, Streptomyces almquistii, Streptomyces alni, Streptomyces althioticus, Streptomyces amagasakensis, Streptomyces amakusaensis, Streptomyces ambofaciens, Streptomyces aminophilus, Streptomyces anandii, Streptomyces angustmyceticus, Streptomyces ansochromogenes* subsp. *ansochromogenes, Streptomyces anthocyanicus, Streptomyces antibioticus, Streptomyces antifibrinolyticus, Streptomyces antimycoticus, Streptomyces anulatus, Streptomyces aomiensis, Streptomyces arabicus, Streptomyces ardus, Streptomyces arenae, Streptomyces argenteolus, Streptomyces argenteolus* subsp. *toyonakensis, Streptomyces argillaceus, Streptomyces armeniacus, Streptomyces armentosus, Streptomyces arsitiensis, Streptomyces ascomycinicus, Streptomyces asiaticus, Streptomyces* asterosporus, Streptomyces atratus, Streptomyces atroaurantiacus, Streptomyces atrocyaneus, Streptomyces atrofaciens, Streptomyces atrolaccus, Streptomyces atroolivaceus, Streptomyces atroviolaceus, Streptomyces atrovirens, Streptomyces aurantiacogriseus, Streptomyces aurantiacus, Streptomyces aurantiogriseus, Streptomyces auratus, Streptomyces aureocirculatus, Streptomyces aureofaciens, Streptomyces aureomonopodiales, Streptomyces aureorectus, Streptomyces aureoverticillatus, Streptomyces aureus, Streptomyces aurigineus, Streptomyces avellaneus, Streptomyces avermectinius, Streptomyces avermitilis, Streptomyces avicenniae, Streptomyces avidinii, Streptomyces axinellae, Streptomyces azureus, Streptomyces baarnensis, Streptomyces bacillaris, Streptomyces badius, Streptomyces baliensis, Streptomyces bambergiensis, Streptomyces bangladeshensis, Streptomyces bangladeshiensis, Streptomyces beijiangensis, Streptomyces bellus, Streptomyces bellus subsp. cirolerosus, Streptomyces bernensis, Streptomyces bicolor, Streptomyces bifurcus, Streptomyces bikiniensis, Streptomyces bikiniensis subsp. zorbonensis, Streptomyces blastmyceticus, Streptomyces bluensis, Streptomyces bobili, Streptomyces bottropensis, Streptomyces brasiliensis, Streptomyces brevisprorus, Streptomyces brunneogriseus, Streptomyces bungoensis, Streptomyces cacaoi, Streptomyces cacaoi subsp. asoensis, Streptomyces cacaoi subsp. cacaoi, Streptomyces caelestis, Streptomyces caelicus, Streptomyces caeruleus, Streptomyces caesius, Streptomyces californicus, Streptomyces calvus, Streptomyces canadiensis, Streptomyces canarius, Streptomyces candidus, Streptomyces canescens, Streptomyces cangkringensis, Streptomyces caniferus, Streptomyces canus, Streptomyces capillispiralis, Streptomyces capoamus, Streptomyces capuensis, Streptomyces carnosus, Streptomyces carpaticus, Streptomyces carpinensis, Streptomyces castaneoglobisporus, Streptomyces castaneus, Streptomyces castelarensis, Streptomyces catenulae, Streptomyces cattleya, Streptomyces cavourensis, Streptomyces cavourensis subsp. cavourensis, Streptomyces cebimarensis, Streptomyces cellostaticus, Streptomyces celluloflavus, Streptomyces cellulosae, Streptomyces champavatii, Streptomyces chartreusis, Streptomyces chattanoogensis, Streptomyces cheonanensis, Streptomyces chiangmaiensis, Streptomyces chibaensis, Streptomyces chlorochromogenes, Streptomyces chrestomyceticus, Streptomyces chrestomyceticus subsp. rubescens, Streptomyces chromofuscus, Streptomyces chromothe genus, Streptomyces chryseus, Streptomyces chrysomallus, Streptomyces chrysomallus subsp. fumigatus, Streptomyces chungwhensis, Streptomyces cinereorectus, Streptomyces cinereoruber, Streptomyces cinereoruber subsp. cinereoruber, Streptomyces cinereoruber subsp. fructofermentans, Streptomyces cinereospinus, Streptomyces cinereus, Streptomyces cinerochromogenes, Streptomyces cinnabarinus, Streptomyces cinnamocastaneus, Streptomyces cinnamonensis, Streptomyces cinnamoneus, Streptomyces cinnamoneus subsp. albosporus, Streptomyces cinnamoneus subsp. forma azacoluta, Streptomyces cinnamoneus subsp. lanosus, Streptomyces cinnamoneus subsp. sparsus, Streptomyces circulatus, Streptomyces cirratus, Streptomyces ciscaucasicus, Streptomyces citreofluorescens, Streptomyces citreus, Streptomyces citricolor, Streptomyces clavifer, Streptomyces clavuligerus, Streptomyces coacervatus, Streptomyces cocklensis, Streptomyces coelescens, Streptomyces coeliatus, Streptomyces coelicoflavus, Streptomyces coelicolor, Streptomyces coeruleoaurantiacus, Streptomyces coeruleofuscus, Streptomyces coeruleoprunus, Streptomyces coeruleorubidus, Streptomyces coerulescens, Streptomyces collinus, Streptomyces collinus subsp. albescens, Streptomyces colombiensis, Streptomyces coralus, Streptomyces corchorusii, Streptomyces coriofaciens, Streptomyces costaricanus, Streptomyces craterifer, Streptomyces cremeus, Streptomyces croceus, Streptomyces crystallinus, Streptomyces curacoi, Streptomyces cuspidosporus, Streptomyces cyaneofuscatus, Streptomyces cyaneogriseus, Streptomyces cyaneus, Streptomyces cyanoalbus, Streptomyces cyanocolor, Streptomyces cyanothe genus, Streptomyces cyanogriseus, Streptomyces cylindosporus, Streptomyces daghestanicus, Streptomyces davawensis, Streptomyces decoyicus, Streptomyces demainii, Streptomyces diastaticus, Streptomyces diastaticus subsp. ardesiacus, Streptomyces diastaticus subsp. diastaticus, Streptomyces diastatochromogenes, Streptomyces diastatochromogenes subsp. luteus, Streptomyces distallicus, Streptomyces djakartensis, Streptomyces drozdowiczii, Streptomyces durhamensis, Streptomyces durmitorensis, Streptomyces eburosporeus, Streptomyces echinatus, Streptomyces echinoruber, Streptomycesederensis, Streptomyces elgreteus, Streptomyces elizabethii, Streptomyces emeiensis, Streptomyces endus, Streptomyces enissocaesilis, Streptomyces eridani, Streptomyces erumpens, Streptomyces erythrochromogenes, Streptomyces erythrogriseus, Streptomyces espinosus, Streptomyces eurocidicus, Streptomyces europaeiscabiei, Streptomyces eurythermus, Streptomyces exfoliatus, Streptomyces fasiculatus, Streptomyces felleus, Streptomyces ferralitis, Streptomyces fervens subsp. melrosporus, Streptomyces ficellus, Streptomyces filamentosus, Streptomyces filipinensis, Streptomyces fimbriatus, Streptomyces fimicarius, Streptomyces finlayi, Streptomyces flaveolus, Streptomyces flaveus, Streptomyces flavidofuscus, Streptomyces flavidovirens, Streptomyces flavidovirens subsp. fuscus, Streptomyces flavisclereoticus, Streptomyces flavochromogenes, Streptomyces flavofungini, Streptomyces flavofuscus, Streptomyces flavogriseus, Streptomyces flavomacrosporus, Streptomyces flavorectus, Streptomyces flavotricini, Streptomyces flavotricini subsp. pseudochromogenes, Streptomyces flavovariabilis, Streptomyces flavovirens, Streptomyces flavoviridis, Streptomyces flavus, Streptomyces flocculus, Streptomyces floridae, Streptomyces fluorescens, Streptomyces fradiae, Streptomyces fradiae subsp. acinicolor, Streptomyces fradiae subsp. italicus, Streptomyces fragilis, Streptomyces fragmentans, Streptomyces fragmentans subsp. aquatica, Streptomyces fulvissimus, Streptomyces fulvorobeus, Streptomyces fulvoviolaceus, Streptomyces fulvoviridis, Streptomyces fumanus, Streptomyces fumigatisclereoticus, Streptomyces fungicidicus, Streptomyces furlongus, Streptomyces furlongus subsp. furlongus, Streptomyces fuscoatrus, Streptomyces gabonae, Streptomyces galbus, Streptomyces galilaeus, Streptomyces gallinarius, Streptomyces gancidicus, Streptomyces gangtokensis, Streptomyces gannmycicus, Streptomyces garden, Streptomyces gardneri, Streptomyces gedanensis, Streptomyces gelaticus, Streptomyces geldanamycininus, Streptomyces geysiriensis, Streptomyces ghanaensis, Streptomyces gibsonii, Streptomyces ginsengisoli, Streptomyces glaucescens, Streptomyces glauciniger, Streptomyces glaucosporus, Streptomyces glaucus, Streptomyces globifer, Streptomyces globisporus, Streptomyces globisporus subsp. caucasicus, Streptomyces globisporus subsp. globisporus, Streptomyces globosus, Streptomyces glomeratus, Streptomyces glomeroaurantiacus, Streptomyces glomerochromogenes, Streptomyces gobitricini, Streptomyces goshikiensis, Streptomyces gougerotii, Streptomyces graminearus, Streptomyces gramineus, Streptomyces graminofaciens, Streptomyces griseiniger, Streptomyces griseinus, Streptomyces griseoaurantiacus, Streptomyces griseobrunneus, Streptomyces griseocarneus, Streptomyces griseochromogenes,

*Streptomyces griseochromogenes* subsp. *suitaensis*, *Streptomyces griseofaciens*, *Streptomyces griseoflavus*, *Streptomyces griseoflavus* subsp. *pyrindicus*, *Streptomyces griseofuscus*, *Streptomyces griseoincarnatus*, *Streptomyces griseoloalbus*, *Streptomyces griseolosuffuscus*, *Streptomyces griseolus*, *Streptomyces griseoluteus*, *Streptomyces griseomycini*, *Streptomyces griseoplanus*, *Streptomyces griseorubens*, *Streptomyces griseoruber*, *Streptomyces griseorubiginosus*, *Streptomyces griseospiralis*, *Streptomyces griseosporeus*, *Streptomyces griseostramineus*, *Streptomyces griseoverticillatus*, *Streptomyces griseoviridis*, *Streptomyces griseus*, *Streptomyces griseus* subsp. *bruneus*, *Streptomyces griseus* subsp. *desideus*, *Streptomyces griseus* subsp. *erizensis*, *Streptomyces griseus* subsp. *formicus*, *Streptomyces griseus* subsp. *griseus*, *Streptomyces griseus* subsp. *purpureus*, *Streptomyces griseus* subsp. *rhodochrous*, *Streptomyces griseus* subsp. *solvifaciens*, *Streptomyces guanduensis*, *Streptomyces gulbargensis*, *Streptomyces gypseus*, *Streptomyces hainanensis*, *Streptomyceshaliclonae*, *Streptomyces halotolerans*, *Streptomyces halstedii*, *Streptomyces hawaiiensis*, *Streptomyces hazeliensis*, *Streptomyceshebeiensis*, *Streptomyces heimi*, *Streptomyces heliomycini*, *Streptomyces helvaticus*, *Streptomyces henetus*, *Streptomyces herbaricolor*, *Streptomyces heteromorphus*, *Streptomyces himgriensis*, *Streptomyces hiroshimensis*, *Streptomyces hirsutus*, *Streptomyces horton*, *Streptomyces humidus*, *Streptomyces humidus* subsp. *antitumoris*, *Streptomyces humifer*, *Streptomyces humiferus*, *Streptomyces hundungensis*, *Streptomyces hyalinus*, *Streptomyces hyderabadensis*, *Streptomyces hydrogenans*, *Streptomyces hygroscopicus*, *Streptomyces hygroscopicus* subsp. *aabomyceticus*, *Streptomyces hygroscopicus* subsp. *angustmyceticus*, *Streptomyces hygroscopicus* subsp. *azalomyceticus*, *Streptomyces hygroscopicus* subsp. *crystallogenes*, *Streptomyces hygroscopicus* subsp. *decoyicus*, *Streptomyces hygroscopicus* subsp. *duamyceticus*, *Streptomyces hygroscopicus* subsp. *geldanus*, *Streptomyces hygroscopicus* subsp. *glebosus*, *Streptomyces hygroscopicus* subsp. *hialomyceticus*, *Streptomyces hygroscopicus* subsp. *hygroscopicus*, *Streptomyces hygroscopicus* subsp. *hygroscopius*, *Streptomyces hygroscopicus* subsp. *limoneus*, *Streptomyces hygroscopicus* subsp. *ossamyceticus*, *Streptomyces hygrospinosus*, *Streptomyces iakyrus*, *Streptomyces inaequalis*, *Streptomyces indiaensis*, *Streptomyces indicus*, *Streptomyces indigocolor*, *Streptomyces indigoferus*, *Streptomyces indonesiensis*, *Streptomyces insignis*, *Streptomyces intermedius*, *Streptomyces inusitatus*, *Streptomyces ipomoeae*, *Streptomyces iranensis*, *Streptomyces ishigakiensis*, *Streptomyces jamaicensis*, *Streptomyces janthinus*, *Streptomycesjavensis*, *Streptomyces jietaisiensis*, *Streptomyces jujuy*, *Streptomyces jumonjinensis*, *Streptomyces kagawaensis*, *Streptomyces kagoshimanus*, *Streptomyces kanamyceticus*, *Streptomyces kaniharaensis*, *Streptomyces karnatakensis*, *Streptomyces kasugaensis*, *Streptomyces kasugaspinus*, *Streptomyces katrae*, *Streptomyces kentuckensis*, *Streptomyces khandalensis*, *Streptomyces kitasatoensis*, *Streptomyces kobenensis*, *Streptomyces koyangensis*, *Streptomyces krainskii*, *Streptomyces kunmingensis*, *Streptomyces kurssanovii*, *Streptomyces kuwaitiensis*, *Streptomyces labedae*, *Streptomyces laceyi*, *Streptomyces laculatusporus*, *Streptomyces laetevioloaceus*, *Streptomyces lanatus*, *Streptomyces lannensis*, *Streptomyces lasaliensis*, *Streptomyces lateritius*, *Streptomyces laurentii*, *Streptomyces lavendofoliae*, *Streptomyces lavendulae*, *Streptomyces lavendulae* subsp. *fuscus*, *Streptomyces lavendulae* subsp. *grasserius*, *Streptomyces lavendulae* subsp. *lavendulae*, *Streptomyces lavendularectus*, *Streptomyces lavenduligriseus*, *Streptomyces lavendulocolor*, *Streptomyces lazureus*, *Streptomyces levis*, *Streptomyces levoris*, *Streptomyces libani*, *Streptomyces libani* subsp. *libani*, *Streptomyces libani* subsp. *rufus*, *Streptomyces lienomycini*, *Streptomyces lieskei*, *Streptomyces lilaceus*, *Streptomyces lilacinofulvus*, *Streptomyces lilacinus*, *Streptomyces limosus*, *Streptomyces lincolnensis*, *Streptomyces lipmanii*, *Streptomyces lisandri*, *Streptomyces litmocidini*, *Streptomyces lividans*, *Streptomyces lividoclavatus*, *Streptomyces lividus*, *Streptomyces loidensis*, *Streptomyces lomondensis*, *Streptomyces longisporoflavus*, *Streptomyces longispororuber*, *Streptomyces longisporus*, *Streptomyces longissimus*, *Streptomyces longwoodensis*, *Streptomyces lucensis*, *Streptomyces lunalinharensis*, *Streptomyces lunalinharesii*, *Streptomyces luridiscabiei*, *Streptomyces luridus*, *Streptomyces lusitanus*, *Streptomyces lusitanus* var. *tetracyclini*, *Streptomyces luteireticuli*, *Streptomyces luteocolor*, *Streptomyces luteogriseus*, *Streptomyces luteolutescens*, *Streptomyces luteosporeus*, *Streptomyces luteoverticillatus*, *Streptomyces lydicus*, *Streptomyces macromomyceticus*, *Streptomyces macrosporeus*, *Streptomyces macrosporus*, *Streptomyces maizeus*, *Streptomyces malachiticus*, *Streptomyces malachiticus* subsp. *griseospinosus*, *Streptomyces malachitofuscus*, *Streptomyces malachitorectus*, *Streptomyces malachitospinus*, *Streptomyces malayensis*, *Streptomyces malaysiensis*, *Streptomyces manipurensis*, *Streptomyces marinus*, *Streptomyces maritimus*, *Streptomyces marokkonensis*, *Streptomyces mashuensis*, *Streptomyces massasporeus*, *Streptomyces matensis*, *Streptomyces mauvecolor*, *Streptomyces mayteni*, *Streptomyces mediocidicus*, *Streptomyces mediolani*, *Streptomyces megasporus*, *Streptomyces melanogenes*, *Streptomyces melanosporofaciens*, *Streptomyces mentougouensis*, *Streptomyces mexicanus*, *Streptomyces michiganensi*, *Streptomyces michiganensis* subsp. *amylolyticus*, *Streptomyces microflavus*, *Streptomyces microsporus*, *Streptomyces miharaensis*, *Streptomyces minoensis*, *Streptomyces minutiscleroticus*, *Streptomyces mirabilis*, *Streptomyces misakiensis*, *Streptomyces misawanensis*, *Streptomyces misionensis*, *Streptomyces mobaraensis*, *Streptomyces moderatus*, *Streptomyces monomycini*, *Streptomyces mordarskii*, *Streptomyces morookaense*, *Streptomyces morookaensis*, *Streptomyces mucoflavus*, *Streptomyces multispiralis*, *Streptomyces murinus*, *Streptomycesmutabilis*, *Streptomyces mutomycini*, *Streptomyces mycarofaciens*, *Streptomyces myxogenes*, *Streptomyces naganishii*, *Streptomyces nanningensis*, *Streptomyces nanshensis*, *Streptomyces naraensis*, *Streptomyces narbonensis*, *Streptomyces nashvillensis*, *Streptomyces natalensis*, *Streptomyces neburosus*, *Streptomyces neocaliberis*, *Streptomyces netropsis*, *Streptomyces neyagawaensis*, *treptomyces nigellus*, *Streptomyces niger*, *Streptomyces nigrescens*, *Streptomyces nigrifaciens*, *Streptomyces nigrogriseolus*, *Streptomyces nigroviolens*, *Streptomyces nitrosporeus*, *Streptomyces niveoruber*, *Streptomyces niveus*, *Streptomyces nobilis*, *Streptomyces noboritoensis*, *Streptomyces nodosus*, *Streptomyces nodosus* subsp. *asukaensis*, *Streptomyces nogalater*, *Streptomyces nojiriensis*, *Streptomyces noursei*, *Streptomyces novaecaesareae*, *Streptomyces novoverticillus*, *Streptomyces ochraceiscleroticus*, *Streptomyces ochrosporus*, *Streptomyces odorifer*, *Streptomyces ogaensis*, *Streptomyces oidiosporus*, *Streptomyces olivaceiscleroticus*, *Streptomyces olivaceoviridis*, *Streptomyces olivaceus*, *Streptomyces olivochromogenes*, *Streptomyces olivochromogenes* subsp. *cytovirinus*, *Streptomyces olivogriseus*, *Streptomyces olivoverticillatus*, *Streptomyces olivoviridis*, *Streptomyces omiyaensis*, *Streptomyces orinoci*, *Streptomyces ornatus*, *Streptomyces osmaniensis*, *Streptomyces ostreogriseus*, *Streptomyces owasiensis*, *Streptomyces pactum*, *Streptomyces padanus*,

*Streptomyces pallidus, Streptomyces panacagri, Streptomyces panaciterrae, Streptomyces panayensis, Streptomyces paradoxus, Streptomyces paraguayensis, Streptomyces parvulus, Streptomyces parvus, Streptomyces paucidiastaticus, Streptomyces paucisporeus, Streptomyces paucisporogenes, Streptomyces paulus, Streptomyces peruviensis, Streptomyces peucetius, Streptomyces peucetius* subsp. *caesius, Streptomyces peucetius* subsp. *carneus, Streptomyces phaeochromogenes, Streptomyces phaeofaciens, Streptomyces phaeoluteichromatogenes, Streptomyces phaeoluteigriseus, Streptomyces phaeopurpureus, Streptomyces phaeoverticillatus* subsp. *takatsukiensis, Streptomyces phaeoviridis, Streptomyces pharetrae, Streptomyces phemorphus, Streptomyces phytohabitans, Streptomyces pilosus, Streptomyces piloviolofuscus, Streptomyces piomothe genus, Streptomyces platensis, Streptomyces platensis* subsp. *clarensis, Streptomyces platensis* subsp. *malvinus, Streptomyces platensis* subsp. *robigocidicus, Streptomyces plicatus, Streptomyces plumbeus, Streptomyces plumbiresistens, Streptomyces pluricolorescens, Streptomyces polyantibioticus, Streptomyces polychromogenes, Streptomyces polychromogenes* subsp. *arenicolus, Streptomyces poonensis, Streptomyces praecox, Streptomyces prasinopilosus, Streptomyces prasinosporus, Streptomyces prasinus, Streptomyces pristinaespiralis, Streptomyces propurpuratus, Streptomyces prunicolor, Streptomyces psammoticus, Streptomyces pseudoechinosporeus, Streptomyces pseudogriseolus, Streptomyces pseudogriseolus* subsp. *glucofermentans, Streptomyces pseudovenezuelae, Streptomyces pulcher, Streptomyces pulveraceus, Streptomyces puniceus, Streptomyces puniceus* subsp. *doliceus, Streptomyces puniciscabiei, Streptomyces purpeochromogenes, Streptomyces purpeofuscus, Streptomyces purpurascens, Streptomyces purpureofuscus, Streptomyces purpureofuscus* subsp. *acoagulans, Streptomyces purpureus, Streptomyces purpurogeneiscleroticus, Streptomyces pyridomyceticus, Streptomyces racemochromogenes, Streptomyces racemosus, Streptomyces radiopugnans, Streptomyces raffinosus, Streptomyces rameus, Streptomyces ramosissimus, Streptomyces ramulosus, Streptomyces rangoon, Streptomyces rangoonensis, Streptomyces rapamycincus, Streptomyces recifensis, Streptomyces rectiviolaceus, Streptomyces refuineus* subsp. *thermotolerans, Streptomyces regalis, Streptomyces regensis, Streptomyces resistomycificus, Streptomyces reticuli* subsp. *protomycicus, Streptomyces reticuliscabiei, Streptomyces rhizosphaericus, Streptomyces ribosidificus, Streptomyces rimofaciens, Streptomyces rimosus, Streptomyces rimosus* subsp. *paromomycinus, Streptomyces rimosus* subsp. *rimosus, Streptomyces rishiriensis, Streptomyces robefuscus, Streptomyces rochei, Streptomyces rosa, Streptomyces rosa* subsp. *notoensis, Streptomyces roseiscleroticus, Streptomyces roseoalbus, Streptomyces roseoaurantius, Streptomyces roseochromogenes, Streptomyces roseochromothe genus, Streptomyces roseochromothe genus* subsp. *albocyclini, Streptomyces roseocinereus, Streptomyces roseodiastaticus, Streptomyces roseoflavus, Streptomyces roseofulvus, Streptomyces roseogriseus, Streptomyces roseolilacinus, Streptomyces roseolus, Streptomyces roseoluteus, Streptomyces roseoplatus, Streptomyces roseorubens, Streptomyces roseosporus, Streptomyces roseoverticillatus, Streptomyces roseoviolaceus, Streptomyces roseoviolascens, Streptomyces roseoviridis, Streptomyces roseus, Streptomyces ruber, Streptomyces rubicolor, Streptomyces rubidus, Streptomyces rubiginosohelvolus, Streptomyces rubiginosus, Streptomyces rubrireticuli, Streptomyces rubrocyanodiastaticus* subsp. *piger, Streptomyces rubrogriseus, Streptomyces rubrolavendulae, Streptomyces rubroverrucosus, Streptomyces rubrus, Streptomyces rufochromogenes, Streptomyces rutgersensis, Streptomyces ryensis, Streptomyces sahachiroi, Streptomyces sakaiensis, Streptomyces salinarum, Streptomyces sampsonii, Streptomyces sanglieri, Streptomyces sannanensis, Streptomyces sannurensis, Streptomyces sanyensis, Streptomyces saprophyticus, Streptomyces saraceticus, Streptomyces sayamaensis, Streptomyces scabiei, Streptomyces scabrisporus, Streptomyces sclerogranulatus, Streptomyces sclerotialus, Streptomyces scopiformis, Streptomyces sedi, Streptomyces senoensis, Streptomyces seoulensis, Streptomyces septatus, Streptomyces serianimatus, Streptomyces setae, Streptomyces setonensis, Streptomyces setonii, Streptomyces shaanxiensis, Streptomyces shiodaensis, Streptomyces showdoensis, Streptomyces sindenensis, Streptomyces sioyaensis, Streptomyces sodiiphilus, Streptomyces somaliensis, Streptomyces spadicis, Streptomyces sparsogenes, Streptomyces sparsus, Streptomyces specialis, Streptomyces spectabilis, Streptomyces speibonae, Streptomyces spheroides, Streptomyces spinichromogenes, Streptomyces spinicoumarensis, Streptomyces spinoverrucosus, Streptomyces spiralis, Streptomyces spiroverticillatus, Streptomyces spongiae, Streptomyces sporocinereus, Streptomyces sporoclivatus, Streptomyces spororaveus, Streptomyces sporoverrucosus, Streptomyces steffisburgensis, Streptomyces steffisburgensis* subsp. *steffisburgensis, Streptomyces stelliscabiei, Streptomyces stramineus, Streptomyces subrutilus, Streptomyces sudanensis, Streptomyces sulfonofaciens, Streptomyces sulphureus, Streptomyces sviceus, Streptomyces synnematoformans, Streptomyces tanashiensis, Streptomyces tanashiensis* subsp. *cephalomyceticus, Streptomyces tateyamensis, Streptomyces tauricus, Streptomyces tendae, Streptomyces tenebrarius, Streptomyces tenjimariensis, Streptomyces termitum, Streptomyces testaceus, Streptomyces tetanusemus, Streptomyces thermoalcalitolerans, Streptomyces thermoatroviridis, Streptomyces thermocarboxydovorans, Streptomyces thermocarboxydus, Streptomyces thermocastaneus, Streptomyces thermocoerulescens, Streptomyces thermocoprophilus, Streptomyces thermocyaneomaculatus, Streptomyces thermocyaneoviolaceus, Streptomyces thermodiastaticus, Streptomyces thermoflavus, Streptomyces thermogriseoviolaceus, Streptomyces thermogriseus, Streptomyces thermohygroscopicus* subsp. *rubiginosus, Streptomyces thermolilacinus, Streptomyces thermolineatus, Streptomyces thermoluteus, Streptomyces thermoluteus* subsp. *fuscus, Streptomyces thermonitrificans, Streptomyces thermoolivaceus* subsp. *fuscus, Streptomyces thermoolivaceus* subsp. *thermoolivaceus, Streptomyces thermophilus, Streptomyces thermospinosisporus, Streptomyces thermotolerans, Streptomyces thermoviolaceus, Streptomyces thermoviolaceus* subsp. *apingens, Streptomyces thermoviolaceus* subsp. *thermoviolaceus, Streptomyces thermovulgaris, Streptomyces thinghirensis, Streptomyces thioluteus, Streptomyces threomyceticus, Streptomyces torulosus, Streptomyces tosaensis, Streptomyces toxifertilis, Streptomyces toxytricini, Streptomyces toyocaensis, Streptomyces triangulatus, Streptomyces tricolor, Streptomyces triculaminicus, Streptomyces triostinicus, Streptomyces tritolerans, Streptomyces tsukiyonensis, Streptomyces tsusimaensis, Streptomyces tubercidicus, Streptomyces tuirus, Streptomyces tumemacerans, Streptomyces tumuli, Streptomyces turgidiscabies, Streptomyces umbrinus, Streptomyces umbrosus, Streptomyces variabilis, Streptomyces variegatus, Streptomyces varius, Streptomyces varsoviensis, Streptomyces vastus, Streptomyces vellosus, Streptomyces vendargensis, Streptomyces venezuelae, Streptomyces verne, Streptomyces versipellis, Streptomyces verticillatus, Streptomyces verticillus, Streptomyces vietnamensis, Streptomy-* ces vinaceus, Streptomyces vinaceusdrappus, Streptomyces violaceochromogenes, Streptomyces violaceolatus, Streptomyces violaceorectus, Streptomyces violaceoruber, Streptomyces violaceorubidus, Streptomyces violaceus, Streptomyces violaceusniger, Streptomyces violarus, Streptomyces violascens, Streptomyces violens, Streptomyces violorubens, Streptomyces virens, Streptomyces virginiae, Streptomyces virginiae subsp. lipoxae, Streptomyces viridans, Streptomyces viridifaciens, Streptomyces viridiflavus, Streptomyces viridis, Streptomyces viridiviolaceus, Streptomyces viridobrunneus, Streptomyces viridochromogenes, Streptomyces viridochromogenes subsp. komabensis, Streptomyces viridochromogenes subsp. sulfomycini, Streptomyces viridodiastaticus, Streptomyces viridogenes, Streptomyces viridosporus, Streptomyces viridoverrucosus, Streptomyces vitaminophilus, Streptomyces vulgaris, Streptomyces wedmorensis, Streptomyces wellingtoniae, Streptomyces werraensis, Streptomyces willmorei, Streptomyces wistariopsis, Streptomyces woolensis, Streptomyces xanthochromogenes, Streptomyces xanthocidicus, Streptomyces xantholiticus, Streptomyces xanthophaeus, Streptomyces xiamenensis, Streptomyces xinghaiensis, Streptomyces xylophagus, Streptomyces yanglinensis, Streptomyces yanii, Streptomyces yatensis, Streptomyces yeochonensis, Streptomyces yerevanensis, Streptomyces yogyakartensis, Streptomyces yokosukanensis, Streptomyces youssoufiensis, Streptomyces yunnanensis, Streptomyces zaomyceticus, Streptomyces zelensis, and Streptomyces zinciresistens.

[Genus Geobacillus]

Examples of the microbes that are classified as the genus Geobacillus include Geobacillus caldoproteolyticus, Geobacillus caldoxylosilyticus, Geobacillus debilis, Geobacillus galactosidasius, Geobacillus gargensis, Geobacillus jurassicus, Geobacillus kaustophilus, Geobacillus lituanicus, Geobacillus pallidus, Geobacillus stearothermophilus, Geobacillus stromboliensis, Geobacillus subterraneus, Geobacillus tepidamans, Geobacillus thermocatenulatus, Geobacillus thermodenitrificans, Geobacillus thermodenitrificans subsp. calidus, Geobacillus thermoglucosidasius, Geobacillus thermoleovorans, Geobacillus toebii, Geobacillus uzensis, Geobacillus vulcani, and Geobacillus zalihae.

[Genus Rhodococcus]

Examples of the microbes that are classified as the genus Rhodococcus include Rhodococcus rhodochrous, Rhodococcus erythropolis, Rhodococcus equi, Rhodococcus rhodnii, Rhodococcus corallinus, Rhodococcus rubropertinctus, Rhodococcus coprophilus, Rhodococcus globerulus, Rhodococcus chlorophenolicus, Rhodococcus luteus, Rhodococcus aichiensis, Rhodococcus chubuensis, Rhodococcus maris, and Rhodococcus fascines.

[Other Preferred Species of Prokaryotes]

Further, as the microbes that are classified as the genus Magnetospirillum, Magnetospirillum magneticum, as the microbes that are classified as the genus Rhodospirillum, Rhodospirillum rubrum, Rhodospirillum centenum and Rhodospirillum photometricum, as the microbes that are classified as the genus Azospirillum, Azospirillum lipoferum and Azospirillum brasilense, as the microbes that are classified as the genus Tistrella, Tistrella mobilis, as the microbes that are classified as the genus Acidiphilium, Acidiphilium cryptum and Acidiphilium multivorum, as the microbes that are classified as the genus Rhodobacter, Rhodobacter sphaeroides and Rhodobacter capsulatus, as the microbes that are classified as the genus Ruegeria, Ruegeria pomeroyi, as the microbes that are classified as the genus Roseobacter, Roseobacter denitrificans and Roseobacter litoralis, as the microbes that are classified as the genus Dinoroseobacter, Dinoroseobacter shibae, as the microbes that are classified as the genus Phaeobacter, Phaeobacter gallaeciensis, as the microbes that are classified as the genus Octadecabacter, Octadecabacter antarcticus and Octadecabacter arcticus, as the microbes that are classified as the genus Hyphomonas, Hyphomonas neptunium, as the microbes that are classified as the genus Maricaulis, Maricaulis maris, as the microbes that are classified as the genus Hirschia, Hirschia baltica, Novosphingobium, Novosphingobium aromaticivorans, Sphingopyxis, Sphingopyxis alaskensis, as the microbes that are classified as the genus Sphingobium, Sphingobium japonicum and Sphingobium chlorophenolicum, as the microbes that are classified as the genus Erythrobacter, Erythrobacter litoralis, as the microbes that are classified as the genus Caulobacter, Caulobacter crescentus and Caulobacter segnis, as the microbes that are classified as the genus Phenylobacterium, Phenylobacterium zucineum, as the microbes that are classified as the genus Asticcacaulis, Asticcacaulis excentricus, as the microbes that are classified as the genus Sinorhizobium, Sinorhizobium meliloti, Sinorhizobium medicae and Sinorhizobium fredii, as the microbes that are classified as the genus Azorhizobium, Azorhizobium caulinodans, as the microbes that are classified as the genus Brucella, Brucella melitensis, Brucella abortus, Brucella suis, Brucella ovis, Brucella canis, Brucella microti, Brucella pinnipedialis and Brucella ceti, as the microbes that are classified as the genus Aurantimonas, Aurantimonas manganoxydans, as the microbes that are classified as the genus Bradyrhizobium, Bradyrhizobium japonicum, as the microbes that are classified as the genus Agromonas, Agromonas oligotrophica, as the microbes that are classified as the genus Rhodopseudomonas, Rhodopseudomonas palustris, as the microbes that are classified as the genus Nitrobacter, Nitrobacter winogradskyi and Nitrobacter hamburgensis, as the microbes that are classified as the genus Methylobacterium, Methylobacterium extorquens, Methylobacterium radiotolerans and Methylobacterium nodulans, as the microbes that are classified as the genus Rhodomicrobium, Rhodomicrobium vannielii, as the microbes that are classified as the genus Pelagibacterium, Pelagibacterium halotolerans, as the microbes that are classified as the genus Parvibaculum, Parvibaculum lavamentivorans, as the microbes that are classified as the genus Parvularcula, Parvularcula bermudensis, as the microbes that are classified as the genus Burkholderia, Burkholderia mallei, Burkholderia pseudomallei, Burkholderia thailandensis, Burkholderia vietnamiensis, Burkholderia cenocepacia, Burkholderia ambifaria, Burkholderia multivorans, Burkholderia cepacia, Burkholderia xenovorans, Burkholderia phymatum, Burkholderia phytofirmans, Burkholderia glumae, Burkholderia rhizoxinica, Burkholderia gladioli, Burkholderia phenoliruptrix and Burkholderia oklahomensis, as the microbes that are classified as the genus Ralstonia, Ralstonia solanacearum, Ralstonia pickettii and Ralstonia eutropha, as the microbes that are classified as the genus Cupriavidus, Cupriavidus metallidurans, Cupriavidus taiwanensis and Cupriavidus necator, as the microbes that are classified as the genus Polynucleobacter, Polynucleobacter necessarius, as the microbes that are classified as the genus Bordetella, Bordetella pertussis, Bordetella parapertussis, Bordetella petrii and Bordetella avium, as the microbes that are classified as the genus Taylorella, Taylorella equigenitalis, as the microbes that are classified as the genus Alicycliphilus, Alicycliphilus denitrificans, as the microbes that are classified as the genus Delftia, Delftia acidovorans, as the microbes that are classified as the genus Ramlibacter, Ramlibacter tataouinensis, as the microbes that are classified as the genus *Rhodoferax*, *Rhodoferax ferrireducens*, as the microbes that are classified as the genus *Variovorax*, *Variovorax paradoxus*, as the microbes that are classified as the genus *Polaromonas*, *Polaromonas naphthalenivorans*, as the microbes that are classified as the genus *Acidovorax*, *Acidovorax citrulli*, *Acidovorax ebreus* and *Acidovorax avenae*, as the microbes that are classified as the genus *Verminephrobacter*, *Verminephrobacter eiseniae*, as the microbes that are classified as the genus *Herminiimonas*, *Herminiimonas arsenicoxydans*, as the microbes that are classified as the genus *Herbaspirillum*, *Herbaspirillum seropedicae*, as the microbes that are classified as the genus *Collimonas*, *Collimonas fungivorans*, as the microbes that are classified as the genus *Chromobacterium*, *Chromobacterium violaceum*, as the microbes that are classified as the genus *Laribacter*, *Laribacter hongkongensis*, as the microbes that are classified as the genus *Pseudogulbenkiania*, *Pseudogulbenkiania ferrooxidans*, as the microbes that are classified as the genus *Nitrosomonas*, *Nitrosomonas europaea*, as the microbes that are classified as the genus *Nitrosospira*, *Nitrosospira multiformis*, as the microbes that are classified as the genus *Aromatoleum*, *Aromatoleum aromaticum*, as the microbes that are classified as the genus *Dechloromonas*, *Dechloromonas aromatica*, as the microbes that are classified as the genus *Azospira* (*Dechlorosoma*), *Azospira oryzae* (*Dechlorosoma suillum*), as the microbes that are classified as the genus *Rheinheimera*, *Rheinheimera nanhaiensis*, *Nitrosococcus*, *Nitrosococcus oceani*, *Halorhodospira*, *Halorhodospira halophila*, as the microbes that are classified as the genus *Xanthomonas*, *Xanthomonas campestris*, *Xanthomonas axonopodis*, *Xanthomonas oryzae*, *Xanthomonas albilineans* and *Xanthomonas citri*, as the microbes that are classified as the genus *Stenotrophomonas*, *Stenotrophomonas maltophilia*, as the microbes that are classified as the genus *Pseudoxanthomonas*, *Pseudoxanthomonas suwonensis* and *Pseudoxanthomonas spadix*, as the microbes that are classified as the genus *Francisella*, *Francisella tularensis* and *Francisella novicida*, as the microbes that are classified as the genus *Cycloclasticus*, *Cycloclasticus zancles*, as the microbes that are classified as the genus *Hahella*, *Hahella chejuensis*, as the microbes that are classified as the genus *Halomonas*, *Halomonas elongata*, as the microbes that are classified as the genus *Alcanivorax*, *Alcanivorax borkumensis* and *Alcanivorax dieselolei*, as the microbes that are classified as the genus *Kangiella*, *Kangiella koreensis*, as the microbes that are classified as the genus *Azotobacter*, *Azotobacter vinelandii*, as the microbes that are classified as the genus *Psychrobacter*, *Psychrobacter arcticus* and *Psychrobacter cryohalolentis*, as the microbes that are classified as the genus *Alishewanella*, *Alishewanella jeotgali*, as the microbes that are classified as the genus *Alteromonas*, *Alteromonas macleodii*, as the microbes that are classified as the genus *Glaciecola*, *Glaciecola nitratireducens*, *Glaciecola psychrophila* and *Glaciecola punicea*, as the microbes that are classified as the genus *Marinobacter*, *Marinobacter aquaeolei*, *Marinobacter hydrocarbonoclasticus*, *Marinobacter adhaerens*, *Marinobacter algicola* and *Marinobacter manganoxydans*, as the microbes that are classified as the genus *Marinobacterium*, *Marinobacterium stanieri*, as the microbes that are classified as the genus *Saccharophagus*, *Saccharophagus degradans*, as the microbes that are classified as the genus *Ferrimonas*, *Ferrimonas balearica*, as the microbes that are classified as the genus *Idiomarina*, *Idiomarina loihiensis* and *Idiomarina baltica*, as the microbes that are classified as the genus *Colwellia*, *Colwellia psychrerythraea*, as the microbes that are classified as the genus *Pseudoalteromonas*, *Pseudoalteromonas haloplanktis*, *Pseudoalteromonas atlantica* and *Pseudoalteromonas tunicata*, as the microbes that are classified as the genus *Vibrio*, *Vibrio parahaemolyticus*, *Vibrio vulnificus*, *Vibrio harveyi*, *Vibrio furnissii*, *Vibrio tubiashii*, *Vibrio sinaloensis*, *Vibrio rotiferianus*, *Vibrio orientalis*, *Vibrio harveyi*, *Vibrio coralliilyticus*, *Vibrio caribbenthicus*, *Vibrio brasiliensis* and *Vibrio alginolyticus*, as the microbes that are classified as the genus *Photobacterium*, *Photobacterium profundum*, as the microbes that are classified as the genus *Aeromonas*, *Aeromonas hydrophila*, *Aeromonas salmonicida* and *Aeromonas veronii*, as the microbes that are classified as the genus *Salinisphaera*, *Salinisphaera shabanensis*, as the microbes that are classified as the genus *Legionella*, *Legionella pneumophila* and *Legionella longbeachae*, as the microbes that are classified as the genus *Coxiella*, *Coxiella burnetii*, as the microbes that are classified as the genus *Desulfococcus*, *Desulfococcus oleovorans*, as the microbes that are classified as the genus *Desulfobacterium*, *Desulfobacterium autotrophicum*, as the microbes that are classified as the genus *Desulfatibacillum*, *Desulfatibacillum alkenivorans*, as the microbes that are classified as the genus *Desulfobulbus*, *Desulfobulbus propionicus*, as the microbes that are classified as the genus *Desulfarculus*, *Desulfarculus baarsii*, as the microbes that are classified as the genus *Geobacter*, *Geobacter metallireducens*, *Geobacter uraniireducens* and *Geobacter bemidjiensis*, as the microbes that are classified as the genus *Syntrophobacter*, *Syntrophobacter fumaroxidans*, as the microbes that are classified as the genus *Syntrophus*, *Syntrophus aciditrophicus*, as the microbes that are classified as the genus *Desulfomonile*, *Desulfomonile tiedjei*, as the microbes that are classified as the genus *Bdellovibrio*, *Bdellovibrio bacteriovorus* and *Bdellovibrio exovorus*, as the microbes that are classified as the genus *Bacteriovorax*, *Bacteriovorax marinus*, as the microbes that are classified as the genus *Stigmatella*, *Stigmatella aurantiaca*, as the microbes that are classified as the genus *Myxococcus*, *Myxococcus xanthus* and *Myxococcus fulvus*, as the microbes that are classified as the genus *Anaeromyxobacter*, *Anaeromyxobacter dehalogenans*, as the microbes that are classified as the genus *Sorangium*, *Sorangium cellulosum*, as the microbes that are classified as the genus *Haliangium*, *Haliangium ochraceum*, as the microbes that are classified as the genus *Acidobacterium*, *Acidobacterium capsulatum*, as the microbes that are classified as the genus *Granulicella*, *Granulicella tundricola*, as the microbes that are classified as the genus *Ilumatobacter*, *Ilumatobacter coccineum*, as the microbes that are classified as the genus *Streptosporangium*, *Streptosporangium roseum*, as the microbes that are classified as the genus *Nocardiopsis*, *Nocardiopsis dassonvillei*, as the microbes that are classified as the genus *Thermobifida*, *Thermobifida fusca*, as the microbes that are classified as the genus *Thermomonospora*, *Thermomonospora curvata*, as the microbes that are classified as the genus *Pseudonocardia*, *Pseudonocardia dioxanivorans*, as the microbes that are classified as the genus *Amycolatopsis*, *Amycolatopsis mediterranei*, as the microbes that are classified as the genus *Saccharomonospora*, *Saccharomonospora viridis* and *Saccharomonospora xinjiangensis*, as the microbes that are classified as the genus *Saccharopolyspora*, *Saccharopolyspora erythraea* and *Saccharopolyspora spinosa*, as the microbes that are classified as the genus *Thermobispora*, *Thermobispora bispora*, as the microbes that are classified as the genus *Actinosynnema*, *Actinosynnema mirum*, as the microbes that are classified as the genus *Micromonospora*, *Micromonospora aurantiaca*, as the microbes that are classified as the genus *Salinispora*, *Salinispora tropica* and

*Salinispora arenicola*, as the microbes that are classified as the genus *Verrucosispora*, *Verrucosispora maris*, as the microbes that are classified as the genus *Kribbella*, *Kribbella flavida*, as the microbes that are classified as the genus *Corynebacterium*, *Corynebacterium jeikeium*, *Corynebacterium urealyticum*, *Corynebacterium glutamicum*, *Corynebacterium ammoniagenes* and *Corynebacterium kroppenstedtii*, as the microbes that are classified as the genus *Nocardia*, *Nocardia farcinica*, *Nocardia brasiliensis* and *Nocardia cyriacigeorgica*, as the microbes that are classified as the genus *Gordonia*, *Gordonia bronchialis*, *Gordonia neofelifaecis* and *Gordonia terrae*, as the microbes that are classified as the genus *Dietzia*, *Dietzia cinnamea*, as the microbes that are classified as the genus *Mycobacterium*, *Mycobacterium tuberculosis*, *Mycobacterium bovis*, *Mycobacterium leprae*, *Mycobacterium avium*, *Mycobacterium smegmatis*, *Mycobacterium ulcerans*, *Mycobacterium vanbaalenii*, *Mycobacterium gilvum*, *Mycobacterium abscessus*, *Mycobacterium marinu*, *Mycobacterium massiliense*, *Mycobacterium phlei*, *Mycobacterium thermoresistibile*, *Mycobacterium tusciae*, *Mycobacterium xenopi* and *Mycobacterium rhodesiae*, as the microbes that are classified as the genus *Amycolicicoccus*, *Amycolicicoccus subflavus*, as the microbes that are classified as the genus *Tsukamurella*, *Tsukamurella paurometabola*, as the microbes that are classified as the genus *Segniliparus*, *Segniliparus rotundus*, as the microbes that are classified as the genus *Microbacterium*, *Microbacterium testaceum*, as the microbes that are classified as the genus *Micrococcus*, *Micrococcus luteus*, as the microbes that are classified as the genus *Arthrobacter*, *Arthrobacter arilaitensis*, *Arthrobacter chlorophenolicus*, *Arthrobacter globiformis* and *Arthrobacter phenanthrenivorans*, as the microbes that are classified as the genus *Renibacterium*, *Renibacterium salmoninarum*, as the microbes that are classified as the genus *Kocuria*, *Kocuria rhizophila*, as the microbes that are classified as the genus *Kytococcus*, *Kytococcus sedentarius*, as the microbes that are classified as the genus *Cellulomonas*, *Cellulomonas fimi*, as the microbes that are classified as the genus *Intrasporangium*, *Intrasporangium calvum*, as the microbes that are classified as the genus *Serinicoccus*, *Serinicoccus profundi*, as the microbes that are classified as the genus *Frankia*, *Frankia alni*, as the microbes that are classified as the genus *Acidothermus*, *Acidothermus cellulolyticus*, as the microbes that are classified as the genus *Nakamurella*, *Nakamurella multipartita*, as the microbes that are classified as the genus *Geodermatophilus*, *Geodermatophilus obscurus*, as the microbes that are classified as the genus *Stackebrandtia*, *Stackebrandtia nassauensis*, as the microbes that are classified as the genus *Catenulispora*, *Catenulispora acidiphila*, as the microbes that are classified as the genus *Rubrobacter*, *Rubrobacter xylanophilus*, as the microbes that are classified as the genus *Conexibacter*, *Conexibacter woesei*, as the microbes that are classified as the genus *Oceanobacillus*, *Oceanobacillus iheyensis*, as the microbes that are classified as the genus *Lysinibacillus*, *Lysinibacillus sphaericus*, as the microbes that are classified as the genus *Halobacillus*, *Halobacillus halophilus*, as the microbes that are classified as the genus *Alicyclobacillus*, *Alicyclobacillus acidocaldarius*, as the microbes that are classified as the genus *Kyrpidia*, *Kyrpidia tusci*, as the microbes that are classified as the genus *Brevibacillus*, *Brevibacillus choshinensis*, as the microbes that are classified as the genus *Lactobacillus*, *Lactobacillus buchneri*, as the microbes that are classified as the genus *Clostridium*, *Clostridium acetobutylicum*, *Clostridium perfringens*, *Clostridium kluyveri*, *Clostridium cellulovorans*, *Clostridium difficile* and *Clostridium sticklandii*, as the microbes that are classified as the genus *Alkaliphilus*, *Alkaliphilus metalliredigens* and *Alkaliphilus oremlandii*, as the microbes that are classified as the genus *Syntrophomonas*, *Syntrophomonas wolfei*, as the microbes that are classified as the genus *Syntrophothermus*, *Syntrophothermus lipocalidus*, as the microbes that are classified as the genus *Eubacterium*, *Eubacterium rectale* and *Eubacterium limosum*, as the microbes that are classified as the genus *Desulfitobacterium*, *Desulfitobacterium hafniense*, as the microbes that are classified as the genus *Desulfotomaculum*, *Desulfotomaculum reducens*, as the microbes that are classified as the genus *Pelotomaculum*, *Pelotomaculum thermopropionicum*, as the microbes that are classified as the genus *Butyrivibrio*, *Butyrivibrio proteoclasticus*, as the microbes that are classified as the genus *Roseburia*, *Roseburia hominis*, *Oscillibacter*, *Oscillibacter valericigenes*, *Thermoanaerobacter*, *Thermoanaerobacter tengcongensis*, *Carboxydothermus*, *Carboxydothermus hydrogenoformans*, as the microbes that are classified as the genus *Natranaerobius*, *Natranaerobius thermophilus*, as the microbes that are classified as the genus *Haliscomenobacter*, *Haliscomenobacter hydrossis*, as the microbes that are classified as the genus *Porphyromonas*, *Porphyromonas gingivalis* and *Porphyromonas asaccharolytica*, as the microbes that are classified as the genus *Odoribacter*, *Odoribacter splanchnicus*, as the microbes that are classified as the genus *Spirosoma*, *Spirosoma linguale*, as the microbes that are classified as the genus *Runella*, *Runella slithyformis*, as the microbes that are classified as the genus *Deinococcus*, *Deinococcus radiodurans*, *Deinococcus geothermalis*, *Deinococcus deserti*, *Deinococcus maricopensis*, *Deinococcus proteolyticus* and *Deinococcus gobiensis*, as the microbes that are classified as the genus *Thermus*, *Thermus thermophilus*, *Thermus agnaticus*, *Thermus flavus*, *Thermus caldophilus*, *Thermus ruder* and *Thermus scotoductus*, as the microbes that are classified as the genus *Meiothermus*, *Meiothermus ruber* and *Meiothermus silvanus*, as the microbes that are classified as the genus *Oceanithermus*, *Oceanithermus profundus*, as the microbes that are classified as the genus *Marinithermus*, *Marinithermus hydrothermalis*, as the microbes that are classified as the genus *Gemmatimonas*, *Gemmatimonas aurantiaca*, as the microbes that are classified as the genus *Fusobacterium*, *Fusobacterium nucleatum*, as the microbes that are classified as the genus *Ilyobacter*, *Ilyobacter polytropus*, as the microbes that are classified as the genus *Roseiflexus*, *Roseiflexus castenholzii*, as the microbes that are classified as the genus *Herpetosiphon*, *Herpetosiphon aurantiacus*, as the microbes that are classified as the genus *Thermomicrobium*, *Thermomicrobium roseum*, as the microbes that are classified as the genus *Thermotoga*, *Thermotoga lettingae*, as the microbes that are classified as the genus *Thermosipho*, *Thermosipho melanesiensis* and *Thermosipho africanus*, as the microbes that are classified as the genus *Fervidobacterium*, *Fervidobacterium nodosum*, as the microbes that are classified as the genus *Deferribacter*, *Deferribacter desulfuricans*, as the microbes that are classified as the genus *Calditerrivibrio*, *Calditerrivibrio nitroreducens*, as the microbes that are classified as the genus *Flexistipes*, *Flexistipes sinusarabici*, as the microbes that are classified as the genus *Metallosphaera*, *Metallosphaera sedula*, as the microbes that are classified as the genus *Aeropyrum*, *Aeropyrum pernix*, as the microbes that are classified as the genus *Pyrobaculum*, *Pyrobaculum aerophilum*, *Pyrobaculum islandicum*, *Pyrobaculum calidifontis* and *Pyrobaculum neutrophilum*, as the microbes that are classified as the genus *Caldivirga*, *Caldivirga maquilingensis*, as the microbes that are classified as the genus *Vulca-

*nisaeta*, *Vulcanisaeta distributa*, as the microbes that are classified as the genus *Acidilobus*, *Acidilobus saccharovorans*, as the microbes that are classified as the genus *Haloarcula*, *Haloarcula marismortui*, as the microbes that are classified as the genus *Haloquadratum*, *Haloquadratum walsbyi*, as the microbes that are classified as the genus *Natronomonas*, *Natronomonas pharaonis*, as the microbes that are classified as the genus *Halorubrum*, *Halorubrum lacusprofundi*, as the microbes that are classified as the genus *Haloterrigena*, *Haloterrigena turkmenica*, as the microbes that are classified as the genus *Natrialba*, *Natrialba magadii*, as the microbes that are classified as the genus *Halalkalicoccus*, *Halalkalicoccus jeotgali*, as the microbes that are classified as the genus *Halogeometricum*, *Halogeometricum borinquense*, as the microbes that are classified as the genus *Thermoplasma*, *Thermoplasma acidophilum* and *Thermoplasma volcanium*, as the microbes that are classified as the genus *Picrophilus*, *Picrophilus torridus*, as the microbes that are classified as the genus *Ferroplasma*, *Ferroplasma acidarmanus*, as the microbes that are classified as the genus *Archaeoglobus*, *Archaeoglobus fulgidus* and *Archaeoglobus veneficus*, as the microbes that are classified as the genus *Ferroglobus*, *Ferroglobus placidus*, as the microbes that are classified as the genus *Polymorphum*, *Polymorphum gilvum*, as the microbes that are classified as the genus *Micavibrio*, *Micavibrio aeruginosavorus*, as the microbes that are classified as the genus *Simiduia*, *Simiduia agarivorans*, as the microbes that are classified as the genus *Leptothrix*, *Leptothrix cholodnii*, as the microbes that are classified as the genus *Thiomonas*, *Thiomonas intermedia*, as the microbes that are classified as the genus *Rubrivivax*, *Rubrivivax gelatinosus*, as the microbes that are classified as the genus *Methylibium*, *Methylibium petroleiphilum*, and as the microbes that are classified as the genus *Anaerococcus*, *Anaerococcus prevotii* are particularly preferable.

[Preferred Order of Eukaryotes]

Examples of the microbes which belong to the eukaryotes include microbes belonging to Eurotiales, Saccharomycetales, Capnodiales, Pleosporales, Ustilaginales, Tremellales, Cystofilobasidiales, Helotiales, Pezizales, Polyporales, Agaricales, Pucciniales, Magnaporthales, Sordariales, Microascales, Hypocreales, Sporidiobolales, Exobasidiales, Malasseziales, Onygenales, Laboulbeniales, or Mucorales.

Further, examples of the particularly preferred microbes which allow experimental confirmation of the production of methacrylic acid derivatives include the microbes belonging to Eurotiales and Saccharomycetales.

[Preferred Family and the Genus of Eukaryotes]

As the microbes that are classified as Capnodiales, the genus *Mycosphaerella*, the genus *Zygophiala*, the genus *Zymoseptoria*, the genus *Cladosporium* and the genus *Capnodium*, as the microbes that are classified as Pleosporales, the genus *Preussia*, the genus *Brachycladium*, the genus *Cochliobolus*, the genus *Pleospora*, the genus *Pleospora*, the genus *Leptosphaeria*, the genus *Leptosphaerulina*, the genus *Phaeosphaeria* and the genus *Pyrenophora*, as the microbes that are classified as the genus Ustilaginales, the genus *Pseudozyma*, the genus *Tolyposporium* and the genus *Ustilago*, as the microbes that are classified as the genus Tremellales, the genus *Bulleromyces*, the genus *Filobasidiella* (*Cryptococcus*), the genus *Bullera*, the genus *Fellomyces*, the genus *Kockovaella* and the genus *Trichosporon*, as the microbes that are classified as the genus Cystofilobasidiales, microbe Mrakia, the genus *Xanthophyllomyces* and genus *Udeniomyces*, as the microbes that are classified as the genus Helotiales, the genus *Botryotinia*, the genus *Monilia*, the genus *Monilinia*, and the genus *Sclerotinia*, as the microbes that are classified as the genus Pezizales, the genus *Peziza*, the genus *Morchella*, the genus *Helvella*, the genus *Ascodesmis*, the genus *Ascobolus*, and the genus *Tuber*, as the microbes that are classified as the genus Polyporales, the genus *Mycoleptodonoides*, the genus *Mycoaciella*, the genus *Parmastomyces* and the genus *Postia*, as the microbes that are classified as the genus Agaricales, the genus *Arthromyces*, the genus *Mycenoporella*, the genus *Laccaria*, the genus *Moniliophthora*, the genus *Coprinopsis* and the genusSchizophyllum, as the microbes that are classified as the genus Pucciniales, the genus *Puccinia*, the genus *Melampsora*, the genus *Cronartium*, the genus *Cyttaria*, the genus *Coleosporium*, the genus *Blastospora* and the genus *Ravenelia*, as the microbes that are classified as the genus Magnaporthales, the genus *Magnaporthe*, as the microbes that are classified as the genus Sordariales, the genus *Podospora*, the genus *Neurospora*, the genus *Sordaria*, the genus *Chaetomium*, the genus *Thielavia*, the genus *Myceliophthora* and the genus *Monotosporella*, as the microbes that are classified as the genus Microascales, the genus *Microascus*, the genus *Nodulosphaeria*, the genus *Okeanomyces*, and the genus *Ceratocystis*, as the microbes that are classified as the genus Hypocreales, the genus *Fusarium*, the genus *Nectria*, the genus *Hypocrea*, the genus *Hypomyces*, the genus *Trichoderma*, the genus *Cordyceps*, the genus *Claviceps*, and the genus *Acremonium*, as the microbes that are classified as the genus Sporidiobolales, the genus *Rhodosporidium*, the genus *Rhodotorula*, the genus *Sporidiobolus*, and the genus *Sporobolomyces*, as the microbes that are classified as the genus Exobasidiales, the genus *Graphiola*, the genus *Exobasidium*, and genus *Dicellomyces*, as the microbes that are classified as the genus Malasseziales, the genus *Malassezia*, as the microbes that are classified as the genus Onygenales, the genus *Gymnoascus*, the genus *Eremascus*, the genus *Arthroderma*, the genus *Coccidioides*, the genus *Paracoccidioides*, the genus *Uncinocarpus*, the genus *Trichophyton*, and the genus *Ajellomyces*, as the microbes that are classified as the genus Laboulbeniales, the genus *Rhachomyces*, the genus *Rickia*, the genus *Stigmatomyces*, and the genus *Ceratomyces*, as the microbes that are classified as the genus Mucorales, gensus Absidia, the genus *Mucor*, the genus *Rhizomucor*, and the genus *Rhizopus* can be mentioned.

As the microbes that are classified as Eurotiales, the genus *Neopetromyces*, the genus *Aspergillus*, the genus *Neosartorya*, the genus *Byssochlamys*, the genus *Emericella*, the genus *Eupenicillium*, the genus *Eurotium*, the genus *Hemicarpenteles*, the genus *Penicillium*, the genus *Talaromyces*, and the genus *Monascus* can be mentioned.

As the microbes that are classified as Saccharomycetales, the genus *Arthroascus*, the genus *Guilliermondella*, the genus *Clavispora*, the genus *Metschnikowia*, the genus *Lipomyces*, the genus *Endomyces*, the genus *Ascoidea*, the genus *Cephaloascus*, the genus *Wickerhamiella*, the genus *Zygoascus*, the genus *Trichomonascus*, the genus *Aciculoconidium*, the genus *Ambrosiozyma*, the genus *Blastobotrys*, the genus *Botryozyma*, the genus *Brettanomyces*, the genus *Myxozyma*, the genus *Ogataea*, the genus *Komagataella*, the genus *Trigonopsis*, the genus *Schizoblastosporion*, and the genus *Sympodiomyces* can be mentioned.

Further, as the microbes belonging to Saccharomycetales, preferred examples include the microbes that are classififed as Saccharomycodaceae, Pichiaceae, Dipodascaceae or mitosporic Saccharomycetales. Examples of the microbes belonging to that family include the genus *Hanseniaspora*, the genus *Kloeckera*, the genus *Saccharomycodes*, the genus

*Nadsonia*, the genus *Ashbya*, the genus *Citeromyces*, the genus *Dekkera*, the genus *Issatchenkia*, the genus *Kluyveromyces*, the genus *Pachysolen*, the genus *Saccharomyces*, the genus *Saturnispora*, the genus *Tetrapisispora*, the genus *Torulaspora*, the genus *Zygosaccharomyces*, the genus *Zygotorulaspora*, the genus *Eremothecium*, the genus *Lachancea*, the genus *Vanderwaltozyma*, the genus *Naumovozyma*, the genus *Kazachstania*, the genus *Eremothecium*, the genus *Williopsis*, the genus *Pichia*, the genus *Yarrowia*, the genus *Dipodascus*, the genus *Arxula*, the genus *Galactomyces*, the genus *Geotrichum*, the genus *Babjevia*, the genus *Debaryomyces*, the genus *Schwanniomyces*, the genus *Priceomyces*, the genus *Yamadazyma*, the genus *Scheffersomyces*, the genus *Meyerozyma*, the genus *Lodderomyces*, the genus *Sporopachydermia*, and the genus *Candida*.

Among those belonging to the eukarytoes, examples of other genus include the genus *Botryosphaeria*, the genus *Helicomyces*, the genus *Aureobasidium*, the genus *Selenophoma*, the genus *Melanotaenium*, the genus *Otospora*, the genus *Glomus*, the genus *Allomyces*, the genus *Rhizidiomyces*, the genus *Hyphochytrium*, the genus *Schizosaccharomyces*, the genus *Filobasidium*, the genus *Lophodermium*, the genus *Dothidea*, the genus *Oidium*, the genus *Amorphotheca*, the genus *Scytalidium*, the genus *Taphrina*, the genus *Strangospora*, the genus *Chytridium*, the genus *Pneumocystis*, the genus *Sclerotium*, the genus *Neolecta*, the genus *Septobasidium*, the genus *Xylaria*, the genus *Pestalotiopsis*, the genus *Phomopsis*, the genus *Sydowiella*, the genus *Coniochaetidium*, the genus *Sporothrix*, the genus *Moleospora*, the genus *Verticillium*, the genus *Microascales*, the genus *Leucosporidium*, the genus *Microstroma*, and the genus *Thraustochytrium*.

Among them, the preferred microbes are the microbes which have been demonstrated to have an enzyme for the metabolism pathway of branched amino acids, that is, microbes classified as the genus *Zymoseptoria*, the genus *Phaeosphaeria*, the genus *Pyrenophora*, the genus *Ustilago*, the genus *Ashbya*, the genus *Kluyveromyces*, the genus *Saccharomyces*, the genus *Yarrowia*, the genus *Debaryomyces*, the genus *Scheffersomyces*, the genus *Meyerozyma*, the genus *Lodderomyces*, the genus *Candida*, the genus *Filobasidiella* (*Cryptococcus*), the genus *Botryotinia*, the genus *Sclerotinia*, the genus *Tuber*, the genus *Postia*, the genus *Laccaria*, the genus *Moniliophthora*, the genus *Coprinopsis*, the genus *Schizophyllum*, the genus *Puccinia*, the genus *Magnaporthe*, the genus *Podospora*, the genus *Neurospora*, the genus *Sordaria*, the genus *Thielavia*, the genus *Myceliophthora*, the genus *Fusarium*, the genus *Nectria*, the genus *Malassezia*, the genus *Aspergillus*, the genus *Neosartorya*, the genus *Arthroderma*, the genus *Coccidioides*, the genus *Paracoccidioides*, the genus *Uncinocarpus*, the genus *Trichophyton*, or the genus *Ajellomyces*.

Further, examples of the particularly preferred microbes which allow experimental confirmation of the production of methacrylic acid derivatives include the microbes that are classified as the genus *Saccharomyces*, the genus *Candida*, or the genus *Aspergillus*.

[Preferred Species of Eukaryotes]
[Genus *Saccharomyces*]

Examples of the microbes that are classified as the genus *Saccharomyces* include *Saccharomyces barnettii*, *Saccharomyces bayanus*, *Saccharomyces bayanus* var. *uvarum*, *Saccharomyces boulardii*, *Saccharomyces bulderi*, *Saccharomyces cariocanus*, *Saccharomyces cerevisiae*, *Saccharomyces castellii*, *Saccharomyces dairenensis*, *Saccharomyces diastaticus*, *Saccharomyces douglasii*, *Saccharomyces exiguus*, *Saccharomyces humaticus*, *Saccharomyces kluyveri*, *Saccharomyces kudriavzevii*, *Saccharomyces kunashirensis*, *Saccharomyces martiniae*, *Saccharomyces mikatae*, *Saccharomyces naganishii*, *Saccharomyces novalvarietatis*, *Saccharomyces paradoxus*, *Saccharomyces pastorianus*, *Saccharomyces rosinii*, *Saccharomyces rouxii*, *Saccharomyces stellatus*, *Saccharomyces servazzii*, *Saccharomyces spencerorum*, *Saccharomyces transvaalensis*, *Saccharomyces turicensis*, *Saccharomyces yakushimaensis* var. *yakushimaensis*, *Saccharomyces unisporus*, and *Saccharomyces uvarum*.

[Genus *Candida*]

Examples of the microbes that are classified as the genus *Candida* include *Candida aaseri*, *Candida africana*, *Candida aglyptinia*, *Candida agrestis*, *Candida akabanensis*, *Candida alai*, *Candida albicans*, *Candida alishanica*, *Candida allociferrii*, *Candida amapae*, *Candida ambrosiae*, *Candida amphixiae*, *Candida anatomiae*, *Candida ancudensis*, *Candida andamanensis*, *Candida anglica*, *Candida anneliseae*, *Candida antillancae*, *Candida anutae*, *Candida apicola*, *Candida apis*, *Candida apis* var. *apis*, *Candida aquaetextoris*, *Candida arabinofermentans*, *Candida arcana*, *Candida ascalaphidarum*, *Candida asiatica*, *Candida atbi*, *Candida atakaporum*, *Candida athensensis*, *Candida atlantica*, *Candida atmosphaerica*, *Candida auringiensis*, *Candida auris*, *Candida aurita*, *Candida austromarina*, *Candida azyma*, *Candida barrocoloradensis*, *Candida batistae*, *Candida beechii*, *Candida bertae*, *Candida berthetii*, *Candida bituminiphila*, *Candida blackwellae*, *Candida blankii*, *Candida blattae*, *Candida blattariae*, *Candida bohiensis*, *Candida boidinii*, *Candida bokatorum*, *Candida boleticola*, *Candida bolitotheri*, *Candida bombi*, *Candida bombicola*, *Candida bondarzewiae*, *Candida bovina*, *Candida bribrorum*, *Candida brumptii*, *Candida buenavistaensis*, *Candida buinensis*, *Candida bullrunensis*, *Candida butyri*, *Candida cacaoi*, *Candida canberraensis*, *Candida cantarellii*, *Candida cariosilignicola*, *Candida carpophila*, *Candida caryicola*, *Candida caseinolytica*, *Candida castellii*, *Candida castrensis*, *Candida catenulata*, *Candida cellulolytica*, *Candida cerambycidarum*, *Candida chauliodes*, *Candida chickasaworum*, *Candida chilensis*, *Candida chiropterorum*, *Candida choctaworum*, *Candida chrysomelidarum*, *Candida cidri*, *Candida ciferrii*, *Candida cleridarum*, *Candida coipomensis*, *Candida colliculosa*, *Candida conglobata*, *Candida corydali*, *Candida cylindracea*, *Candida dajiaensis*, *Candida danieliae*, *Candida davenportii*, *Candida davisiana*, *Candida deformans*, *Candida dendrica*, *Candida dendronema*, *Candida derodonti*, *Candida deserticola*, *Candida diddensiae*, *Candida digboiensis*, *Candida diversa*, *Candida dosseyi*, *Candida drimydis*, *Candida drosophilae*, *Candida dubliniensis*, *Candida easanensis*, *Candida edax*, *Candida elateridarum*, *Candida elegans*, *Candida emberorum*, *Candida endomychidarum*, *Candida entomophila*, *Candida eppingiae*, *Candida eremophlia*, *Candida ergatensis*, *Candida ernobii*, *Candida etchellsii*, *Candida ethanolica*, *Candida famata*, *Candida famata* var. *famata*, *Candida fennica*, *Candida fermentati*, *Candida fermenticarens*, *Candida floricola*, *Candida fluviatilis*, *Candida fragi*, *Candida fragicola*, *Candida freyschussii*, *Candida friedrichii*, *Candida frijolensensis*, *Candida fructus*, *Candida fukazawae*, *Candida fukuyamanensis*, *Candida fungicola*, *Candidafusiformata*, *Candida galacta*, *Candida galis*, *Candida gatunensis*, *Candida geochares*, *Candida germanica*, *Candida ghanaensis*, *Candida gigantensis*, *Candida glabrata*, *Candida glaebosa*, *Candida globosa*, *Candida glucosophila*, *Candida golubevii*, *Candida gorgasii*, *Candida gosingica*, *Candida gotoi*, *Candida gropengiesseri*, *Candida guaymorum*, *Candida guilliermondii*, *Candida*

*haemulonii, Candida halonitratophila, Candida halophila, Candida hasegawae, Candida hellenica, Candida holmii, Candida homilentoma, Candida hordei, Candida hsintzibuensis, Candida humilis, Candida hungarica, Candida hungchunana, Candida incommunis, Candida inconspicua, Candida ingens, Candida insectalens, Candida insectamans, Candida insectorum, Candida insectosa, Candida intermedia, Candida intermedia* var. *intermedia, Candida ipomoeae, Candida ishiwadae, Candida japonica, Candida jaroonii, Candida jeffriesii, Candida jianshihensis, Candida jiufengensis, Candida kanchanaburiensis, Candida kaohsiungensis, Candida karawaiewii, Candida kashinagacola, Candida kazuoi, Candida kefyr, Candida khaoyaiensis, Candida khmerensis, Candida kofuensis, Candida krabiensis, Candida krissii, Candida kruisii, Candida krusei, Candida krusoides, Candida kunorum, Candida kunwiensis, Candida labiduridarum, Candida lactis-condensi, Candida laemsonensis, Candida lambica, Candida lassenensis, Candida laureliae, Candida leandrae, Candida lessepsii, Candida levantina, Candida lidongshanica, Candida lignicola, Candida lignohabitans, Candida lignophila, Candida lignosa, Candida lipolytica, Candida litsaeae, Candida llanquihuensis, Candida lodderae, Candida lundiana, Candida lusitaniae, Candida lycoperdinae, Candida lyxosophila, Candida maesa, Candida magnoliae, Candida maltosa, Candida mannitofaciens, Candida maris, Candida maritima, Candida maxii, Candida melibiosica, Candida melinii, Candida membranifaciens, Candida mesenterica, Candida metapsilosis, Candida methanolovescens, Candida methanosorbosa, Candida methylica, Candida michaelii, Candida milleri, Candida mogii, Candida mokoenaii, Candida molischiana, Candida montana, Candida morakotiae, Candida mucifera, Candida multigemmis, Candida musae, Candida mycetangii, Candida naeodendra, Candida nakhonratchasimensis, Candida nanaspora, Candida natalensis, Candida neerlandica, Candida nemodendra, Candida neustonensis, Candida nitrativorans, Candida nitratophila, Candida nodaensis, Candida nonsorbophila, Candida norvegensis, Candida norvegica, Candida novakii, Candida obtusa* var. *obtusa, Candida odintsovae, Candida oleophila, Candida olivae, Candida ontarioensis, Candida ooitensis, Candida orba, Candida oregonensis, Candida orthopsilosis, Candida ortonii, Candida ovalis, Candida oxycentoniae, Candida pallodes, Candida palmioleophila, Candida palmyrensis, Candida paludigena, Candida panamensis, Candida panamericana, Candida parapolymorpha, Candida parapsilosis, Candida parapsilosis* var. *parapsilosis, Candida pararugosa, Candida pattaniensis, Candida peltata, Candida peoriaensis, Candida petrohuensis, Candida phangngensis, Candida picachoensis, Candida piceae, Candida pignaliae, Candida pimensis, Candida pini, Candida pintolopesii, Candida pintolopesii* var. *pintolopesii, Candida pintolopesii* var. *sloofiae, Candida pinus, Candida plutei, Candida polymorpha, Candida pomiphila, Candida ponderosae, Candida populi, Candida powellii, Candida prachuapensis, Candida prunicola, Candida pseudoflosculorum, Candida pseudoglaebosa, Candida pseudohaemulonii, Candida pseudointermedia, Candida pseudojiufengensis, Candida pseudolambica, Candida pseudovanderkliftii, Candida psychrophila, Candida pulcherrima, Candida pyralidae, Candida quercitrusa, Candida quercuum, Candida railenensis, Candida ralunensis, Candida ranongensis, Candida ratchasimensis, Candida restingae, Candida reversa, Candida rhagii, Candida robnettiae, Candida rugopelliculosa, Candida rugosa, Candida rugosa* var. *rugosa, Candida sagamina, Candida saitoana, Candida sake, Candida salmanticensis, Candida sanitii, Candida santamariae, Candida santamariae* var. *membranifaciens, Candida santamariae* var. *santamariae, Candida santjacobensis, Candida sanyiensis, Candida saraburiensis, Candida savonica, Candida schatavii, Candida sekii, Candida sequanensis, Candida sergipensis, Candida shehatae, Candida shehatae* var. *insectosa, Candida shehatae* var. *lignosa, Candida shehatae* var. *shehatae, Candida siamensis, Candida silvae, Candida silvanorum, Candida silvatica, Candida silvicultrix, Candida sinolaborantium, Candida sithepensis, Candida slooffiae, Candida smagusa, Candida smithsonii, Candida sojae, Candida solani, Candida solicola, Candida sonckii, Candida songkhlaensis, Candida sonorensis, Candida sophiaereginae, Candida sorbophila, Candida sorbosa, Candida sorbosivorans, Candida sorboxylosa, Candida spandovensis, Candida sphaerica, Candida stauntonica, Candida stellata, Candida stellimalicola, Candida stri, Candida succiphila, Candida suecica, Candida suthepensis, Candida suwanaritii, Candida suzukii, Candida takamatsuzukensis, Candida takata, Candida taliae, Candida tammaniensis, Candida tannotolerans, Candida tanticharoeniae, Candida tanzawaensis, Candida taoyuanica, Candida tartarivorans, Candida temnochilae, Candida tenuis, Candida tepae, Candida terebra, Candida terraborum, Candida tetrigidarum, Candida thailandica, Candida thaimueangensis, Candida theae, Candida thermophila, Candida tilneyi, Candida tolerans, Candida torresii, Candida tritomae, Candida tropicalis, Candida tropicalis* var. *tropicalis, Candida trypodendroni, Candida tsuchiyae, Candida tsukubaensis, Candida tumulicola, Candida ulmi, Candida utilis, Candida vaccinii, Candida valdiviana, Candida valida, Candida vanderwaltii, Candida variabilis, Candida vartiovaarae, Candida veronae, Candida versatilis, Candida vinaria, Candida vini, Candida viswanathii, Candida wanchemiae, Candida wickerhamii, Candida wounanorum, Candida wyomingensis, Candida xestobii, Candida xyloterini, Candida yuanshanicus, Candida yuchorum, Candida zemplinina, Candida zeylanoides,* and *Candida zeylanoides* var. *zeylanoides.*

[Genus *Aspergillus*]

Examples of the microbes that are classified as the genus *Aspergillus* include *Aspergillus acanthosporus, Aspergillus acolumnaris, Aspergillus aculeatus, Aspergillus aeneus, Aspergillus affinis, Aspergillus allahabadii, Aspergillus alliaceus, Aspergillus alutaceus, Aspergillus ambiguus, Aspergillus amstelodami, Aspergillus amylovorus, Aspergillus anomalus, Aspergillus anthodesmis, Aspergillus apica, Aspergillus appendiculatus, Aspergillus arenarius, Aspergillus asperescens, Aspergillus athecius, Aspergillus aurantiobrunneus, Aspergillus auratus, Aspergillus aureus* var. *acidus, Aspergillus aureus* var. *minor, Aspergillus aureofulgens, Aspergillus aureolatus, Aspergillus aureolus, Aspergillus auricomus, Aspergillus avenaceus, Aspergillus awamori, Aspergillus awamori* var. *fumeus, Aspergillus awamori* var. *fuscus, Aspergillus awamori* var. *minimus, Aspergillus awamori* var. *piceus, Aspergillus batatas, Aspergillus bicolor, Aspergillus biplanus, Aspergillus bisporus, Aspergillus bombycis, Aspergillus brasiliensis, Aspergillus brevipes, Aspergillus bridgeri, Aspergillus brunneo-uniseriatus, Aspergillus brunneo-uniseriatus* var. *nanus, Aspergillus caelatus, Aspergillus caesiellus, Aspergillus caespitosus, Aspergillus campestris, Aspergillus candidus, Aspergillus carbonarius, Aspergillus carneus, Aspergillus carnoyi, Aspergillus cellulosae, Aspergillus cervinus, Aspergillus chevalieri, Aspergillus chevalieri* var. *intermedius, Aspergillus chrysellus, Aspergillus cinnamomeus, Aspergillus citrisporus, Aspergillus clavatoflavus, Aspergillus clavatonanica, Aspergillus clavatonanicus, Aspergillus clavatus,*

*Aspergillus cleistominutus, Aspergillus conicus, Aspergillus conjunctus, Aspergillus coremiiformis, Aspergillus corrugatus, Aspergillus crassihyphae, Aspergillus cremeus, Aspergillus cristatus, Aspergillus crustosus, Aspergillus crystallinus, Aspergillus deflectus, Aspergillus dimorphicus, Aspergillus diversus, Aspergillus dorothicus, Aspergillus duricaulis, Aspergillus eburneocremeus, Aspergillus echinulatus, Aspergillus egyptiacus, Aspergillus elegans, Aspergillus ellipticus, Aspergillus elongatus, Aspergillus fennelliae, Aspergillus ficuum, Aspergillus fischeri, Aspergillus fischeri* var. *brasiliensis, Aspergillus fischeri* var. *glaber, Aspergillus fischeri* var. *spinosus, Aspergillus flaschentraegeri, Aspergillus flavipes, Aspergillus flavofurcatus, Aspergillus flavus, Aspergillus flavus* var. *columnaris, Aspergillus flavus* var. *flavus, Aspergillus flavus* var. *sojae, Aspergillus flocculosus, Aspergillus floriformis, Aspergillus foetidus, Aspergillus foetidus* var. *acidus, Aspergillus foetidus* var. *pallidus, Aspergillus foveolatus, Aspergillus fresenii, Aspergillus fruticulosus, Aspergillus fumaricus, Aspergillus fumigatus, Aspergillus fumigatus* var. *acolumnaris, Aspergillus fumigatus* var. *ellipticus, Aspergillus fumigatus* var. *fumigatus, Aspergillus fumigatus* var. *helvolus, Aspergillus funiculosus, Aspergillus giganteus, Aspergillus glaber, Aspergillus glaucus, Aspergillus gorakhpurensis, Aspergillus gracilis, Aspergillus granulatus, Aspergillus granulosus, Aspergillus gymnosardae, Aspergillus halophilicus, Aspergillus helicothrix, Aspergillus hennebergii, Aspergillus heterocaryoticus, Aspergillus heteromorphus, Aspergillus heterothallicus, Aspergillus iizukae, Aspergillus implicatus, Aspergillus insuetus, Aspergillus insulicola, Aspergillus inuii, Aspergillus itaconicus, Aspergillus ivoriensis, Aspergillus janus, Aspergillus janus* var. *brevis, Aspergillus janus* var. *janus, Aspergillus japonicus, Aspergillus japonicus* var. *atrofuscus, Aspergillus japonicus* var. *viridiflavus, Aspergillus kambarensis, Aspergillus kanagawaensis, Aspergillus kawachii, Aspergillus lanosus, Aspergillus lentulus, Aspergillus leporis, Aspergillus leucocarpus, Aspergillus longivesica, Aspergillus luchuensis, Aspergillus lucknowensis, Aspergillus luteo-niger, Aspergillus malignus, Aspergillus malodoratus, Aspergillus manginii, Aspergillus medius, Aspergillus melleus, Aspergillus microcephalus, Aspergillus microviridicitrinus, Aspergillus microcysticus, Aspergillus minimus, Aspergillus miyokoensis, Aspergillus montevidensis, Aspergillus multicolor, Aspergillus mutabilis, Aspergillus nidulans, Aspergillus nidulans* var. *acristatus, Aspergillus nidulans* var. *dentatus, Aspergillus nidulans* var. *echinulatus, Aspergillus nidulans* var. *latus, Aspergillus nidulans* var. *roseus, Aspergillus niger, Aspergillus niger* mut. *cinnamomeus, Aspergillus niger* var. *intermedius, Aspergillus niger* var. *macrosporus, Aspergillus niger* var. *nanus, Aspergillus niger* var. *niger, Aspergillus niger* var. *niger f. hennebergii, Aspergillus niger* var. *phoenicis, Aspergillus niger* mut. *schiemanni, Aspergillus niveoglaucus, Aspergillus niveus, Aspergillus niveus* ver. *indica, Aspergillus nomius, Aspergillus nutans, Aspergillus ochraceoroseus, Aspergillus ochraceus, Aspergillus ornatus, Aspergillus oryzae, Aspergillus oryzae* var. *brunneus, Aspergillus oryzae* var. *effusus, Aspergillus oryzae* var. *magnasporus, Aspergillus oryzae* var. *oryzae, Aspergillus oryzae* var. *sporoflavus, Aspergillus oryzae* var. *variabilis, Aspergillus oryzae* var. *viridis, Aspergillus ostianus, Aspergillus pallidus, Aspergillus panamensis, Aspergillus paradoxus, Aspergillus parasiticus, Aspergillus parasiticus* var. *globosus, Aspergillus parvathecius, Aspergillus parvulus, Aspergillus penicillioformis, Aspergillus penicillioides, Aspergillus persii, Aspergillus petrakii, Aspergillus peyronelii, Aspergillus phialiseptus, Aspergillus phoenicis, Aspergillus proliferans, Aspergillus protuberus, Aspergillus pseudodeflectus, Aspergillus pseudoglaucus, Aspergillus pseudotamarii, Aspergillus pulverulentus, Aspergillus pulvinus, Aspergillus puniceus, Aspergillus quadricinctus, Aspergillus quadrilineatus, Aspergillus quercinus, Aspergillus quercinus* var. *petrakii, Aspergillus raperi, Aspergillus recurvatus, Aspergillus repens, Aspergillus restrictus, Aspergillus rhizopodus, Aspergillus robustus, Aspergillus ruber, Aspergillus rugulosus, Aspergillus saitoi* var. *kagoshimaensis, Aspergillus salviicola, Aspergillus sclerotiorum, Aspergillus sepultus, Aspergillus silvaticus, Aspergillus sojae, Aspergillus sparsus, Aspergillus spathulatus, Aspergillus spectabilis, Aspergillus spelunceus, Aspergillus speluneus, Aspergillus spinulosus, Aspergillus stellatus, Aspergillus stellatus* var. *astellatus, Aspergillus stramenius, Aspergillus striatus, Aspergillus stromatoides, Aspergillus subolivaceus, Aspergillus subsessilis, Aspergillus sulphureus, Aspergillus sulphureus* var. *minimus, Aspergillus sunderbanii, Aspergillus sydowii, Aspergillus tamarii, Aspergillus tardus, Aspergillus terreus, Aspergillus terreus* var. *africanus, Aspergillus terreus* var. *aureus, Aspergillus terreus* var. *baedijnii, Aspergillus terreus* var. *globosus, Aspergillus terreus* var. *terreus, Aspergillus terricola, Aspergillus terricola* var. *americana, Aspergillus terricola* var. *indicus, Aspergillus testaceocolorans, Aspergillus thermomutatus, Aspergillus thomii, Aspergillus togoensis, Aspergillus tonophilus, Aspergillus toxicarius, Aspergillus tubingensis, Aspergillus umbrosus, Aspergillus unguis, Aspergillus unilateralis, Aspergillus usamii* mut. *shirousamii, Aspergillus usamii* var. *shiro-usamii, Aspergillus ustus, Aspergillus uvarum, Aspergillus vadensis, Aspergillus varians, Aspergillus versicolor, Aspergillus violaceofuscus, Aspergillus violaceus, Aspergillus viridinutans, Aspergillus vitis, Aspergillus vitis* var. *montevidensis, Aspergillus wentii, Aspergillus wentii* var. *minimus, Aspergillus zhaoqingensis,* and *Aspergillus zonatus.*

[Other Preferred Species of Eukaryotes]

Further, as the microbes that are classified as the genus *Zymoseptoria, Zymoseptoria tritici,* as the microbes that are classified as the genus *Phaeosphaeria, Phaeosphaeria nodorum,* as the microbes that are classified as the genus *Pyrenophora, Pyrenophora teres,* as the microbes that are classified as the genus *Ustilago, Ustilago maydis,* as the microbes that are classified as the genus *Ashbya, Ashbya gossypii (Eremothecium gossypii),* as the microbes that are classified as the genus *Kluyveromyces, Kluyveromyces lactis,* as the microbes that are classified as the genus *Yarrowia, Yarrowia lipolytica,* as the microbes that are classified as the genus *Debaryomyces, Debaryomyces hansenii,* as the microbes that are classified as the genus *Scheffersomyces, Scheffersomyces stipitis,* as the microbes that are classified as the genus *Meyerozyma, Meyerozyma guilliermondii,* as the microbes that are classified as the genus *Lodderomyces, Lodderomyces elongisporus,* as the microbes that are classified as the genus *Filobasidiella (Cryptococcus), Cryptococcus neoformans, Cryptococcus gattii* and *Cryptococcus amylolentus,* as the microbes that are classified as the genus *Botryotinia, Botryotinia fuckeliana,* as the microbes that are classified as the genus *Sclerotinia, Sclerotinia sclerotiorum,* as the microbes that are classified as the genus *Tuber, Tuber melanosporum,* as the microbes that are classified as the genus *Postia, Postia placenta,* as the microbes that are classified as the genus *Laccaria, Laccaria bicolor,* as the microbes that are classified as the genus *Moniliophthora, Moniliophthora perniciosa,* as the microbes that are classified as the genus *Coprinopsis, Coprinopsis cinerea,* as the microbes that are classified as the genus *Schizophyllum, Schizophyllum commune,* as the microbes that are classified as the genus *Puccinia*, *Puccinia graminis*, as the microbes that are classified as the genus *Magnaporthe*, *Magnaporthe oryzae*, as the microbes that are classified as the genus *Podospora*, *Podospora anserina*, as the microbes that are classified as the genus *Neurospora*, *Neurospora crassa*, as the microbes that are classified as the genus *Sordaria*, *Sordaria macrospora*, as the microbes that are classified as the genus *Thielavia*, *Thielavia terrestris*, as the microbes that are classified as the genus *Myceliophthora*, *Myceliophthora thermophila*, as the microbes that are classified as the genus *Fusarium*, *Fusarium graminearum*, as the microbes that are classified as the genus *Nectria*, *Nectria haematococca*, as the microbes that are classified as the genus *Malassezia*, *Malassezia globosa*, as the microbes that are classified as the genus *Neosartorya*, *Neosartorya fischeri*, as the microbes that are classified as the genus *Arthroderma*, *Arthroderma benhamiae*, as the microbes that are classified as the genus *Coccidioides*, *Coccidioides immitis* and *Coccidioides posadasii*, as the microbes that are classified as the genus *Paracoccidioides*, *Paracoccidioides brasiliensis*, as the microbes that are classified as the genus *Uncinocarpus*, *Uncinocarpus reesii*, as the microbes that are classified as the genus *Trichophyton*, *Trichophyton verrucosum*, as the microbes that are classified as the genus *Ajellomyces*, *Ajellomyces capsulatus*, as the microbes that are classified as the genus *Hypocrea*, *Hypocrea rufa*, as the microbes that are classified as the genus *Acremonium*, *Acremonium chrysogenum*, as the microbes that are classified as the genus *Penicillium*, *Penicillium camembertii*, as the microbes that are classified as the genus *Ogataea*, *Ogataea minuta*, as the microbes that are classified as the genus *Komagataella*, *Komagataella pastoris*, as the microbes that are classified as the genus *Trigonopsis*, *Trigonopsis variabilis*, as the microbes that are classified as the genus *Schizosaccharomyces*, *Schizosaccharomyces pombe*, and as the microbes that are classified as the genus *Scytalidium*, *Scytalidium thermophirum* can be mentioned.

Among the aforementioned prokaryotes and eukaryotes, examples of the particularly preferred microbes which allow experimental confirmation of the production of methacrylic acid derivatives include the microbes which belong to the genus *Pseudomonas*, the genus *Bacillus*, the genus *Sphingobacterium*, the genus *Comamonas*, the genus *Brevundimonas*, the genus *Sphingomonas*, the genus *Ochrobactrum*, the genus *Pedobacter*, the genus *Paenibacillus*, the genus *Achromobacter*, the genus *Acinetobacter*, the genus *Shewanella*, the genus *Listonella*, the genus *Agrobacterium*, the genus *Mesorhizobium*, the genus *Rhizobium*, the genus *Paracoccus*, the genus *Xanthobacter*, the genus *Streptomyces*, the genus *Geobacillus*, the genus *Rhodococcus*, the genus *Saccharomyces*, the genus *Candida*, or the genus *Aspergillus*.

Among them, more preferred are the microbes which belong to the genus *Sphingobacterium*, the genus *Comamonas*, the genus *Brevundimonas*, the genus *Sphingomonas*, the genus *Ochrobactrum*, the genus *Pedobacter*, the genus *Paenibacillus*, the genus *Achromobacter*, the genus *Acinetobacter*, the genus *Shewanella*, the genus *Listonella*, the genus *Agrobacterium*, the genus *Mesorhizobium*, the genus *Paracoccus*, the genus *Xanthobacter*, the genus *Geobacillus*, the genus *Rhodococcus*, or the genus *Candida*.

[Preferred Microbial Strains]

Particularly preferred examples of the microbes having the ability to produce methacrylic acid, which are used for the method for producing methacrylic acid of the invention, include the following microbial strains having high ability to produce methacrylic acid (see, Examples described below).

[Correction of Nov. 27, 2013 Based on Rule 91]

(i) B25-2 strain (The National Institute of Technology and Evaluation (NITE), Patent Microorganisms Depository (zip code 292-0818, 2-5-8 Kazusakamatari, Kisarazu-shi, Chiba-ken, 292-0818, Japan), Accession number: NITE BP-1451), D22-1 strain (Accession number: NITE BP-1452), D43-1 strain (Accession number: NITE BP-1453), D25 strain (Accession number: NITE BP-1454), D26 strain (Accession number: NITE BP-1455), D29 strain (Accession number: NITE BP-1456), D41-2 strain (Accession number: NITE BP-1457), and *Pseudomonas putida* NBRC12996 which belong to the genus *Pseudomonas*, or (ii) G1 strain (Accession number: NITE BP-1458), G2 strain (Accession number: NITE BP-1459) strain, R1 strain (Accession number: NITE BP-1460), *Bacillus subtilis* NBRC12210, *Bacillus badius* ATCC14574, *Bacillus megaterium* NBRC15308, and *Bacillus simplex* ATCC49097 which belong to the genus *Bacillus*

(iii) B13 strain (Accession number: NITE BP-1461) which belongs to the genus *Sphingobacterium*.

(iv) *Comamonas terrigena* NBRC13299 which belongs to the genus *Comamonase*.

(v) *Brevundimonas diminuta* ATCC11568, *Brevundimonas vesicularis* ATCC11426 or *Brevundimonas subvibrioides* NBRC16000 which belongs to the genus *Brevundimonas*.

(vi) *Sphingomonas paucimobilis* NBRC 13935 which belongs to the genus *Sphingomonas*.

(vii) *Ochrobactrum* sp. NBRC12951, *Ochrobactrum intermedium* NBRC15820, *Ochrobactrum intermedium* NBRC13694, *Ochrobactrum anthropic* ATCC49237, *Ochrobactrum grignonense* NBRC 102586 or *Ochrobactrum lupini* NBRC 102587 which belongs to the genus *Ochrobactrum*.

(viii) *Pedobacter heparinus* NBRC12017 which belongs to the genus *Pedobacter*.

(ix) *Paenibacillus* sp. NBRC 13157 which belongs to the genus *Paenibacillus*.

(x) *Achromobacter denitrificans* NBRC 12669 which belongs to the genus *Achromobacter*.

(xi) *Acinetobacter haemolyticus* ATCC17906 or *Acinetobacter junii* ATCC17908 which belongs to the genus *Acinetobacter*.

(xii) *Shewanella fodinae* NBRC105216 which belongs to the genus *Shewanella*.

(xiii) *Listonella anguillarum* ATCC19264 which belongs to the genus *Listonella*.

(xiv) *Agrobacterium luteum* NBRC15768 which belongs to the genus *Agrobacterium*.

(xv) *Mesorhizobium loti* ATCC700743 which belongs to the genus *Mesorhizobium*.

(xvi) *Rhizobium leguminosarum* ATCC10004 which belongs to the genus *Rhizobium*.

(xvii) *Paracoccus aminophilus* NBRC16710 which belongs to the genus *Paracoccus*.

(xviii) *Xanthobacter autotrophicus* ATCC35674 which belongs to the genus *Xanthobacter*.

(xix) *Streptomyces griseus* NBRC13350 which belongs to the genus *Streptomyces*.

(xx) *Geobacillus stearothermophilus* NBRC 12983 which belongs to the genus *Geobacillus*.

(xxi) *Rhodococcus erythropolis* can be mentioned. More preferred examples of the strain include *Rhodococcus erythropolis* PR-4 strain, *Rhodococcus erythropolis* KA2-5-1 strain, *Rhodococcus erythropolis* IGTS8 strain, *Rhodococcus erythropolis* D-1 strain, *Rhodococcus erythropolis* H-2 strain, *Rhodococcus erythropolis* N1-36 strain, *Rhodococcus erythropolis* 1-19 strain, *Rhodococcus erythropolis*

ECRD-1 strain, *Rhodococcus erythropolis* B1 strain, *Rhodococcus erythropolis* SY-1 strain, *Rhodococcus erythropolis* UM3 strain, *Rhodococcus erythropolis* UM9 strain, and *Rhodococcus erythropolis* T09 strain. Particularly preferred examples include *Rhodococcus erythropolis* PR-4 strain.
(xxii) *Saccharomyces cerevisiae* NBRC1136, *Saccharomyces cerevisiae* NBRC2347 or *Saccharomyces paradoxus* NBRC 10609 which belongs to the genus *Saccharomyces*.
(xxiii) *Candida utilis* NBRC1086 or *Candida parapsilosis* ATCC22019 which belongs to the genus *Candida*.
(xxiv) *Aspergillus niger* ATCC6275, *Aspergillus flavus* NBRC8558 or *Aspergillus oryzae* NBRC4255 which belongs to the genus *Aspergillus*.

[Method for Selecting Microbes by Screening or the Like]

The microbes having the ability to produce methacrylic acid can be identified from soil, river water, lake water, sea water, sludge, animal, plant, insect, or the like based on screening such as a flat plate separation or direct culture method by using the assimilating property of amino acids or fatty acids.

Specifically, according to evaluation of the assimilating property of valine or isobutyric acid and/or the property for producing methacrylic acid, the microbes appropriate for the invention can be selected. The assimilating property of valine or isobutyric acid can be evaluated by observing the growth on a synthetic medium which uses 0.1 to 1% valine or isobutyric acid as a carbon source. The property for producing methacrylic acid can be evaluated by analyzing the production of methacrylic acid in the aforementioned broth. Alternatively, the evaluation can be made by contacting the cells obtained by the culture with a solution containing valine or isobutyric acid at 0.1 to 1% and analyzing the production of methacrylic acid in the same reaction solution. The reaction can be performed at 30° C. with shaking for 5 to 120 hours. Preferably, it is the microbes having the ability to produce methacrylic acid derivatives at 0.04 ppm or more as determined by the aforementioned evaluation.

Alternatively, the microbes appropriate for the invention can be selected according to mycological properties of microbes (that is, cultural property, morphological property, physiological property, chemosystematic property, and genetic property). For example, the microbes of the invention can be selected in view of the identity of the rRNA gene of the microbes. Specifically, the selection can be made from the microbes having rRNA gene which includes a nucleotide sequence having the identity of 81% or more, preferably 88% or more, more preferably 95% or more, more preferably 97% or more, more preferably 98% or more, and even more preferably 99.5% or more to any one of the nucleotide sequences described in SEQ ID NOS. 1 to 49.

Further, the microbes appropriate for the invention can be efficiently narrowed by selecting from microbes belonging to the taxonomic order including the order, family, or the genus described above and combining the information of rRNA gene.

Meanwhile, with regard to the method for analyzing and identifying the rRNA gene, reference can be made to "Determination method of 16S rRNA gene sequence (In The Isolation and Characterization of Actinomycetes, pp. 88-117, Edited by The Society Actinomycetes, Japan, 2001)", "Bulletin of Japanese Society of Microbial Ecology Vol. 10, 31-42, 1995", and "Japanese Pharmacopoeia, 16 revised edition; Method for quick identification of microbes based on gene analysis", or the like. Preferably, the microbes appropriate for the invention are selected by combining those mycological properties, property of assimilating valine or isobutyric acid, and property for producing methacrylic acid. It is also possible to select them from existing type culture according to the same procedure.

[Derivative Strain]

A derivative strain which is derived either naturally or by a chemical or physical treatment from the microbes having the ability to produce methacrylic acid (for example, the aforementioned microbial strains of (i) to (xxiv)) and maintains the ability to produce methacrylic acid by using renewable raw materials and/or biomass as a carbon source and/or energy source can be also used as microbes. The derivative strain encompasses the "variant strain" and "gene modified strain" that are described below.

[Variant Strain]

The variant strain can be obtained by causing a genetic variation in the microbes having the ability to produce methacrylic acid according to a chemical or physical treatment (for example, γ ray irradiation).

[Gene Modified Strain]

The gene modified strain is a strain of the microbes having the ability to produce methacrylic acid with enhanced activity or deleted or lowered activity as described below.

Enhanced activity means that the expression amount of an enzyme gene (regardless of its origin) is increased in microbes based on the gene incorporated from outside of the microbial cells to the microbes. In addition to the incorporation of a gene encoding an enzyme from outside of the microbial cells to inside of the microbial cells, enhancing the promoter activity of an enzyme gene which is included on the microbes on genome, expressing strongly an enzyme gene by substituting with other promoter, and enhancing the activity of an enzyme gene as a result of lowering or inactivating the activity of the repressor of the enzyme gene are included. Meanwhile, the gene introduction or substitution of a gene on genome can be performed according to a general method.

The gene modified strain can be a modified strain having gene modification for deleting or lowering the activity of an enzyme which suppresses the reaction for synthesizing methacrylic acid. "Deleting" or "lowering" the activity means that completely removed or lowered expression of the enzyme gene, and in addition to an occurrence of substitution, deletion, or insertion in the enzyme gene, suppressing the activity of the promoter of the enzyme gene which is contained on a gene of the microbes, suppressing the expression of the enzyme gene by substituting with other promoter, and lowering the activity of an enzyme gene as a result of enhancing or activating the activity of the repressor of the enzyme are included. Meanwhile, those gene modifications can be performed to a general method.

Examples of the preferred modified gene include a modified gene having at least one of the following (a) and (b).
(a) According to introduction of the BCKAD gene and/or ACD gene, the activity of producing methacrylic acid is enhanced.
(b) According to deletion of inactivation of enoyl CoA hydratase gene, 3-hydroxyisobutyryl CoA hydrolase gene, and/or 3-hydroxyisobutyric acid dehydrogenase gene, the activity of producing methacrylic acid is enhanced. The deletion or inactivation is performed by substitution, deletion, or insertion in the entire or partial nucleotide sequence of a gene.

[Gene Recombinant Strain]

Further, a strain newly given with an ability to produce methacrylic acid by using renewable raw materials and/or biomass as a carbon source and/or energy source according to introduction of an enzyme involved with methacrylic acid synthesis, which is identified from microbes having the ability to produce methacrylic acid, to microbes not having the ability to produce methacrylic acid can be also used as microbes. With regard to the production of the gene recombinant strain, it can be performed with the same method as the production of a gene modified strain described above.

[Homologous Strain]

Further, a strain which is a homologous strain of the microbes having the ability to produce methacrylic acid (for example, the aforementioned microbial strains of (i) to (xxiv)) and maintains the ability to produce methacrylic acid by using renewable raw materials and/or biomass as a carbon source and/or energy source can be also used as microbes. The homologous strain can be obtained by performing molecular phylogenetic analysis based on the base sequence information of nucleic acid, for example. Specifically, the homologous strain can be obtained by a homology analysis of the nucleotide sequence of ribosomal RNA gene (rRNA gene; hereinbelow, rDNA).

Examples of the preferred homologous strain include the followings.

(1) Microbes which belong to the genus *Pseudomonas* and have 16S rDNA containing the nucleotide sequence with the identity of 81% or more, preferably 88% or more, more preferably 95% or more, more preferably 97% or more, more preferably 98% or more, and even more preferably 99.5% or more to any one of the partial nucleotide sequence of 16S rDNA of the strain of (i) above (SEQ ID NOS. 1 to 8).

(2) Microbes which belong to the genus *Bacillus* and have 16S rDNA containing the nucleotide sequence with the identity of 81% or more, preferably 88% or more, more preferably 95% or more, more preferably 97% or more, more preferably 98% or more, and even more preferably 99.5% or more to any one of the partial nucleotide sequence of 16S rDNA of the strain of (ii) above (SEQ ID NOS. 9 to 15).

(3) Microbes which belong to the genus *Sphingobacterium* and have 16S rDNA containing the nucleotide sequence with the identity of 81% or more, preferably 88% or more, more preferably 95% or more, more preferably 97% or more, more preferably 98% or more, and even more preferably 99.5% or more to the partial nucleotide sequence of 16S rDNA of the strain of (iii) above (SEQ ID NO. 16).

(4) Microbes which belong to the genus *Comamonas* and have 16S rDNA containing the nucleotide sequence with the identity of 81% or more, preferably 88% or more, more preferably 95% or more, more preferably 97% or more, more preferably 98% or more, and even more preferably 99.5% or more to the partial nucleotide sequence of 16S rDNA of the strain of (iv) above (SEQ ID NO. 17).

(5) Microbes which belong to the genus *Brevundimonas* and have 16S rDNA containing the nucleotide sequence with the identity of 81% or more, preferably 88% or more, more preferably 95% or more, more preferably 97% or more, more preferably 98% or more, and even more preferably 99.5% or more to any one of the partial nucleotide sequence of 16S rDNA of the strain of (v) above (SEQ ID NOS. 18 to 20).

(6) Microbes which belong to the genus *Sphingomonas* and have 16S rDNA containing the nucleotide sequence with the identity of 81% or more, preferably 88% or more, more preferably 95% or more, more preferably 97% or more, more preferably 98% or more, and even more preferably 99.5% or more to the partial nucleotide sequence of 16S rDNA of the strain of (vi) above (SEQ ID NO. 21).

(7) Microbes which belong to the genus *Ochrobactrum* and have 16S rDNA containing the nucleotide sequence with the identity of 81% or more, preferably 88% or more, more preferably 95% or more, more preferably 97% or more, more preferably 98% or more, and even more preferably 99.5% or more to any one of the partial nucleotide sequence of 16S rDNA of the strain of (vii) above (SEQ ID NOS. 22 to 26).

(8) Microbes which belong to the genus *Pedobacter* and have 16S rDNA containing the nucleotide sequence with the identity of 81% or more, preferably 88% or more, more preferably 95% or more, more preferably 97% or more, more preferably 98% or more, and even more preferably 99.5% or more to any one of the partial nucleotide sequence of 16S rDNA of the strain of (viii) above (SEQ ID NO. 27).

(9) Microbes which belong to the genus *Paenibacillus* and have 16S rDNA containing the nucleotide sequence with the identity of 81% or more, preferably 88% or more, more preferably 95% or more, more preferably 97% or more, more preferably 98% or more, and even more preferably 99.5% or more to the partial nucleotide sequence of 16S rDNA of the strain of (ix) above (SEQ ID NO. 28).

(10) Microbes which belong to the genus *Achromobacter* and have 16S rDNA containing the nucleotide sequence with the identity of 81% or more, preferably 88% or more, more preferably 95% or more, more preferably 97% or more, more preferably 98% or more, and even more preferably 99.5% or more to the partial nucleotide sequence of 16S rDNA of the strain of (x) above (SEQ ID NO. 29).

(11) Microbes which belong to the genus *Acinetobacter* and have 16S rDNA containing the nucleotide sequence with the identity of 81% or more, preferably 88% or more, more preferably 95% or more, more preferably 97% or more, more preferably 98% or more, and even more preferably 99.5% or more to any one of the partial nucleotide sequence of 16S rDNA of the strain of (xi) above (SEQ ID NOS. 30 and 31).

(12) Microbes which belong to the genus *Shewanella* and have 16S rDNA containing the nucleotide sequence with the identity of 81% or more, preferably 88% or more, more preferably 95% or more, more preferably 97% or more, more preferably 98% or more, and even more preferably 99.5% or more to the partial nucleotide sequence of 16S rDNA of the strain of (xii) above (SEQ ID NO. 32).

(13) Microbes which belong to the genus *Listonella* and have 16S rDNA containing the nucleotide sequence with the identity of 81% or more, preferably 88% or more, more preferably 95% or more, more preferably 97% or more, more preferably 98% or more, and even more preferably 99.5% or more to the partial nucleotide sequence of 16S rDNA of the strain of (xiii) above (SEQ ID NO. 33).

(14) Microbes which belong to the genus *Agrobacterium* and have 16S rDNA containing the nucleotide sequence with the identity of 81% or more, preferably 88% or more, more preferably 95% or more, more preferably 97% or more, more preferably 98% or more, and even more preferably 99.5% or more to the partial nucleotide sequence of 16S rDNA of the strain of (xiv) above (SEQ ID NO. 34).

(15) Microbes which belong to the genus *Mesorhizobium* and have 16S rDNA containing the nucleotide sequence with the identity of 81% or more, preferably 88% or more, more preferably 95% or more, more preferably 97% or more, more preferably 98% or more, and even more preferably 99.5% or more the partial nucleotide sequence of 16S rDNA of the strain of (xv) above (SEQ ID NO. 35).

(16) Microbes which belong to the genus *Rhizobium* and have 16S rDNA containing the nucleotide sequence with the identity of 81% or more, preferably 88% or more, more preferably 95% or more, more preferably 97% or more, more preferably 98% or more, and even more preferably 99.5% or more to the partial nucleotide sequence of 16S rDNA of the strain of (xvi) above (SEQ ID NO. 36).

(17) Microbes which belong to the genus *Paracoccus* and have 16S rDNA containing the nucleotide sequence with the identity of 81% or more, preferably 88% or more, more preferably 95% or more, more preferably 97% or more, more preferably 98% or more, and even more preferably 99.5% or more to any one of the partial nucleotide sequence of 16S rDNA of the strain of (xvii) above (SEQ ID NO. 37).

(18) Microbes which belong to the genus *Xanthobacter* and have 16S rDNA containing the nucleotide sequence with the identity of 81% or more, preferably 88% or more, more preferably 95% or more, more preferably 97% or more, more preferably 98% or more, and even more preferably 99.5% or more to the partial nucleotide sequence of 16S rDNA of the strain of (xviii) above (SEQ ID NO. 38).

(19) Microbes which belong to the genus *Streptomyces* and have 16S rDNA containing the nucleotide sequence with the identity of 81% or more, preferably 88% or more, more preferably 95% or more, more preferably 97% or more, more preferably 98% or more, and even more preferably 99.5% or more to any one of the partial nucleotide sequence of 16S rDNA of the strain of (xix) above (SEQ ID NO. 39).

(20) Microbes which belong to the genus *Geobacillus* and have 16S rDNA containing the nucleotide sequence with the identity of 81% or more, preferably 88% or more, more preferably 95% or more, more preferably 97% or more, more preferably 98% or more, and even more preferably 99.5% or more to the partial nucleotide sequence of 16S rDNA of the strain of (xx) above (SEQ ID NO. 40).

(21) Microbes which have 16S rDNA containing the nucleotide sequence with the identity of 81% or more, preferably 88% or more, more preferably 95% or more, more preferably 97% or more, more preferably 98% or more, and even more preferably 99.5% or more to the partial nucleotide sequence of 16S rDNA of the *Rhodococcus* erythropolis PR-4 strain (SEQ ID NO. 41).

(22) Microbes which belong to the genus *Saccharomyces* and have LSUrDNA containing the nucleotide sequence with the identity of 81% or more, preferably 88% or more, more preferably 95% or more, more preferably 97% or more, more preferably 98% or more, and even more preferably 99.5% or more to any one of the partial nucleotide sequence of LSUrDNA of the strain of (xxii) above (SEQ ID NOS. 42 to 44).

(23) Microbes which belong to the genus *Candida* and have LSUrDNA containing the nucleotide sequence with the identity of 81% or more, preferably 88% or more, more preferably 95% or more, more preferably 97% or more, more preferably 98% or more, and even more preferably 99.5% or more to any one of the partial nucleotide sequence of LSUrDNA of the strain of (xxiii) above (SEQ ID NOS. 45 and 46).

(24) Microbes which belong to the genus *Aspergillus* and have LSUrDNA containing the nucleotide sequence with the identity of 81% or more, preferably 88% or more, more preferably 95% or more, more preferably 97% or more, more preferably 98% or more, and even more preferably 99.5% or more to any one of the partial nucleotide sequence of LSUrDNA of the strain of (xxiv) above (SEQ ID NOS. 47 to 49).

Further, the homologous strain can be selected from existing type culture based on the information in which mycological properties are suitably combined.

As described herein, the "identity" of a sequence indicates the percentage that is obtained by, in case of a nucleotide sequence, aligning two nucleotide sequences for comparison such that they are in match with each other as much as possible and dividing the number of nucleotides in match by the number of total nucleotides. For the aligning, a gap is suitably inserted to one or both sequences for comparison, if necessary. The aligning of a sequence can be performed by using a known program such as BLAST, FASTA, or CLUSTALW. In case of inserting a gap, the number of total nucleotides corresponds to the number of nucleotides after counting one gap as one nucleotide. When the number of total nucleotides counted as above is different between two sequences for comparison, the identity (%) is calculated by dividing the number of nucleotides in match by the number of total nucleotides with longer length. The same applies to the identity of an amino acid sequence.

Further, according to the method for producing methacrylic acid and/or a methacrylic acid ester of the invention, it is also possible that, with a step of using recombinant microbes in which AAT gene and/or ACD gene is introduced to the microbes having the ability to produce methacrylic acid and contacting them with renewable raw materials and/or biomass, methacrylic acid and/or a methacrylic acid ester is produced.

[Production of Recombinant Microbes in which AAT Gene is Introduced to the Microbes Having Ability to Produce Methacrylic Acid]

[AAT]

AAT is an enzyme having a catalytic function of transferring an acyl group of acyl-CoA to alcohols or phenols to synthesize ester. AAT is believed to be involved with production of esters in various fruits. AAT is known to be present in a plant such as Zingiberales (banana), Rosales (strawberry, apple, pear, and peach), Cucurbitales (melon), Ericales (kiwi), Lamiales (olive), Solanales (tomato), and Sapindales (lemon and mango).

Regardless of the type and origin, the AAT used in the invention is not particularly limited if it is a catalyst derived from a living microorganism having the ability to produce methacrylic acid by using methacrylyl-CoA and alcohols or phenols as a raw material. As an enzyme source, those derived from a plant are preferable. Among them, those classified as an angiosperm plant are preferable.

The AAT suitable for the invention can be selected from the aforementioned plants according to the following method. A suitable area of a tissue is obtained by cutting, if necessary. To the cut area, a solution containing methacrylyl-CoA and alcohols or phenols is added, shaken, and allowed to proceed with the reaction for a certain time. By confirming the presence or absence of a methacrylic acid ester in the reaction solution using GC (gas chromatography), the synthetic activity can be confirmed. Specifically, fruit flesh or fruit skin is cut and added with a solution containing 1 to 10 mM methacrylyl-CoA, 0.35 M KCl, and 5 to 50× molar amount of n-butanol, and shaken for 1 to 10 hours at 30° C. Once the reaction is completed, by confirming the presence or absence of a methacrylic acid ester by GC, the AAT applicable to the invention can be selected.

The alcohols or phenols are a compound represented by the following formula "R—OH". Because the structure of the alcohols or phenols corresponds to methacrylic acid ester, the structure has the same definition as R of Formula 1 above, and it represents a linear or branched hydrocarbon group having 1 to 20 carbon atoms. The hydrocarbon group can be a saturated or unsaturated noncyclic type, or a saturated or unsaturated cyclic type. Preferably, it is a linear or branched unsubstituted alcohol, aralkyl alcohols or phenols having 1 to 10 carbon atoms. Particularly preferred examples include alkyl alcohol having 1 to 8 carbon atoms such as a methyl group, an ethyl group, a n-propyl group, an isopropyl group, a n-butyl group, an isobutyl group, a sec-butyl group, a tert-butyl group, a n-pentyl alcohol, isopentyl alcohol, tert-pentyl alcohol, n-hexyl alcohol, isohexyl alcohol, 2-hexyl alcohol, dimethylbutyl alcohol, or ethylbutyl alcohol, heptyl alcohol, octyl alcohol, or 2-ethylhexyl alcohol, benzyl alcohol, and phenol.

Specific examples of the AAT enzyme source which is suitable for the invention include those belonging to any order selected from a group consisting of Zingiberales, Rosales, Ericales, Cucurbitales, Brassicales, Laurales, Poales, Arecales, Asparagales, Saxifragales, Caryophyllales, Vitales, Malpighiales, Oxalidales, Fabales, Sapindales, Malvales, Myrtales, Ranunculales, Solanales, Lamiales, Gentianales, and Asterales. Among them, preferred are those belonging to any order selected from a group consisting of Zingiberales, Rosales, Ericales, Cucurbitales, Brassicales, and Laurales.

Preferred are as follows; Musaceae and Zingiberaceae as those belonging to the order Zingiberales, Rosaceae and Moraceae as those belonging to the order Rosales, Ericaceae, Actinidiaceae, Ebenaceae and Theaceae as those belonging to the order Ericales, Cucurbitaceae as those belonging to the order Cucurbitales, Caricaceae and Brassicaceae as those belonging to the order Brassicales, Lauraceae as those belonging to the order Laurales, Bromeliaceae and Poaceae as those belonging to the order Poales, Arecaceae as those belonging to the order Arecales, Orchidaceae and Iridaceae as those belonging to the order Asparagales, Grossulariaceae as those belonging to the order Saxifragales, Caryophyllaceae as those belonging to the order Caryophyllales, Vitaceae as those belonging to the order Vitales, Malpighiaceae, Passifloraceae, Euphorbiaceae and Salicaceae as those belonging to the order Malpighiales, Oxalidaceae as those belonging to the order Oxalidales, Fabaceae as those belonging to the order Fabales, Rutaceae, Sapindaceae and Anacardiaceae as those belonging to the order Sapindales, Malvaceae as those belonging to the order Malvales, Lythraceae, Onagraceae and Myrtaceae as those belonging to the order Myrtales, Ranunculaceae and Papaveraceae as those belonging to the order Ranunculales, Solanaceae as those belonging to the order Solanales, Oleaceae, Verbenaceae and Lamiaceae as those belonging to the order Lamiales, Apocynaceae as those belonging to the order Gentianales, and Asteraceae as those belonging to the order Asterales. Homologous species of the aforementioned plant can be also used. Among them, more preferred is a plant belonging to Musaceae, Rosaceae, Ericaceae, Actinidiaceae, Cucurbitaceae, Caricaceae or Lauraceae.

Specifically, preferred are as follows: the genus *Musa* as those belonging to *Musaceae*, the genus *Zingiber* as those belonging to Zingiberales, the genus *Fragaria*, the genus *Malus*, the genus *Prunus*, the genus *Pyrus*, the genus *Eriobotrya*, the genus *Chaenomeles*, the genus *Rubus* and the genus *Rosa* as those belonging to Rosaceae, the genus *Ficus* as those belonging to Moraceae, the genus *Vaccinium* as those belonging to Ericaceae, the genus *Actinidia* as those belonging to Bower *actinidia*, the genus *Diospyros* as those belonging to Ebenaceae, the genus *Camellia* as those belonging to Theaceae, the genus *Cucumis* and the genus *Citrullus* as those belonging to Cucurbitaceae, the genus *Carica* and the genus *Vasconcellea* as those belonging to Caricaceae, the genus *Arabidopsis* as those belonging to Brassicaceae, the genus *Persea* as those belonging to Lauraceae, the genus *Ananas* as those belonging to Bromeliaceae, the genus *Oryza*, the genus *Triticum*, the genus *Hordeum*, the genus *Zea*, the genus *Sorghumm* and the genus *Brachypodium* as those belonging to Poaceae, the genus *Cocos* as those belonging to Arecaceae, the genus *Vanda* as those belonging to Orchidaceae, the genus Iris as those belonging to Iridaceae, the genus *Ribes* as those belonging to Grossulariaceae, the genus *Gypsophila* as those belonging to Caryophyllaceae, the genus *Vitis* as those belonging to Vitaceae, the genus *Malpighia* as those belonging to Malpighiaceae, the genus *Passiflora* as those belonging to Passifloraceae, the genus *Ricinus* as those belonging to Euphroniaceae, the genus *Populus* as those belonging to Salicaceae, the genus *Averrhoa* as those belonging to Oxalidaceae, the genus *Medicago*, the genus *Lupinus*, the genus *Glycine*, and the genus *Clitoria* as those belonging to Fabaceae, the genus *Citrus* and the genus *Aegle* as those belonging to Rutaceae, the genus *Litchi* as those belonging to Sapindaceae, the genus *Mangifera* as those belonging to Anacardiaceae, the genus *Durio* and the genus *Theobroma* as those belonging to Malvaceae, the genus *Punica* as those belonging to Lythraceae, the genus *Clarkia* as those belonging to Onagraceae, the genus *Psidium* as those belonging to Myrtaceae, the genus *Actaea* as those belonging to Ranunculaceae, the genus *Papaver* as those belonging to Papaveraceae, the genus the genus *Solanum*, the genus *Capsicum*, the genus *Nicotiana* and the genus *Petunia* as those belonging to Solanaceae, the genus *Olea* as those belonging to Oleaceae, the genus *Glandularia* as those belonging to Verbenaceae, the genus *Salvia* as those belonging to Lamiaceae, the genus *Rauvolfia* and the genus *Catharanthus* as those belonging to Apocynaceae, and the genus *Chamaemelum* as those belonging to Asteraceae. Among them, a plant belonging to the genus *Musaceae*, the genus *fragaria*, the genus *Malus*, the genus *Purunus*, the genus *Pyrus*, the genus *Vaccinium hirtum*, the genus *Bower actinidia*, the genus *Cucumis*, the genus *Carica* or the genus *Persea* is more preferable. A plant belonging to the genus *Musaceae*, the genus *Malus*, the genus *Purunus*, the genus *Pyrus*, the genus *Vaccinium hirtum*, the genus *Bower actinidia*, the genus *Cucumis*, the genus *Carica* or the genus *Persea* is particularly preferable. A plant belonging to the genus *Musaceae*, the genus *Malus*, the genus *Pyrus*, the genus *Bower actinidia*, the genus *Cucumis*, the genus *Carica*, or the genus *Persea* is particularly preferable.

Further, specific examples of the particularly preferred are as follows: *Musa×paradisiaca*, *Musa basjoo*, *Musa coccinea* and *Musa acuminate* as those belonging to the genus *Musa*, *Zingiber officinale* as those belonging to the genus *Zingiber*, *Fragaria×ananassa*, *Fragaria virginiana*, *Fragaria chiloensis* and *Fragaria vesca* as those belonging to the genus *Fragaria*, *Malus pumila*, *Malus domestica*, *Malus baccata*, *Malus halliana*, *Malus floribunda* and *Malus prunifolia* as those belonging to the genus *Malus*, *Prunus mume*, *Prunus avium*, *Prunus persica*, *Prunus armeniaca*, *Prunus dulcis*, *Prunus salicina* and *Prunus domestica* as those belonging to the genus *Prunus*, *Pyrus communis*, *Pyrus pyrifolia*, *Pyrus calleryana* and *Pyrus pyraster* as those belonging to the genus *Pyrus*, *Eriobotrya japonica* as those belonging to the genus *Eriobotrya*, *Chaenomeles sinensis* as those belonging to the genus *Chaenomeles*, *Rubus idaeus* and *Rubus fruticosus* as those belonging to the genus *Rubus*, *Rosa rugosa* as those belonging to the genus *Rosa*, *Ficus carica* as those belonging to the genus *Ficus*, *Vaccinium corymbosum* (*Vaccinium angustifolium*), *Vaccinium myrtillus*, *Vaccinium vitis-idaea* and *Vaccinium oxycoccos* as those belonging to the genus *Vaccinium hirtum*,

*Actinidia chinensis* (*Actinidia deliciosa*), *Actinidia arguta*, *Actinidia rufa* and *Actinidia polygama* as those belonging to the genus *Bower actinidia*, *Diospyros kaki* as those belonging to the genus *Diospyros*, *Camellia sinensis* as those belonging to the genus *Camellia*, *Cucumis sativus*, *Cucumis melo*, *Cucumis anguria* and *Cucumis metulifer* as those belonging to the genus *Cucumis*, *Citrullus lanatus* as those belonging to the genus *Citrullus*, *Carica papaya* as those belonging to the genus *Carica*, *Vasconcellea cundinamarcensis* as those belonging to the genus *Vasconcellea*, *Arabidopsis thaliana* and *Arabidopsis lyrata* as those belonging to the genus *Arabidopsis*, *Persea americana* as those belonging to the genus *Persea*, *Ananas comosu* as those belonging to the genus *Ananas*, *Oryza sativa* as those belonging to the genus *Oryza*, *Triticum aestivum* as those belonging to the genus *Triticum*, *Hordeum vulgare* as those belonging to the genus *Cerealia*, *Zea mays* as those belonging to the genus *Zea*, *Sorghum bicolor* as those belonging to the genus *Sorghum*, *Brachypodium distachyon* as those belonging to the genus *Brachypodium*, *Cocos nucifera* as those belonging to the genus palm tree, *Vanda* hybrid cultivar as those belonging to the genus *Vanda*, *Iris×hollandica* as those belonging to the genus *Iris*, *Ribes nigrum* as those belonging to the genus *Ribes*, *Gypsophila paniculata* (*Gypsophila elegans*) as those belonging to the genus *Gypsophila*, *Vitis vinifera* (*Vitis labrusca*) as those belonging to the genus *Vits*, *Malpighia glabra* as those belonging to the genus *Malpighia coccigera*, *Passiflora edulis* as those belonging to the genus *Passiflora*, *Ricinus communis* as those belonging to the genus *Ricinus*, *Populus trichocarpa* as those belonging to the genus *Populus*, *Averrhoa carambola* as those belonging to the genus *Carambola*, *Medicago truncatula* as those belonging to the genus *Medicago*, *Lupinus albus* as those belonging to the genus *Lupinus*, *Glycine max* as those belonging to the genus *Glycine mas*, *Clitoria ternatea* as those belonging to the genus *Clitoria*, *Citrus limon*, *Citrus sudachi*, *Citrus sphaerocarpa*, *Citrus×paradisi*, *Citrus junos*, *Citrus aurantifolia*, *Citrus unshiu* and *Citrus sinensis* as those belonging to the genus *Citrus*, *Aegle marmelos* as those belonging to the genus *Aegle*, *Litchi chinensis* as those belonging to the genus *Litchi*, *Mangifera indica* as those belonging to the genus *Mangifera*, *Durio zibethinus* as those belonging to the genus *Durio*, *Theobroma cacao* as those belonging to the genus *Theobroma*, *Punica granatum* as those belonging to the genus *Punica*, fairy fans (*Clarkia breweri*) and Red ribbons (*Clarkia concinna*) as those belonging to the genus *Clarkia*, *Psidium guajava* as those belonging to the genus *Psidium*, *Actaea racemosa* as those belonging to the genus *Actaea*, *Papaver somniferum*, *Papaver orientale* and *Papaver bracteatum* as those belonging to the genus *Papaver*, *Solanum lycopersicum* as those belonging to the genus *Solanum*, *Capsicum annuum* and *Capsicum chinense* as those belonging to the genus *Capsicum*, *Nicotiana tabacum* (*Nicotiana attenuata*) as those belonging to the genus *Nicotiana*, *Petunia×hybrida* as those belonging to the genus *Petunia*, *Olea europaea* as those belonging to the genus *Olea*, *Glandularia×hybrida* as those belonging to the genus *Glandularia*, *Salvia splendens* as those belonging to the genus *Salvia*, *Rauvolfia serpentina* as those belonging to the genus *Rauwolfia*, *Catharanthus roseus* as those belonging to the genus *Catharanthus*, and *Chamaemelum nobile* as those belonging to *Chamaemelum*. Among them, banana, strawberry, apple, Japanese apricot, pear, blueberry, kiwi, melon, papaya, and avocado are preferable. Banana, apple, Japanese apricot, pear, blueberry, kiwi, melon, papaya, and avocado are more preferable. Banana, apple, pear, kiwi, melon, papaya, and avocado are particularly preferable.

In the invention, plant classification is based on the APG plant classification system III (Botanical Journal of the Linnean Society, 2009, 161, 105121).

At the time of selecting AAT, it is also possible that the AAT gene is isolated, introduced to a common host vector system, for example, and then evaluated and selected by using microbes that are transformed with the vector system. For example, several AAT genes have been known (for example, see Patent Document 7). Based on the information, the gene can be isolated by producing a DNA probe, producing a primer used for PCR, for example, and performing PCR. It is also possible that the entire nucleotide sequence of AAT gene is synthesized by a general method. According to the same method as described above, it is possible to determine whether or not the genetic information has the activity of synthesizing a methacrylic acid ester of known AAT. Meanwhile, with regard to the AAT with unclear genetic information, it is possible that the genetic information can be obtained based on genetic engineering of a protein resulting from purification of the AAT.

As for the AAT gene preferred in the invention, it is not particularly limited if the translated product has an ability to produce a methacrylic acid ester, and it is suitably selected from the AAT enzyme sources described above. Examples of the particularly preferred include the AAT gene derived from an apple (SEQ ID NO. 77), the AAT gene derived from strawberry (SEQ ID NO. 79), and the AAT gene derived from strawberry (SEQ ID NO. 81).

Meanwhile, the AAT gene of the invention also encompasses a gene which contains an amino acid sequence of having one or several substitutions, deletions, or additions of the amino acids in the amino acid sequence of the wild type and encodes a protein having an activity of producing a methacrylic acid ester from methacrylyl-CoA and alcohol.

As described herein, the term "several" indicates 1 to 40, preferably 1 to 20, and more preferably 10 or less. In order to introduce a mutation to a gene, a kit for introducing mutation which uses a site specific mutagenesis, such as QuikChange™ Site-Directed Mutagenesis Kit (manufactured by Stratagene), GeneTailor™ Site-Directed Mutagenesis System (manufactured by Invitrogen), TaKaRa Site-Directed Mutagenesis System (manufactured by Takara Bio Inc., Mutan-K, Mutan-Super Express Km or the like), can be used based on a known method like Kunkel method or Gapped duplex method. Alternatively, the entire gene having a sequence in which a mutation is contained can be artificially synthesized.

In the invention, identification of the nucleotide sequence of a DNA can be performed by determining the sequence by a commonly used method. For example, the sequence can be identified based on Sanger method by using a suitable DNA sequencer.

Further, the AAT gene of the invention encompasses a gene which exhibits the identity of 90% or more, preferably 95% or more, more preferably 99.5% or more, and even more preferably 99.9% or more to the protein consisting of an amino acid sequence of the wild type and encodes a protein having an activity of producing a methacrylic acid ester from methacrylyl-CoA and alcohol.

Further, the AAT gene of the invention encompasses a gene which hybridizes under stringent conditions to a polynucleotide having a nucleotide sequence complementary to the nucleotide sequence of the wild type and encodes a protein having an activity of producing a methacrylic acid ester from methacrylyl-CoA and alcohol.

In the specification, reference can be made to "Molecular Cloning, A Laboratory Manual 2nd ed." (Cold Spring Harbor Laboratory Press (1989)), "Current Protocols in Molecular Biology" (John Wiley & Sons (1987-1997)) or the like with regard to the method for hybridization.

In the specification, the stringent conditions may be a condition in which the hybridization is performed by incubating a nylon membrane having immobilized DNA with a probe in a solution containing 6×SSC (1×SSC indicates 8.76 g of sodium chloride and 4.41 g of sodium citrate are dissolved in 1 liter water), 1% SDS, 100 µg/ml salmon sperm DNA, 0.1% bovine serum albumin, 0.1% polyvinylpyrrolidone, and 0.1% Ficoll for 20 hours at 65° C., but it is not limited thereto. A skilled person in the pertinent art can set the conditions for hybridization by considering, in addition to the conditions like salt concentration of a buffer, temperature, or the like, various conditions such as probe concentration, probe length, or reaction time. For example, with regard to cleaning condition after the hybridization, a condition like "1×SSC, 0.1% SDS, 65° C.", "0.5×SSC, 0.1% SDS, 50° C." can be mentioned as a more stringent condition than "2×SSC, 0.1% SDS, 42° C.", "1×SSC, 0.1% SDS, 37° C.".

Further, in the invention, the AAT gene also encompasses a gene consisting of a nucleotide sequence having the identity of 80% or more, preferably 90% or more, and most preferably 95% or more to the nucleotide sequence of the wild type when calculation is made by using BLAST (for example, default, that is, parameters of initial setting) and encoding the protein having an activity of producing a methacrylic acid ester from methacrylyl-CoA and alcohol. Further, the codon of the AAT gene may be modified in response to the codon usage frequency of the microbes that are used for transformation.

[Production of Recombinant Microbes Introduced with AAT Gene]

By introducing the DNA encoding the AAT gene to the microbes having the ability to produce methacrylic acid as a host and performing transcription and translation into a protein in the microbes, methacrylic acid ester can be produced. It is also possible that a gene of the enzyme which enhances the methacrylic acid producing activity (for example, gene like ACD and BCKAD) can be simultaneously introduced.

The gene introduction method is not particularly limited. However, the DNA to be introduced is preferably in a state in which it is bound to a vector. Specifically, the AAT gene is bound to the vector in a state in which it can be expressed in a host cell, and introduced to the host cell. Examples of the vector include those capable of self-replication in host microbes and those capable of binding to the genome of microbes. However, as long as the AAT gene is maintained, it is not limited and a vector that is suitable for each microbe can be used. In case of bacteria of the genus *Rhodococcus* and analog bacteria, it is also possible to insert a DNA fragment containing the AAT gene that can be expressed to a genome by taking advantage of the property that a DNA introduced by electroporation or the like can be easily bound to a genome. When it is desired to introduce plural genes containing the AAT gene, it can be bound to one or plural expression vectors, each in expressible state.

The vector which may be used in the invention encompasses a plasmid vector, a phage (virus) vector, a cosmid vector, and an artificial chromosome vector, and it may also contain one or several selectable marker genes and suitable sequence for expression regulation. Although many host and vector systems are known, they can be developed by the same method, if necessary.

As for the vector for introduction into microbes which belong to the genus *Rhodococcus*, a known vector such as pK1, pK2, pK3, pK4, or pSJ034 (see JP-A No. 10-337185), pSJ023 and pSJ002 (see JP-A No. 10-24867) can be used (but not limited thereto). Further, a known vector modified to have a desired constitution can be also used. pSJ023 has been deposited with National Institute of Advanced Industrial Science and Technology as the transformant *Rhodococcus rhodochrous* ATCC12674/pSJ023 (FERM BP-6232) as *Rhodococcus rhodochrous* ATCC12674/pSJ023 (FERM BP-6232).

Insertion of the AAT gene to a vector can be performed by using a genetic recombination technique which is known to a skilled person in the pertinent art. Examples of the method which can be used include a method of using restriction with a restriction enzyme and a ligation kit, a method of using topoisomerase, and a method of using In Fusion kit (Takara Bio). The gene to be inserted to a vector is inserted by ligating it to the downstream of a promoter, which can regulate transcription and translation of a protein encoded by each gene in a host organism. Further, if required for insertion, a suitable linker may be added. Further, if necessary, a terminator sequence, an enhancer sequence, a splicing signal sequence, a signal sequence for adding polyA, a ribosome-binding sequence such as SD sequence or Kozak sequence, and a selection marker gene, which can be used in a host microbe to which a gene is introduced, can be added. Examples of the selection marker gene include, in addition to a drug-resistant gene such as ampicillin resistant gene, tetracycline resistant gene, neomycin resistant gene, kanamycin resistant gene, or chloramphenicol resistant gene, a gene involved with cellular biosynthesis of nutrients such as amino acid or nucleic acid, and a gene encoding a fluorescent protein such as luciferase. Part of the amino acid sequence encoded by DNA can be also substituted in conjunction with the insertion.

In view of the above, it is particularly preferable to use, in an example of the invention, pLK005 obtained by performing a mutagenic treatment of pK4 as a vector for the genus *Rhodococcus*. By ligating and inserting the AAT gene such that it is located 3' downstream of the promoter of pLK005, an expression plasmid vector for expressing the AAT gene as caused by the promoter can be constructed.

In the vector, the AAT gene alone or any one gene selected from a group consisting of enzyme genes which enhance the activity of producing methacrylic acid can be inserted. It is also possible that two or more genes are inserted. When used in relation to the gene to be introduced to a vector, the term "two or more" means that 2 to 5, 2 to 4, and preferably 2 to 3 genes can be inserted. Further, when two or more genes are inserted to a single vector, it is preferable that those genes form an operon. As described herein, the term "operon" means a unit of nucleic acids consisting of one or more genes that are transcribed under control of the same promoter.

The aforementioned gene, and preferably the gene present in the form of a vector, is introduced to a host microbe according to a method known to a person skilled in the pertinent art. Examples of the method for introducing a recombinant vector to a host microbe is not particularly limited if it is a method suitable for the host microbe. Examples thereof include electroporation, spheroplasting, lithium acetate method, calcium phosphate method, lipofection, and transconjugation.

(2) Step for Producing Methacrylic Acid
(2-1) Production of Methacrylic Acid by Culture With the method for producing methacrylic acid according to the invention, methacrylic acid can be obtained in culture by culturing the aforementioned microbes in an aqueous medium containing renewable raw materials and/or biomass.

[Medium]

The aqueous medium containing renewable raw materials and/or biomass (that is, medium) which is used for the culture of microbes is a solid medium or a liquid medium containing sufficient nutrients which include at least one kind of carbon source, on which the microbes can proliferate. According to one embodiment, the medium is prepared advantageously to have pH and salt concentration that are optimum for survival and proliferation of cells.

The renewable raw materials and biomass are not particularly limited if it can produce methacrylic acid. The renewable raw materials and biomass can be a plant material, an animal material, or a biodegradable waste. Examples of the preferred renewable raw materials and biomass include polypeptone, meat extract, yeast extract, corn steep liquor, or an extract of bean or the like. The extract is used as it is or after partial purification. The renewable raw materials can be polysaccharides, oligosaccharides and monosaccharides such as glucose, galactose, mannose, fructose, xylose, or arabinose, or derivatives thereof. Further, as the renewable raw materials and biomass, lipids, amino acids, organic acids, and alcohols that are generated by derivatization or metabolism of those sugars can be used. Examples of the preferred renewable raw materials include sugars such as glucose, fructose, or xylose; amino acids such as valine, alanine, leucine, lysine, or glutamic acid; acids such as acetic acid, pyruvic acid, lactic acid, acetoacetic acid, acetolactic acid, 2-oxoisovaleric acid, butyric acid, isobutyric acid, propionic acid, malic acid, fumaric acid, citric acid, or succinic acid; and alcohols such as ethanol, n-propanol, isopropanol, n-butanol, or isobutanol. The renewable raw materials can be used either singly or in combination of two or more types.

A concentration of the renewable raw materials and/or biomass in the medium is not particularly limited as long as methacrylic acid can be produced. The concentration is, for example, 0.05 to 20 (w/v) %, preferably 0.1 to 15 (w/v) %, and more preferably 0.2 to 10 (w/v) %. The reason for using them at 0.2 (w/v) % or higher is to have enhanced property of the microbes to produce methacrylic acid, and the reason for using them at 10 (w/v) % or lower is that no significant increase in effect is observed even when they are added at higher concentration.

An inorganic nitrogen source or an inorganic metal salts may be added to the medium. As the inorganic nitrogen source, ammonium salts of inorganic acid or organic acid such as ammonium chloride, ammonium sulfate, ammonium acetate, or ammonium phosphate are used.

A concentration of the nitrogen source in the medium is not particularly limited as long as methacrylic acid can be produced. The concentration is, for example, 0.01 to 10 (w/v) %, preferably 0.05 to 8 (w/v) %, and more preferably 0.1 to 4 (w/v) %.

Examples of the inorganic metal salt which can be used include monobasic potassium phosphate, dibasic potassium phosphate, magnesium phosphate, magnesium sulfate, sodium chloride, ferrous sulfate, manganese sulfate, copper sulfate, and calcium carbonate.

A concentration of the inorganic salts in the medium is not particularly limited as long as methacrylic acid can be produced. The concentration is, for example, 0.001 to 1.6 (w/v) %, preferably 0.005 to 1.3 (w/v) %, and more preferably 0.01 to 1 (w/v) %. The reason for using them at 0.01 (w/v) % or higher is to have enhanced property of the microbes to produce methacrylic acid, and the reason for using them at 1 (w/v) % or lower is that no significant increase in effect is observed even when they are added at higher concentration.

In addition to them, a trace amount of a metal, a vitamin, or the like can be added to the medium, if necessary. Further, if necessary, various organic substances, inorganic substances, surfactants, that are required for growth of microbes, or anti-foaming agents that are generally used can be added to the medium.

[Culture Conditions]

Seeding of the microbes on the medium can be performed by a known method of the related art. The culture method is not particularly limited either, and a known method such as shaking culture, aeration and agitation culture, or static culture can be used.

Conditions for culturing microbes are not particularly limited as long as the microbes can grow and produce methacrylic acid. Culture can be performed under aerobic conditions or anaerobic conditions.

A pH, temperature, and culture time are not particularly limited as long as they are the conditions allowing growth of the microbes and production of methacrylic acid. pH is preferably 3 to 10, more preferably 4 to 9, and even more preferably 5 to 8. The temperature is preferably 10 to 45° C., more preferably 15 to 40° C., and even more preferably 20 to 35° C. The culture time is preferably 10 to 1000 hours, more preferably 15 to 480 hours, and even more preferably 20 to 240 hours.

Those culture conditions are selected or optimized for each strain so as to maximize the ratio of the methacrylic acid production amount compared to the use amount of the renewable raw materials and/or biomass. Meanwhile, by suitably controlling the amount of carbon sources and culture conditions, the methacrylic acid production amount can be also controlled.

As the conditions preferred for accumulating methacrylic acid at 0.04 ppm or higher, the reaction is allowed to occur for three hours or longer at conditions of pH 5.5 to 7.5, while maintaining directly or indirectly the concentration of the renewable raw materials and/or biomass at 0.1% or higher and adjusting the temperature in the range of 20 to 40° C. Further, within the range that death ratio does not increase as the environment of broth becomes inappropriate for growth of microbes or cultured cells, the concentration of the microbes in broth is preferably maintained at high level in terms of obtaining efficient productivity. For example, by maintaining it at 2 g/l or more in dry weight, good production efficiency is obtained and the accumulated concentration of the product can be increased.

(2-2) Production of Methacrylic Acid Based on Reaction of Resting Cells

For the method for producing methacrylic acid according to the invention, the following method can be also adopted in addition to the method which involves performing, in an aqueous medium containing renewable raw materials and/or biomass, culture of microbes accompanied with proliferation. The microbes may or may not have a proliferation property, and methacrylic acid can be also produced based on a resting cell reaction which is substantially not accompanied with proliferation, by contacting the microbes cultured in advance with an aqueous medium containing renewable raw materials and/or biomass.

[Reaction Solution]

The renewable raw materials that are contained in an aqueous medium containing renewable raw materials and/or biomass used for the resting cell reaction (that is, reaction solution) and the concentration can be the same as those for the production of methacrylic acid by culture.

To the reaction solution, inorganic metal salt or the like may be added. Examples of the inorganic metal salt which can be used include monobasic potassium phosphate, dibasic potassium phosphate, magnesium phosphate, magnesium sulfate, sodium chloride, ferrous sulfate, manganese sulfate, copper sulfate, and calcium carbonate.

A concentration of the inorganic salts in the reaction solution is not particularly limited as long as methacrylic acid can be produced. The concentration is, for example, 0.0001 to 2 (w/v) %, preferably 0.0003 to 1.3 (w/v) %, and more preferably 0.001 to 1 (w/v) %.

In addition to them, a trace amount of a metal, a vitamin, or the like is added to the reaction solution. Further, if necessary, various organic substances, inorganic substances, surfactants, that are required for the reaction or anti-foaming agents that are generally used can be added to the reaction solution.

[Reaction Conditions]

For the resting cell reaction, the broth of the microbes which have been cultured in advance may be used as it is, or the cells collected by filtration or centrifugal separation are used. The collected microbes can be used at any microbial concentration after re-suspending them in a suitable buffer solution or the like. Examples of the buffer solution which may be used include physiological saline, potassium phosphate buffer solution, tris-hydrochloric acid buffer solution, glycine-sodium hydroxide buffer solution, and borate-sodium hydroxide buffer solution.

Further, a processed product of the collected microbes (for example, disrupted product, co-enzymes, or purified enzymes) can be used for the resting cell reaction. Further, it is also possible that the microbes or their processed products are immobilized on a suitable carrier by a known method and the immobilized product is used for the reaction.

The conditions for culturing microbes are not particularly limited as long as it allows production of methacrylic acid. A culture can be performed under aerobic conditions or anaerobic conditions. The reaction method is not particularly limited either, and a known method such as shaking reaction, aeration and agitation reaction, or static reaction can be used.

A pH, temperature, and reaction time are not particularly limited as long as they are the conditions allowing the production of methacrylic acid. The pH is preferably 3 to 10, more preferably 4 to 9, and even more preferably 5 to 8. The temperature is preferably 10 to 45° C., more preferably 15 to 40° C., and even more preferably 20 to 35° C. The culture time is preferably 10 to 180 hours, more preferably 15 to 150 hours, and even more preferably 20 to 120 hours.

Further, for purpose of isolating methacrylic acid produced, it is also possible to add an organic solvent in advance and performing the reaction in a biphasic system. Examples of the organic acid include a linear, branched, or cyclic and saturated or unsaturated aliphatic hydrocarbon, a saturated or unsaturated aromatic hydrocarbon or the like, and they can be used either singly or as a mixture of two or more types. Specific examples include a hydrocarbon solvent (for example, pentane, hexane, cyclohexane, benzene, toluene, and xylene), a halogenated hydrocarbon solvent (for example, methylene chloride and chloroform), an ether solvent (for example, diethyl ether, dipropyl ether, diisopropyl ether, dibutyl ether, tert-butyl methyl ether, and dimethoxyethane), and an ester solvent (for example, methyl formate, methyl acetate, ethyl acetate, butyl acetate, and methyl propionate). By adding the organic solvent in advance, methacrylic acid produced may migrate to an organic phase to have efficient progress of the reaction.

The reaction conditions are suitably selected or optimized for each strain so as to maximize the ratio of the methacrylic acid production amount compared to the use amount of the renewable raw materials and/or biomass. Meanwhile, by suitably controlling the amount of carbon sources and reaction conditions, the methacrylic acid production amount can be also controlled.

With regard to the method for producing methacrylic acid according to the invention, the aforementioned production of methacrylic acid based on culture and production of methacrylic acid based on the resting cell reaction can be suitably combined. According to the combination of the two methods, more efficient production of methacrylic acid can be achieved. Further, for the method for producing methacrylic acid according to the invention, a method of directly contacting the microbes with renewable raw materials and/or biomass can be also adopted, in addition to the method of contacting the microbes with an aqueous medium containing renewable raw materials and/or biomass, which is prepared as a medium or solution for the resting cell reaction.

As the conditions preferred for accumulating methacrylic acid at 0.04 ppm or higher, the reaction is allowed to occur for three hours or longer at conditions of pH 5.5 to 7.5, while maintaining directly or indirectly the concentration of the renewable raw materials and/or biomass at 0.1% or higher and adjusting the temperature in the range of 20 to 40° C. Further, the concentration of the microbes in reaction solution is preferably maintained at high level in terms of obtaining efficient productivity. For example, by maintaining it at 2 g/l or more in dry weight, good production efficiency is obtained and the accumulated concentration of the product can be increased.

(2-3) Recovery of Methacrylic Acid

The methacrylic acid produced in a medium or reaction solution and its production amount can be detected and measured by using a common method like high speed liquid chromatography and LC-MS.

Methacrylic acid can be isolated and purified from the medium or reaction solution by suitably using, if necessary in combination, a known process like filtration, centrifugal separation, vacuum concentration, ion exchange or adsorptive chromatography, solvent extraction, distillation, and crystallization.

Methacrylic acid ester can be produced from the obtained methacrylic acid based on an esterification. Further, according to genetic introduction of an enzyme involved with esterification of methacrylic acid to microbes having the ability to produce a methacrylic acid ester (for example, microbial strains of (i) to (xxiv) described above), it is also possible to produce a methacrylic acid ester.

(3) Step for Producing Methacrylic Acid Ester (3-1) Production of Methacrylic Acid Ester by Culture In the invention, production of methacrylic acid ester is performed by producing and accumulating methacrylic acid ester in cultured cells or culture by culturing the microbes having the ability of producing methacrylic acid and the genetic recombinant microbes, obtained by introducing the AAT gene to the derivative strain, in an aqueous medium containing the renewable raw materials and/or biomass, and collecting methacrylic acid ester from the cultured cells, culture, or vapor phase of the culture container.

[Medium]

The aqueous medium containing renewable raw materials and/or biomass (that is, medium) which is used for culturing the microbes is a solid medium or a liquid medium containing sufficient nutrients which include at least one kind of carbon source, on which the microbes can proliferate. According to one embodiment, the medium is prepared advantageously to have pH and salt concentration that are optimum for survival and proliferation of cells.

The renewable raw materials and biomass are not particularly limited if it can produce methacrylic acid ester. The renewable raw materials and biomass can be a plant material, an animal material, or a biodegradable waste. Examples of the preferred renewable raw materials and biomass include polypeptone, meat extract, yeast extract, corn steep liquor, or an extract of bean or the like. The extract is used as it is or after partial purification. The renewable raw materials can be polysaccharides, oligosaccharides and monosaccharides such as glucose, galactose, mannose, fructose, xylose, or arabinose, or derivatives thereof. Further, as the renewable raw materials and biomass, lipids, amino acids, organic acids, and alcohols that are generated by derivatization or metabolism of those sugars can be used. Examples of the preferred renewable raw materials include sugars such as glucose, fructose, or xylose; amino acids such as valine, alanine, leucine, lysine, or glutamic acid; acids such as acetic acid, pyruvic acid, lactic acid, acetoacetic acid, acetolactic acid, 2-oxoisovaleric acid, butyric acid, isobutyric acid, propionic acid, malic acid, fumaric acid, citric acid, or succinic acid; and alcohols such as ethanol, n-propanol, isopropanol, n-butanol, or isobutanol. The renewable raw materials can be used either singly or in combination of two or more types.

A concentration of the renewable raw materials and/or biomass in the medium is not particularly limited as long as methacrylic acid ester can be produced. The concentration is, for example, 0.05 to 20 (w/v) %, preferably 0.1 to 15 (w/v) %, and more preferably 0.2 to 10 (w/v) %. The reason for using them at 0.2 (w/v) % or higher is to have enhanced property of the microbes to produce methacrylic acid, and the reason for using them at 10 (w/v) % or lower is that no significant increase in effect is observed even when they are added at higher concentration.

To the medium, alcohols or phenols are added depending on desired methacrylic acid ester. As for the alcohols or phenols, those described before are preferably used. The alcohols or phenols can be used either singly or in combination of two or more types.

A concentration of the alcohols or phenols in the medium is not particularly limited as long as methacrylic acid ester can be produced. The concentration is, for example, 0.01 to 20 (w/v) %, preferably 0.05 to 10 (w/v) %, and more preferably 0.1 to 5 (w/v) %. Further, the alcohols or phenols can be added in advance to the medium, or continuously or intermittently added two or more divided times while performing the culture.

An inorganic nitrogen source or an inorganic metal salts may be added to the medium. As the inorganic nitrogen source, ammonium salts of inorganic acid or organic acid such as ammonium chloride, ammonium sulfate, ammonium acetate, or ammonium phosphate are used.

A concentration of the nitrogen source in the medium is not particularly limited as long as methacrylic acid ester can be produced. The concentration is, for example, 0.01 to 10 (w/v) %, preferably 0.05 to 8 (w/v) %, and more preferably 0.1 to 4 (w/v) %.

Examples of the inorganic metal salt which can be used include monobasic potassium phosphate, dibasic potassium phosphate, magnesium phosphate, magnesium sulfate, sodium chloride, ferrous sulfate, manganese sulfate, copper sulfate, and calcium carbonate.

A concentration of the inorganic salts in the medium is not particularly limited as long as methacrylic acid ester can be produced. The concentration is, for example, 0.001 to 1.6 (w/v) %, preferably 0.005 to 1.3 (w/v) %, and more preferably 0.01 to 1 (w/v) %. The reason for using them at 0.01 (w/v) % or higher is to have enhanced property of the microbes to produce methacrylic acid, and the reason for using them at 1 (w/v) % or lower is that no significant increase in effect is observed even when they are added at higher concentration.

In addition to them, a trace amount of a metal, a vitamin, or the like can be added to the medium, if necessary. Further, if necessary, various organic substances, inorganic substances, surfactants, that are required for growth of microbes, or anti-foaming agents that are generally used can be added to the medium.

[Culture Conditions]

A seeding of the microbes on the medium can be performed by a known method of the related art. The culture method is not particularly limited either, and a known method such as shaking culture, aeration and agitation culture, or static culture can be used.

The conditions for culturing microbes are not particularly limited as long as the microbes can grow and produce methacrylic acid ester. Culture can be performed under aerobic conditions or anaerobic conditions.

A pH, temperature, and culture time are not particularly limited as long as they are the conditions allowing growth of the microbes and production of methacrylic acid ester. The pH is preferably 3 to 10, more preferably 4 to 9, and even more preferably 5 to 8. The temperature is preferably 10 to 45° C., more preferably 15 to 40° C., and even more preferably 20 to 35° C. The culture time is preferably 10 to 1000 hours, more preferably 15 to 480 hours, and even more preferably 20 to 240 hours.

Those culture conditions are selected or optimized for each strain so as to maximize the ratio of the methacrylic acid ester production amount compared to the use amount of the renewable raw materials and/or biomass. Meanwhile, by suitably controlling the amount of carbon sources and culture conditions, the methacrylic acid ester production amount can be also controlled.

As the conditions preferred for accumulating methacrylic acid ester at 0.04 ppm or higher, the reaction is allowed to occur for three hours or longer at conditions of pH 5.5 to 7.5, while maintaining directly or indirectly the concentration of the renewable raw materials and/or biomass at 0.1% or higher and the concentration of the alcohols or phenols at 0.1% or higher and adjusting the temperature in the range of 20 to 40° C. Further, within the range that death ratio does not increase as the environment of broth becomes inappropriate for growth of microbes or cultured cells, the concentration of the microbes in broth is preferably maintained at high level in terms of obtaining efficient productivity. For example, by maintaining it at 2 g/l or more in dry weight, good production efficiency is obtained and the accumulated concentration of the product can be increased.

(3-2) Production of Methacrylic Acid Ester Based on Reaction of Resting Cells

For the method for producing a methacrylic acid ester according to the invention, the following method can be also adopted in addition to the method which involves performing, in an aqueous medium containing renewable raw materials and/or biomass, culture of microbes accompanied with proliferation. The microbes may or may not have a proliferation property, and methacrylic acid ester can be also produced based on a resting cell reaction which is substantially not accompanied with proliferation, by contacting the microbes cultured in advance with an aqueous medium containing renewable raw materials and/or biomass.

[Reaction Solution]

The renewable raw materials that are contained in an aqueous medium containing renewable raw materials and/or biomass used for the resting cell reaction (that is, reaction solution) and the concentration can be the same as those for the production of methacrylic acid ester by culture.

The alcohols or phenols that are used for the resting cell reaction and the concentration can be the same as those for the production of methacrylic acid ester by culture.

To the reaction solution, inorganic metal salt or the like may be added. Examples of the inorganic metal salt which can be used include monobasic potassium phosphate, dibasic potassium phosphate, magnesium phosphate, magnesium sulfate, sodium chloride, ferrous sulfate, manganese sulfate, copper sulfate, and calcium carbonate.

A concentration of the inorganic salts in the reaction solution is not particularly limited as long as methacrylic acid ester can be produced. The concentration is, for example, 0.0001 to 2 (w/v) %, preferably 0.0003 to 1.3 (w/v) %, and more preferably 0.001 to 1 (w/v) %.

In addition to them, a trace amount of a metal, a vitamin, or the like is added to the reaction solution. Further, if necessary, various organic substances, inorganic substances, surfactants, that are required for the reaction or anti-foaming agents that are generally used can be added to the reaction solution.

[Reaction Conditions]

For the resting cell reaction, the broth of the microbes which have been cultured in advance may be used as it is, or the cells collected by filtration or centrifugal separation are used. The collected microbes can be used at any microbial concentration after re-suspending them in a suitable buffer solution or the like. Examples of the buffer solution which may be used include physiological saline, potassium phosphate buffer solution, tris-hydrochloric acid buffer solution, glycine-sodium hydroxide buffer solution, and borate-sodium hydroxide buffer solution.

Further, a processed product of the collected microbes (for example, disrupted product, co-enzymes, or purified enzymes) can be used for the resting cell reaction. Further, it is also possible that the microbes or their processed products are immobilized on a suitable carrier by a known method and the immobilized product is used for the reaction.

The conditions for the reaction are not particularly limited as long as it allows production of methacrylic acid ester. The reaction can be performed under aerobic conditions or anaerobic conditions. The reaction method is not particularly limited either, and a known method such as shaking reaction, aeration and agitation reaction, or static reaction can be used.

A pH, temperature, and reaction time are not particularly limited as long as they are the conditions allowing production of methacrylic acid ester. The pH is preferably 3 to 10, more preferably 4 to 9, and even more preferably 5 to 8. The temperature is preferably 10 to 45° C., more preferably 15 to 40° C., and even more preferably 20 to 35° C. The culture time is preferably 5 to 180 hours, more preferably 10 to 150 hours, and even more preferably 15 to 120 hours.

Further, for purpose of isolating methacrylic acid ester produced, it is also possible to add an organic solvent in advance and performing the reaction in a biphasic system. Examples of the organic acid include a linear, branched, or cyclic and saturated or unsaturated aliphatic hydrocarbon, a saturated or unsaturated aromatic hydrocarbon or the like, and they can be used either singly or as a mixture of two or more types. Specific examples include a hydrocarbon solvent (for example, pentane, hexane, cyclohexane, benzene, toluene, and xylene), a halogenated hydrocarbon solvent (for example, methylene chloride and chloroform), an ether solvent (for example, diethyl ether, dipropyl ether, diisopropyl ether, dibutyl ether, tert-butyl methyl ether, and dimethoxyethane), and an ester solvent (for example, methyl formate, methyl acetate, ethyl acetate, butyl acetate, and methyl propionate). By adding the organic solvent in advance, methacrylic acid ester produced may migrate to an organic phase to have efficient progress of the reaction.

The reaction conditions are suitably selected or optimized for each strain so as to maximize the ratio of the methacrylic acid ester production amount compared to the use amount of the renewable raw materials and/or biomass. Meanwhile, by suitably controlling the amount of carbon sources and reaction conditions, the methacrylic acid ester production amount can be also controlled.

As the conditions preferred for accumulating methacrylic acid ester at 0.04 ppm or higher, the reaction is allowed to occur for three hours or longer at conditions of pH 5.5 to 7.5, while maintaining directly or indirectly the concentration of the renewable raw materials and/or biomass at 0.1% or higher and the concentration of the alcohols or phenols at 0.1% or higher and adjusting the temperature in the range of 20 to 40° C. Further, the concentration of the microbes in reaction liquid is preferably maintained at high level in terms of obtaining efficient productivity. For example, by maintaining it at 2 g/l or more in dry weight, good production efficiency is obtained and the accumulated concentration of the product can be increased.

For performing the method for producing a methacrylic acid ester according to the invention, the aforementioned production of methacrylic acid ester based on culture and production of methacrylic acid ester based on the resting cell reaction can be suitably combined. According to the combination of the two methods, more efficient production of methacrylic acid ester can be achieved. Further, for the method for producing a methacrylic acid ester according to the invention, a method of directly contacting the microbes with renewable raw materials and/or biomass can be also adopted, in addition to the method of contacting the microbes with an aqueous medium containing renewable raw materials and/or biomass, which is prepared as a medium or solution for the resting cell reaction.

(3-3) Recovery of Methacrylic Acid Ester

The methacrylic acid ester produced in a medium or reaction solution and its production amount can be detected and measured by using a common method like high speed liquid chromatography and LC-MS. Further, the methacrylic acid ester vaporized in the reaction container or the vapor phase of the reaction container (that is, head space part) and the production amount can be defected and measured by using a common method like gas chromatography.

Methacrylic acid ester can be isolated and purified from the medium or reaction solution by suitably using, if necessary in combination, a known process like filtration, centrifugal separation, vacuum concentration, ion exchange or adsorptive chromatography, solvent extraction, distillation, and crystallization.

2. Enzymes Involved with Synthesis of Methacrylic Acid and their Genes

Hereinbelow, the enzymes that are involved with synthesis of methacrylic acid and their genes as one aspect of the invention will be described in detail.

The inventors of the invention found that, as a result of conducting extensive searches for microbes having the ability to produce methacrylic acid derivatives, methacrylic acid can be produced by using microbes. Based on history of the searches and techniques of the related art, the synthetic route is presumably the decomposition pathway of valine.

In view of the relationship with a genetic disease, studies on the decomposition pathway of valine are made for a human or a rat (Methods in Enzymology, 324: 241-258 (2000)). However, little is known about the enzymes of the decomposition pathway of valine in microbes, and the details have remained unclear. With regard to the mold *Aspergillus nidulans*, there are results demonstrating that scdA gene product is involved with metabolism of isoleucine, valine, and short chain fatty acid and has an activity of acyl CoA dehydrogenase acting on several metabolic pathways, based on the analysis of the variant strain deficient of scdA gene (Fungal Genet. Biol. 45: 180-189 (2008)). Those results are an indirect evaluation, and it remained uncertain whether or not the enzyme is actually effective for producing methacrylic acid. Other than that, there is the information only about the genus *Streptomyces*, which are actinomycetes as one type of bacteria, with regard to the enzyme derived microbes (Microbiology 145: 2323-2334 (1999)). In the literature, ACD gene (acdH) is cloned from *Streptomyces coelicolor*, and by using partially purified enzyme which has been produced from recombinant *E. coli*, production of methacrylyl-CoA from isobutyryl-CoA was confirmed. The inventors of the invention also followed the test to recognize the significant expression of the enzyme protein in a recombinant which uses *E. coli* as a host. However, regarding the ACD activity, only an extremely weak activity was recognized and it was determined that the enzyme is not suitable for synthesis of methacrylic acid.

Accordingly, for the purpose of using effectively the enzyme involved with synthesis of methacrylic acid in microbes, the inventors made investigations about the enzyme gene of other microbes. As a result, the following useful enzymes were found.

Among the microbes having the ability to produce methacrylic acid as described in the invention, the genus *Pseudomonas* and the genus *Rhodococcus* were selected.

With regard to the microbes of the genus *Pseudomonas*, *Pseudomonas putida* and *Pseudomonas aeruginosa* are known to have a valine-assimilating property (Bacteriol. Review 40: 42-54 (1976)). Although the valine-assimilating property is not known for the microbes of the genus *Rhodococcus*, the inventors of the invention experimentally confirmed that they have an ability to produce methacrylic acid. Among them, for *Pseudomonas aeruginosa* PAO1 and *Rhodococcus erythropolis* PR4 which have a known genome sequence, list-up of candidates was performed by homology search under the assumption that they have ACD believed to be involved with synthesis of methacrylic acid.

With regard to the presence of a homolog gene of bacteria which exhibits high identity to ACAD8 which becomes human ACD, there have been descriptions in the literature (J. Mol. Evol. 69: 176-193 (2009)) (however, the activity has not been confirmed experimentally). Further, for the two bacteria of *Pseudomonas aeruginosa* PAO1 and *Rhodococcus erythropolis* PR4 which have a known genome sequence, only the information regarding the presence of Open Reading Frame (ORF), which is annotated to acyl CoA dehydrogenase, has been known.

Against the genome sequence information of the two bacteria, homology search was performed for the amino acid sequence of human ACAD8. Genes of the total six kinds of ORF found to have the homology were amplified and obtained by PCR and ligated to the expression vector for *E. coli*. By using them, a recombinant was produced, and expression of the homolog protein in the recombinant and the ACD activity of the recombinant cell extract were determined

[ACD]

As a result, a very high activity was obtained from the recombinant introduced with the gene named PA_acd1 from *Pseudomonas aeruginosa* PAO1 and the gene named RE_acd1 from *Rhodococcus erythropolis* PR4 (SEQ ID NOS. 51 and 53). PA_acd1 and RE_acd1 exhibited 57% identity to each other in terms of the amino acid sequence encoded by them (SEQ ID NOS. 50 and 52). Meanwhile, the amino acid-level identity of PA_acd2, RE_acd2 not observed with any activity or acdH (*Streptomyces*) observed only with weak activity to PA_acd1 and RE_acd1 observed with high activity is as described below. PA_acd2 exhibited the identity of 40% and 41% to PA_acd1 and RE_acd1, respectively. RE_acd2 exhibited the identity of 36% to PA_acd1 and RE_acd1, respectively. acdH exhibited the identity of 38% and 36% to PA_acd1 and RE_acd1, respectively.

In other words, as one of ACD useful for synthesis of methacrylic acid, there are (A) the enzyme consisting of the amino acid sequence (SEQ ID NO. 50 or 52) encoded by PA_acd1 or RE_acd1 and (B) the enzyme consisting of an amino acid which exhibits the amino acid-level identity of 45% or more, more preferably 60% or more, and even more preferably 80% or more to the amino acid sequence (SEQ ID NO. 50 or 52) encoded by PA_acd1 or RE_acd1 and exhibiting the ACD activity. Alternatively, it is (C) the enzyme having the ACD activity and consisting of an amino acid sequence with deletion, substitution, or addition of one or several amino acids in the amino acid sequence (SEQ ID NO. 50 or 52) encoded by PA_acd1 or RE_acd1.

Further, PA_acd1 and RE_acd1 exhibited 69% identity for the 70 amino acids from the C terminus of the amino acid sequence encoded by them (SEQ ID NOS. 50 and 52). Meanwhile, with regard to PA_acd2, RE_acd2 not observed with any activity or acdH (*Streptomyces*) observed only with weak activity, the amino acid-level homology of 70 amino acids from the C terminus of PA_acd1 and RE_acd1 that have been observed with high activity are as described below. PA_acd2 exhibited the identity of 43% and 43% to PA_acd1 and RE_acd1, respectively. RE_acd2 exhibited the identity of 38% to PA_acd1 and RE_acd1, respectively. acdH exhibited the identity of 43% and 38% to PA_acd1 and RE_acd1, respectively.

In the invention, another embodiment of the ACD which is useful for the synthesis of methacrylic acid is (D) the enzyme having the ACD activity and consisting of an amino acid sequence which exhibits the identity of 60% or more, more preferably 65% or more, and even more preferably 80% or more to the amino acid sequence of the 70 amino acid residues from C terminus of the amino acid sequence encoded by PA_acd1 or RE_acd1 (SEQ ID NO. 50 or 52).

One of the ACD gene particularly useful for the method for producing methacrylic acid of the invention is a gene selected from the group consisting of the followings.

(a) a gene encoding the protein consisting of an amino acid sequence represented by SEQ ID NO. 50 or 52, (b) a gene consisting of a nucleotide sequence represented by SEQ ID NO. 51 or 52, (c) a gene encoding the protein consisting of an amino acid sequence, which exhibits the identity of 45% or more to the protein consisting of an amino acid sequence represented by SEQ ID NO. 50 or 52, and having the ACD activity, and (d) a gene encoding the protein consisting of an amino acid sequence with deletion, substitution, or addition of one or several amino acids in the amino acid sequence represented by SEQ ID NO. 50 or 52 and having the ACD activity.

In the invention, ACD is not particularly limited if it is useful as an enzyme for synthesizing methacrylic acid and also derived from microbes having the ability to produce methacrylic acid as described in the invention.

More preferably, it is those derived from *Pseudomonas* or *Rhodococcus* erythropolis, and examples of the preferred strain include *Rhodococcus* erythropolis PR-4 strain, *Rhodococcus* erythropolis KA2-5-1 strain, *Rhodococcus* erythropolis IGTS8 strain, *Rhodococcus erythropolis* D-1 strain, *Rhodococcus erythropolis* H-2 strain, *Rhodococcus erythropolis* N1-36 strain, *Rhodococcus erythropolis* 1-19 strain, *Rhodococcus erythropolis* ECRD-1 strain, *Rhodococcus erythropolis* B1 strain, *Rhodococcus erythropolis* SY-1 strain, *Rhodococcus erythropolis* UM3 strain, *Rhodococcus erythropolis* UM9 strain and *Rhodococcus erythropolis* T09 strain. Particularly preferred is *Rhodococcus erythropolis* PR-4 strain.

Hereinabove, the ACD as one of the enzymes involved with synthesis of methacrylic acid and obtainment of the gene thereof will be described.

[BCKAD]

Next, descriptions are made with regard to BCKAD which is involved with synthesis of methacrylic acid. BCKAD is an enzyme capable of producing isobutyryl-CoA from 2-oxoisovaleric acid. From the microbes of the invention having the ability to produce methacrylic acid, BCKAD and the gene thereof can be obtained.

BCKAD derived from *Pseudomonas putida* or *Pseudomonas aeruginosa* is a complex consisting of four polypeptides (SEQ ID NOS. 54, 56, 58 and 60), and their genes (SEQ ID NOS. 55, 57, 59 and 61) are known to form an operon (Methods in Enzymology (2000) 324: 129-138).

As a method for obtainment, a vector for expressing BCKAD can be constructed, for example, by designing a primer for amplifying the entire BCKAD operon from the genome sequence of *Pseudomonas aeruginosa* PAO1, amplifying the entire BCKAD operon by PCR reaction using the genomic DNA as a template, and ligating it to an expression vector for *E. coli*. By using the vector, a recombinant can be produced and the BCKAD gene and BCKAD can be obtained.

With regard to the BCKAD of the invention, there is no particular limitation on the gene thereof, if it is useful as one enzyme useful for synthesis of methacrylic acid and is derived from microbes having the ability to produce methacrylic acid as described in the invention. However, examples thereof include a gene selected from the group consisting of the following (e) to (h), (i) to (l), or (m) to (p).

(e) a gene encoding the four polypeptides having an amino acid sequence represented by SEQ ID NOS. 54, 56, 58, and 60.

(f) a gene consisting of a nucleotide sequence represented by SEQ ID NOS. 55, 57, 59, and 61.

(g) a gene capable of hybridizing under stringent conditions to a complementary sequence of the gene encoding the four polypeptides having an amino acid sequence represented by SEQ ID NOS. 54, 56, 58, and 60 and encoding the protein having the BCKAD activity.

(h) a gene consisting of an amino acid sequence with deletion, substitution, and/or addition of one or several amino acids in the amino acid sequence represented by SEQ ID NOS. 54, 56, 58, and 60, and encoding the protein having the BCKAD activity.

(i) a gene encoding the four polypeptides having an amino acid sequence represented by SEQ ID NOS. 62, 64, 66, and 68.

(j) a gene consisting of a nucleotide sequence represented by SEQ ID NOS. 63, 65, 67, and 69.

(k) a gene capable of hybridizing under stringent conditions to a complementary sequence of the gene encoding the four polypeptides having an amino acid sequence represented by SEQ ID NOS. 62, 64, 66, and 68 and encoding the protein having the BCKAD activity.

(l) a gene consisting of an amino acid sequence with deletion, substitution, and/or addition of one or several amino acids in the amino acid sequence represented by SEQ ID NOS. 62, 64, 66, and 68, and encoding the protein having the BCKAD activity.

(m) a gene encoding the three polypeptides having an amino acid sequence represented by SEQ ID NOS. 70, 72, and 74.

(n) a gene consisting of a nucleotide sequence represented by SEQ ID NOS. 71, 73, and 75.

(o) a gene capable of hybridizing under stringent conditions to a complementary sequence of the gene encoding the three polypeptides having an amino acid sequence represented by SEQ ID NOS. 70, 72, and 74 and encoding the protein having the BCKAD activity.

(p) a gene consisting of an amino acid sequence with deletion, substitution, and/or addition of one or several amino acids in the amino acid sequence represented by SEQ ID NOS. 70, 72, and 74, and encoding the protein having the BCKAD activity.

In the invention, the gene encoding BCKAD is not limited to the aforementioned sequences, and a gene having a nucleotide sequence which has the identity of about 50% or more, preferably about 60% or more, more preferably about 70% or more, even more preferably about 80% or more, particularly preferably about 90% or more, particularly even more preferably about 95% or more, and most preferably about 98% or more to the nucleotide sequence described with the aforementioned SEQ ID NOs is also included in the gene encoding BCKAD as long as a protein having the BCKAD activity is encoded by it.

In the invention, examples of the BCKAD include those having an amino acid sequence represented by SEQ ID NOS. 54, 56, 58, and 60, an amino acid sequence represented by SEQ ID NOS. 62, 64, 66, and 68, or an amino acid sequence represented by SEQ ID NOS. 70, 72, and 74.

In the invention, the BCKAD is not limited to those having the aforementioned sequences, and a protein having the BCKAD activity and containing an amino acid sequence which has the identity of about 50% or more, preferably about 60% or more, more preferably about 70% or more, even more preferably about 80% or more, particularly preferably about 90% or more, particularly even more preferably about 95% or more, and most preferably about 98% or more to the amino acid sequence described with the aforementioned SEQ ID NOs is also included in the gene encoding BCKAD.

The identity value described above is obtained by running a program for analyzing homology with use of GENETYX (manufactured by GENETYX Corporation), which is a software for sequence analysis. Parameters at that time are the same as the default setting (initial setting).

In the BCKAD of the invention, a protein having the BCKAD activity and containing an amino acid sequence with deletion, substitution, and/or addition of one or several amino acids in the amino acid sequence represented by SEQ ID NOS. 54, 56, 58, and 60, the amino acid sequence represented by SEQ ID NOS. 62, 64, 66, and 68, or the amino acid sequence represented by the amino acid sequence represented by SEQ ID NOS. 70, 72, and 74 is also included.

More specific examples thereof include a protein containing the following amino acid sequence and having the BCKAD activity.

(i) An amino acid sequence with deletion of 1 to 20 (for example, 1 to 10, preferably 1 to 5, and even more preferably 1 to 2) amino acids in the amino acid sequence represented by SEQ ID NOS. 54, 56, 58, and 60, the amino acid sequence represented by SEQ ID NOS. 62, 64, 66, and 68, or the amino acid sequence represented by SEQ ID NOS. 70, 72, and 74.

(ii) An amino acid sequence with substitution of 1 to 20 (for example, 1 to 10, preferably 1 to 5, and even more preferably 1 to 2) amino acids in the amino acid sequence represented by SEQ ID NOS. 54, 56, 58, and 60, the amino acid sequence represented by SEQ ID NOS. 62, 64, 66, and 68, or the amino acid sequence represented by SEQ ID NOS. 70, 72, and 74 with other amino acids.

(iii) An amino acid sequence with addition of 1 to 20 (for example, 1 to 10, preferably 1 to 5, and even more preferably 1 to 2) amino acids in the amino acid sequence represented by SEQ ID NOS. 54, 56, 58, and 60, the amino acid sequence represented by SEQ ID NOS. 62, 64, 66, and 68, or the amino acid sequence represented by SEQ ID NOS. 70, 72, and 74.

(iv) An amino acid sequence with insertion of 1 to 20 (for example, 1 to 10, preferably 1 to 5, and even more preferably 1 to 2) amino acids to the amino acid sequence represented by SEQ ID NOS. 54, 56, 58, and 60, the amino acid sequence represented by SEQ ID NOS. 62, 64, 66, and 68, or the amino acid sequence represented by SEQ ID NOS. 70, 72, and 74.

(v) An amino acid sequence having a combination of (i) to (iv).

When one or more amino acids of the amino acid sequence are substituted, it is preferable to have conservative substitution between similar amino acid residues. For example, amino acids are classified into hydrophobic amino acids (A, I, L, M, F, P, W, Y, V), hydrophilic amino acids (R, D, N, C, E, Q, G, H, K, S, T), amino acids having aliphatic side chains (G, A, V, L, I, P), amino acids having side chains that contain a hydroxy group (S, T, Y), amino acids having side chains that contain a sulfur atom (C, M), amino acids having side chains that contain carboxylic acid and amide (D, N, E, Q), amino acids having side chains that contain a base (R, K, H), amino acids having side chains that contain aromatics (H, F, Y, W), based on the characteristics of the side chains. The amino acids classified into each group are known to have a high possibility of maintaining the activity of the polypeptide when substitution is made between them, and it is preferable to have mutual substitution between such amino acids. Examples include substitution between glycine and proline, glycine and alanine or valine, leucine and isoleucine, glutaminic acid and glutamine, asparaginic acid and asparagine, cysteine and threonine, threonine and serine or alanine, and lysine and arginine.

Further, in response to the aforementioned deletion, substitution, addition, and/or insertion of the amino acid sequence, a nucleotide sequence having a mutation like deletion, substitution, addition, and/or insertion occurred in several nucleotides of the nucleotide sequence represented by SEQ ID NOS. 55, 57, 59, and 61, the nucleotide sequence represented by SEQ ID NOS. 63, 65, 67, and 69, or the nucleotide sequence represented by SEQ ID NOS. 71, 73, and 75 is also included in the gene which encodes BCKAD, as long as it encodes the protein having the BCKAD activity described in the invention. Meanwhile, the number of the nucleotides that are subjected to deletion, substitution, addition, and/or insertion is 30 or less, preferably 15 or less, and particularly preferably 6 or less. Further, a DNA capable of hybridizing, under a stringent condition, to a DNA consisting of a nucleotide sequence complementary to the gene consisting of the nucleotide sequence represented by SEQ ID NOS. 55, 57, 59, and 61, the gene consisting of the nucleotide sequence represented by SEQ ID NOS. 63, 65, 67, and 69, or the gene consisting of the nucleotide sequence represented by SEQ ID NOS. 71, 73, and 75 is also included in the gene which encodes BCKAD, as long as it encodes the protein having the BCKAD activity.

Hereinabove, descriptions are made regarding enzyme proteins and obtainment of their genes for ACD and BCKAD, as an example of an enzyme that is involved with synthesis of methacrylic acid. In the invention, other enzymes and genes thereof that are involved either directly or indirectly with synthesis of methacrylic acid can be also obtained in a similar manner.

For example, enzymes involved with synthesis of methacrylic acid can be purified by using a common method with a use of the enzyme activity as an indicator. Further, the genetic information can be obtained by a genetic engineering method based on the proteins. Alternatively, the entire genome sequence is determined for the microbes having the ability to synthesize methacrylic acid as described in the invention. Selection can be made by searching a gene sequence having high homology by using homology search based on known information about the sequence of a gene which encodes the target enzyme, isolating or synthesizing the entire gene with a known method and introducing it to a general host vector system, expressing the candidate protein using microbes transformed with the vector system, and evaluating the activity of the target enzyme. Meanwhile, due to the availability of a next generation sequencer, a skilled person in the pertinent art can easily analyze the entire genome sequence of microbes.

Further, the microbes having the ability to synthesize methacrylic acid as described in the invention include an acceptor of electrons, which are released in accordance with the dehydrogenation of ACD, proteins relating to the transfer system, and the genes thereof, and they are also included in the invention.

In addition, the enzymes involved with synthesis of methacrylic acid, which are obtained from microbes having the ability to synthesize methacrylic acid can produce, either singly or collectively with others, methacrylic acid derivatives and intermediates thereof. For example, with BCKAD, isobutyryl-CoA can be produced from 2-oxoisovaleric acid, and with ACD, methacrylyl-CoA can be produced from isobutyryl-CoA. Thus, by combining the reactions of both BCKAD and ACD, it becomes possible to produce methacrylyl-CoA from 2-oxoisovaleric acid. Alternatively, by adding an enzyme which has an activity of hydrolyzing AAT or methacrylyl-CoA, each of methacrylic acid ester and methacrylic acid can be produced.

The enzymes involved with synthesis of methacrylic acid can be obtained by isolating the gene as described above, producing a recombinant (transformant) by using a general host vector, and culturing the recombinant. Examples of the host include *E. coli*, the genus *Rhodococcus*, the genus *Pseudomonas*, the genus *Corynebacterium*, the genus *Bacillus*, the genus *Streptococcus*, and the genus *Streptomyces* as bacteria, *Saccharomyces*, the genus *Candida*, the genus *Shizosaccharomyces*, and the genus *Pichia* as yeast, and the genus *Aspergillus* as mold. For a case in which obtainment of the enzyme (protein) is the object, using *E. coli* is preferred due to convenience and good efficiency. It is also possible to express plural enzymes involved with synthesis of methacrylic acid in the same host. With regard to the obtainment of the enzymes from culture of a transformant, collection can be made by disruption, extraction, or centrifugal separation of the cells after recovery.

By contacting the enzymes obtained accordingly with a compound as a raw material under conditions allowing the enzymes to work, each target product can be obtained.

EXAMPLES

Hereinbelow, the invention is explained in greater detail on the basis of the examples, but the invention is not limited to them.

Example 1: Search for Methacrylic Acid-Producing Microbes

Using the soils and insects which have been collected from different areas in Japan as a source of microbes, search for methacrylic acid-producing microbes was conducted based on enrichment culture. Because the metabolitic intermediates of valine include methacrylyl-CoA, which is a derivative of methacrylic acid, a medium containing L-valine was used and the screening was performed using the assimilation property of valine as an indicator.

[Isolation from Soils]

An appropriate amount of soils was added to 5 mL of sterilized water and stirred. After allowing it to stand, a suitable amount of the supernatant was added to 10 ml liquid medium. The composition of the medium is shown below.
$K_2HPO_4$ 1.0 μl
$MgSO_4.7H_2O$ 0.2 g/l
$FeSO_4.7H_2O$ 0.01 g/l
$CaCl_2$ 0.01 g/l
L-Valine 5.0 g/l
pH 7.0

Shake culture was performed at 30° C. for 3 to 7 days. The grown strain was transferred to the same medium and acclimated culture was performed for several times. After that, they were inoculated on an agar medium, that is, the same medium added with 1.5% agar, and cultured at 30° C. for 48 hours to form a colony. Using a platinum loop, the colony was scraped and inoculated on an agar medium (LB medium, 1.5% agar) and cultured at 30° C. for 48 hours to obtain the isolated strains (B25-2 strain, D22-1 strain, D43-1 strain, D25 strain, D26 strain, D29 strain, D41-2 strain, R1 strain, B13 strain). The composition of the LB medium is as follows: 1% bactotrypton, 0.5% bactoyeast extract, and 0.5% NaCl.

[Isolation from Insect]

The collected *Carabus insulicola* was kept for 2 days in starvation state, and the body of the insect was washed with 95% ethanol and sterilized physiological saline, two times for each. The abdomen part of the insect body was separated and suspended in 0.3 mL sterilized water. 0.1 mL of the supernatant was added to the LB liquid medium and cultured at 30° C. for 48 hours. A suitable amount of the culture supernatant was added to 10 ml liquid medium. The composition of the medium is shown below.
$K_2HPO_4$ 1.0 g/l
$MgSO_4.7H_2O$ 0.2 g/l
$FeSO_4.7H_2O$ 0.01 g/l
$CaCl_2$ 0.01 g/l
L-Valine 5.0 g/l
pH 7.0

Shake culture was performed at 30° C. for 3 to 7 days. The cultured strain was transferred to the same medium and acclimated culture was performed for several times. After that, they were inoculated on an agar medium, that is, the same medium added with 1.5% agar, and cultured at 30° C. for 48 hours to form a colony. Using a platinum loop, the colony was scraped and inoculated on an agar medium (LB medium, 1.5% agar) and cultured at 30° C. for 48 hours to obtain the isolated strains (G1 strain, G2 strain).

The mycological properties of the isolated strains are shown in the following table. In the table, "+" indicates positive, "−" indicates negative and "+w" indicates a weak response.

(1) Mycological Properties of *Pseudomonas* sp. B25-2

TABLE 1-1

| 1. Morphological properties | |
|---|---|
| Culture conditions | Nutrient agar medium 30° C. |
| Shape of cell | Bacillus (0.6 to 0.7 × 1.5 to 2.0 μm) |
| Presence or absence of cell pleomorphism | − |
| Motility (attachment state of flagella) | + |
| Presence or absence of spore (spore location) | − |
| 2. Cultural properties | |
| Culture conditions | Nutrient agar medium 30° C. |
| Color | Pale yellow color |
| Gloss | + |
| Pigment production | − |
| Culture conditions | Nutrient broth medium 30° C. |
| Presence or absence of surface growth | − |
| Presence or absence of turbidity in medium | + |
| Culture conditions | Gelatin stab culture 30° C. |
| Growth state | + |
| Gelatin liquefaction | − |
| Culture conditions | Litmus milk 30° C. |
| Solidification | − |
| Liquefaction | − |
| 3. Physiological properties | |
| Gram stain | − |
| Nitrate salt reduction | − |
| Denitrification | − |
| MR test | − |
| VP test | + |
| Indole production | − |
| Hydrogen sulfide production | − |
| Hydrolysis of starch | − |
| Use of citric acid (Koser) | + |
| (Christensen) | + |
| Use of inorganic nitrogen source Nitrate salt | + |
| Ammonium salt | + |

TABLE 1-2

| Urease activity | − |
|---|---|
| Catalase | + |
| Oxidase | + |

TABLE 1-2-continued

| | | |
|---|---|---|
| Growth range pH | 5 | + |
| | 8 | + |
| | 9 | + |
| Growth range Temperature (° C.) | 15 | + |
| | 20 | + |
| | 37 | − |
| | 45 | − |
| Anaerobic growing property | | + |
| O•F Test (oxidation/fermentation) | | +/− |
| 4. Acid production/gas production from carbohydrates | | |
| L-Arabinose | +/− | D-Xylose −/− |
| D-Glucose | +/− | D-Mannose +/− |
| D-Fructose | −/− | D-Galactose +/− |
| Maltose | −/− | Saccharose −/− |
| Lactose | −/− | Trehalose −/− |
| D-Sorbitol | −/− | D-Mannitol −/− |
| Inositol | −/− | Glycerin −/− |
| 5. Other physiological properties | | |
| β-Galactosidase activity | | − |
| Arginine dehydrolase activity | | + |
| Lysine decarboxylase activity | | − |
| Tryptophan deaminase activity | | − |
| Gelatinase activity | | − |

According to a common method, the partial nucleotide sequence of 16S rDNA of the B25-2 strain (SEQ ID NO. 1) was determined.

The partial nucleotide sequence of 16S rDNA of the B25-2 strain exhibited high homology to the nucleotide sequence of 16S rDNA of *Pseudomonas*, and it exhibited the highest identity of 99.2% to the *Pseudomonas orizihabitans* IAM (Institute of Molecular and Cellular Biology Culture Collection (University of Tokyo)) 1568 strain (NBRC102199) and *Pseudomonas japonica* IAM 15071 strain (NBRC 103040) (NBRC strain is obtainable from Biotechnology Center of National Institute of Technology and Evaluation, Independent Administrative Institution).

As a result of a brief molecular phylogenetic analysis based on the partial nucleotide sequence of 16S rDNA, B25-2 strain is included in a cluster formed of the species of *Pseudomonas*. Further, unlike any other known species, B25-2 strain showed an independent molecular phylogenetic position in the cluster of *Pseudomonas*.

B25-2 strain does not reduce a nitrate salt, exhibits an arginine hydrolase activity, does not hydrolyze gelatin, but assimilates glucose, D-mannose, potassium gluconate, or the like. Further, it does not assimilate L-arabinose and D-mannitol, produces a fluorescent pigment in Kings'B agar medium, shows motility, shows a positive response for both the catalase reaction and oxidase reaction, and does not hydrolyze starch. Those properties are believed not to contradict with the properties of *Pseudomonas*, but they are not in match with the properties of any other known species.

As such, B25-2 strain was identified as *Pseudomonas* sp. On Nov. 7, 2012, B25-2 strain was subjected to international deposition with National Institute of Technology and Evaluation (NITE), Independent Administrative Institution (zip code: 292-0818, Kazusakamatari, Kisarazu-shi, Chiba, Japan, 2-5-8), under accession number of NITE BP-1451.

(2) Mycological Properties of *Pseudomonas* sp. D22-1

TABLE 2-1

| 1. Morphological properties | |
|---|---|
| Culture conditions | Nutrient agar medium 30° C. |
| Shape of cell | Bacillus (0.7 to 0.8 × 1.2 to 2.0 μm) |
| Presence or absence of cell pleomorphism | − |
| Motility (attachment state of flagella) | +(Ciliate) |
| Presence or absence of spore (spore location) | − |
| 2. Cultural properties | |
| Culture conditions | Nutrient agar medium 30° C. |
| Color | Pale yellow color |
| Gloss | + |
| Pigment production | − |
| Culture conditions | Nutrient broth medium 30° C. |
| Presence or absence of surface growth | − |
| Presence or absence of turbidity in medium | + |
| Culture conditions | Gelatin stab culture 30° C. |
| Growth state | + |
| Gelatin liquefaction | − |
| Culture conditions | Litmus milk 30° C. |
| Solidification | − |
| Liquefaction | − |
| 3. Physiological properties | |
| Gram stain | − |
| Nitrate salt reduction | − |
| Denitrification | − |
| MR test | + |
| VP test | + |
| Indole production | − |
| Hydrogen sulfide production | − |
| Hydrolysis of starch | − |
| Use of citric acid (Koser) | − |
| (Christensen) | + |
| Use of inorganic nitrogen source Nitrate salt | + |
| Ammonium salt | + |

TABLE 2-2

| | | |
|---|---|---|
| Urease activity | | − |
| Catalase | | + |
| Oxidase | | + |
| Growth range pH | 5 | + |
| | 8 | + |
| | 9 | − |
| Growth range Temperature (° C.) | 15 | + |
| | 20 | + |
| | 37 | − |
| | 45 | − |
| Anaerobic growing property | | + |
| O•F Test (oxidation/fermentation) | | +/− |
| 4. Acid production/gas production from carbohydrates | | |
| L-Arabinose | −/− | D-Xylose −/− |
| D-Glucose | +/− | D-Mannose +/− |
| D-Fructose | −/− | D-Galactose +/− |
| Maltose | −/− | Saccharose −/− |
| Lactose | −/− | Trehalose −/− |
| D-Sorbitol | −/− | D-Mannitol −/− |
| Inositol | −/− | Glycerin +w/− |
| 5. Other physiological properties | | |
| β-Galactosidase activity | | − |
| Arginine dehydrolase activity | | + |
| Lysine decarboxylase activity | | + |
| Tryptophan deaminase activity | | − |
| Gelatinase activity | | − |

According to a common method, the partial nucleotide sequence of 16S rDNA of the D22-1 strain (SEQ ID NO. 2) was determined.

The partial nucleotide sequence of 16S rDNA of the D22-1 strain exhibited high homology to the nucleotide sequence of 16S rDNA of *Pseudomonas*, and it exhibited the highest identity of 98.8% to the *Pseudomonas agarici* LMG2112 strain.

As a result of a brief molecular phylogenetic analysis based on the partial nucleotide sequence of 16S rDNA, D22-1 strain is included in a cluster formed of the species of *Pseudomonas*. Further, although D22-1 strain formed a cluster with *Pseudomonas abietaniphila*, a distance is recognized between them.

D22-1 strain does not reduce a nitrate salt, exhibits an arginine hydrolase activity but no urease activity, does not hydrolyze gelatin but assimilates glucose, D-mannose and N-acetyl-D-glucosamine, or the like. Further, it does not assimilate L-arabinose and D-mannitol, does not produce a fluorescent pigment in Kings'B agar medium, shows motility, and shows a positive response to both the catalase reaction and oxidase reaction. Those properties are believed to be in match with the properties of *Pseudomonas*, but they are not in match with the properties of any other known species.

As such, D22-1 strain was identified as *Pseudomonas* sp. On Nov. 7, 2012, D22-1 strain was subjected to international deposition under accession number of NITE BP-1452.

(3) Mycological Properties of *Pseudomonas umsongensis* D43-1

TABLE 3-1

| 1. Morphological properties | |
|---|---|
| Culture conditions | Nutrient agar medium 30° C. |
| Shape of cell | Bacillus (0.8 to 0.9 × 1.2 to 1.5 μm) |
| Presence or absence of cell pleomorphism | − |
| Motility (attachment state of flagella) | +(Ciliate) |
| Presence or absence of spore (spore location) | − |
| 2. Cultural properties | |
| Culture conditions | Nutrient agar medium 30° C. |
| Color | Pale yellow color |
| Gloss | + |
| Pigment production | − |
| Culture conditions | Nutrient broth medium 30° C. |
| Presence or absence of surface growth | − |
| Presence or absence of turbidity in medium | + |
| Culture conditions | Gelatin stab culture 30° C. |
| Growth state | + |
| Gelatin liquefaction | − |
| Culture conditions | Litmus milk 30° C. |
| Solidification | − |
| Liquefaction | − |
| 3. Physiological properties | |
| Gram stain | − |
| Nitrate salt reduction | + |
| Denitrification | − |
| MR test | − |
| VP test | + |
| Indole production | − |
| Hydrogen sulfide production | − |
| Hydrolysis of starch | − |
| Use of citric acid (Koser) | + |
| (Christensen) | + |
| Use of inorganic nitrogen source  Nitrate salt | + |
| Ammonium salt | + |

TABLE 3-2

| Urease activity | | − |
|---|---|---|
| Catalase | | + |
| Oxidase | | + |
| Growth range | 5 | + |
| pH | 8 | + |
| | 9 | +w |
| Growth range Temperature (° C.) | 15 | + |
| | 20 | + |
| | 37 | − |
| | 45 | − |

TABLE 3-2-continued

| Anaerobic growing property | | + |
|---|---|---|
| O•F Test (oxidation/fermentation) | | +/− |
| 4. Acid production/gas production from carbohydrates | | |
| L-Arabinose | +/− | D-Xylose | −/− |
| D-Glucose | +/− | D-Mannose | +/− |
| D-Fructose | −/− | D-Galactose | +/− |
| Maltose | −/− | Saccharose | −/− |
| Lactose | −/− | Trehalose | −/− |
| D-Sorbitol | −/− | D-Mannitol | −/− |
| Inositol | −/− | Glycerin | +/− |
| 5. Other physiological properties | | | |
| β-Galactosidase activity | | − | |
| Arginine dehydrolase activity | | + | |
| Lysine decarboxylase activity | | + | |
| Tryptophan deaminase activity | | − | |
| Gelatinase activity | | − | |

According to a common method, the partial nucleotide sequence of 16S rDNA of the D43-1 strain (SEQ ID NO. 3) was determined.

The partial nucleotide sequence of 16S rDNA of the D43-1 strain exhibited high homology to the nucleotide sequence of 16S rDNA of *Pseudomonas*, and it exhibited the highest identity of 100% to the *Pseudomonas umsongensis* Ps33-10 strain.

As a result of a brief molecular phylogenetic analysis based on the partial nucleotide sequence of 16S rDNA, D43-1 strain is included in a cluster formed of the species of *Pseudomonas*. Further, D43-1 strain formed a cluster with *Pseudomonas umsongensis* and *Pseudomonas mohnii*, and it exhibited the same molecular phylogenetic position as those two species.

D43-1 strain reduces a nitrate salt, exhibits an arginine hydrolase activity but no urease activity, does not hydrolyze gelatin but assimilates glucose, L-arabinose and D-mannose, or the like. Further, it does not assimilate D-mannitol and N-acetyl-D-glucosamine, produces a fluorescent pigment in Kings'B agar medium, shows motility, and shows a positive response to both the catalase reaction and oxidase reaction. Those properties are almost in match with the properties of *Pseudomonas umsongensis*.

As such, D43-1 strain was identified as *Pseudomonas umsongensis*. On Nov. 7, 2012, D43-1 strain was subjected to international deposition under accession number of NITE BP-1453.

(4) Mycological Properties of *Pseudomonas* sp. D25

TABLE 4-1

| 1. Morphological properties | |
|---|---|
| Culture conditions | Nutrient agar medium 30° C. |
| Shape of cell | Bacillus (0.8 to 0.9 × 1.2 to 2.0 μm) |
| Presence or absence of cell pleomorphism | − |
| Motility (attachment state of flagella) | +(Ciliate) |
| Presence or absence of spore (spore location) | − |
| 2. Cultural properties | |
| Culture conditions | Nutrient agar medium 30° C. |
| Color | Pale yellow color |
| Gloss | + |
| Pigment production | − |
| Culture conditions | Nutrient broth medium 30° C. |
| Presence or absence of surface growth | − |
| Presence or absence of turbidity in medium | + |

TABLE 4-1-continued

| Culture conditions | Gelatin stab culture 30° C. |
|---|---|
| Growth state | + |
| Gelatin liquefaction | − |
| Culture conditions | Litmus milk 30° C. |
| Solidification | − |
| Liquefaction | − |
| 3. Physiological properties | |
| Gram stain | − |
| Nitrate salt reduction | − |
| Denitrification | − |
| MR test | − |
| VP test | + |
| Indole production | − |
| Hydrogen sulfide production | − |
| Hydrolysis of starch | − |
| Use of citric acid (Koser) | + |
| (Christensen) | + |
| Use of inorganic nitrogen source  Nitrate salt | + |
| Ammonium salt | + |

TABLE 4-2

| Urease activity | | − | | |
|---|---|---|---|---|
| Catalase | | + | | |
| Oxidase | | + | | |
| Growth range pH | 5 | + | | |
| | 8 | + | | |
| | 9 | − | | |
| Growth range Temperature (° C.) | 15 | + | | |
| | 20 | + | | |
| | 37 | − | | |
| | 45 | − | | |
| Anaerobic growing property | | + | | |
| O•F Test (oxidation/fermentation) | | +/− | | |
| 4. Acid production/gas production from carbohydrates | | | | |
| L-Arabinose | | +/− | D-Xylose | −/− |
| D-Glucose | | +/− | D-Mannose | −/− |
| D-Fructose | | −/− | D-Galactose | −/− |
| Maltose | | −/− | Saccharose | −/− |
| Lactose | | −/− | Trehalose | −/− |
| D-Sorbitol | | −/− | D-Mannitol | −/− |
| Inositol | | −/− | Glycerin | +/− |
| 5. Other physiological properties | | | | |
| β-Galactosidase activity | | − | | |
| Arginine dehydrolase activity | | + | | |
| Lysine decarboxylase activity | | + | | |
| Tryptophan deaminase activity | | − | | |
| Gelatinase activity | | − | | |

According to a common method, the partial nucleotide sequence of 16S rDNA of the D25 strain (SEQ ID NO. 4) was determined.

The partial nucleotide sequence of 16S rDNA of the D25 strain exhibited high homology to the nucleotide sequence of 16S rDNA of *Pseudomonas*, and it exhibited the highest identity of 99.0% to the *Pseudomonas putida* ATCC12633 strain, *Pseudomonas fuscovaginae* MAFF 301177 strain, *Pseudomonas asplenii* ATCC 23835 strain and *Pseudomonas agarici* LMG 2112 strain.

As a result of a brief molecular phylogenetic analysis based on the partial nucleotide sequence of 16S rDNA, D25 strain is included in a cluster formed of the species of *Pseudomonas*. Further, D25 strain showed, in the cluster of *Pseudomonas*, an independent molecular phylogenetic position unlike any other known species.

D25 strain reduces a nitrate salt, exhibits an arginine hydrolase activity but no urease activity, does not hydrolyze gelatin but assimilates glucose, L-arabinose and D-mannitol, or the like. Further, it does not assimilate D-mannose or maltose, does not produce a fluorescent pigment in Kings'B agar medium, shows motility, and shows a positive response to both the catalase reaction and oxidase reaction. Those properties are believed to be in match with the properties of *Pseudomonas*, but a difference is recognized with *Pseudomonas putida*, *Pseudomonas fuscovaginae*, *Pseudomonas asplenii* and *Pseudomonas agarici* for which high homology has been demonstrated in terms of the assimilation property or producing a fluorescent pigment.

As such, D25 strain was identified as *Pseudomonas* sp. On Nov. 7, 2012, D25 strain was subjected to international deposition under accession number of NITE BP-1454.

(5) Mycological Properties of *Pseudomonas* sp. D26

TABLE 5-1

| 1. Morphological properties | |
|---|---|
| Culture conditions | Nutrient agar medium 30° C. |
| Shape of cell | Bacillus (0.7 to 0.8 × 1.2 to 1.5 μm) |
| Presence or absence of cell pleomorphism | − |
| Motility (attachment state of flagella) | +(Ciliate) |
| Presence or absence of spore (spore location) | − |
| 2. Cultural properties | |
| Culture conditions | Nutrient agar medium 30° C. |
| Color | Pale yellow color |
| Gloss | + |
| Pigment production | − |
| Culture conditions | Nutrient broth medium 30° C. |
| Presence or absence of surface growth | − |
| Presence or absence of turbidity in medium | + |
| Culture conditions | Gelatin stab culture 30° C. |
| Growth state | + |
| Gelatin liquefaction | − |
| Culture conditions | Litmus milk 30° C. |
| Solidification | − |
| Liquefaction | − |
| 3. Physiological properties | |
| Gram stain | − |
| Nitrate salt reduction | + |
| Denitrification | − |
| MR test | − |
| VP test | + |
| Indole production | − |
| Hydrogen sulfide production | − |
| Hydrolysis of starch | − |
| Use of citric acid (Koser) | + |
| (Christensen) | + |
| Use of inorganic nitrogen source  Nitrate salt | + |
| Ammonium salt | + |

TABLE 5-2

| Urease activity | | − | | |
|---|---|---|---|---|
| Catalase | | + | | |
| Oxidase | | + | | |
| Growth range pH | 5 | + | | |
| | 8 | + | | |
| | 9 | − | | |
| Growth range Temperature (° C.) | 15 | + | | |
| | 20 | + | | |
| | 37 | − | | |
| | 45 | − | | |
| Anaerobic growing property | | + | | |
| O•F Test (oxidation/fermentation) | | +/− | | |
| 4. Acid production/gas production from carbohydrates | | | | |
| L-Arabinose | | +/− | D-Xylose | −/− |
| D-Glucose | | +/− | D-Mannose | +/− |
| D-Fructose | | −/− | D-Galactose | +/− |
| Maltose | | −/− | Saccharose | −/− |
| Lactose | | −/− | Trehalose | −/− |
| D-Sorbitol | | −/− | D-Mannitol | −/− |
| Inositol | | −/− | Glycerin | +/− |

TABLE 5-2-continued

5. Other physiological properties

| | |
|---|---|
| β-Galactosidase activity | – |
| Arginine dehydrolase activity | – |
| Lysine decarboxylase activity | – |
| Tryptophan deaminase activity | – |
| Gelatinase activity | – |

According to a common method, the partial nucleotide sequence of 16S rDNA of the D26 strain (SEQ ID NO. 5) was determined.

The partial nucleotide sequence of 16S rDNA of the D26 strain exhibited high homology to the nucleotide sequence of 16S rDNA of *Pseudomonas*, and it exhibited the highest identity of 98.6% to the *Pseudomonas putida* ATCC 12633 strain, *Pseudomonas fuscovaginae* MAFF 301177 strain and *Pseudomonas asplenii* ATCC 23835 strain.

As a result of a brief molecular phylogenetic analysis based on the partial nucleotide sequence of 16S rDNA, D26 strain is included in a cluster formed of the species of *Pseudomonas*. Further, D25 strain forms a cluster with *Pseudomonas putida*, *Pseudomonas fuscovaginae*, *Pseudomonas asplenii* and *Pseudomonas agarici*, and among them, it showed the same molecular phylogenetic position as the three species, that is, *Pseudomonas putida*, *Pseudomonas fuscovaginae* and *Pseudomonas asplenii*.

D26 strain reduces a nitrate salt, does not exhibit an arginine hydrolase activity and urease activity, does not hydrolyze gelatin but assimilates glucose, L-arabinose and D-mannose, or the like. Further, it does not assimilate maltose and adipic acid, produces a fluorescent pigment in Kings'B agar medium, shows motility, shows a positive response to both the catalase reaction and oxidase reaction, and does not hydrolyze starch. Although those properties have a similarity to those of *Pseudomonas putida*, *Pseudomonas fuscovaginae* and *Pseudomonas asplenii* for which the homologous property has been demonstrated, differences are also confirmed. In particular, reducing a nitrate salt but not exhibiting the arginine hydrolase activity is different from those species.

As such, D26 strain was identified as *Pseudomonas* sp. On Nov. 7, 2012, D26 strain was subjected to international deposition under accession number of NITE BP-1455.

(6) Mycological Properties of *Pseudomonas* sp. D29

TABLE 6-1

1. Morphological properties

| | |
|---|---|
| Culture conditions | Nutrient agar medium 30° C. |
| Shape of cell | Bacillus (0.7 to 0.8 × 1.5 to 2.0 μm) |
| Presence or absence of cell pleomorphism | – |
| Motility (attachment state of flagella) | +(Ciliate) |
| Presence or absence of spore (spore location) | – |

2. Cultural properties

| | |
|---|---|
| Culture conditions | Nutrient agar medium 30° C. |
| Color | Pale yellow color |
| Gloss | + |
| Pigment production | – |
| Culture conditions | Nutrient broth medium 30° C. |
| Presence or absence of surface growth | – |
| Presence or absence of turbidity in medium | + |
| Culture conditions | Gelatin stab culture 30° C. |
| Growth state | + |
| Gelatin liquefaction | – |
| Culture conditions | Litmus milk 30° C. |
| Solidification | – |
| Liquefaction | – |

3. Physiological properties

| | | |
|---|---|---|
| Gram stain | | – |
| Nitrate salt reduction | | + |
| Denitrification | | – |
| MR test | | – |
| VP test | | + |
| Indole production | | – |
| Hydrogen sulfide production | | – |
| Hydrolysis of starch | | – |
| Use of citric acid | (Koser) | + |
| | (Christensen) | + |
| Use of inorganic nitrogen source | Nitrate salt | + |
| | Ammonium salt | + |

TABLE 6-2

| | | |
|---|---|---|
| Urease activity | | – |
| Catalase | | + |
| Oxidase | | + |
| Growth range pH | 5 | + |
| | 8 | + |
| | 9 | +w |
| Growth range Temperature (° C.) | 15 | + |
| | 20 | + |
| | 37 | +w |
| | 45 | – |
| Anaerobic growing property | | + |
| O•F Test (oxidation/fermentation) | | +/– |

4. Acid production/gas production from carbohydrates

| | | | |
|---|---|---|---|
| L-Arabinose | +/– | D-Xylose | –/– |
| D-Glucose | +/– | D-Mannose | +/– |
| D-Fructose | –/– | D-Galactose | +/– |
| Maltose | –/– | Saccharose | –/– |
| Lactose | –/– | Trehalose | –/– |
| D-Sorbitol | –/– | D-Mannitol | –/– |
| Inositol | –/– | Glycerin | +w/– |

5. Other physiological properties

| | |
|---|---|
| β-Galactosidase activity | – |
| Arginine dehydrolase activity | + |
| Lysine decarboxylase activity | + |
| Tryptophan deaminase activity | – |
| Gelatinase activity | – |

According to a common method, the partial nucleotide sequence of 16S rDNA of the D29 strain (SEQ ID NO. 6) was determined.

The partial nucleotide sequence of 16S rDNA of the D29 strain exhibited high homology to the nucleotide sequence of 16S rDNA of *Pseudomonas*, and it exhibited the highest identity of 99.6% to the *Pseudomonas vancouverensis* DhA-51 strain.

As a result of a brief molecular phylogenetic analysis based on the partial nucleotide sequence of 16S rDNA, D29 strain forms a cluster with *Pseudomonas umsongensis*, *Pseudomonas mohnii*, *Pseudomonas graminis*, and among them, it showed the same molecular phylogenetic position as *Pseudomonas umsongensis* and *Pseudomonas mohnii*.

D29 strain reduces a nitrate salt, exhibits an arginine hydrolase activity but no urease activity, does not hydrolyze gelatin but assimilates glucose, L-arabinose and D-mannose, or the like. Further, it does not assimilate N-acetyl-D-glucosamine, maltose and adipic acid, does not produce a fluorescent pigment in Kings'B agar medium, shows motility, and shows a positive response to both the catalase reaction and oxidase reaction. Although those properties have a similarity to those of *Pseudomonas umsongensis* and

*Pseudomonas mohnii* for which the homologous property has been demonstrated, differences are also confirmed. In particular, not exhibiting the arginine hydrolase activity is different from those two species while reducing a nitrate salt is different from the properties of *Pseudomonas mohnii*

As such, D29 strain was identified as *Pseudomonas* sp. On Nov. 7, 2012, D29 strain was subjected to international deposition under accession number of NITE BP-1456.

(7) Mycological Properties of *Pseudomonas* sp. D41-2

TABLE 7-1

| 1. Morphological properties | |
| --- | --- |
| Culture conditions | Nutrient agar medium 30° C. |
| Shape of cell | Bacillus (0.7 to 0.8 × 1.2 to 1.5 μm) |
| Presence or absence of cell pleomorphism | – |
| Motility (attachment state of flagella) | +(Ciliate) |
| Presence or absence of spore (spore location) | – |
| 2. Cultural properties | |
| Culture conditions | Nutrient agar medium 30° C. |
| Color | Pale yellow color |
| Gloss | + |
| Pigment production | – |
| Culture conditions | Nutrient broth medium 30° C. |
| Presence or absence of surface growth | – |
| Presence or absence of turbidity in medium | + |
| Culture conditions | Gelatin stab culture 30° C. |
| Growth state | + |
| Gelatin liquefaction | – |
| Culture conditions | Litmus milk 30° C. |
| Solidification | – |
| Liquefaction | – |
| 3. Physiological properties | |
| Gram stain | – |
| Nitrate salt reduction | + |
| Denitrification | – |
| MR test | – |
| VP test | + |
| Indole production | – |
| Hydrogen sulfide production | – |
| Hydrolysis of starch | – |
| Use of citric acid (Koser) | – |
| (Christensen) | + |
| Use of inorganic nitrogen source  Nitrate salt | + |
| Ammonium salt | + |

TABLE 7-2

| Urease activity | | – |
| --- | --- | --- |
| Catalase | | + |
| Oxidase | | + |
| Growth range pH | 5 | + |
| | 8 | + |
| | 9 | +w |
| Growth range Temperature (° C.) | 15 | + |
| | 20 | + |
| | 37 | – |
| | 45 | – |
| Anaerobic growing property | | + |
| O•F Test (oxidation/fermentation) | | +/– |
| 4. Acid production/gas production from carbohydrates | | |
| L-Arabinose | +/– | D-Xylose  –/– |
| D-Glucose | –/– | D-Mannose  +/– |
| D-Fructose | –/– | D-Galactose  +/– |
| Maltose | –/– | Saccharose  –/– |
| Lactose | –/– | Trehalose  –/– |
| D-Sorbitol | –/– | D-Mannitol  –/– |
| Inositol | –/– | Glycerin  +w/– |

TABLE 7-2-continued

| 5. Other physiological properties | |
| --- | --- |
| β-Galactosidase activity | – |
| Arginine dehydrolase activity | + |
| Lysine decarboxylase activity | + |
| Tryptophan deaminase activity | – |
| Gelatinase activity | – |

According to a common method, the partial nucleotide sequence of 16S rDNA of the D41-2 strain (SEQ ID NO. 7) was determined.

The partial nucleotide sequence of 16S rDNA of the D41-2 strain exhibited high homology to the nucleotide sequence of 16S rDNA of *Pseudomonas*, and it exhibited the highest identity of 99.8% to the *Pseudomonas vancouverensis* DhA-51 strain.

As a result of a brief molecular phylogenetic analysis based on the partial nucleotide sequence of 16S rDNA, D41-2 is included in a cluster formed of the species *Pseudomonas*. Further, D41-2 strain forms a cluster with *Pseudomonas vancouverensis* and *Pseudomonas moorei*, and it showed the same molecular phylogenetic position as those two species.

D41-2 strain reduces a nitrate salt, exhibits an arginine hydrolase activity, does not hydrolyze gelatin but assimilates glucose, L-arabinose and D-mannose, or the like. Further, it does not assimilate maltose and adipic acid, produces a fluorescent pigment in Kings'B agar medium, shows motility, and shows a positive response to both the catalase reaction and oxidase reaction. Although those properties have a similarity to those of *Pseudomonas vancouverensis* and *Pseudomonas moorei* for which the homology has been demonstrated, differences are also confirmed. In particular, producing a fluorescent pigment and reducing a nitrate salt are different from the properties of *Pseudomonas moorei* while exhibiting the arginine hydrolase activity is different from the properties of *Pseudomonas vancouverensis*.

As such, D41-2 strain was identified as *Pseudomonas* sp. On Nov. 7, 2012, D41-2 strain was subjected to international deposition under accession number of NITE BP-1457.

(8) Mycological Properties of *Bacillus thuringiensis* G1

TABLE 8-1

| 1. Morphological properties | |
| --- | --- |
| Culture conditions | Nutrient agar medium 30° C. |
| Shape of cell | Bacillus (1.0 × 1.5 to 2.5 μm) |
| Presence or absence of cell pleomorphism | – |
| Motility (attachment state of flagella) | +(Peritrichous flagella) |
| Presence or absence of spore (spore location) | +(Center to closed to end) |
| 2. Cultural properties | |
| Culture conditions | Nutrient agar medium 30° C. |
| Color | Cream color |
| Gloss | – |
| Pigment production | – |
| Culture conditions | Nutrient broth medium 30° C. |
| Presence or absence of surface growth | – |
| Presence or absence of turbidity in medium | + |
| Culture conditions | Gelatin stab culture 30° C. |
| Growth state | + |
| Gelatin liquefaction | + |
| Culture conditions | Litmus milk 30° C. |
| Solidification | + |
| Liquefaction | – |

TABLE 8-1-continued

| 3. Physiological properties | | |
|---|---|---|
| Gram stain | | + |
| Nitrate salt reduction | | − |
| Denitrification | | + |
| MR test | | + |
| VP test | | + |
| Indole production | | − |
| Hydrogen sulfide production | | − |
| Hydrolysis of starch | | + |
| Use of citric acid | (Koser) | − |
| | (Christensen) | + |
| Use of inorganic nitrogen source | Nitrate salt | − |
| | Ammonium salt | − |

TABLE 8-2

| Urease activity | | − |
|---|---|---|
| Catalase | | + |
| Oxidase | | + |
| Growth range pH | 5 | + |
| | 8 | + |
| | 9 | + |
| Growth range Temperature (° C.) | 15 | + |
| | 20 | + |
| | 37 | + |
| | 45 | − |
| Anaerobic growing property | | + |
| O•F Test (oxidation/fermentation) | | −/− |
| 4. Acid production/gas production from carbohydrates | | | |

| L-Arabinose | −/− | D-Xylose | −/− |
|---|---|---|---|
| D-Glucose | +/− | D-Mannose | −/− |
| D-Fructose | +/− | D-Galactose | −/− |
| Maltose | +/− | Saccharose | −/− |
| Lactose | −/− | Trehalose | +/− |
| D-Sorbitol | −/− | D-Mannitol | −/− |
| Inositol | −/− | Glycerin | +/− |
| 5. Other physiological properties | | | |

| β-Galactosidase activity | − |
|---|---|
| Arginine dehydrolase activity | + |
| Lysine decarboxylase activity | − |
| Tryptophan deaminase activity | − |
| Gelatinase activity | + |

According to a common method, the partial nucleotide sequence of 16S rDNA of the G1 strain (SEQ ID NO. 9) was determined The partial nucleotide sequence of 16S rDNA of the G1 strain exhibited high homology to the nucleotide sequence of 16S rDNA of *Bacillus*, and it exhibited the highest identity of 99.8% to the *Bacillus thuringiensis* ATCC 10792 strain.

As a result of a brief molecular phylogenetic analysis based on the partial nucleotide sequence of 16S rDNA, G1 strain is included in a cluster formed of the species of *Bacillus*. Further, G1 strain forms a cluster with *Bacillus thuringiensis* and both exhibits the same molecular phylogenetic position.

G1 strain ferments glycerol, ribose, and glucose, does not ferment D-xylose, L-xylose, and galactose, does not exhibit the β-galactosidase activity or urease activity, uses citric acid, does not produce indole, produces acetoin, does not reduce a nitrate salt, does not grow at 45° C., grows under anaerobic conditions, and hydrolyzes starch. Although those properties are almost in match with those of *Bacillus thuringiensis* for which the homology has been demonstrated, not reducing a nitrate salt is different from the typical properties of *Bacillus thuringiensis*. With regard to the physiological biochemical differences, the possibility of having a difference at strain level cannot be ruled out.

As such, G1 strain was identified as *Bacillus thuringiensis*. On Nov. 7, 2012, G1 strain was subjected to international deposition under accession number of NITE BP-1458.

(9) Mycological Properties of *Bacillus thuringiensis* G2

TABLE 9-1

| 1. Morphological properties | | |
|---|---|---|
| Culture conditions | | Nutrient agar medium 30° C. |
| Shape of cell | | Bacillus (1.0 × 1.5 to 2.5 μm) |
| Presence or absence of cell pleomorphism | | − |
| Motility (attachment state of flagella) | | +(Peritrichous flagella) |
| Presence or absence of spore (spore location) | | +(Center to close to end) |
| 2. Cultural properties | | |
| Culture conditions | | Nutrient agar medium 30° C. |
| Color | | Cream color |
| Gloss | | − |
| Pigment production | | − |
| Culture conditions | | Nutrient broth medium 30° C. |
| Presence or absence of surface growth | | − |
| Presence or absence of turbidity in medium | | + |
| Culture conditions | | Gelatin stab culture 30° C. |
| Growth state | | + |
| Gelatin liquefaction | | + |
| Culture conditions | | Litmus milk 30° C. |
| Solidification | | + |
| Liquefaction | | − |
| 3. Physiological properties | | |
| Gram stain | | + |
| Nitrate salt reduction | | − |
| Denitrification | | + |
| MR test | | + |
| VP test | | + |
| Indole production | | − |
| Hydrogen sulfide production | | − |
| Hydrolysis of starch | | + |
| Use of citric acid | (Koser) | − |
| | (Christensen) | + |
| Use of inorganic | Nitrate salt | − |
| nitrogen source | Ammonium salt | − |

TABLE 9-2

| | | | | |
|---|---|---|---|---|
| Urease activity | | − | | |
| Catalase | | + | | |
| Oxidase | | + | | |
| Growth range | 5 | + | | |
| pH | 8 | + | | |
| | 9 | + | | |
| Growth range | 15 | + | | |
| Temperature | 20 | + | | |
| (° C.) | 37 | + | | |
| | 45 | − | | |
| Anaerobic growing property | | + | | |
| O•F Test (oxidation/fermentation) | | −/− | | |
| 4. Acid production/gas production from carbohydrates | | | | |
| L-Arabinose | −/− | D-Xylose | −/− | |
| D-Glucose | +/− | D-Mannose | −/− | |
| D-Fructose | +/− | D-Galactose | −/− | |
| Maltose | +/− | Saccharose | +/− | |
| Lactose | −/− | Trehalose | +/− | |
| D-Sorbitol | −/− | D-Mannitol | −/− | |
| Inositol | −/− | Glycerin | +/− | |
| 5. Other physiological properties | | | | |
| β-Galactosidase activity | | − | | |
| Arginine dehydrolase activity | | + | | |
| Lysine decarboxylase activity | | − | | |
| Tryptophan deaminase activity | | − | | |
| Gelatinase activity | | + | | |

According to a common method, the partial nucleotide sequence of 16S rDNA of the G2 strain (SEQ ID NO. 10) was determined.

The partial nucleotide sequence of 16S rDNA of the G2 strain exhibited high homology to the nucleotide sequence of 16S rDNA of *Bacillus*, and it exhibited the highest identity of 99.2% to the *Bacillus thuringiensis* ATCC 17092 strain.

As a result of a brief molecular phylogenetic analysis based on the partial nucleotide sequence of 16S rDNA, G2 strain is included in a cluster formed of the species of *Bacillus*. Further, G2 strain forms a cluster with *Bacillus thuringiensis* and both exhibits the same molecular phylogenetic position.

G2 strain ferments glycerol, ribose and glucose, does not ferment D-xylose, L-xylose, and galactose, does not exhibit the β-galactosidase activity or urease activity, uses citric acid, does not produce indole, produces acetoin, does not reduce a nitrate salt, does not grow at 45° C., grows under anaerobic conditions, and hydrolyzes starch. Although those properties are almost in match with those of *Bacillus thuringiensis* for which the homology has been demonstrated, not reducing a nitrate salt is different from the typical properties of *Bacillus thuringiensis*. With regard to the physiological biochemical differences, the possibility of having a difference at strain level cannot be ruled out.

As such, G2 strain was identified as *Bacillus thuringiensis*. On Nov. 7, 2012, G2 strain was subjected to international deposition under accession number of NITE BP-1459.

(10) Mycological Properties of *Bacillus* sp. R1

TABLE 10-1

| 1. Morphological properties | |
|---|---|
| Culture conditions | Nutrient agar medium 30° C. |
| Shape of cell | Bacillus (0.7 to 0.8 × 1.5 to 2.5 μm) |
| Presence or absence of cell pleomorphism | – |
| Motility (attachment state of flagella) | +(Peritrichous flagella) |
| Presence or absence of spore (spore location) | +(Center to close to end) |
| 2. Cultural properties | |
| Culture conditions | Nutrient agar medium 30° C. |
| Color | Pale yellow color |
| Gloss | + |
| Pigment production | – |
| Culture conditions | Nutrient broth medium 30° C. |
| Presence or absence of surface growth | – |
| Presence or absence of turbidity in medium | + |
| Culture conditions | Gelatin stab culture 30° C. |
| Growth state | + |
| Gelatin liquefaction | – |
| Culture conditions | Litmus milk 30° C. |
| Solidification | – |
| Liquefaction | – |
| 3. Physiological properties | |
| Gram stain | + |
| Nitrate salt reduction | + |
| Denitrification | – |
| MR test | – |
| VP test | – |
| Indole production | – |
| Hydrogen sulfide production | – |
| Hydrolysis of starch | – |
| Use of citric acid (Koser) | – |
| (Christensen) | – |
| Use of inorganic nitrogen source   Nitrate salt | – |
| Ammonium salt | – |

TABLE 10-2

| Urease activity | | – | |
|---|---|---|---|
| Catalase | | + | |
| Oxidase | | – | |
| Growth range pH | 5 | – | |
| | 8 | + | |
| | 9 | + | |
| Growth range Temperature (° C.) | 15 | + | |
| | 20 | + | |
| | 37 | + | |
| | 45 | – | |
| Anaerobic growing property | | – | |
| O•F Test (oxidation/fermentation) | | –/– | |
| 4. Acid production/gas production from carbohydrates | | | |
| L-Arabinose | –/– | D-Xylose | +/– |
| D-Glucose | +/– | D-Mannose | –/– |
| D-Fructose | +/– | D-Galactose | –/– |
| Maltose | +/– | Saccharose | +/– |
| Lactose | –/– | Trehalose | +/– |
| D-Sorbitol | –/– | D-Mannitol | +/– |
| Inositol | –/– | Glycerin | +/– |
| 5. Other physiological properties | | | |
| β-Galactosidase activity | | – | |
| Arginine dehydrolase activity | | – | |
| Lysine decarboxylase activity | | – | |
| Tryptophan deaminase activity | | – | |
| Gelatinase activity | | + | |

According to a common method, the partial nucleotide sequence of 16S rDNA of the R1 strain (SEQ ID NO. 11) was determined.

The partial nucleotide sequence of 16S rDNA of the R1 strain exhibited high homology to the nucleotide sequence of 16S rDNA of *Bacillus*, and it exhibited the highest identity of 98.9% to the *Bacillus oceanisediminis* H2 strain.

As a result of a brief molecular phylogenetic analysis based on the partial nucleotide sequence of 16S rDNA, R1 strain is included in a cluster formed of the species of *Bacillus*. Further, R1 strain forms a cluster with *Bacillus oceanisediminis* and they are found to be homologous to each other.

R1 strain oxidizes glycerol, ribose and D-xylose, does not oxidize D-arabinose and L-xylose, does not exhibit the arginine hydrolase activity, hydrolyzes gelatin, reduces a nitrate salt, forms a spore, does not grow at 45° C., and does not hydrolyze starch. Although those properties are similar to those of *Bacillus* oceanisediminis for which the homology has been demonstrated, a difference is also recognized. In particular, not exhibiting the arginine hydrolase activity, not growing at 45° C., and not hydrolyzing starch are different from the properties of *Bacillus* oceanisediminis.

As such, R1 strain was identified as *Bacillus* sp. On Nov. 7, 2012, R1 strain was subjected to international deposition under accession number of NITE BP-1460.

(11) Mycological Properties of *Sphingobacterium* sp. B13

TABLE 11-1

| 1. Morphological properties | |
|---|---|
| Culture conditions | Nutrient agar medium 30° C. |
| Shape of cell | Bacillus (0.6 to 0.77 × 1.2 to 1.5 μm) |
| Presence or absence of cell pleomorphism | – |
| Motility (attachment state of flagella) | – |
| Presence or absence of spore (spore location) | – |
| 2. Cultural properties | |
| Culture conditions | Nutrient agar medium 30° C. |
| Color | Yellow color |

TABLE 11-1-continued

| | |
|---|---|
| Gloss | + |
| Pigment production | + |
| Culture conditions | Nutrient broth medium 30° C. |
| Presence or absence of surface growth | − |
| Presence or absence of turbidity in medium | + |
| Culture conditions | Gelatin stab culture 30° C. |
| Growth state | + |
| Gelatin liquefaction | + |
| Culture conditions | Litmus milk 30° C. |
| Solidification | + |
| Liquefaction | − |
| 3. Physiological properties | |
| Gram stain | − |
| Nitrate salt reduction | − |
| Denitrification | − |
| MR test | − |
| VP test | + |
| Indole production | − |
| Hydrogen sulfide production | − |
| Hydrolysis of starch | − |
| Use of citric acid (Koser) | − |
| (Christensen) | − |
| Use of inorganic nitrogen source  Nitrate salt | + |
| Ammonium salt | + |

TABLE 11-2

| | | |
|---|---|---|
| Urease activity | | + |
| Catalase | | + |
| Oxidase | | + |
| Growth range pH | 5 | − |
| | 8 | + |
| | 9 | + |
| Growth range Temperature (° C.) | 15 | + |
| | 20 | + |
| | 37 | + |
| | 45 | − |
| Anaerobic growing property | | + |
| O•F Test (oxidation/fermentation) | | +/− |
| 4. Acid production/gas production from carbohydrates | | |
| L-Arabinose | −/− | D-Xylose −/− |
| D-Glucose | +/− | D-Mannose +/− |
| D-Fructose | −/− | D-Galactose +/− |
| Maltose | +/− | Saccharose −/− |
| Lactose | +/− | Trehalose −/− |
| D-Sorbitol | −/− | D-Mannitol −/− |
| Inositol | −/− | Glycerin +/− |
| 5. Other physiological properties | | |
| β-Galactosidase activity | | + |
| Arginine dehydrolase activity | | − |
| Lysine decarboxylase activity | | − |
| Tryptophan deaminase activity | | − |
| Gelatinase activity | | + |

According to a common method, the partial nucleotide sequence of 16S rDNA of the B13 strain (SEQ ID NO. 16) was determined.

The partial nucleotide sequence of 16S rDNA of the B13 strain exhibited high homology to the nucleotide sequence of 16S rDNA of *Sphingobacterium*, and it exhibited the highest identity of 97.4% to the *Sphingobacterium siyangense* SY1 strain.

B13 strain does not reduce a nitrate salt, does not ferment glucose, exhibits the urease and β-galactosidase activity, hydrolyzes exculin and gelatin, assimilates glucose, D-mannose and maltose, does not assimilate L-arabinose and D-mannitol, does not exhibit motility, exhibits the catalase activity, and does not produce indole. Although those properties are believed to be in match with the properties of *Sphingobacterium*, no known species having the properties that are in match with those of B13 strain was found.

As such, B13 strain was identified as *Sphingobacterium* sp. On Nov. 7, 2012, R1 strain was subjected to international deposition under accession number of NITE BP-1461.

Example 2: Production of Methacrylic Acid Using Synthetic Medium

Using the isolated strains obtained from Example 1, production of methacrylic acid in a synthetic medium was performed.

D22-1 strain, D41-2 strain or D43-1 strain was grown on an agar medium (LB medium, 1.5% agar) and one platinum loop of the cells was inoculated on 10 ml liquid medium. The composition of the medium is shown below. Under aerobic conditions at 30° C. with a rotary shaker (230 rpm), culture was performed for 19 to 22 hours (pre-culture).

$K_2HPO_4$ 1.0 g/l
$MgSO_4 \cdot 7H_2O$ 0.2 g/l
$FeSO_4 \cdot 7H_2O$ 0.01 g/l
$CaCl_2$ 0.01 g/l
L-Valine 5.0 g/l
pH 7.0

2 ml of the pre-culture was inoculated to 100 mL liquid medium (100 ml medium/500 ml volume conical flask). The composition of the medium is the same as that of the pre-culture medium. Under aerobic conditions at 30° C. with a rotary shaker (230 rpm), culture was performed for 44 to 72 hours (main culture).

After the main culture, the main culture was subjected to centrifugal separation (12000 rpm, 10 min) and the supernatant fraction was fractionated. Compounds contained the culture supernatant were analyzed by HPLC. Conditions for HPLC analysis are as follows.

Apparatus: e2695 (manufactured by Waters)
Column: Ion exclusion type polymer column T-132-E for analysis of organic acids (manufactured by WAKO)
Eluent: 0.1% (v/v) phosphoric acid solution
Flow rate: 0.5 ml/min
Column temperature: 40° C.
Sample injection amount: 10 μl
Time for analysis: 40 min
Detector: UV The sample for analysis was suitably diluted with the eluent, filtered with a DISMIC-13CP Cellulose Acetate 0.2 μm filter (manufactured by ADVANTEC), and used. As a result of the analysis, a peak was observed at the same elution time (31.15 min) as methacrylic acid. In "Table 12", the concentration of methacrylic acid which is in the supernatant of each culture at the time of terminating the main culture is shown.

TABLE 12

| Microbial strain | Time for pre-culture (hr) | Time for main culture (hr) | Concentration of methacrylic acid (ppm) |
|---|---|---|---|
| D22-1 | 22 | 72 | 0.05 |
| D41-2 | 19 | 44 | 0.06 |
| D43-1 | 22 | 72 | 0.06 |

GC/MS analysis was performed for the above peak.
Conditions for the GC/MS analysis are as follows.
Apparatus: 6890/5875A (manufactured by Agilent Technologies) Column: DB-FFAP column (manufactured by J&W)
Carrier: He
Oven temperature: after 50° C. (1 min), temperature was raised to 150° C. at 5° C./min, and again raised to 250° C. at 20° C./min.
Inlet temperature: 200° C.

Column flow rate: 1 ml/min (constant flow mode)
Split ratio: 1/50
Sample injection amount: 1 µl
Detector: MSD (EI)

Figure 2:
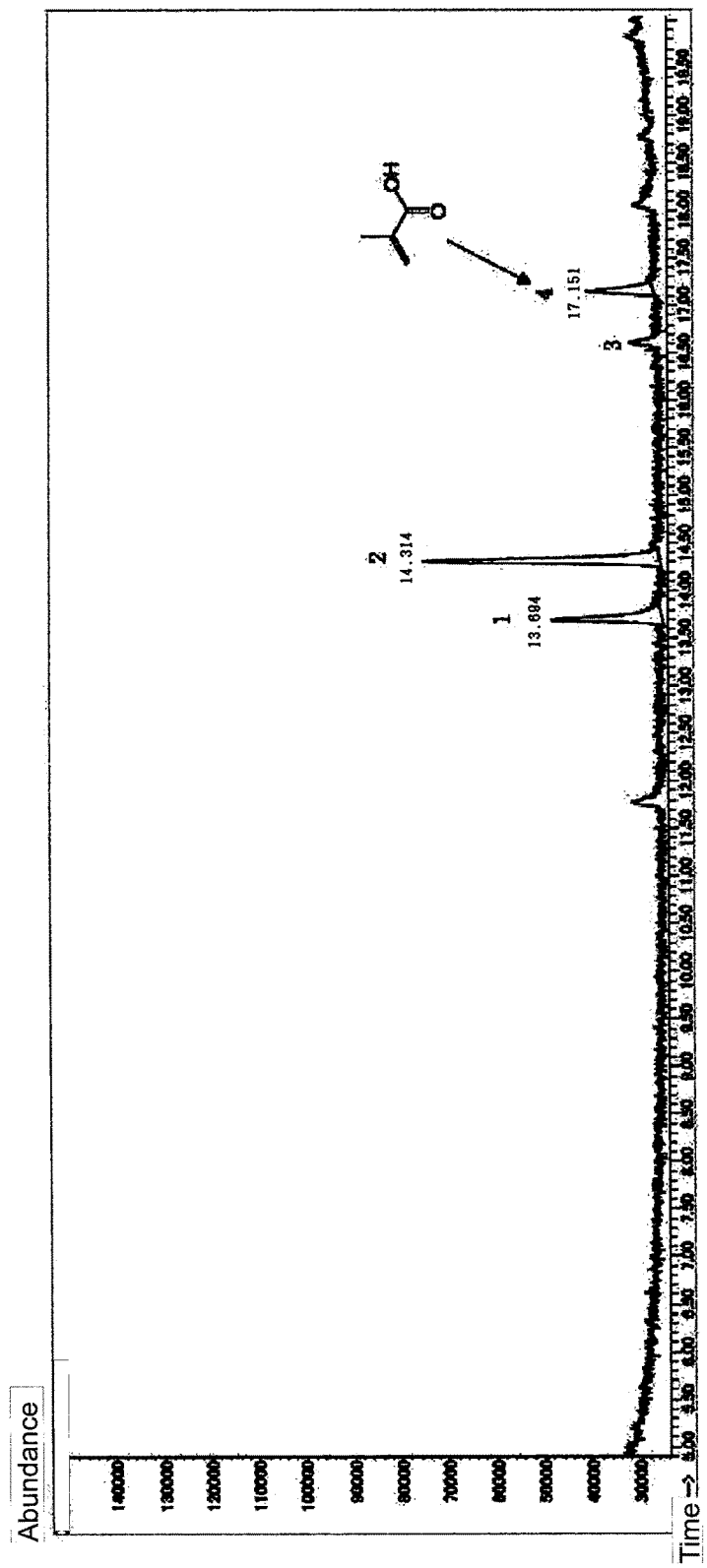
FIG. 2 is a total ion chromatograph illustrating the result of GC/MS analysis of methacrylic acid which has been produced in a broth of methacrylic acid-producing microbes (Example 2).
Figure 3:
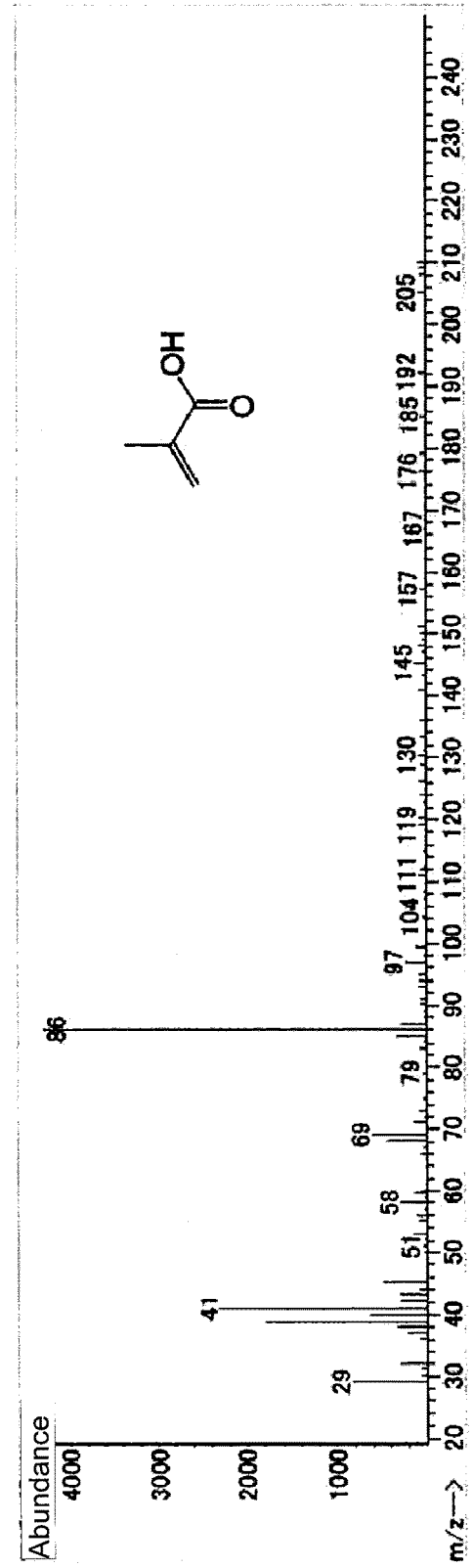
FIG. 3 is a mass spectrum illustrating the result of GC/MS analysis of methacrylic acid which has been produced in a broth of methacrylic acid-producing microbes (Example 2).

The obtained total ion chromatograph is shown in FIG. 2 and the mass spectrum of the observed peak is shown in FIG. 3. As a result of the analysis, it was able to confirm that the peak observed at the same retention time (17.15 min) as methacrylic acid corresponds to methacrylic acid.

Example 3: Production of Methacrylic Acid Using Natural Medium

Using the isolated strains obtained from Example 1, production of methacrylic acid in a natural medium was performed.

G2 strain was grown on an agar medium (LB medium, 1.5% agar) and one platinum loop of the cells was inoculated on 10 ml liquid medium. The composition of the medium is shown below. Under aerobic conditions at 37° C. with a rotary shaker (230 rpm), culture was performed for 24 hours (pre-culture).

Tryptone (manufactured by Becton, Dickinson and Company) 10 g/l
Yeast extract (manufactured by Becton, Dickinson and Company) 5 g/l
NaCl 10 g/l
pH 7.0

1 ml of the pre-culture was inoculated to 100 mL liquid medium (100 ml medium/500 ml volume conical flask). The composition of the medium is the same as that of the pre-culture medium. Under aerobic conditions at 37° C. with a rotary shaker (230 rpm), culture was performed for 24 hours (main culture).

After the main culture, the main culture was subjected to centrifugal separation (12000 rpm, 10 min) and the supernatant fraction was fractionated. Compounds contained the culture supernatant were analyzed by the method described in Example 2. As a result, a peak was observed at the same elution time (31.15 min) as methacrylic acid. The concentration of methacrylic acid in the culture was 1.0 ppm.

Example 4: Production of Methacrylic Acid Based on Resting Cell Reaction

Using the isolated strains obtained from Example 1, production of methacrylic acid was performed based on resting cell reaction.

B25-2 strain, D22-1 strain, D43-1 strain, D25 strain, D26 strain, D29 strain, D41-2 strain, G1 strain, G2 strain, R1 strain, and B13 strain were grown on an agar medium (LB medium, 1.5% agar) and one platinum loop of the cells was inoculated on 10 ml liquid medium. The composition of the medium is shown below. Under aerobic conditions at 30° C. with a rotary shaker (230 rpm), culture was performed for 19 to 22 hours (pre-culture).

$K_2HPO_4$ 1.0 g/l
$MgSO_4 \cdot 7H_2O$ 0.2 g/l
$FeSO_4 \cdot 7H_2O$ 0.01 g/l
$CaCl_2$ 0.01 g/l
L-Valine 5.0 g/l
pH 7.0

2 ml of the pre-culture was inoculated to 100 mL liquid medium (100 ml medium/500 ml volume conical flask). The composition of the medium is the same as that of the pre-culture medium. Under aerobic conditions at 30° C. with a rotary shaker (230 rpm), culture was performed for 69 to 76 hours (main culture).

After the main culture, 40 mL of the main broth was transferred to a conical tube with volume of 50 mL and separated by centrifuge (12000 rpm, 10 min) to obtain the cells. To the cells, 10 mL solution for resting cell reaction was added to perform the resting cell reaction. The composition of the solution for resting cell reaction includes 5.0 g/l L-valine, 50 mM phosphate buffer, and pH 7.0. The reaction was performed for 24 hours under aerobic conditions at 30° C. with a rotary shaker (230 rpm).

According to the method shown in Example 2, the compounds contained the solution for resting cell reaction were analyzed. As a result, a peak was observed at the same elution time (31.15 min) as methacrylic acid. In "Table 13", the concentration of methacrylic acid which is in each reaction solution at the time of terminating the resting cell reaction is shown.

TABLE 13

| Microbial strain | Resting cell reaction OD | Concentration of methacrylic acid (ppm) |
| --- | --- | --- |
| B25-2 | 17 | 0.2 |
| D22-1 | 17 | 0.3 |
| D43-1 | 15 | 0.2 |
| D25 | 17 | 1.0 |
| D26 | 18 | 0.8 |
| D29 | 18 | 0.2 |
| D41-2 | 13 | 0.7 |
| G1 | 21 | 10 |
| G2 | 21 | 10 |
| R1 | 20 | 12 |
| B13 | 31 | 10 |

Example 5: Production of Methacrylic Acid in Synthetic Medium Using Genus Pseudomonas Pseudomonas putida NBRC12996 was grown on an agar medium (LB medium, 1.5% agar) and one platinum loop of the cells was inoculated on 10 ml liquid medium. Under aerobic conditions at 30° C. with a rotary shaker (230 rpm), culture was performed for 1 to 4 days (pre-culture). The composition of the medium for the pre-culture is described below.

$Na_2HPO_4$ (anhydrous) 6.0 g/l
$KH_2PO_4$ 3.0 g/l
NaCl 0.5 g/l
$NH_4Cl$ 1.0 g/l
1M $MgSO_4 \cdot 7H_2O$ 1 ml
1M $CaCl_2$ 0.1 ml
1% Thiamine 1 ml
Glucose 2.0 g/l 1 ml of the pre-culture was inoculated to 100 mL liquid medium (100 ml medium/500 ml volume conical flask). Under aerobic conditions at 30° C. with a rotary shaker (230 rpm), culture was performed for 2 days (main culture). The composition of the medium for the main culture is described below.

$Na_2HPO_4$ (anhydrous) 6.0 g/l
$KH_2PO_4$ 3.0 g/l
NaCl 0.5 g/l
$NH_4Cl$ 1.0 g/l
1M $MgSO_4 \cdot 7H_2O$ 1 ml
1M $CaCl_2$ 0.1 ml
1% Thiamine 1 ml
L-Valine 2.0 g/l After the main culture, the main broth was separated by centrifuge (7500 rpm, 15 min) and the supernatant fraction was subjected to a filtration treatment which uses a DISMIC-13CP Cellulose Acetate 0.2 µm filter (manufactured by ADVANTEC). The compounds contained in the culture supernatant were analyzed according to two kinds of analysis conditions. Conditions for HPLC analysis are as follows.

Analysis condition A
  Apparatus: e2695 (manufactured by Waters)
  Column: Ion exclusion type polymer column T-132-E for analysis of organic acids (manufactured by WAKO)
  Eluent: 0.1% (v/v) phosphoric acid solution
  Flow rate: 0.5 ml/min
  Column temperature: 40° C.
  Sample injection amount: 10 µl
  Time for analysis: 40 min
  Detector: UV Analysis Condition B
  Apparatus: JASCO UV-970, CO-960, PU-980, DG-1580-54 (manufactured by JASCO, Japan)
  Column: Inertsil RODS-3V (manufactured by GL Sciences)
  Eluent: 20% (v/v) methanol, 0.2% (v/v) phosphoric acid solution
  Flow rate: 1.0 ml/min
  Column temperature: 40° C.
  Sample injection amount: 5 µl
  Time for analysis: 15 min
  Detector: UV As a result of the analysis, a peak was observed at the same elution time as methacrylic acid for both the analysis condition A and the analysis condition B. The concentration of methacrylic acid in the supernatant of the culture was 0.2 ppm at the time of terminating the main culture.

Example 6: Production of Methacrylic Acid in Synthetic Medium Using Genus *Brevundimonas*, Genus *Ochrobactrum*, and Genus *Paracoccus*

*Brevundimonas subvibrioides* NBRC 16000, *Ochrobactrum grignonense* NBRC102586, *Ochrobactrum lupini* NBRC102587, and *Paracoccus aminophilus* NBRC 16710 were grown on an agar medium (plate culture). The composition of the medium for plate culture is shown below.
  Polypeptone (manufactured by Becton, Dickinson and Company) 10 g
  Yeast extract (manufactured by Becton, Dickinson and Company) 2 g
  $MgSO_4 \cdot 7H_2O$ 1 g
  Distilled water 1 l
  Ager 15 g
  pH 7.0

Cells grown by plate culture were inoculated in 10 ml liquid medium (one platinum loop) and cultured under aerobic conditions at 30° C. with a rotary shaker (230 rpm) for 3 to 4 days (pre-culture). The composition of the medium for the pre-culture is described below.
  $Na_2HPO_4$ (anhydrous) 6.0 g/l
  $KH_2PO_4$ 3.0 g/l
  NaCl 0.5 g/l
  $NH_4Cl$ 1.0 g/l
  1M $MgSO_4 \cdot 7H_2O$ 1 ml
  1M $CaCl_2$ 0.1 ml
  1% Thiamine 1 ml
  Glucose 2.0 g/l 1 ml of the pre-culture was inoculated to 100 mL liquid medium (100 ml medium/500 ml volume conical flask). Under aerobic conditions at 30° C. with a rotary shaker (230 rpm), culture was performed for 2 days (main culture). The composition of the medium for the main culture is described below.
  $Na_2HPO_4$ (anhydrous) 6.0 g/l
  $KH_2PO_4$ 3.0 g/l
  NaCl 0.5 g/l
  $NH_4Cl$ 1.0 g/l
  1M $MgSO_4 \cdot 7H_2O$ 1 ml
  1M $CaCl_2$ 0.1 ml
  1% Thiamine 1 ml
  L-Valine 2.0 g/l
  Glucose 2.0 g/l After the main culture, the main broth was separated by centrifuge (7500 rpm, 15 min) and the supernatant fraction was subjected to a filtration treatment which uses a DISMIC-13CP Cellulose Acetate 0.2 µm filter (manufactured by ADVANTEC). The compounds contained in the culture supernatant were analyzed according to the analysis condition A described in Example 5. As a result, a peak was observed at the same elution time as methacrylic acid. In "Table 14", the concentration of methacrylic acid which is in each culture supernatant at the time of terminating the main culture is shown.

TABLE 14

| Microbial strain | Number of days for plate culture (days) | Number of days for pre-culture (days) | Number of days for main culture (days) | Concentration of methacrylic acid (ppm) |
|---|---|---|---|---|
| Brevundimonas subvibrioides NBRC16000 | 3 | 3 | 2 | 0.1 |
| Ochrobactrum grignonense NBRC102586 | 3 | 3 | 2 | 1.0 |
| Ochrobactrum lupini NBRC102587 | 3 | 3 | 2 | 0.2 |
| Paracoccus aminophilus NBRC16710 | 3 | 4 | 2 | 0.3 |

Example 7: Production of Methacrylic Acid in Synthetic Medium Using Genus *Sphingomonas*, Genus *Ochrobactrum*, Genus *Paenibacillus*, and Genus *Mesorhizobium*

*Sphingomonas paucimobilis* NBRC13935, *Ochrobactrum intermedium* NBRC15820, *Paenibacillus* sp. NBRC13157, *Mesorhizobium loti* ATCC700743 were grown on a nutrient agar medium (manufactured by Becton, Dickinson and Company, agar 1.5%). The grown cells were inoculated (one platinum loop) to 10 ml liquid medium and cultured under aerobic conditions at 30° C. with a rotary shaker (230 rpm) for 1 to 4 days (pre-culture). The composition of the medium for the pre-culture is described below.
  $Na_2HPO_4$ (anhydrous) 6.0 g/l
  $KH_2PO_4$ 3.0 g/l
  NaCl 0.5 g/l
  $NH_4Cl$ 1.0 g/l
  1M $MgSO_4 \cdot 7H_2O$ 1 ml
  1M $CaCl_2$ 0.1 ml
  1% Thiamine 1 ml
  Glucose 2.0 g/l 1 ml of the pre-culture was inoculated to 100 mL liquid medium (100 ml medium/500 ml volume conical flask). Under aerobic conditions at 30° C. with a rotary shaker (230 rpm), culture was performed for 3 to 6 days (main culture). The composition of the medium for the main culture is described below.

$Na_2HPO_4$ (anhydrous) 6.0 g/l
$KH_2PO_4$ 3.0 g/l
NaCl 0.5 g/l
$NH_4Cl$ 1.0 g/l
1M $MgSO_4.7H_2O$ 1 ml
1M $CaCl_2$ 0.1 ml
1% Thiamine 1 ml
L-Valine 2.0 g/l
Glucose 2.0 g/l After the main culture, the main broth was separated by centrifuge (7500 rpm, 15 min) and the supernatant fraction was subjected to a filtration treatment which uses a DISMIC-13CP Cellulose Acetate 0.2 μm filter (manufactured by ADVANTEC). The compounds contained in the culture supernatant were analyzed according to the analysis condition B described in Example 5. As a result, a peak was observed at the same elution time as methacrylic acid. In "Table 15", the concentration of methacrylic acid which is in each culture supernatant at the time of terminating the main culture is shown.

TABLE 15

| Microbial strain | Number of days for plate culture (days) | Number of days for pre-culture (days) | Number of days for main culture (days) | Concentration of methacrylic acid (ppm) |
|---|---|---|---|---|
| Sphingomonas paucimobilis NBRC13935 | 3 | 1 | 6 | 0.2 |
| Ochrobactrum intermedium NBRC15820 | 3 | 3 | 3 | 0.6 |
| Paenibacillus sp. NBRC13157 | 3 | 2 | 3 | 0.1 |
| Mesorhizobium loti ATCC700743 | 6 | 4 | 3 | 0.2 |

Example 8: Production of methacrylic acid in synthetic medium using genus *Bacillus*

*Bacillus badius* ATCC 14574 was grown on a nutrient agar medium (manufactured by Becton, Dickinson and Company, agar 1.5%). The grown cells were inoculated (one platinum loop) to 10 ml liquid medium and cultured under aerobic conditions at 30° C. with a rotary shaker (230 rpm) for 1 day (pre-culture).

1 ml of the pre-culture was inoculated to 100 mL liquid medium (100 ml medium/500 ml volume conical flask). Under aerobic conditions at 30° C. with a rotary shaker (230 rpm), culture was performed for 8 days (main culture). Composition of the medium for the main culture is described below.

$Na_2HPO_4$ (anhydrous) 6.0 g/l
$KH_2PO_4$ 3.0 g/l
NaCl 0.5 g/l
$NH_4Cl$ 1.0 g/l
1M $MgSO_4.7H_2O$ 1 ml
1M $CaCl_2$ 0.1 ml
1% Thiamine 1 ml
L-Valine 2.0 g/l
Glucose 2.0 g/l After the main culture, the main broth was separated by centrifuge (7500 rpm, 15 min) and the supernatant fraction was subjected to a filtration treatment which uses a DISMIC-13CP Cellulose Acetate 0.2 μm filter (manufactured by ADVANTEC). The compounds contained in the culture supernatant were analyzed according to the two kinds of analysis condition described in Example 5. As a result, a peak was observed at the same elution time as methacrylic acid for both the analysis condition A and the analysis condition B. Concentration of methacrylic acid in the culture supernatant at the time of terminating the main reaction was 2.0 ppm and 2.4 ppm for the analysis condition A and the analysis condition B, respectively.

Example 9: Production of Methacrylic Acid in Natural Medium Using Genus *Ochrobactrum*

*Ochrobactrum* sp. NBRC 12951 was grown on a nutrient agar medium (manufactured by Becton, Dickinson and Company, agar 1.5%). The grown cells were inoculated (one platinum loop) to 100 mL liquid medium (100 ml medium/500 ml volume conical flask) and cultured under aerobic conditions at 30° C. with a rotary shaker (230 rpm) for 8 days (main culture). Composition of the medium for the main culture is described below.

Nutrient medium 8 g/l
L-Valine 2.0 g/l

After the main culture, the main broth was separated by centrifuge (7500 rpm, 15 min) and the supernatant fraction was subjected to a filtration treatment which uses a DISMIC-13CP Cellulose Acetate 0.2 μm filter (manufactured by ADVANTEC). The compounds contained in the culture supernatant were analyzed according to the analysis condition B described in Example 5. As a result, a peak was observed at the same elution time as methacrylic acid. Concentration of methacrylic acid in the culture supernatant at the time of terminating the main reaction was 3.1 ppm.

Example 10: Production of Methacrylic Acid in Natural Medium Using Genus *Brevundimonas*

*Brevundimonas diminuta* ATCC11568 was grown on a nutrient agar medium (manufactured by Becton, Dickinson and Company, agar 1.5%). The grown cells were inoculated (one platinum loop) to 10 mL nutrient medium and cultured under aerobic conditions at 30° C. with a rotary shaker (230 rpm) for 1 day (pre-culture). The pre-culture and 40% glycerol were mixed with each other at 1:1 and subjected to cryopreservation at −80° C.

The pre-culture which has been remained under cryopreservation was thawed at room temperature and 0.5 mL was inoculated to 100 ml liquid medium (100 ml medium/500 ml volume conical flask). It was then cultured under aerobic conditions at 30° C. with a rotary shaker (230 rpm) for 2 days (main culture). Composition of the medium for the main culture is described below.

Nutrient medium 8 g/l
L-Valine 2.0 g/l

After the main culture, the main broth was separated by centrifuge (7500 rpm, 15 min) and the supernatant fraction was subjected to a filtration treatment which uses a DISMIC-13CP Cellulose Acetate 0.2 μm filter (manufactured by ADVANTEC). The compounds contained in the culture supernatant were analyzed according to the analysis condition B described in Example 5. As a result, a peak was observed at the same elution time as methacrylic acid and the concentration of methacrylic acid in the culture supernatant at the time of terminating the main culture was 37.0 ppm.

Example 11: Production of Methacrylic Acid Using Yeast

*Candida utilis* NBRC 1086 was grown on a nutrient agar medium (manufactured by Becton, Dickinson and Company, agar 1.5%). The grown cells were inoculated (one platinum loop) to 10 mL liquid medium and cultured under aerobic conditions at 24° C. with a rotary shaker (230 rpm) for 1 day (pre-culture). Composition of the medium for the pre-culture is described below.

Yeast extract (manufactured by Becton, Dickinson and Company) 20 g/l
Polypeptone (manufactured by Becton, Dickinson and Company) 20 g/l
Glucose 20 g/l 1 ml of the pre-culture was inoculated to 100 mL liquid medium (100 ml medium/500 ml volume conical flask) and cultured under aerobic conditions at 24° C. with a rotary shaker (230 rpm) for 2 days (main culture). Composition of the medium for the main culture is described below.

Glucose 2.0 g/l
L-Valine 2.0 g/l
$(NH_4)_2SO_4$ 6.0 g/l
KCl 2.4 g/l
NaCl 0.12 g/l
$H_3PO_4$ 3.0 g/l
$MgSO_4.7H_2O$ 2.4 g/l
$FeSO_4.7H_2O$ 0.01 g/l
$ZnSO_4.7H_2O$ 0.12 g/l
$MnSO_4 0.4-6H_2O$ 0.024 g/l
$CuSO_4.5H_2O$ 0.006 g/l
$CaCl_2$ 0.12 g/l
Vitamin Mix 30 ml Composition of Vitamin Mix is shown below.
Biotin 0.2 g/l
Calcium pantothenate 2 g/l
Folic acid 0.002 g/l
Thiamine hydrochloride 0.4 g/l
Rivoflavin 0.2 g/l
Nicotinic acid 0.4 g/l
Pyridoxine hydrochloride 0.4 g/l
Inositol 1 g/l
p-Aminobenzoic acid 0.2 g/l After the main culture, the main broth was separated by centrifuge (7500 rpm, 15 min) and the supernatant fraction was subjected to a filtration treatment which uses a DISMIC-13CP Cellulose Acetate 0.2 μm filter (manufactured by ADVANTEC). The compounds contained in the culture supernatant were analyzed according to the analysis condition A described in Example 5. As a result, a peak was observed at the same elution time as methacrylic acid and the concentration of methacrylic acid in the culture supernatant at the time of terminating the main culture was 0.1 ppm.

Example 12: Production of Methacrylic Acid Using Mildew

*Aspergillus flavus* NBRC8558, *Aspergillus oryzae* NBRC4255 was grown on a potato dextrose agar medium (manufactured by Nissui Pharmaceutical Co., Ltd.). The grown mycelia and spores were suspended in 5 ml sterilized water, and 1 ml of the resultant was inoculated to 100 mL liquid medium (100 ml medium/500 ml volume conical flask) and cultured under aerobic conditions at 24° C. with a rotary shaker (230 rpm) for 2 days (main culture). Composition of the medium for the main culture is described below.

L-Valine 2.0 g/l
$NaNO_3$ 2.5 g/l
$K_2HPO_4$ 1.25 g/l
$MgSO_4.7H_2O$ 0.63 g/l
KCl 0.63 g/l
$FeSO_4.7H_2O$ 0.013 g/l
Wheat bran 5 g/l
pH 7.0

After the main culture, the main broth was separated by centrifuge (7500 rpm, 15 min) and the supernatant fraction was subjected to a filtration treatment which uses a DISMIC-13CP Cellulose Acetate 0.2 μm filter (manufactured by ADVANTEC). The compounds contained in the culture supernatant were analyzed according to the analysis condition A and the condition B described in Example 5. As a result, a peak was observed at the same elution time as methacrylic acid for both the condition A and the condition B. In "Table 16", concentration of methacrylic acid which is in the supernatant of each culture at the time of terminating the main culture is shown.

TABLE 16

| | Concentration of methacrylic acid (ppm) | |
|---|---|---|
| Microbial strain | Analysis condition A | Analysis condition B |
| Aspergillus flavus NBRC8558 | 0.3 | 0.5 |
| Aspergillus oryzae NBRC4255 | 0.1 | 0.04 |

Example 13: Production of Methacrylic Acid Based on Resting Cell Reaction Using Genus *Sphingomonas*, Genus *Pedobacter*, Genus *Bacillus*, and Genus *Listonella*

*Sphingomonas paucimobilis* NBRC13935, *Pedobacter heparinus* NBRC12017, *Bacillus subtilis* NBRC12210, and *Listonella anguillarum* ATCC19264 were grown on a nutrient agar medium (manufactured by Becton, Dickinson and Company, agar 1.5%). The cells were inoculated (one platinum loop) to 10 mL liquid medium (one platinum loop) and cultured under aerobic conditions at 30° C. with a rotary shaker (230 rpm) for 1 to 3 days (pre-culture). Composition of the medium for the pre-culture is described below.

$Na_2HPO_4$ (anhydrous) 6.0 g/l
$KH_2PO_4$ 3.0 g/l
NaCl 0.5 g/l
$NH_4Cl$ 1.0 g/l
1M $MgSO_4.7H_2O$ 1 ml
1M $CaCl_2$ 0.1 ml
1% Thiamine 1 ml
Glucose 2.0 g/l 1 ml of the pre-culture was inoculated to 100 mL liquid medium (100 ml medium/500 ml volume conical flask) and cultured under aerobic conditions at 30° C. with a rotary shaker (230 rpm) for 3 to 6 days (main culture). Composition of the medium for the main culture is described below.

$Na_2HPO_4$ (anhydrous) 6.0 g/l
$KH_2PO_4$ 3.0 g/l
NaCl 0.5 g/l
$NH_4Cl$ 1.0 g/l 1M MgSO$_4$.7H$_2$O 1 ml
1M CaCl$_2$ 0.1 ml
1% Thiamine 1 ml
L-Valine 2.0 g/l
Glucose 2.0 g/l After the main culture, the entire volume of the main culture was transferred to a centrifuge tube with volume of 225 ml and then centrifuged (5000 rpm, 15 min). By removing the supernatant, the cells were obtained. To the cells, 40 ml of 50 mM phosphate buffer (pH 7.0) were added and the cells were suspended and centrifuged again under the same conditions. By removing the supernatant, the washed cells were obtained. To the washed cells, 3 ml of 50 mM phosphate buffer (pH 7.0) were added to prepare a cell suspension. To a conical tube with volume of 50 mL, 3 ml of the cell suspension and 3 ml of the solution for resting cell reaction were added to perform the resting cell reaction. The reaction was allowed to occur under aerobic conditions at 30° C. with a rotary shaker (230 rpm) for 24 hours. Composition of the solution for resting cell reaction includes 5.0 g/l L-valine and 50 mM phosphate buffer (pH 7.0).

Five hours and twenty-four hours after starting the resting cell reaction, 1.6 ml of the reaction solution were collected. The reaction solution was separated by centrifuge (15000 rpm, 5 min) and the supernatant fraction was subjected to a filtration treatment which uses a DISMIC-13CP Cellulose Acetate 0.2 μm filter (manufactured by ADVANTEC). The compounds contained in the culture supernatant were analyzed according to the analysis condition A described in Example 5. As a result, a peak was observed at the same elution time as methacrylic acid. In "Table 17", concentration of methacrylic acid which is in the supernatant of the reaction solution of the resting cell reaction is shown.

TABLE 17

| Microbial strain | Number of days for pre-culture (days) | Number of days for main culture (days) | Concentration of methacrylic acid (ppm) | |
|---|---|---|---|---|
| | | | After 5 hours | After 24 hours |
| Sphingomonas paucimobilis NBRC 13935 | 1 | 6 | 0.2 | 0.1 |
| Pedobacter heparinus NBRC12017 | 3 | 3 | 1.2 | 2.8 |
| Bacillus subtilis NBRC12210 | 2 | 3 | 0.1 | 0.4 |
| Listonella anguillarum ATCC19264 | 3 | 3 | ND | 0.4 |

(ND: Not Detected)

Example 14: Production of Methacrylic Acid Based on Resting Cell Reaction Using Genus *Ochrobactrum* and Genus *Paracoccus*

*Ochrobactrum grignonense* NBRC102586, *Ochrobactrum lupini* NBRC102587, and *Paracoccus aminophilus* NBRC16710 were grown on an agar medium (plate culture). Composition of the medium for plate culture is shown below.

Polypeptone (manufactured by Becton, Dickinson and Company) 10 g
Yeast extract (manufactured by Becton, Dickinson and Company) 2 g
MgSO$_4$ 7.H$_2$O 1 g
Distilled water 1 l
Ager 15 g
pH 7.0

Cells grown by plate culture were inoculated (one platinum loop) to 10 ml liquid medium and cultured under aerobic conditions at 30° C. with a rotary shaker (230 rpm) for 3 to 4 days (pre-culture). Composition of the medium for the pre-culture is described below.

Na$_2$HPO$_4$ (anhydrous) 6.0 g/l
KH$_2$PO$_4$ 3.0 g/l
NaCl 0.5 g/l
NH$_4$Cl 1.0 g/l
1M MgSO$_4$.7H$_2$O 1 ml
1M CaCl$_2$ 0.1 ml
1% Thiamine 1 ml
Glucose 2.0 g/l 1 ml of the pre-culture was inoculated to 100 mL liquid medium (100 ml medium/500 ml volume conical flask). Under aerobic conditions at 30° C. with a rotary shaker (230 rpm), culture was performed for 2 days (main culture). Composition of the medium for the main culture is described below.

Na$_2$HPO$_4$ (anhydrous) 6.0 g/l
KH$_2$PO$_4$ 3.0 g/l
NaCl 0.5 g/l
NH$_4$Cl 1.0 g/l
1M MgSO$_4$.7H$_2$O 1 ml
1M CaCl$_2$ 0.1 ml
1% Thiamine 1 ml
L-Valine 2.0 g/l
Glucose 2.0 g/l After the main culture, the entire volume of the main culture was transferred to a centrifuge tube with volume of 225 ml and then centrifuged (5000 rpm, 15 min) By removing the supernatant, the cells were obtained. To the cells, 40 ml of 50 mM phosphate buffer (pH 7.0) were added and the cells were suspended and centrifuged again under the same conditions. By removing the supernatant, the washed cells were obtained. To the washed cells, 3 ml of 50 mM phosphate buffer (pH 7.0) were added to prepare a cell suspension. To a conical tube with volume of 50 mL, 3 ml of the cell suspension and 3 ml of the solution for resting cell reaction were added to perform the resting cell reaction. The reaction was allowed to occur under aerobic conditions at 30° C. with a rotary shaker (230 rpm) for 24 hours. Composition of the solution for resting cell reaction includes 5.0 g/l L-valine and 50 mM phosphate buffer (pH 7.0).

Five hours and twenty-four hours after starting the resting cell reaction, 1.6 ml of the reaction solution were collected. The reaction solution was separated by centrifuge (15000 rpm, 5 min) and the supernatant fraction was subjected to a filtration treatment which uses a DISMIC-13CP Cellulose Acetate 0.2 μm filter (manufactured by ADVANTEC). The compounds contained in the culture supernatant were analyzed according to the analysis condition A described in Example 5. As a result, a peak was observed at the same elution time as methacrylic acid. In "Table 18", concentration of methacrylic acid which is in the supernatant of the reaction solution of the resting cell reaction is shown.

TABLE 18

| Microbial strain | Number of days for pre-culture (days) | Number of days for main culture (days) | Concentration of methacrylic acid (ppm) | |
|---|---|---|---|---|
| | | | After 5 hours | After 24 hours |
| Ochrobactrum grignonense NBRC 102586 | 3 | 2 | 1.4 | 18.1 |
| Ochrobactrum lupini NBRC 102587 | 3 | 2 | 1.0 | 4.9 |
| Paracoccus aminophilus NBRC16710 | 4 | 2 | 0.3 | 2.5 |

Example 15: Production of Methacrylic Acid Based on Resting Cell Reaction Using Genus *Bacillus* and Genus *Streptomyces*

*Bacillus megaterium* NBRC15308, *Bacillus simplex* ATCC49097, and *Streptomyces griseus* NBRC 13350 were grown on a nutrient agar medium (manufactured by Becton, Dickinson and Company, agar 1.5%). The cells were inoculated (one platinum loop) to 10 mL liquid medium (one platinum loop) and cultured under aerobic conditions at 30° C. with a rotary shaker (230 rpm) for 1 day (pre-culture).

1 ml of the pre-culture was inoculated to 100 mL liquid medium (100 ml medium/500 ml volume conical flask) and cultured under aerobic conditions at 30° C. with a rotary shaker (230 rpm) for 2 days (main culture). Composition of the medium for the main culture is described below.

Na$_2$HPO$_4$ (anhydrous) 6.0 g/l
KH$_2$PO$_4$ 3.0 g/l
NaCl 0.5 g/l
NH$_4$Cl 1.0 g/l
1M MgSO$_4$.7H$_2$O 1 ml
1M CaCl$_2$ 0.1 ml
1% Thiamine 1 ml
L-Valine 2.0 g/l
Glucose 2.0 g/l After the main culture, the entire volume of the main culture was transferred to a centrifuge tube with volume of 225 ml and then centrifuged (5000 rpm, 15 min). By removing the supernatant, the cells were obtained. To the cells, 40 ml of 50 mM phosphate buffer (pH 7.0) were added and the cells were suspended and centrifuged again under the same conditions. By removing the supernatant, the washed cells were obtained. To the washed cells, 3 ml of 50 mM phosphate buffer (pH 7.0) were added to prepare a cell suspension. To a conical tube with volume of 50 mL, 3 ml of the cell suspension and 3 ml of the solution for resting cell reaction were added to perform the resting cell reaction. The reaction was allowed to occur under aerobic conditions at 30° C. with a rotary shaker (230 rpm) for 24 hours. Composition of the solution for resting cell reaction includes 5.0 g/l L-valine and 50 mM phosphate buffer (pH 7.0).

Five hours (*Streptomyces griseus* NBRC13350) or twenty-four hours (*Bacillus megaterium* NBRC 15308 and *Bacillus simplex* ATCC49097) after starting the resting cell reaction, 1.6 ml of the reaction solution were collected. The reaction solution was separated by centrifuge (15000 rpm, 5 min) and the supernatant fraction was subjected to a filtration treatment which uses a DISMIC-13CP Cellulose Acetate 0.2 μm filter (manufactured by ADVANTEC). The compounds contained in the supernatant of the reaction solution were analyzed according to the analysis condition A described in Example 5. As a result, a peak was observed at the same elution time as methacrylic acid. In "Table 19", concentration of methacrylic acid which is in the supernatant of the reaction solution of the resting cell reaction is shown.

TABLE 19

| Microbial strain | Concentration of methacrylic acid (ppm) |
|---|---|
| Bacillus megaterium NBRC15308 | 0.1 |
| Bacillus simplex ATCC49097 | 0.1 |
| Streptomyces griseus NBRC13350 | 0.1 |

Example 16: Production of Methacrylic Acid Based on Resting Cell Reaction Using Genus *Comamonas*, Genus *Acinetobacter*, and Genus *Xanthobacter*

*Comamonas terrigena* NBRC13299, *Acinetobacter junii* ATCC17908, and *Xanthobacter autotrophicus* ATCC35674 were grown on a nutrient agar medium (manufactured by Becton, Dickinson and Company, agar 1.5%). The cells were inoculated (one platinum loop) to 10 mL nutrient medium (one platinum loop) and cultured under aerobic conditions at 30° C. with a rotary shaker (230 rpm) for 1 day (pre-culture).

1 ml of the pre-culture was inoculated to 100 mL liquid medium (100 ml medium/500 ml volume conical flask) and cultured under aerobic conditions at 30° C. with a rotary shaker (230 rpm) for 2 days (main culture). Composition of the medium for the main culture is described below.

Nutrient medium 8 g/l
L-Valine 2.0 g/l

After the main culture, the entire volume of the main culture was transferred to a centrifuge tube with volume of 225 ml and then centrifuged (5000 rpm, 15 min). By removing the supernatant, the cells were obtained. To the cells, 40 ml of 50 mM phosphate buffer (pH 7.0) were added and the cells were suspended and centrifuged again under the same conditions. By removing the supernatant, the washed cells were obtained. To the washed cells, 3 ml of 50 mM phosphate buffer (pH 7.0) were added to prepare a cell suspension. To a conical tube with volume of 50 mL, 3 ml of the cell suspension and 3 ml of the solution for resting cell reaction were added to perform the resting cell reaction. The reaction was allowed to occur under aerobic conditions at 30° C. with a rotary shaker (230 rpm) for 24 hours. Composition of the solution for resting cell reaction includes 5.0 g/l L-valine or isobutyric acid and 50 mM phosphate buffer (pH 7.0).

Five hours and twenty-four hours after starting the resting cell reaction, 1.6 ml of the reaction solution were collected. The reaction solution was separated by centrifuge (15000 rpm, 5 min) and the supernatant fraction was subjected to a filtration treatment which uses a DISMIC-13CP Cellulose Acetate 0.2 μm filter (manufactured by ADVANTEC). The compounds contained in the culture supernatant were analyzed according to the analysis condition A described in Example 5. As a result, a peak was observed at the same elution time as methacrylic acid. In "Table 20", concentration of methacrylic acid which is in the supernatant of the reaction solution of the resting cell reaction is shown.

TABLE 20

| Microbial strain | Substrate for resting reaction | Concentration of methacrylic acid (ppm) | |
|---|---|---|---|
| | | After 5 hours | After 24 hours |
| Comamonas terrigena NBRC13299 | Isobutyric acid | 1.7 | 5.2 |
| Acinetobacter junii ATCC17908 | Valine | ND | 0.3 |
| Xanthobacter autotrophicus ATCC35674 | Valine | 0.1 | 0.1 |

(ND: Not Detected)

Example 17: Production of Methacrylic Acid Based on Resting Cell Reaction Using Genus *Ochrobactrum*, Genus *Achromobacter*, and Genus *Acinetobacter*

*Ochrobactrum* sp. NBRC12951, *Ochrobactrum intermedium* NBRC13694, *Ochrobactrum anthropi* ATCC49237, *Achromobacter denitrificans* NBRC12669, and *Acinetobacter haemolyticus* ATCC 17906 were grown on a nutrient agar medium (manufactured by Becton, Dickinson and Company, agar 1.5%). The grown cells were inoculated (one platinum loop) to 100 mL liquid medium (100 ml medium/500 ml volume conical flask) and cultured under aerobic conditions at 30° C. with a rotary shaker (230 rpm) for 3 to 4 days (main culture). Composition of the medium for the main culture is described below.
Nutrient medium 8 g/l
L-Valine 2.0 g/l
After the main culture, the entire volume of the main culture was transferred to a centrifuge tube with volume of 225 ml and then centrifuged (5000 rpm, 15 min). By removing the supernatant, the cells were obtained. To the cells, 40 ml of 50 mM phosphate buffer (pH 7.0) were added and the cells were suspended and centrifuged again under the same conditions. By removing the supernatant, the washed cells were obtained. To the washed cells, 3 ml of 50 mM phosphate buffer (pH 7.0) were added to prepare a cell suspension. To a conical tube with volume of 50 mL, 3 ml of the cell suspension and 3 ml of the solution for resting cell reaction were added to perform the resting cell reaction. The reaction was allowed to occur under aerobic conditions at 30° C. with a rotary shaker (230 rpm) for 24 hours. Composition of the solution for resting cell reaction includes 5.0 g/l L-valine or isobutyric acid and 50 mM phosphate buffer (pH 7.0).

Five hours and twenty-four hours (genus *Ochrobactrum*) or five hours (*Achromobacter denitrificans* NBRC 12669 and *Acinetobacter haemolyticus* ATCC17906) after starting the resting cell reaction, 1.6 ml of the reaction solution were collected. The reaction solution was separated by centrifuge (15000 rpm, 5 min) and the supernatant fraction was subjected to a filtration treatment which uses a DISMIC-13CP Cellulose Acetate 0.2 µm filter (manufactured by ADVANTEC). The compounds contained in the culture supernatant were analyzed according to the analysis condition A described in Example 5. As a result, a peak was observed at the same elution time as methacrylic acid. In "Table 21" and "Table 22" concentration of methacrylic acid which is in the supernatant of the reaction solution of the resting cell reaction is shown.

TABLE 21

| Microbial strain | Number of days for main culture (days) | Concentration of methacrylic acid (ppm) | |
|---|---|---|---|
| | | After 5 hours | After 24 hours |
| Ochrobactrum sp. NBRC12951 | 3 | 2.9 | 5.7 |
| Ochrobactrum intermedium NBRC13694 | 4 | 3.4 | 14.4 |
| Ochrobactrum anthropi ATCC49237 | 4 | 0.7 | 1.6 |

TABLE 22

| Microbial strain | Number of days for main culture (days) | Concentration of methacrylic acid (ppm) |
|---|---|---|
| Achromobacter denitrificans NBRC12669 | 3 | 0.3 |
| Acinetobacter haemolyticus ATCC17906 | 3 | 0.1 |

Example 18: Production of Methacrylic Acid Based on Resting Cell Reaction Using Genus *Shewanella*

*Shewanella fodinae* NBRC 105216 was grown on a nutrient agar medium (manufactured by Becton, Dickinson and Company, agar 1.5%). The grown cells were inoculated (one platinum loop) to 100 mL liquid medium (100 ml medium/500 ml volume conical flask) and cultured under aerobic conditions at 30° C. with a rotary shaker (230 rpm) for 3 days (main culture). Composition of the medium for the main culture is described below.
Polypeptone (manufactured by Becton, Dickinson and Company) 10 g
Yeast extract (manufactured by Becton, Dickinson and Company) 2 g
$MgSO_4 \cdot 7H_2O$ 1 g
Sea water (Daigo's artificial sea water SP for marine microalgae, manufactured by Nihon Seiyaku Co. Japan) 750 ml
Distilled water 250 ml
L-Valine 2.0 g/l
pH 7.2-7.4
After the main culture, the entire volume of the main culture was transferred to a centrifuge tube with volume of 225 ml and then centrifuged (5000 rpm, 15 min). By removing the supernatant, the cells were obtained. To the cells, 40 ml of 50 mM phosphate buffer (pH 7.0) were added and the cells were suspended and centrifuged again under the same conditions. By removing the supernatant, the washed cells were obtained. To the washed cells, 3 ml of 50 mM phosphate buffer (pH 7.0) were added to prepare a cell suspension. To a conical tube with volume of 50 mL, 3 ml of the cell suspension and 3 ml of the solution for resting cell reaction were added to perform the resting cell reaction. The reaction was allowed to occur under aerobic conditions at 30° C. with a rotary shaker (230 rpm) for 24 hours. Composition of the solution for resting cell reaction includes 5.0 g/l L-valine and 50 mM phosphate buffer (pH 7.0).

Twenty-four hours after starting the resting cell reaction, 1.6 ml of the reaction solution were collected. The reaction solution was separated by centrifuge (15000 rpm, 5 min) and the supernatant fraction was subjected to a filtration treatment which uses a DISMIC-13CP Cellulose Acetate 0.2 μm filter (manufactured by ADVANTEC). The compounds contained in the supernatant of the reaction solution were analyzed according to the analysis condition A described in Example 5. As a result, a peak was observed at the same elution time as methacrylic acid and the concentration of methacrylic acid was 0.1 ppm.

Example 19: Production of Methacrylic Acid Based on Resting Cell Reaction Using Genus Agrobacterium Agrobacterium luteum NBRC15768 was grown at 25° C. on an agar medium (plate culture). Composition of the medium for plate culture is shown below.
Polypeptone (manufactured by Becton, Dickinson and Company) 10 g
Yeast extract (manufactured by Becton, Dickinson and Company) 2 g
$MgSO_4 \cdot 7H_2O$ 1 g
Sea water (Daigo's artificial sea water SP for marine microalgae, manufactured by Nihon Seiyaku Co. Japan) 750 ml
Distilled water 250 ml
Ager 15 g
pH 7.2-7.4
The grown cells were inoculated to 100 mL liquid medium (100 ml medium/500 ml volume conical flask) and cultured under aerobic conditions at 30° C. with a rotary shaker (230 rpm) for 3 days (main culture). Composition of the medium for the main culture is described below.
Polypeptone (manufactured by Becton, Dickinson and Company) 10 g
Yeast extract (manufactured by Becton, Dickinson and Company) 2 g
$MgSO_4 \cdot 7H_2O$ 1 g
Sea water (Daigo's artificial sea water SP for marine microalgae, manufactured by Nihon Seiyaku Co. Japan) 750 ml
Distilled water 250 ml
L-Valine 2.0 g/l
pH 7.2-7.4
After the main culture, the entire volume of the main culture was transferred to a centrifuge tube with volume of 225 ml and then centrifuged (5000 rpm, 15 min). By removing the supernatant, the cells were obtained. To the cells, 40 ml of 50 mM phosphate buffer (pH 7.0) were added and the cells were suspended and centrifuged again under the same conditions. By removing the supernatant, the washed cells were obtained. To the washed cells, 3 ml of 50 mM phosphate buffer (pH 7.0) were added to prepare a cell suspension. To a conical tube with volume of 50 mL, 3 ml of the cell suspension and 3 ml of the solution for resting cell reaction were added to perform the resting cell reaction. The reaction was allowed to occur under aerobic conditions at 30° C. with a rotary shaker (230 rpm) for 24 hours. Composition of the solution for resting cell reaction includes 5.0 g/l L-valine and 50 mM phosphate buffer (pH 7.0).
Five hours and twenty-four hours after starting the resting cell reaction, 1.6 ml of the reaction solution were collected. The reaction solution was separated by centrifuge (15000 rpm, 5 min) and the supernatant fraction was subjected to a filtration treatment which uses a DISMIC-13CP Cellulose Acetate 0.2 μm filter (manufactured by ADVANTEC). The compounds contained in the supernatant of the reaction solution were analyzed according to the analysis condition A and condition B described in Example 5. As a result, a peak was observed at the same elution time as methacrylic acid and the concentration of methacrylic acid was 0.1 ppm after 5 hours and 0.1 ppm after 24 hours.

Example 20: Production of methacrylic acid based on resting cell reaction using genus Brevundimonas and genus Rhizobium Brevundimonas vesicularis ATCC11426 and Rhizobium leguminosarum ATCC10004 were grown on a nutrient agar medium (manufactured by Becton, Dickinson and Company, agar 1.5%). The grown cells were inoculated (one platinum loop) to 10 mL liquid medium and cultured under aerobic conditions at 30° C. with a rotary shaker (230 rpm) for 4 days (pre-culture). Composition of the medium for the main culture is described below. The pre-culture and 40% glycerol were mixed with each other at 1:1 and subjected to cryopreservation at −80° C.
$Na_2HPO_4$ (anhydrous) 6.0 g/l
$KH_2PO_4$ 3.0 g/l
NaCl 0.5 g/l
$NH_4Cl$ 1.0 g/l
1M $MgSO_4 \cdot 7H_2O$ 1 ml
1M $CaCl_2$ 0.1 ml
1% Thiamine 1 ml
Glucose 2.0 g/l
The pre-culture which has been remained under cryopreservation was thawed at room temperature and 0.5 ml was inoculated to 100 ml liquid medium (100 ml medium/500 ml volume conical flask). It was then cultured under aerobic conditions at 30° C. with a rotary shaker (230 rpm) for 2 days (main culture). Composition of the medium for the main culture is described below.
Nutrient medium 8 g/l
L-Valine 2.0 g/l
After the main culture, the entire volume of the main culture was transferred to a centrifuge tube with volume of 225 ml and then centrifuged (5000 rpm, 15 min). By removing the supernatant, the cells were obtained. To the cells, 40 ml of 50 mM phosphate buffer (pH 7.0) were added and the cells were suspended and centrifuged again under the same conditions. By removing the supernatant, the washed cells were obtained. To the washed cells, 3 ml of 50 mM phosphate buffer (pH 7.0) were added to prepare a cell suspension. To a conical tube with volume of 50 mL, 3 ml of the cell suspension and 3 ml of the solution for resting cell reaction were added to perform the resting cell reaction. The reaction was allowed to occur under aerobic conditions at 30° C. with a rotary shaker (230 rpm) for 24 hours. Composition of the solution for resting cell reaction includes 5.0 g/l L-valine and 50 mM phosphate buffer (pH 7.0).
Five hours (Brevundimonas vesicularis ATCC11426) or twenty-four hours (Rhizobium leguminosarum ATCC 10004) after starting the resting cell reaction, 1.6 ml of the reaction solution were collected. The reaction solution was separated by centrifuge (15000 rpm, 5 min) and the supernatant fraction was subjected to a filtration treatment which uses a DISMIC-13CP Cellulose Acetate 0.2 μm filter (manufactured by ADVANTEC). The compounds contained in the supernatant of the reaction solution were analyzed according to the analysis condition B described in Example 5. As a result, a peak was observed at the same elution time as methacrylic acid and the concentration of methacrylic acid was 0.7 ppm for Brevundimonas vesicularis ATCC 11426 and 1.6 ppm for Rhizobium leguminosarum ATCC 10004.

Example 21: Production of Methacrylic Acid Based on Resting Cell Reaction Using Genus *Brevundimonas*

*Brevundimonas diminuta* ATCC 11568 was grown on a nutrient agar medium (manufactured by Becton, Dickinson and Company, agar 1.5%). The grown cells were inoculated (one platinum loop) to 10 mL nutrient medium and cultured under aerobic conditions at 30° C. with a rotary shaker (230 rpm) for 1 day (pre-culture). The pre-culture and 40% glycerol were mixed with each other at 1:1 and subjected to cryopreservation at −80° C.

The pre-culture which has been remained under cryopreservation was thawed at room temperature and 0.5 ml was inoculated to 100 ml liquid medium (100 ml medium/500 ml volume conical flask). It was then cultured under aerobic conditions at 30° C. with a rotary shaker (230 rpm) for 2 days (main culture). Composition of the medium for the main culture is described below.

Nutrient medium 8 g/l
L-Valine 2.0 g/l

After the main culture, the entire volume of the main culture was transferred to a centrifuge tube with volume of 225 ml and then centrifuged (5000 rpm, 15 min). By removing the supernatant, the cells were obtained. To the cells, 40 ml of 50 mM phosphate buffer (pH 7.0) were added and the cells were suspended and centrifuged again under the same conditions. By removing the supernatant, the washed cells were obtained. To the washed cells, 3 ml of 50 mM phosphate buffer (pH 7.0) were added to prepare a cell suspension. To a conical tube with volume of 50 mL, 3 ml of the cell suspension and 3 ml of the solution for resting cell reaction were added to perform the resting cell reaction. The reaction was allowed to occur under aerobic conditions at 30° C. with a rotary shaker (230 rpm) for 24 hours. Composition of the solution for resting cell reaction includes 5.0 g/l L-valine and 50 mM phosphate buffer (pH 7.0).

Five hours and twenty-four hours after starting the resting cell reaction, 1.6 ml of the reaction solution were collected. The reaction solution was separated by centrifuge (15000 rpm, 5 min) and the supernatant fraction was subjected to a filtration treatment which uses a DISMIC-13CP Cellulose Acetate 0.2 μm filter (manufactured by ADVANTEC). The compounds contained in the supernatant of the reaction solution were analyzed according to the analysis condition B described in Example 5. As a result, a peak was observed at the same elution time as methacrylic acid and the concentration of methacrylic acid was 33.0 ppm after 5 hours and 37.0 ppm after 24 hours.

Example 22: Production of Methacrylic Acid Based on Resting Cell Reaction Using Thermophillic Bacteria

*Geobacillus stearothermophilus* NBRC 12983 was grown on a nutrient agar medium (manufactured by Becton, Dickinson and Company, agar 1.5%). The cells were inoculated (one platinum loop) to 10 mL liquid medium and cultured under aerobic conditions at 37° C. with a rotary shaker (230 rpm) for 2 days (pre-culture). Composition of the medium for the pre-culture is described below.

Nutrient medium 8 g/l
Glucose 2.0 g/l

The grown cells were inoculated to 100 ml liquid medium (100 ml medium/500 ml volume conical flask) and cultured under aerobic conditions at 25° C. with a rotary shaker (230 rpm) for 5 days (main culture). Composition of the medium for the main culture is described below.

Nutrient medium 8 g/l
L-Valine 2.0 g/l

After the main culture, the entire volume of the main culture was transferred to a centrifuge tube with volume of 225 ml and then centrifuged (5000 rpm, 15 min). By removing the supernatant, the cells were obtained. To the cells, 40 ml of 50 mM phosphate buffer (pH 7.0) were added and the cells were suspended and centrifuged again under the same conditions. By removing the supernatant, the washed cells were obtained. To the washed cells, 3 ml of 50 mM phosphate buffer (pH 7.0) were added to prepare a cell suspension. To a conical tube with volume of 50 mL, 3 ml of the cell suspension and 3 ml of the solution for resting cell reaction were added to perform the resting cell reaction. The reaction was allowed to occur under aerobic conditions at 30° C. with a rotary shaker (230 rpm) for 24 hours. Composition of the solution for resting cell reaction includes 5.0 g/l L-valine and 50 mM phosphate buffer (pH 7.0).

Five hours and twenty-four hours after starting the resting cell reaction, 1.6 ml of the reaction solution were collected. The reaction solution was separated by centrifuge (15000 rpm, 5 min) and the supernatant fraction was subjected to a filtration treatment which uses a DISMIC-13CP Cellulose Acetate 0.2 μm filter (manufactured by ADVANTEC). The compounds contained in the supernatant of the reaction solution were analyzed according to the analysis condition A described in Example 5. As a result, a peak was observed at the same elution time as methacrylic acid and the concentration of methacrylic acid was 0.4 ppm after 5 hours and 0.3 ppm after 24 hours.

Example 23: Production of Methacrylic Acid Based on Resting Cell Reaction Using Yeast

*Saccharomyces cerevisiae* NBRC1136, *Saccharomyces cerevisiae* NBRC2347, *Saccharomyces paradoxus* NBRC10609, and *Candida parapsilosis* ATCC22019 were grown on an agar medium (plate culture). Composition of the medium for plate culture is shown below. The culture was performed at 30° C. (genus *Saccharomyces*) or at 24° C. (genus *Candida*).

Yeast extract (manufactured by Becton, Dickinson and Company) 20 g/l
Polypeptone (manufactured by Becton, Dickinson and Company) 20 g/l
Glucose 20 g/l
Ager 15 g/l The grown cells were inoculated (one platinum loop) to 10 ml liquid medium and cultured under aerobic conditions at 30° C. with a rotary shaker (230 rpm) for 2 to 7 days (pre-culture). The culture was performed at 30° C. (genus *Saccharomyces*) or at 24° C. (genus *Candida*), and as a medium for the pre-culture, the medium 1 or 2 was used. Composition of the medium is shown below.

Medium 1
Yeast extract (manufactured by Becton, Dickinson and Company) 20 g/l
Polypeptone (manufactured by Becton, Dickinson and Company) 20 g/l
Glucose 20 g/l
Medium 2
Glucose 2.0 g/l
L-Valine 2.0 g/l
$(NH_4)_2SO_4$ 6.0 g/l
KCl 2.4 g/l NaCl 0.12 g/l
H₃PO₄ 3.0 g/l
MgSO₄·7H₂O 2.4 g/l
FeSO₄·7H₂O 0.01 g/l
ZnSO₄·7H₂O 0.12 g/l
MnSO₄0.4-6H₂O 0.024 g/l
CuSO₄·5H₂O 0.006 g/l
CaCl₂ 0.12 g/l
Vitamin Mix 30 ml
Composition of Vitamin Mix is shown below.
Biotin 0.2 g/l
Calcium pantothenate 2 g/l
Folic acid 0.002 g/l
Thiamine hydrochloride 0.4 g/l
Riboflavin 0.2 g/l
Nicotinic acid 0.4 g/l
Pyridoxine hydrochloride 0.4 g/l
Inositol 1 g/l
p-Aminobenzoic acid 0.2 g/l 1 ml of the pre-culture was inoculated to 100 ml liquid medium (100 ml medium/500 ml volume conical flask). It was then cultured under aerobic conditions at 30° C. with a rotary shaker (230 rpm) for 2 to 3 days (main culture). The culture was performed at 30° C. (genus *Saccharomyces*) or at 24° C. (genus *Candida*). Composition of the medium for the main culture is described below.

Glucose 2.0 g/l
L-Valine or Isobutyric acid 2.0 g/l
(NH₄)₂SO₄ 6.0 g/l
KCl 2.4 g/l
NaCl 0.12 g/l
H₃PO₄ 3.0 g/l
MgSO₄·7H₂O 2.4 g/l
FeSO₄·7H₂O 0.01 g/l
ZnSO₄·7H₂O 0.12 g/l
MnSO₄·4-6H₂O 0.024 g/l
CuSO₄·5H₂O 0.006 g/l
CaCl₂ 0.12 g/l
Vitamin Mix 30 ml
Composition of Vitamin Mix is shown below.
Biotin 0.2 g/l
Calcium pantothenate 2 g/l
Folic acid 0.002 g/l
Thiamine hydrochloride 0.4 g/l
Riboflavin 0.2 g/l
Nicotinic acid 0.4 g/l
Pyridoxine hydrochloride 0.4 g/l
Inositol 1 g/l
p-Aminobenzoic acid 0.2 g/l After the main culture, the entire volume of the main culture was transferred to a centrifuge tube with volume of 225 ml and then centrifuged (5000 rpm, 15 min) By removing the supernatant, the cells were obtained. To the cells, 40 ml of 50 mM phosphate buffer (pH 7.0) were added and the cells were suspended and centrifuged again under the same conditions. By removing the supernatant, the washed cells were obtained. To the washed cells, 3 ml of 50 mM phosphate buffer (pH 7.0) were added to prepare a cell suspension. To a conical tube with volume of 50 mL, 3 ml of the cell suspension and 3 ml of the solution for resting cell reaction were added to perform the resting cell reaction. The reaction was allowed to occur under aerobic conditions at 30° C. with a rotary shaker (230 rpm) for 24 hours. Composition of the solution for resting cell reaction includes 5.0 g/l L-valine or isobutyric acid and 50 mM phosphate buffer (pH 7.0). In "Table 23", conditions for the culture and resting cell reaction are shown.

TABLE 23

| Microbial strain | Pre-culture Medium | Pre-culture Number of days | Main culture Substrate | Main culture Number of days | Resting cell Substrate |
|---|---|---|---|---|---|
| Saccharomyces cerevisiae NBRC1136 | Medium 1 | 1 | Isobutyric acid | 3 | Isobutyric acid |
| Saccharomyces cerevisiae NBRC2347 | Medium 1 | 1 | Isobutyric acid | 3 | Isobutyric acid |
| Saccharomyces paradoxus NBRC10609 | Medium 2 | 4 | Isobutyric acid | 2 | Isobutyric acid |
| Candida parapsilosis ATCC22019 | Medium 2 | 3 | Valine | 2 | Valine |

Five hours (*Saccharomyces cerevisiae* NBRC2347 and *Candida parapsilosis* ATCC22019) or twenty-four hours (*Saccharomyces cerevisiae* NBRC1136 and *Saccharomyces paradoxus* NBRC10609) after starting the resting cell reaction, 1.6 ml of the reaction solution were collected. The reaction solution was separated by centrifuge (15000 rpm, 5 min) and the supernatant fraction was subjected to a filtration treatment which uses a DISMIC-13CP Cellulose Acetate 0.2 µm filter (manufactured by ADVANTEC). The compounds contained in the supernatant of the reaction solution were analyzed according to the analysis condition A described in Example 5. As a result, a peak was observed at the same elution time as methacrylic acid. In "Table 24", concentration of methacrylic acid which is in the supernatant of the reaction solution of the resting cell reaction is shown.

TABLE 24

| Microbial strain | Concentration of methacrylic acid (ppm) |
|---|---|
| Saccharomyces cerevisiae NBRC1136 | 0.1 |
| Saccharomyces cerevisiae NBRC2347 | 0.2 |
| Saccharomyces paradoxus NBRC10609 | 0.2 |
| Candida parapsilosis ATCC22019 | 0.2 |

Example 24: Production of Methacrylic Acid Based on Resting Cell Reaction Using Mildew

*Aspergillus niger* ATCC6275, *Aspergillus flavus* NBRC8558, and *Aspergillus oryzae* NBRC4255 was grown on a potato dextrose agar medium (manufactured by Nissui Pharmaceutical Co., Ltd.). The grown mycelia and spores were suspended in 5 ml sterilized water, and 1 ml of the resultant was inoculated to 100 mL liquid medium (100 ml medium/500 ml volume conical flask) and cultured under aerobic conditions at 24° C. with a rotary shaker (230 rpm) for 2 days (main culture). Composition of the medium for the main culture is described below.

L-Valine 2.0 g/l
NaNO₃ 2.5 g/l
K₂HPO₄ 1.25 g/l
MgSO₄·7H₂O 0.63 g/l

KCl 0.63 g/l
FeSO$_4$.7H$_2$O 0.013 g/l
Wheat bran 5 g/l
pH 7.0

After the main culture, the entire volume of the main culture was transferred to a centrifuge tube with volume of 225 ml and then centrifuged (5000 rpm, 15 min). By removing the supernatant, the cells were obtained. To the cells, 40 ml of 50 mM phosphate buffer (pH 7.0) were added and the cells were suspended and centrifuged again under the same conditions. By removing the supernatant, the washed cells were obtained. To the washed cells, 10 ml of 50 mM phosphate buffer (pH 7.0) were added to prepare a cell suspension. To a conical tube with volume of 50 mL, the cell suspension was transferred and 10 ml of the solution for resting cell reaction were added to perform the resting cell reaction. The reaction was allowed to occur under aerobic conditions at 30° C. with a rotary shaker (230 rpm) for 24 hours. Composition of the solution for resting cell reaction includes 5.0 g/l L-valine and 50 mM phosphate buffer (pH 7.0).

Five hours and twenty-four hours after starting the resting cell reaction, about 2 ml of the reaction solution were collected. The reaction solution was separated by centrifuge (15000 rpm, 5 min) and the supernatant fraction was subjected to a filtration treatment which uses a DISMIC-13CP Cellulose Acetate 0.2 μM filter (manufactured by ADVANTEC). The compounds contained in the culture supernatant were analyzed according to the analysis condition A and condition B described in Example 5. As a result, a peak was observed at the same elution time as methacrylic acid. In "Table 25", concentration of methacrylic acid which is in the supernatant of the reaction solution of the resting cell reaction is shown.

TABLE 25

| | Concentration of methacrylic acid (ppm) | | | |
| | After 5 hours | | After 24 hours | |
| Microbial strain | Analysis condition A | Analysis condition B | Analysis condition A | Analysis condition B |
|---|---|---|---|---|
| Aspergillus niger ATCC6275 | ND | ND | 0.1 | 1.7 |
| Aspergillus flavus NBRC8558 | 0.5 | 0.7 | 1.1 | 1.4 |
| Aspergillus oryzae NBRC4255 | 0.4 | 0.4 | 0.7 | 0.8 |

(ND: Not Detected)

Example 25: Identity Comparison Using Genus *Pseudomonas*, Genus *Bacillus*, Genus *Brevundimonas*, Genus *Ochrobactrum*, and Genus *Acinetobacter*

By using the homology analysis program GENETYX ver. 10, which is a software for processing genetic information by GENETYX CORPORATION, identity between nucleotide sequences of 16S rDNA or LSU rDNA in each microbe, which are shown in SEQ ID NOS. 1 to 8, 9 to 15, 18 to 20, 22 to 26, 30 to 31, 42 to 44, 45 to 46, and 47 to 49, was compared. The results are shown in "Table 26 to 33."

SEQ ID NO. 1 to 8

TABLE 26

| | Pseudomonas sp. D29 | Pseudomonas sp. D41-2 | Pseudomonas sp. D43-1 | Pseudomonas putida NBRC12996 | Pseudomonas sp. B25-2 | Pseudomonas sp. B22-1 | Pseudomonas sp. D25 | Pseudomonas sp. D26 |
|---|---|---|---|---|---|---|---|---|
| Pseudomonas sp. D29 | | 99% | 98% | 97% | 97% | 96% | 95% | 95% |
| Pseudomonas sp. D41-2 | 99% | | 98% | 97% | 97% | 95% | 96% | 96% |
| Pseudomonas sp. D43-1 | 98% | 98% | | 98% | 98% | 97% | 96% | 96% |
| Pseudomonas putida NBRC12996 | 97% | 97% | 98% | | 98% | 97% | 98% | 97% |
| Pseudomonas sp. B25-2 | 97% | 97% | 98% | 98% | | 96% | 97% | 97% |
| Pseudomonas sp. B22-1 | 96% | 95% | 97% | 97% | 96% | | 99% | 98% |
| Pseudomonas sp. D25 | 95% | 96% | 96% | 98% | 97% | 99% | | 98% |
| Pseudomonas sp. D26 | 95% | 96% | 96% | 97% | 97% | 98% | 98% | |

SEQ ID NO. 9 to 15

TABLE 27

| | Bacillus subtilis NBRC12210 | Bacillus sp. R1 | Bacillus badius ATCC14574 | Bacillus megaterium NBRC15308 | Bacillus simplex ATCC49097 | Bacillus sp. G1 | Bacillus sp. G2 |
|---|---|---|---|---|---|---|---|
| Bacillus subtilis NBRC12210 | | 93% | 90% | 89% | 89% | 92% | 91% |
| Bacillus sp. R1 | 93% | | 92% | 92% | 91% | 89% | 89% |
| Bacillus badius ATCC14574 | 90% | 92% | | 89% | 90% | 88% | 88% |
| Bacillus megaterium NBRC15308 | 89% | 92% | 89% | | 92% | 90% | 90% |
| Bacillus simplex ATCC49097 | 89% | 91% | 90% | 92% | | 89% | 89% |
| Bacillus sp. G1 | 92% | 89% | 88% | 90% | 89% | | 99% |
| Bacillus sp. G2 | 91% | 89% | 88% | 90% | 89% | 99% | |

SEQ ID NOS. 18 to 20

TABLE 28

|  | Brevundimonas diminuta ATCC11568 | Brevundimonas subvibrioides NBRC16000 | Brevundimonas vesicularis ATCC11426 |
|---|---|---|---|
| Brevundimonas diminuta ATCC11568 |  | 96% | 96% |
| Brevundimonas subvibrioides NBRC16000 | 96% |  | 95% |
| Brevundimonas vesicularis ATCC11426 | 96% | 95% |  |

SEQ ID NOS. 22 to 26

TABLE 29

|  | Ochrobactrum intermedium NBRC13694 | Ochrobactrum lupini NBRC 102587 | Ochrobactrum sp. NBRC12951 | Ochrobactrum intermedium NBRC15820 | Ochrobactrum grignonense NBRC102586 |
|---|---|---|---|---|---|
| Ochrobactrum intermedium NBRC13694 |  | 100% | 100% | 98% | 97% |
| Ochrobactrum lupini NBRC 102587 | 100% |  | 100% | 98% | 97% |
| Ochrobactrum sp. NBRC12951 | 100% | 100% |  | 98% | 97% |
| Ochrobactrum intermedium NBRC15820 | 98% | 98% | 98% |  | 97% |
| Ochrobactrum grignonense NBRC102586 | 97% | 97% | 97% | 97% |  |

SEQ ID NOS. 30 to 31

TABLE 30

|  | Acinetobacter haemolyticus ATCC17906 | Acinetobacter junii ATCC17908 |
|---|---|---|
| Acinetobacter haemolyticus ATCC17906 |  | 95% |
| Acinetobacter junii ATCC17908 | 95% |  |

SEQ ID NOS. 42 to 44

TABLE 31

|  | Saccharomyces cerevisiae NBRC1136 | Saccharomyces cerevisiae NBRC2347 | Saccharomyces paradoxus NBRC10609 |
|---|---|---|---|
| Saccharomyces cerevisiae NBRC1136 |  | 100% | 98% |
| Saccharomyces cerevisiae NBRC2347 | 100% |  | 98% |
| Saccharomyces paradoxus NBRC10609 | 98% | 98% |  |

SEQ ID NOS. 45 to 46

TABLE 32

|  | Candida utilis NBRC1086 | Candida parapsilosis ATCC22019 |
|---|---|---|
| Candida utilis NBRC1086 |  | 81% |
| Candida parapsilosis ATCC22019 | 81% |  |

SEQ ID NOS. 47 to 49

TABLE 33

|  | Aspergillus niger ATCC6275 | Aspergillus flavus NBRC8558 | Aspergillus oryzae NBRC4255 |
|---|---|---|---|
| Aspergillus niger ATCC6275 |  | 96% | 96% |
| Aspergillus flavus NBRC8558 | 96% |  | 100% |
| Aspergillus oryzae NBRC4255 | 96% | 100% |  |

Reference Example 1: Preparation of Recipient PR4KS for Conjugal Transfer

*Rhodococcus erythropolis* PR4 (Biological and genetic resource division of The National Institute of Technology and Evaluation; Accession number: NBRC 100887) was modified by a method described in JP-A No. 2011-200133, and a derivative strain which exhibits resistance to 120 mg/l chloramphenicol and is deficient of the kanamycin resistant gene was produced and named PR4KS strain.

Specifically, to enhance the chloramphenicol resistance, a natural mutation was caused by subculturing the strain PR4 while the concentration of chloramphenicol in MYK medium (0.5% polypeptone, 0.3% bact yeast extract, 0.3% malt extract, 0.2% $KH_2PO_4$, 0.2% $K_2HPO_4$) is gradually increased from 10 mg/mL to 120 mg/mL. Accordingly, the derivative strain RhCmSR-09 strain having resistance to 120 mg/mL chloramphenicol was obtained.

Subsequently, the RhCmSR-09 strain was admixed with the *E. coli* strain described in JP-A No. 2011-200133, which contains plasmid pKM043 for introducing kanamycin resistant gene deletion mutation, at ratio of 1:1. After introducing the pKM043 to the RhCmSR-09 strain by conjugal transfer, with culture in the MYK agar medium (0.5% polypeptone, 0.3% bact yeast extract, 0.3% malt extract, 0.2% $KH_2PO_4$, 0.2% $K_2HPO_4$, 1.5% agar) containing kanamycin sulfate at 200 mg/L and chloramphenicol at 50 mg/L, the homologues recombinant strain having the pKM043 inserted to the genome of the RhCmSR-09 strain was obtained. The homologous recombinant strain was cultured in the MYK agar medium containing 10% sucrose to obtain from the resulting colonies a derivative strain which becomes a kanamycin-sensitive strain, that is, the mutant derivative strain PR4KS strain deleted with the kanamycin resistant gene.

Reference Example 2: Cloning of LigD Homolog Gene and Production of Plasmid for Gene Deletion LigD homolog gene (Accession No.: YP_002767969) of the PR4KS strain was the target gene. After amplification by PCR of about 5.4 kb DNA containing peripheral sequences of the LigD gene, it was cloned into the plasmid vector pK19mobsacB1 described in JP-A No. 2011-200133, in which the sacB gene is introduced in the downstream or in the same direction of the kanamycin resistant gene, to obtain the plasmid pTJ001. Conditions for PCR are as follows.

```
Primers
GB-138:
                                     (SEQ ID NO. 94)
5'-GGCCTGCAGGTACCGATCATCACCATCGGTGTC-3'

GB-139:
                                     (SEQ ID NO. 95)
5'-GGTCTAGACTGAGCAGTGTTCCAATGCG-3'
```

Figure 4:
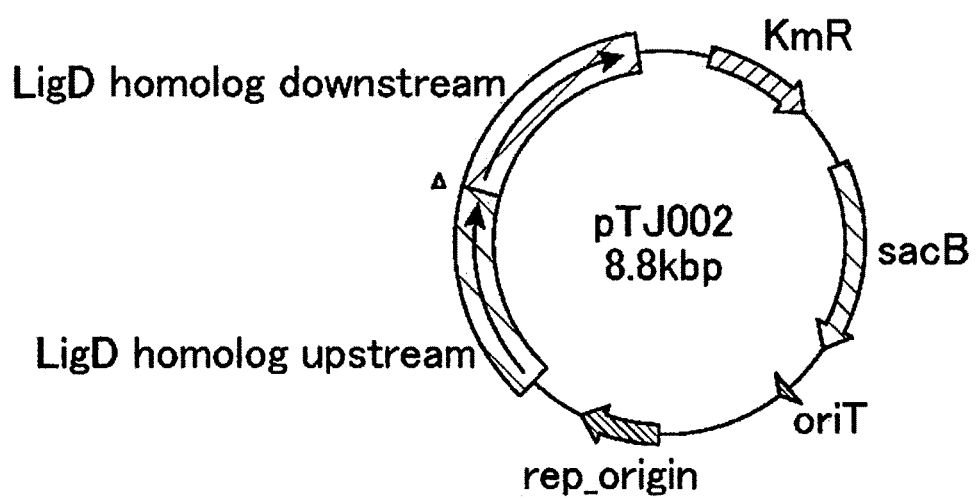
FIG. 4 is a drawing illustrating the structure of a plasmid for deleting LigD homolog gene.

Composition of Reaction Solution
  Sterilized water 22 µl
  2×PrimeSTAR (manufactured by Takara Bio Inc.) 25 µl
  GB-138 1 µl
  GB-139 1 µl
  PR4KS genome (50 ng/µl) 1 µl
  Total volume 50
Temperature Cycle
35 Cycles of the Reaction Including 98° C. for 10 Seconds, 55° C. for 10 Seconds, and 72° C. for 120 Seconds Plasmid pTJ002 for deletion of LigD homolog gene in which the full-length sequence of the LigD homolog gene (about 2.3 kb) inside pTJ001 is deleted to maintain only the upstream and downstream sequences of the LigD homolog gene was produced (see, FIG. 4). pTJ002 was produced by transforming E. coli JM109 strain with a PCR product not containing the LigD homolog gene, which has been obtained by amplifying internal sequence of pTJ001 using primers GB-140 and GB-141 designed so as to contain both the sequences near the start codon and the sequence near the stop codon of the LigD homolog gene as a target and to elongate respectively in the upstream direction from the start codon or in the downstream direction from the stop codon, to yield a cyclic DNA (see, FIG. 4). PCR conditions are as follows.

```
Primers
GB-140:
                                     (SEQ ID NO. 96)
GAGGAAATGGTCACAGGGCGAGAATAGGTTG GB-141:
                                     (SEQ ID NO. 97)
GCCCTGTGACCATTTCCTCATTGTGCTGG
```

Composition of Reaction Solution
  Sterilized water 22 µl
  2×PrimeSTAR (manufactured by Takara Bio Inc.) 25 µl
  GB-140 1 µl
  GB-141 1 µl
  pTJ001 1 µl
  Total volume 50 µl
Temperature Cycle
30 Cycles of the Reaction Including 98° C. for 10 Seconds, 50° C. for 10 Seconds, and 72° C. for 180 Seconds Upon the completion of PCR, determination of the fragment was performed by using 1 µl sample and 0.7% agarose gel electrophoresis. As a result, the fragment amplification was observed. With regard to the aforementioned steps for producing the plasmid pTJ002, Wizard Genomic DNA Purification Kit (manufactured by Promega) was used for the genome extraction form the PR4 strain, Gel/PCR Purification Kit (manufactured by FAVORGEN) was used for purification of the DNA fragment digested with restrictions enzymes and the PCR product, DNA Ligation Kit <Mighty Mix> (manufactured by Takara Bio Inc.) was used for conjugation between DNAs, and QIAprep miniprep kit (manufactured by QIAGEN) was used for the plasmid extraction.

Reference Example 3: Production of the PR4KS Derivative Strain in which LigD Homolog Gene is Deleted By having the E. coli (Escherichia coli) S17-1λpir which has been transformed with pTJ002 as a donor and PR4KS obtained by the method of Reference example 1 as a recipient, conjugal transfer was performed according to the method described in JP-A No. 2011-200133 to obtain by homologous recombination a derivative strain of thirteen strains generated in which LigD homolog gene is deleted. One strain was selected from the above derivative strain with deletion and named PR4KSΔligD derivative strain.

Example 26: Production of Plasmid pLK005 for Bacteria of Genus Rhodococcus and Plasmid pSJ201 for Expression of Nitrile Hydratase Using it (1) Obtainment and Analysis of pLK005

By using pK4 (see, JP-A No. 5-64589), Rhodococcus sp. N775 (Accession number of FERM BP-961, Patent Microorganisms Depository Center of National Institute of Advanced Industrial Science and Technology, Independent Administrative Institution) was transformed by electroporation. The obtained transformant was inoculated to 10 ml MYK medium and cultured at 30° C. for 1 day. According to UV irradiation on it in a clean bench, a mutagenic treatment was performed. The culture after the mutagenic treatment was applied to an agar medium containing 50 to 400 µg/ml kanamycin and cultured at 30° C. for 3 days.

Each of the plural colonies shown on the agar medium was cultured on the MYK medium and the plasmid was recovered from the transformant. By using the recovered plasmid, Rhodococcus sp. N775 was transformed again and an examination was made to see if there is any increase in the resistance of the transformant to kanamycin. As a result, several strains of the transformant were observed with clearly increased kanamycin resistance.

As a result of examining the nucleotide sequence of the plasmid for which increased kanamycin resistance is observed, a change in the sequence in the upstream region of the kanamycin resistant gene of pK4 was observed (eight-nucleotide sequence of GTTGTAGG is repeated). The plasmid observed with increased kanamycin resistance was named pLK005.

(2) Production of pSJ040

Plasmid pSJ034 was produced from plasmid pSJ023 according to the method described in JP-A No. 10-337185. There are three sites for the restriction enzyme EcoRI in pSJ034, and plasmid pSJ040 was produced in which one of those sites is modified to SpeI. With regard to the production method, pSJ034 was partially degraded by the restriction enzyme EcoRI and blunting of the restriction sites were performed by using Takara Blunting Kit. In the presence of SpeI linker, the ligation reaction was performed and the E.

coli JM109 strain was transformed by using the reaction solution. After culturing the transformant, the plasmid was extracted and the plasmid inserted with SpeI linker was selected. Among the three EcoRI sites in pSJ034, the one having SpeI linker inserted to EcoRI site, which is located downstream of the kanamycin resistant gene, was named pSJ040.

(3) Construction of pSJ201

By digesting pLK005 with HindIII, a fragment of about 2.1 kb was produced. Meanwhile, by digesting pSJ040 with HindIII, a fragment of about 9.8 kb was produced. By using those two fragments, the ligation reaction was performed and the E. coli JM109 strain was transformed by using the reaction solution. After culturing the transformant, the plasmid was extracted and, as a result of determining the nucleotide sequence, the plasmid having the mutated sequence derived from pLK005 (repetition of GTTGTAGG) but basically the same sequence as pSJ040 other than that was named pSJ201.

Figure 5:
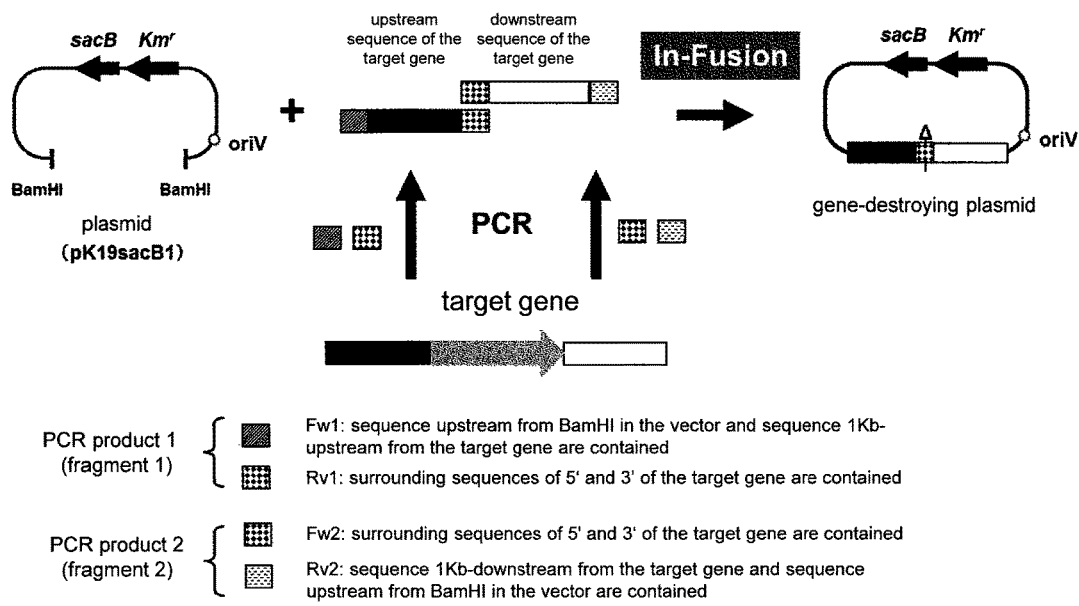
FIG. 5 is a drawing explaining the method for producing a plasmid for deleting a gene In Fusion method.

Example 27: Production of Derivative Strain in which RE_acd1/RE_echA/RE_hchA/RE_mmsB gene of PR4KSΔligD Derivative Strain is Deleted (1) Production of Plasmid for Gene Deletion Using in Fusion Method Production of plasmid for gene deletion using In-Fusion HD Cloning kit (manufactured by Takara Bio Inc.) which uses RE_acd1/RE_echA/RE_hchA/RE_mmsB of PR4KS strain as a target gene was performed (see, FIG. 5).

DNA of the upstream and downstream of the target gene was amplified by PCR. PCR conditions are as described below.

```
Primer for fragment 1
MMA-061:
                                        (SEQ ID NO. 98)
CGACTCTAGAGGATCGCTCAGTACATCTACGAGAC MMA-062:
                                        (SEQ ID NO. 99)
AGTGTGAGGAAAGTGTTCCGATCAGTTCAT Primer for fragment 2
MMA-063:
                                       (SEQ ID NO. 100)
CACTTTCCTCACACTCGTCGAGAGTATGAG MMA-064:
                                       (SEQ ID NO. 101)
CGGTACCCGGGGATCAGCGCGACGAACAACGAGAC
```

Composition of Reaction Solution
Template (PR4 wild type genomic DNA) 1 μl
2× PrimeSTAR Max Premix (manufactured by Takara Inc.) 25 μl
Fw Primer (20 μM) 1 μl
Rv Primer (20 μM) 1 μl
D.W. 22 μl
Total 50 μl
Temperature Cycle
30 Cycles of the Reaction Including 98° C. for 10 Seconds, 60° C. for 10 Seconds, and 72° C. for 120 Seconds Upon the completion of PCR, determination of the fragment was performed by using 1 μl sample and 0.7% agarose gel electrophoresis. As a result, the fragment amplification was observed. The PCR product (fragment 1 and fragment 2) was subjected to buffer exchange by using Gel/PCR Purification Kit (manufactured by FAVORGEN) and used for the reaction using In-Fusion HD Cloning Kit which is described below.

(2) Ligation Between Vector and Target Fragment Using in-Fusion HD Cloning Kit and Transformation By using In-Fusion HD Cloning Kit, ligation between the above fragment and vector was performed. The reactions conditions are described below.
Composition of Reaction Solution
5× In-Fusion HD Enzyme Premix 2 μl
Vector fragment 1.5 μl
DNA fragment 1 1 μl
DNA fragment 2 2 μl
D.W. 3.5 μl
Total 10 μl After incubating for 15 minutes at 50° C., the above reaction solution was cooled on ice and used for transformation of E. coli JM109 strain. Selection of the E. coli transformant was performed on an LB agar medium containing kanamycin sulfate at 50 mg/l (hereinbelow, LB Km50 agar medium). From the obtained transformant, a plasmid was prepared by using Mini prep Kit (manufactured by QIAGEN) to obtain the target plasmid. Confirmation of the plasmid was performed by examining the fragment size after treatment with the restriction enzyme XbaI and the sequence of the linking region between the insertion fragment and the vector. The target plasmid was named pMMA302.

(3) Production of Homologous Recombinant Derivative Strain of PR4KSΔligD Derivative Strain and Derivative Strain with Deleted Gene To 20 μl of competent cells of PR4KSΔligD strain, 1 μl of pMMA302 was added and incubated on ice for 10 minutes. Entire volume of the solution after the incubation was transferred to an ice-cooled electroporation cuvette (0.1 cm) and applied with high voltage of 1.5 kV (200Ω). Immediately thereafter, 600 μl of the LB liquid medium was added and kept for 6 hours at 30° C. 200 μl was added to a LB Km10 agar medium and cultured at 30° C. for 4 days. The grown colonies were streaked on a LB Km10 agar medium and, after growing for 4 days, colony PCR was performed according to the following conditions to confirm the homologous recombinant derivative strain.

```
Primer
MMA-069:
                                       (SEQ ID NO. 102)
GCGCATCTACAAGGAAGAGATC MMA-070:
                                       (SEQ ID NO. 103)
GCGACGCTCATCGAGATCTC
```

Composition of Reaction Solution
Template 4.0 μl
2× MightyAmp Buffer (manufactured by Takara Inc.) 5.0 μl
Fw Primer (20 μM) 0.25 μl
Rv Primer (20 μM) 0.25 μl
D.W. 0.3 μl
MightyAmp DNAPolymerase (manufactured by Takara Inc.) 0.2 μl
Total 10.0 μl
Temperature Cycle
30 Cycles of the Reaction Including 98° C. for 10 Seconds and 68° C. for 180 Seconds Colonies recognized to be a homologous recombinant derivative strain was suspended in 200 µl of LB medium and 100 µl was applied to LB+10% Sucrose agar medium followed by culture for 3 days. From the grown colonies, those having kanamycin sensitivity were selected and deletion of the target gene was confirmed from them by colony PCR. As a result, a strain in which 4 genes, that is, RE_acd1, RE_echA, RE_hchA, RE_mmsB, are deleted from the PR4KSΔligD derivative strain was obtained, and it was named DMA008 strain.

Example 28: Production of Plasmid for Expression of ACD or AAT in Bacteria of genus Rhodococcus A plasmid for expression of ACD or AAT in microbes that belong to the genus Rhodococcus was produced.

In order to produce a plasmid for expressing each of ACD or AAT, DNA of each gene was amplified by PCR. PCR conditions are as described below.

```
Primer for RE_acd1
MMA-114
                                    (SEQ ID NO. 126)
GGTCTAGAATGTTTACTCTGACCGATGACGAGCG MMA-022
                                    (SEQ ID NO. 115)
GGCCTGCAGGCCGTCACGCTTTTCGATCAATAC Primer for MpAAT1
MMA-109
                                    (SEQ ID NO. 127)
GGTCTAGAATGAAATCATTCTCAGTACTTCAG MMA-045
                                    (SEQ ID NO. 83)
CGGTACGCGCGGATCTTCCAGAG
```

Template for RE_acd1
Rhodococcus erythropolis PR4 wild type strain genomic DNA
Template for MpAAT1
plasmid pAAT001 (see Example 45)
Composition of Reaction Solution
Template 1 µl
2× PrimeSTAR Max Premix (manufactured by TAKARA Inc.) 25 µl
Fw Primer (20 µM) 1 µl
Rv Primer (20 µM) 1 µl
D.W. 22 µl
Total 50 µl
Temperature Cycle:
30 Cycles of the Reaction Including 98° C. for 10 Seconds, 60° C. for 10 Seconds, and 72° C. for 60 Seconds Upon the completion of PCR, the PCR product was subjected to buffer exchange by using Gel/PCR Purification Kit (manufactured by FAVORGEN) and the obtained fragment was treated with restriction enzymes XbaI and Sse8387I. Further, pSJ201 produced in Example 26 was also treated with the restriction enzymes XbaI and Sse8387I. After performing ethanol precipitation, it was dissolved again with sterilized water and subjected to the Shrimp Alkaline Phosphatase (SAP) treatment. The PCR fragment and a large fragment derived from pSJ201 were purified by, after 0.7% agarose gel electrophoresis, using Gel/PCR Purification Kit (manufactured by FAVORGEN). The reaction conditions for the restriction enzyme treatment, conditions for SAP treatment, and the ligation reaction conditions are as follows.

Composition for Restriction Enzyme Treatment Reaction
PCR amplified fragment 20 µl
10×M 5 µl
0.1% BSA 5 µl
XbaI (manufactured by TAKARA Inc.) 2 µl
Sse8387I (manufactured by TAKARA Inc.) 2 µl
D.W. 16 µl
Total 50 µl
Composition for SAP Treatment Reaction
Vector fragment (pSJ201) 44 µl
10×SAP Buffer 5 µl
SAP (manufactured by Promega) 1 µl
Total 50 µl
Composition for Ligation Reaction
Vector fragment 4 µl
Target fragment 1 µl
Ligation Mix (manufactured by TAKARA Inc.) 3 µl
Total 8 µl By using the reaction solution for ligation as a mixture of the above composition, transformation of E. coli JM109 strain was performed. From the transformant obtained, the plasmid was extracted, and by performing agarose electrophoresis after treatment with the restriction enzyme XbaI and Sse8387I, it was confirmed that the fragment of a desired size is inserted. Further, according to nucleotide sequence analysis of a linking region between the insertion fragment and vector, it is confirmed to be the target plasmid. The plasmid incorporated with RE_acd1 gene for MpAAT1 gene was named pMMA401 and pAAT301, respectively.

Example 29: Production of Plasmid for Expression of Both ACD and AAT for Transformation of Genus Rhodococcus Plasmid production was performed for producing a methacrylic acid ester using microbes of the genus Rhodococcus, which has been obtained in Example 27.

At the downstream of RE_acd1 gene of plasmid pMMA401 for expressing RE_acd1, the "nitrilase promoter+MpAAT1 gene" fragment, which has been obtained by PCR using as a template the plasmid pAAT301 for expression of MpAAT1 gene, was inserted.

Amplification of the "nitrilase promoter+MpAAT1 gene" fragment was performed as described below.

```
Primer
MMA-133 (Sse-ProFw):
                                    (SEQ ID NO. 104)
TGACCTGCAGGTGCACTCCGCTGCGACATGTATCGA MMA-131 (Sse-001Rv):
                                    (SEQ ID NO. 105)
ACTCTAGCCTGCAGGTCATTGACTAGTTGATCTAAGGTTGTTACA
```

Composition for PCR Reaction
Template (pAAT301) 1 µl
2× PrimeSTAR Max Premix (manufactured by TAKARA Inc.) 10 µl
Fw Primer (10 µM) 0.6 µl
Rv Primer (10 µM) 0.6 µl
D.W. 7.8 µl
Total 20 µl
Temperature Cycle:
30 Cycles of the Reaction Including 98° C. for 5 Seconds, 60° C. for 5 Seconds, and 72° C. for 45 Seconds The "nitrilase promoter+MpAAT1 gene" fragment as obtained above was treated with the restriction enzyme Sse8387I. Meanwhile, pMMA401 was also subjected to the SAP treatment after being treated with Sse8387I. Those DNA fragments were purified, after performing 0.7% agarose gel electrophoresis, by using Gel/PCR Purification Kit (manufactured by FAVORGEN). The conditions for restriction enzyme treatment reaction and the conditions for ligation reaction are as described below.

Figure 6:
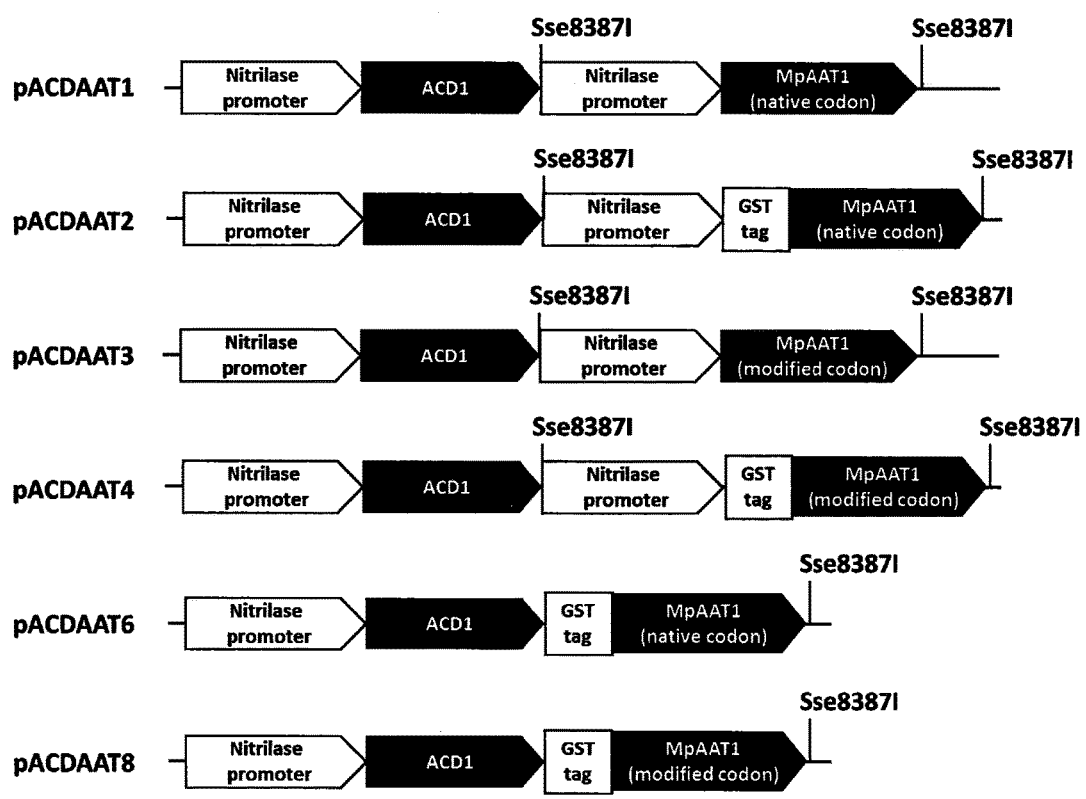
FIG. 6 is a drawing illustrating the structure of a plasmid for co-expressing ACD-AAT.

Composition for the Restriction Enzyme Treatment Reaction (AAT Fragment)
    PCR amplification fragment 40 µl
    10×M buffer 5 µl
    0.1% BSA 4 µl
    Sse8387I (manufactured by TAKARA Inc.) 1 µl
    Total 50 µl
    Composition for the restriction enzyme treatment reaction (Vector fragment)
    pMMA401 (vector) 3 µl
    10×M buffer 4 µl
    0.1% BSA 4 µl
    AP 1 µl
    Sse8387I (manufactured by Promega) 1 µl
    D.W. 27 µl
    Total 40 µl Composition for Ligation Reaction
    pMMA401 1 µl
    Insertion fragment 2 µl
    Ligation Mix (manufactured by TAKARA Inc.) 3 µl
    Total 6 µl By using the ligation reaction solution which has been mixed according to the above composition, transformation of *E. coli* JM109 strain was performed. From the obtained transformant, the plasmid was extracted, and by performing agarose electrophoresis after treatment with the restriction enzyme Sse8387I, it was confirmed that the fragment of a desired size is inserted. Further, according to nucleotide sequence analysis of a linking region of the insertion fragment of the obtained plasmid, it was confirmed to be the target plasmid, and the plasmid was named pACDAAT1. By using the same method as described above, total six plasmids with a different sequence for co-expressing ACD and AAT (pACDAAT2, pACDAAT3, pACDAAT4, pACDAAT6, and pACDAAT8) were prepared (see, FIG. 6).

Example 30: Production of Methacrylic Acid Using Genus *Rhodococcus*

DMA008 strain obtained from Example 27 (3) was transformed with the plasmid pMMA401. The obtained recombinant (DMA008/pMMA401) was used for producing methacrylic acid based on the resting cell reaction. One platinum loop inoculation was made to 2 mL of M9/Frc/Km10 liquid medium shown below (wassermann test tube), and cultured for 2 days under aerobic conditions at 30° C. using a rotary shaker (180 rpm) (pre-culture).

M9/Frc/Km10 Liquid Medium
    6.0 g/l $Na_2HPO_4$
    3.0 g/l $KH_2PO_4$
    0.5 g/l NaCl
    1.0 g/l $NH_4Cl$
    1 mM $MgSO_4.7H_2O$
    1 mM $CaCl_2$
    0.01 g/l Thiamine
    2.0 g/l Fructose
    10 µg/l Kanamycin 1 µl of the pre-broth was inoculated to 100 mLM9/Frc/Km10 liquid medium (100 µl medium/500 µl volume conical flask), and under aerobic conditions at 30° C. with a rotary shaker (230 rpm), culture was performed for 3 days (main culture).

After the main culture, 40 µl of the main-broth was transferred to a conical tube with volume of 50 mL and subjected to centrifugal separation (12000 rpm, 10 min) to obtain cells. The following reaction was performed by using the cells. To a conical tube with volume of 50 mL, 1 mL of the reaction solution was added and the reaction was performed for 24 hours under aerobic conditions at 30° C. with a rotary shaker (180 rpm).

Composition of Reaction Solution
    OD630=10 bacterial cells (final concentration)
    5.0 g/l 2-oxoisovaleric acid (final concentration)
    50 mM phosphate buffer/pH 7.0 (final concentration)

After the reaction, an appropriate amount of the supernatant of the reaction solution was collected and subjected to the analysis according to the following HPLC conditions. As a result, methacrylic acid of 12 ppm was detected.

Conditions for HPLC Analysis
    Apparatus: Waters 2695
    Column: ICsep USP L-17, φ4.0 mm×250 mm
    Mobile phase: 0.01 N $H_2SO_4$
    Flow amount: 0.35 µl/min
    Run time: 20 min
    Column temperature: 40° C.
    Sample temperature: 20° C.
    Detection: UV 210 nm Example 31: Production of Butyl Methacrylate Using Genus *Rhodococcus*

DMA008 strain obtained from Example 27 (3) was transformed with each of the plasmid pACDAAT1, pACDAAT2, pACDAAT3, pACDAAT4, pACDAAT6, and pACDAAT8. The obtained recombinant (DMA008/pACDAAT1, DMA008/pACDAAT2, DMA008/pACDAAT3, DMA008/pACDAAT4, DMA008/pACDAAT6 and DMA008/pACDAAT8) was used for producing a methacrylic acid ester based on the resting cell reaction. One platinum loop inoculation was made to 2 mL of LB Km10 liquid medium (wassermann test tube), and cultured for 2 days under aerobic conditions at 30° C. using a rotary shaker (180 rpm) (pre-culture). 1 µl of the pre-broth was inoculated to 100 mL LB Km10 (100 µl medium/500 µl volume conical flask), and under aerobic conditions at 30° C. with a rotary shaker (230 rpm), culture was performed for 3 days (main culture). Meanwhile, as a control, plasmid DMA008/pLK005 was used.

After the main culture, 40 µl of the main-broth was transferred to a conical tube with volume of 50 mL and subjected to centrifugal separation (12000 rpm, 10 min) to obtain cells. The following reaction was performed by using the cells. To a glass sample bottle with volume of 10 mL, 1 mL of the reaction solution was added and the reaction was performed for 18 hours under aerobic conditions at 30° C. with a rotary shaker (180 rpm).

Composition of Reaction Solution
    OD630=10 bacterial cells (final concentration)
    5.0 g/l 2-oxoisovaleric acid (final concentration)
    40 mM alcohol (final concentration)
    50 mM phosphate buffer/pH 7.5 (final concentration)
    As an alcohol, n-butanol was used.

After the reaction, 1 mL acetonitrile was added to the reaction solution and mixed well. After filtration using a syringe filter DISMIC/hole diameter 0.45 µm (manufactured by ADVANTEC), analysis was made by the HPLC analysis described in Example 49. In Table 34, the results of analyzing the product after 18 hours are shown.
Production of Butyl Methacrylate by *Rhodococcus* Recombinant which Co-Expresses ACD and AAT

TABLE 34

| Recombinant | Production amount of butyl methacrylate (μM) |
|---|---|
| DMA008/pLK005 | 0 |
| DMA008/pACDAAT1 | 7.51 |
| DMA008/pACDAAT2 | 2.06 |
| DMA008/pACDAAT3 | 4.34 |
| DMA008/pACDAAT4 | 0.46 |
| DMA008/pACDAAT6 | 2.18 |
| DMA008/pACDAAT8 | 0.52 |

Example 32: Production of Methacrylic Acid Ester Using Genus *Rhodococcus*

DMA008 strain obtained from Example 27 (3) was transformed with plasmid pACDAAT1. The obtained recombinant (DMA008/pACDAAT1) was used for producing a methacrylic acid ester based on the resting cell reaction. Further, as a control, plasmid DMA008/pLK005 was used. By using the method described in Example 31, the recombinant was cultured to obtain the cells.
Composition of Reaction Solution
  OD630=10 microbial cells (final concentration)
  5.0 g/l 2-oxoisovaleric acid (final concentration)
  40 mM alcohol (final concentration)
  50 mM phosphate buffer/pH 7.5 (final concentration)
As an alcohol, n-butanol, isobutanol, and 2-ethylhexylalcohol were used.

After the reaction, 1 mL acetonitrile was added to the reaction solution and mixed well. After filtration using a syringe filter DISMIC/hole diameter 0.45 μm (manufactured by ADVANTEC), analysis was made by the HPLC analysis described in Example 9B. In Table 35, the results of analyzing the product after 18 hours are shown.
Production of Methacrylic Acid Ester by *Rhodococcus* Recombinant which Co-Expresses ACD and AAT

TABLE 35

| | Production amount (mM) | | |
|---|---|---|---|
| Recombinant | Butyl methacrylate | Isobutyl methacrylate | 2-Ehtylhexyl methacrylate |
| DMA008/pLK005 | 0 | 0 | 0 |
| DMA008/pACDAAT1 | 0.01 | 0.006 | 0.02 |

Example 33: Cloning of ACD Homolog (ACD) Gene from *Pseudomonas aeruginosa* PAO1 and Production of Recombinant with High Expression Isolation of a gene which is involved with synthesis of methacrylic acid in microbes of the genus *Pseudomonas* having an ability to produce methacrylic acid was performed.
<Production of Genomic DNA>
*Pseudomonas aeruginosa* PAO1 strain (NBRC 106052) grown in a LB agar medium (1% bactotrypton, 0.5% bactoyeast extract, 0.5% NaCl, 1.5% agar) was inoculated to 10 mL of a LB liquid medium and cultured under shaking for 15 hours at 37° C. Once the culture is completed, the cells were collected by centrifuge from 2 mL of the culture, and 50 μL of genomic DNA was obtained by using Wizard Genomic DNA Purification Kit (manufactured by Promega).
<Cloning into Expression Vector>
By using the genomic DNA as a template and designing an oligonucleotide such that it is in the form in which a restriction enzyme recognition site, which is easily introducible to an expression vector, is added, a DNA fragment containing a gene presumed to encode ACD was produced by PCR method.

TABLE 36

| Isobutyryl CoA | | | Obtained plasmid | |
|---|---|---|---|---|
| dehydrogenase | PCR Primer | | pTrc99A | |
| homolog | Forward | Reverse | Vector | pET Vector |
| PA_acd1 | MMA-003 | MMA-004 | pMMA002 | pMMA102 |
| PA_acd2 | MMA-020 | MMA-006 | pMMA003 | pMMA103 |
| PA_acd3 | MMA-018 | MMA-008 | pMMA004 | pMMA104 |
| PA_acd4 | MMA-019 | MMA-010 | pMMA005 | pMMA105 |

```
Oligonucleotide primer
MMA-003:
                              (SEQ ID NO. 106)
5'-GACCCATGGATTTCGACCTCACCGAAGAAC-3'

MMA-004:
                              (SEQ ID NO. 107)
5'-GCCCTGCAGGATGCGATGGTTCGCGGCGTTC-3'

MMA-020:
                              (SEQ ID NO. 108)
5'-GGACATGTTTCGTGATCCGGAAACCCTGAAC-3'

MMA-006:
                              (SEQ ID NO. 109)
5'-GGCCTGCAGGCGAAGGATCGACGCTAGCCCTG-3'

MMA-018:
                              (SEQ ID NO. 110)
5'-GGACATGTTTCCCTGCGAAGAAGAGATCCAG-3'

MMA-008:
                              (SEQ ID NO. 111)
5'-GGCCTGCAGGCGCCGTTGCGGAAACGACGG-3'

MMA-019:
                              (SEQ ID NO. 112)
5'-GGCCATGGTACCGAGAACCCTGTTCAGCTC-3'

MMA-010:
                              (SEQ ID NO. 113)
5'-GGCCTGCAGGCTGGACGAGGAGGTGCTCGC-3'
```

Composition of Reaction Solution
  Sterilized water 22 μL
  2× PrimeSTAR (manufactured by Takara Bio Inc.) 25 μL
  Forward primer 1 μL
  Reverse primer 1 μL
  Genomic DNA 1 μL
  Total volume 50 μL
Temperature Cycle:
30 Cycles of the Reaction Including 98° C. for 10 Seconds, 55° C. for 15 Seconds, and 72° C. for 150 Seconds
The band of the obtained amplified product was purified with QIAquick Gel Extraction Kit (QIAGEN). For PA_acd1, the purified DNA was digested with the restriction enzyme NcoI (the restriction recognition site is included in the forward primer) and Sse8387I (the restriction recognition site is included in the reverse primer). For PA_acd2 to PA_acd4, the restriction was made with the restriction enzyme BspHI (the restriction recognition site is included in the forward primer) and Sse8387I (the restriction recognition site is included in the reverse primer). Separation was performed by agarose gel electrophoresis, and the target band was cut out from the gel and purified. For the purification, Gel/PCR Purification Kit (manufactured by FAVORGEN) was used, and 30 µL of sterilized water was used for elution.

By mixing the purified DNA (5 µL), vector pTrc99A (1 µL) previously digested with NcoI and Sse8387I, distilled water (4 µL) and solution I (DNA Ligation Kit ver. 2 (Takara Bio Inc.)) (10 µL) and incubating for 12 hours at 16° C., ligation between the PCR amplified product and the vector was made.

After inoculating the E. coli JM109 strain to 1 mL of the LB medium and performing aerobic pre-culture at 37° C. for 5 hours, 0.4 mL of the culture product was added to 40 mL of the SOB medium (2% bactotrypton, 0.5% bactoyeast extract, 10 mM NaCl, 2.5 mM KCl, 1 mM MgSO$_4$, 1 mM MgCl$_2$) and cultured at 18° C. for 20 hours. The culture product was collected by centrifugation, added with 13 mL of cooled TF solution (20 mM PIPES-KOH (pH 6.0), 200 mM KCl, 10 mM CaCl$_2$, 40 mM MnCl$_2$), and allowed to stand for 10 minutes at 0° C. After that, it was centrifuged again to remove the supernatant, and the precipitated E. coli was suspended in 3.2 µl cooled TF solution. After adding 0.22 µl dimethyl sulfoxide, it was allowed to stand for 10 minutes at 0° C.

To 200 µL of the competent cells as prepared above, 10 µL of the ligation solution was added, maintained for 30 minutes at 0° C., and applied with a heat shock at 42° C. for 30 seconds. After cooling at 0° C. for 2 minutes, 1 mL of the SOC medium (20 mM glucose, 2% bactotrypton, 0.5% bactoyeast extract, 10 mM NaCl, 2.5 mM KCl, 1 mM MgSO$_4$, 1 mM MgCl$_2$) was added and followed by culture under shaking at 37° C. for 1 hour.

After the culture, each was applied in an amount of 100 µL to the LBAmp agar medium (LB medium containing ampicillin 100 mg/l and 1.5% agar) and further cultured at 37° C. Plural colonies of the transformant which have been grown on the agar medium were cultured overnight at 37° C. on 1.5 µl LBAmp medium (LB medium containing ampicillin at 100 mg/l). After collecting the cells, the plasmid DNA was prepared by using QIAprep Spin Miniprep kit (manufactured by QIAGEN).

The nucleotide sequence of the obtained recombinant plasmid DNA was determined by using CEQ DTCS Quick Start Kit and Fluorescence sequence CEQ 2000XL DNA Analysis (both manufactured by BECKMAN COULTER, USA), and named plasmid pMMA002 to pMMA005 (Table 36).

ACD homolog gene was also inserted to the pET16b vector according to the same procedure as above, and the obtained plasmids were named pMMA102 to pMMA105 (Table 36). Meanwhile, since pET16b has no Sse8387I site, a linker containing the Sse8387I restriction site inserted to BamHI site of pET16b was prepared in advance, and it was used as a vector.

Example 34: Cloning of ACD Homolog Gene from Rhodococcus erythropolis PR4 Strain and Production of Recombinant with High Expression Isolation of a gene which is involved with synthesis of methacrylic acid in microbes of the genus Pseudomonas was performed.

<Production of Genomic DNA>

Rhodococcus erythropolis PR4 strain (NBRC100887) grown in a LB agar medium (LB medium, 1.5% agar) was inoculated to 10 mL of a LB liquid medium and cultured under shaking for 36 hours at 30° C. Once the culture is completed, the cells from 2 mL of the culture were collected by centrifuge, and 100 µL of genomic DNA was obtained by using Wizard Genomic DNA Purification Kit (manufactured by Promega).

<Cloning into High Expression Vector>

By using the genomic DNA as a template and designing an oligonucleotide such that it is in the form in which a restriction enzyme recognition site, which is easily introducible to an expression vector, is added, a DNA fragment containing a gene presumed to encode ACD was produced by PCR method.

TABLE 37

| Isobutyryl CoA dehydrogenase homolog | PCR Primer | | Obtained plasmid | |
|---|---|---|---|---|
| | Forward | Reverse | pTrc99A Vector | pET Vector |
| RE_acd1 | MMA 021 | MMA 022 | pMMA009 | pMMA109 |
| RE_acd2 | MMA 023 | MMA 024 | pMMA010 | pMMA110 |

```
Oligonucleotide primer
MMA-021:
                            (SEQ ID NO. 114)
5'-GGACATGTTTACTCTGACCGATGACGAGCG-3'

MMA-022:
                            (SEQ ID NO. 115)
5'-GGCCTGCAGGCCGTCACGCTTTTCGATCAATAC-3'

MMA-023:
                            (SEQ ID NO. 116)
5'-CCACATGTCCGATTACCTTGCCACCGGAGC-3'

MMA-024:
                            (SEQ ID NO. 117)
5'-GGCCTGCAGGATCTTCTTGGGGTTCGTCACAAC-3'
```

Amplification by a PCR reaction was performed in the same manner as Example 33.

The band of the obtained amplified product was purified with QIAquick Gel Extraction Kit (QIAGEN) and digested with the restriction enzyme PciI (the restriction recognition site is included in the forward primer) and Sse8387I (the restriction recognition site is included in the reverse primer). The following operations were performed like Example 33 to obtain plasmid pMMA009 and 010 having pTrc99A as a vector and plasmid pMMA109 and 110 having pET16b as a vector (Table 37).

Example 35: Production of Cell Extract from Recombinant in which ACD Homolog Gene is Expressed and Analysis of Protein Expression By using the expression plasmid containing ACD homolog gene produced in Example 33 and 34, E. coli JM109 (for pMMA002 to pMMA005, pMMA009 and 010) or E. coli BL21 (DE3) (for pMMA102 to pMMA105, pMMA109 and 110) was transformed. Transformed E. coli JM109 strains were cultured as described below.

The recombinant E. coli was inoculated to LB medium containing 1 mL of 100 µg/mL ampicillin and subjected to pre-culture at 37° C. for 7 hours. 0.1 µl of the culture was harvested and added to 100 µl of the same medium (containing 100 µg/mL ampicillin, 1 mM isopropyl-β-D-thiogalactopyranoside (hereinbelow, IPTG)) and cultured under shaking at 37° C. for 15 hours. From the obtained culture, the cells were collected by centrifuge (3,700×g, 10 minutes, 4° C.), washed with 10 mM sodium phosphate buffer (pH 7.0), and suspended in the same buffer solution. As a control strain, JM109/pTrc99A was used.

The transformed E. coli BL21 (DE3) strain was cultured as follows. The recombinant E. coli was added to LB medium containing 1 mL of 100 μg/mL ampicillin and subjected to pre-culture at 37° C. for 14 hours. 0.1 mL of the culture was collected, added to 100 mL of the same medium (100 μg/mL ampicillin), and cultured under shaking until OD at 37° C. becomes 0.3. Then, IPTG was added to have final concentration of 1 mM and it was cultured again under shaking for several hours. From the obtained culture, the cells were collected by centrifuge (3,700×g, 10 minutes, 4° C.), washed with 10 mM sodium phosphate buffer (pH 7.0), and suspended in the same buffer solution. As a control strain, BL21 (DE3)/pET16b was used.

1 mL was collected from the obtained cell suspension, and the cell extract was prepared as follows. By using ultrasonic homogenizer VP-300 (manufactured by DYTEC, Japan), disruption was performed for 3 minutes with pulse output at interval of 1 second under ice cooling. Next, by performing centrifuge (10,000×g, 5 minutes, 4° C.), the obtained supernatant was collected as cell extract.

Figure 7:
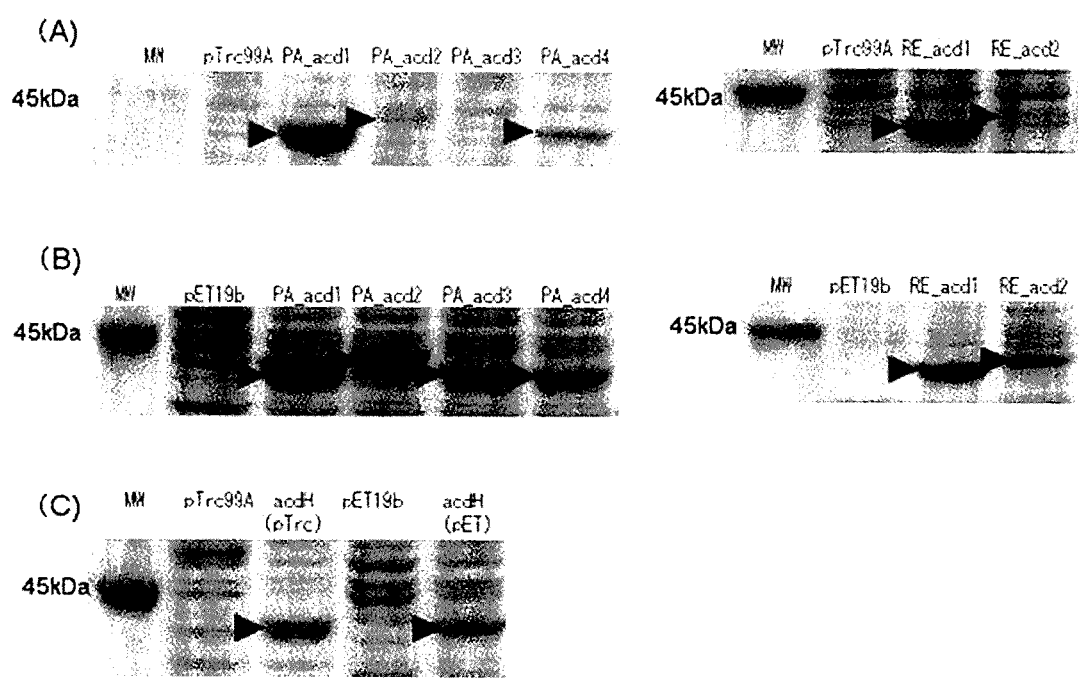
FIG. 7 is a drawing illustrating the expression of the recombinant protein based on SDS polyacrylamide gel electrophoresis. The arrow indicates the position of the target protein. (A) Cell extract of the recombinant with the described gene introduced therein, in which E. coli JM109 is used as a host and pTrc99A is used as a vector, (B) a cell extract of the recombinant with the described gene introduced therein in which E. coli BL21 (DE3) is used as a host and pET19b is used as a vector, and (C) a cell extract of the recombinant with the acdH gene introduced therein.

The protein analysis by SDS gel electrophoresis was performed as follows. After appropriately diluting the cell extract, it was mixed with a sample solution for polyacrylamide gel electrophoresis (0.1M Tris-HCl (pH 6.8), 4% w/v SDS, 0.2M dithiothreitol, 20% v/v glycerol, trace amount of bromophenol blue) and heated at 98° C. for 5 minutes for denaturation. 10% polyacrylamide gel was prepared, and by using 5 μL of the denatured sample per lane, the electrophoretic analysis was performed (FIG. 7).

Example 36: Measurement of ACD Activity of Cell Extract

The ACD activity was measured according to production of methacrylyl-CoA having isobutyryl-CoA as a substrate. To a solution (1.84 mL) containing 1-methoxy-5-methylphenazinum methyl sulfate, flavine adenine dinucleotide, and isobutyryl-CoA at final concentration of 6 mM, 0.4 mM, and 1 mM, respectively in 100 mM sodium phosphate buffer (pH 8.0), 0.16 μl of the cell extract which has been obtained like Example 35 was added to have 2 μl. After the reaction at 37° C. for 30 minutes, protein removal was performed by ultrafiltration using Centricut Ultramini W-10 (manufactured by Kurashiki Boseki), the reaction was terminated and analysis by HPLC was performed under following conditions. The results are shown in Table 38. It was able to confirm that high ACD activity is observed from PA_acd1 and RE_acd1 and methacrylyl-CoA can be produced from isobutyryl-CoA by those enzymes.

Conditions for HPLC Analysis

Column: Inertsil ODS-3V, 4.6 mm×250 mm

Mobile phase: 30% MeOH, 50 mM $H_3PO_4$, pH 5.7

Flow amount: 1.0 μl/min column temperature: 35° C. Detection: UV 254 nm (210 nm)

Injection amount 10 μl reaction solution was diluted by 10 times with a mobile phase and measured

TABLE 38

| Vector | Isobutyryl CoA dehydrogenase homolog | Recombinant | Activity (U/mg protein) |
|---|---|---|---|
| pTrc99A | PA_acd1 | JM109/pMMA002 | 0.63 |
| | PA_acd2 | JM109/pMMA003 | 0 |
| | PA_acd3 | JM109/pMMA004 | <0.01 |
| | PA_acd4 | JM109/pMMA005 | 0.024 |
| | RE_acd1 | JM109/pMMA009 | 0.063 |
| | RE_acd2 | JM109/pMMA010 | 0 |
| | acdH | JM109/pMMA001 | <0.01 |
| pET19b | PA_acd1 | BL21(DE3)/pMMA102 | 0.44 |
| | PA_acd2 | BL21(DE3)/pMMA103 | 0 |
| | PA_acd3 | BL21(DE3)/pMMA104 | 0.010 |
| | PA_acd4 | BL21(DE3)/pMMA105 | <0.01 |
| | RE_acd1 | BL21(DE3)/pMMA109 | 0.009 |
| | RE_acd2 | BL21(DE3)/pMMA110 | 0 |
| | acdH | BL21(DE3)/pMMA102 | <0.01 |

Example 37: Cloning of BCKAD Gene, Production of Recombinant with High Expression, Preparation of Cell Extract, and Analysis of Protein Expression Gene cloning, production of an expression plasmid, and production of a recombinant were performed in the same manner as Example 33. The DNA fragment containing the entire gene operon which encodes the BCKAD complex gene was produced, by using the genomic DNA of Pseudomonas aeruginosa PAO1 strain as a template, by PCR method with the primer shown in Table 39. The obtained fragment was digested with the restriction enzyme BspHI and Sse8387I, and by inserting to the vector pTrc99A and pET16b in the same manner as Example 33, the recombinant plasmid (pWA108 and pWA008) was obtained.

TABLE 39

| Gene of | | | Obtained plasmid | |
|---|---|---|---|---|
| 2-oxoisovaleric acid | PCR Primer | | pTrc99A | pET |
| dehydrogenase complex | Forward | Reverse | Vector | Vector |
| BCKAD | MMA 15 | MMA 16 | pWA108 | pWA008 |

```
Oligonucleotide primer
MAA-15:
                                    (SEQ ID NO. 118)
5'-GGCCTGTCATGAGTGATTACGAGCCG-3'

MAA-16:
                                    (SEQ ID NO. 119)
5'-CGGCCCTGCAGGTTCGCGGGAATCAGATGTGC-3'
```

The recombinant E. coli JM109/pWA108 as obtained above was cultured in the same manner as Example 35 (in case of this recombinant, high protein expression was observed even without adding IPTG, and thus, although the reason remains unclear, the culture was performed without adding IPTG). In case of the recombinant E. coli BL21 (DE3)/pWA008, the culture was performed in the same manner as Example 35. Preparation of cell extract and analysis of protein expression by SDS polyacrylamide gel electrophoresis were performed in the same manner as Example 35.

Example 38: Cloning of BCKAD Gene from Bacteria of Genus *Rhodococcus* (Cluster 1) and Production of Recombinant with High Expression Because there was no knowledge about BCKAD gene from the bacteria of the genus *Rhodococcus*, by performing homology search for the genome sequence of the *Rhodococcus erythropolis* PR4 strain based on the amino acid sequence of the BCKAD complex gene of *Pseudomonas aeruginosa* PAO1 strain, two candidate gene clusters were found. They are referred to as Cluster 1 and Cluster 2.

With regard to Cluster 1, the four genes consist of a nucleotide sequence represented by SEQ ID NOS. 63, 65, 67, 69 like the *Pseudomonas aeruginosa* PAO1 strain, and the amino acid sequence encoded by them are SEQ ID NOS. 62, 64, 66, 68. With regard to Cluster 2, three genes consist of the nucleotide sequence represented by SEQ ID NOS. 71, 73, and 75, respectively, and the amino acid encoded by them are SEQ ID NOS. 70, 72, and 74, respectively.

Cloning of BCKAD complex gene of Cluster 1, production of an expression plasmid, and production of a recombinant were performed in the same manner as Example 33. The DNA fragment containing the entire gene operon which encodes the BCKAD complex gene was produced, by using the genomic DNA of *Rhodococcus* erythropolis PR4 strain as a template, by PCR method with use of the primer shown below. The obtained fragment was digested with the restriction enzyme BspHI and Sse8387I, and by inserting to the vector pTrc99A in the same manner as Example 33, the recombinant plasmid (pMMA019) was obtained.

```
Oligonucleotide primer
MMA-187:
                                       (SEQ ID NO. 120)
5'-GGTCATGACTCTTGTCGAGCCCTTG-3'

MMA-140:
                                       (SEQ ID NO. 121)
5'-GACCTGCAGGTCCTCTTCTGGTCATGGTTC-3'
```

Example 39: Cloning of BCKAD Gene from Bacteria of Genus *Rhodococcus* (Cluster 2) and Production of Recombinant with High Expression Cloning of BCKAD complex gene of Cluster 2, production of an expression plasmid, and production of a recombinant were performed as follows. It was produced, by using the genomic DNA of *Rhodococcus erythropolis* PR4 strain as a template, by PCR method with use of the primer shown below.

```
Oligonucleotide primer
MMA-188:
                                       (SEQ ID NO. 122)
5'-AGGAAACAGACCATGATCGACAACCTCGATTA-3'

MMA-189:
                                       (SEQ ID NO. 123)
5'-CTTGCATGCCTGCAGGCTCACTCGTTCCTTTTTACAG-3'
```

The above PCR product and vector pTrc99A which has been digested in advance with the NcoI and Sse8387I were linked by performing recombination of terminal sequence using In-Fusion HD Cloning Kit (manufactured by Takara Bio) and following the manufacturer's instruction. 2 µL of the infusion reaction solution was used and transformation of the *E. coli* JM109 was performed in the same manner as Example 33. From the obtained transformant, the recombinant plasmid (pMMA020) was obtained.

Example 40: Measurement of Activity of Cell Extract of Recombinant which Expresses BCKAD Gene at High Level The BCKAD activity was measured according to production of methacrylyl-CoA having 2-oxoisovaleric acid as a substrate.

To a solution (0.7 mL) containing $MgCl_2$, thiamine pyro acid, CoA-SH, and DTT at final concentration of 1 mM, 0.2 mM, 1 mM and 2 mM, respectively in 100 mM sodium phosphate buffer (pH 7.0), 0.2 µl of the cell extract obtained like Example 37 was added to have 0.9 µl. After the reaction at 37° C. for 30 minutes by adding 0.1 mL of calcium 2-oxoisovalerate (final concentration 4 mM), protein removal was performed by ultrafiltration using Centricut Ultramini W-10 (manufactured by Kurashiki Boseki), the reaction was terminated and analysis by HPLC was performed under following conditions. As a result, production of isobutyryl-CoA was observed at 0.83 mM or 0.88 mM for JM109/pWA108 and BL21 (DE3)/pWA008, respectively.

Conditions for HPLC Analysis

Column: Inertsil ODS-3V, 4.6 mm×250 mm

Mobile phase: 35% MeOH, 50 mM $H_3PO_4$, pH 5.7

Flow amount: 1.0 µl/min column temperature: 35° C.

Detection: UV 254 nm (210 nm)

Injection amount 10 µl reaction solution was diluted by 10 times with a mobile phase and measured

Example 41: Synthesis of Methacrylyl-CoA from 2-Oxoisovaleric Acid Using Mixture of Cell Extracts of Recombinant with High Expression of BCKAD Gene and Recombinant in which ACD Homolog Gene is Expressed To a solution (0.6 mL) containing 1 mM $MgCl_2$, 0.2 mM thiamine pyro acid, 1 mM CoA-SH, 2 mM DTT, 2 mM nicotine amide adenine nucleotide (NAD), 0.04 mM flavine adenine dinucleotide (FAD), 2 mM valine, each in final concentration in 100 mM sodium phosphate buffer (pH 7.0), 0.1 µl of the cell extract (JM109/pMMA002 and JM109/pWA108) obtained like Example 35 and 40 was added to have 0.8 ml. After the reaction at 37° C. for 30 minutes with addition of 0.1 mL calcium 2-oxoisovalerate (final concentration of 4 mM), production of isobutyryl-CoA was confirmed by HPLC. By adding 0.1 mL of 1-methoxy-5-methylphenazinum methyl sulfate (final concentration 6 mM), the reaction was allowed to occur again for 3 hours. After the reaction, ultrafiltration was performed by using Centricut Ultramini W-10 (manufactured by Kurashiki Boseki). The reaction was terminated by removing proteins and analysis by HPLC was performed. As a result, production of methacrylyl-CoA of 2 mM was observed.

Example 42: Synthesis of Butyl Methacrylate

To a solution (1.84 mL) containing 6 mM 1-methoxy-5-methylphenazinum methyl sulfate, 0.4 mM FAD and 1 mM isobutyryl-CoA, each in final concentration in 100 mM sodium phosphate buffer (pH 8.0), 0.16 ml of the cell extract having an ACD activity, which has been obtained like Example 35, was added and adjusted to 2 µl. After the reaction at 37° C. for 30 minutes, the analysis was performed under HPLC conditions shown in Example 41. As a result, production of methacrylyl-CoA was observed while the peak of isobutyryl-CoA has disappeared.

By using the reaction solution obtained as above in which methacrylyl-CoA is produced and reacting it with banana flesh having the AAT activity and n-butyl alcohol, production of butyl methacrylate was observed. Specifically, after removing the skin, banana flesh was sliced to a thickness of about 1 mm, and cut again to four pieces. 1 g of the sliced banana, 0.9 mL of the reaction solution for synthesizing methacrylyl-CoA, 0.1 mL of 3.5 M KCl solution, and 5 µL of n-butyl alcohol were added to a 50 ml flask and sealed, and the reaction was allowed to occur at 30° C. for 2 hours. After the reaction, 150 µL was collected from of head space of the 100 mL flask and analyzed according to the following GC conditions. As a result, it was found that butyl methacrylate of 0.015 mM was produced.

Conditions for GC Analysis
  Column: DB-WAX, 30 m×0.32 mm
  Column temperature: 50° C. 5 min→5° C./min→100° C. (total 15 min)
  Carrier gas: He
  Inject: 200° C. splitless (sampling time of 1 min)
  Detect: 250° C. FID Injection amount: 150 µL Meanwhile, concentration of butyl methacrylate was calculated as follows: an aqueous solution with known concentration is prepared, 2 mL of the aqueous solution is added to a 100 mL flask, and after incubation at 30° C. for 30 min, collection is made from the head space with the same method as above, GC analysis is made, and then a calibration curve is constructed.

Example 43: Production of Plasmid for *E. coli* for Co-Expressing BCKAD and ACD

The DNA fragment which contains the ACD gene (PA_acd1 gene) is inserted to the downstream of BCKAD of pWA108 produced in Example 37 by using In-Fusion HD Cloning kit (manufactured by Takara Bio Inc.) to prepare the plasmid pMMA201 and pMMA202 for co-expressing BCKAD and ACD. Further, in the same manner, the DNA fragment which contains the BCKAD gene is inserted to the downstream of PA_acd1 of pMMA002 produced in Example 33 to produce the plasmid pMMA203 and pMMA204 for co-expression. Details are described below.

(1) Production of Plasmid pMMA201
By using pMMA102 produced in Example 33 as a template, PA_acd1 gene was amplified by PCR method. PCR conditions are as described below.

```
Fw Primer
MMA-039
                                      (SEQ ID NO. 128)
TAGAGTCGACCTGCACGAGATCTCGATCCCGCGAAAT Rv Primer
MMA-040
                                      (SEQ ID NO. 129)
GCTTGCATGCCTGCACAGCAGCCAACTCAGCTTCCTTT
```

Composition of Reaction Solution
  Template (pMMA102) 1 µl
  2× PrimeSTAR Max Premix (manufactured by TAKARA Inc.) 25 µl
  FW Primer (20 µM) 1 µl
  Rv Primer (20 µM) 1 µl
  D.W. 22 µl
  Total 50 µl Temperature Cycle:
30 Cycles of the Reaction Including 98° C. for 10 Seconds, 60° C. for 10 Seconds, and 72° C. for 120 Seconds When the PCR is completed, the fragment was determined based on 0.7% agarose gel electrophoresis by using 1 µl sample. As a result, amplification of a fragment of about 1.1 kb was observed. The PCR product was briefly purified by Gel/PCR Purification Kit (manufactured by FAVORGEN) to obtain a PCR fragment.

Meanwhile, the plasmid pWA108 with the restriction enzyme Sse8387I was digested to have a vector-side fragment. Both fragments described above were used for the reaction shown below which uses In-Fusion HD Cloning Kit.

Composition of Reaction Solution
  5× In-Fusion HD Enzyme Premix 2 µl
  Vector-side fragment 1.5 µl
  PCR fragment 1 µl
  D.W. 3.5 µl
  Total 10 µl After incubating for 15 minutes at 50° C., the above reaction solution was cooled on ice and used for transformation of *E. coli* JM109 strain. Selection of the *E. coli* transformant was performed on an LBAmp medium. From the obtained transformant, a plasmid was prepared by the method described in Example 33 to obtain the target plasmid. Confirmation of the plasmid was performed by examining the fragment size after treatment with the restriction enzyme XbaI and Sse8387I and the sequence of the linking region between the insertion fragment and the vector. The target plasmid was named pMMA201.

(2) Production of Plasmid pMMA202
By using pMMA102 produced in Example 33 as a template, PA_acd1 gene was amplified by PCR method. PCR primers are as described below.

```
Fw Primer
MMA-042
                                      (SEQ ID NO. 130)
TAGAGTCGACCTGCACCTCTAGAAATAATTTTGTTTA Rv Primer
MMA-040
                                      (SEQ ID NO. 129)
GCTTGCATGCCTGCACAGCAGCCAACTCAGCTTCCTTT
```

In the same manner as above, the PCR fragment and the plasmid pWA108 digested with the restriction enzyme Sse8387I were ligated to each other by using In-Fusion HD Cloning Kit and the target plasmid was named pMMA202.

(3) Production of Plasmid pMMA203
By using p pWA008 produced in Example 37 as a template, BCKAD gene was amplified by PCR method. PCR primers are as described below.

```
Fw Primer
MMA-041
                                      (SEQ ID NO. 131)
CCATCGCATCCTGCACGAGATCTCGATCCCGCGAAAT Rv Primer
MMA-040
                                      (SEQ ID NO. 129)
GCTTGCATGCCTGCACAGCAGCCAACTCAGCTTCCTTT
```

The reaction method and obtaining the PCR fragment are performed in the same manner as those described in (1) above.

Meanwhile, the plasmid pMMA002 containing PA_acd1 gene was digested with the restriction enzyme Sse8387I to give a vector-side fragment. In the same manner as above (1), both fragments were subjected to the reaction using In-Fusion HD Cloning Kit, and transformation of E. coli JM109 strain was performed by using the reaction solution. A plasmid was obtained from the obtained transformant, and in the same manner as (1) above, plasmid confirmation was carried out. The target plasmid was named pMMA203.

(4) Production of Plasmid pMMA204

By using pWA008 produced in Example 37 as a template, BCKAD gene was amplified by PCR method. PCR primers are as described below.

```
Fw Primer
MMA-043
                              (SEQ ID NO. 132)
CCATCGCATCCTGCACCTCTAGAAATAATTTTGTTTA Rv Primer
MMA-040
                              (SEQ ID NO. 129)
GCTTGCATGCCTGCACAGCAGCCAACTCAGCTTCCTTT
```

The reaction method and obtaining the PCR fragment are performed in the same manner as those described in (1) above. In the same manner as above, the PCR fragment and the plasmid pMMA002 which has been digested with the restriction enzyme Sse8387I were ligated to each other by using In-Fusion HD Cloning Kit and the target plasmid was named pMMA204.

Example 44: (In Vitro) Synthesis of Methacrylyl-CoA from 2-Oxoisovaleric Acid Using Cell Extract of E. coli Recombinant in which BCKAD and ACD are Expressed Cell extract of the JM109/pMMA204 strain was obtained in the same manner as the method described in Example 35. As a control strain, JM109/pTrc99A was used. With the same method as the method described in Example 40, 0.1 ml of calcium 2-oxoisovalerate (final concentration of 4 mM) was added to the cell extract of JM109/pMMA204. After the reaction at 37° C. for 30 minutes, production of isobutyryl-CoA was confirmed by HPLC, and 0.1 mL of 1-methoxy-5-methylphenazinum methyl sulfate (final concentration 6 mM) was added. The reaction was allowed to occur again for 3 hours. After the reaction, removal of the protein (terminating the reaction) was performed by ultrafiltration using Centricut Ultramini W-10 (manufactured by Kurashiki Boseki). Then, analysis was made by HPLC according to the following conditions.

Conditions for HPLC Analysis
  Column: Capcell Pak ODS-UG120 (Shiseido), particle diameter μm, 2.0 mm I.D.×250 mm
  Mobile phase: 25% MeOH, 50 mM $H_3PO_4$, pH 5.7
  Flow amount: 1.0 μl/min
  Column temperature: 35° C.
  Detection: UV 254 nm (210 nm)
  Injection amount 10 μl reaction solution was diluted by 10 times with a mobile phase and measured As a result, production of 0.1 mM methacrylyl-CoA was observed. It was possible to confirm that BCKAD and ACD expressed by E. coli recombinant can produce methacrylyl-CoA from 2-oxoisovaleric acid in the presence of 1-methoxy-5-methylphenazinum methyl.

Reference Example 4: (In Vivo) Synthesis of Methacrylyl-CoA from 2-Oxoisovaleric Acid Using Recombinant E. coli in which BCKAD and ACD are Expressed By using the recombinant E. coli in which BCKAD and ACD are expressed, synthesis of methacrylic acid or methacrylyl-CoA from 2-oxoisovaleric acid was performed.

JM109/pMMA201 strain, JM109/pMMA202 strain, JM109/pMMA203 strain and JM109/pMMA204 strain were inoculated to LBAmp medium (ampicillin 100 mg/l) containing 1 ml of 100 μg/mL ampicillin and pre-cultured at 37° C. for 6 hours. 0.1 mL of the culture was collected and added to the same medium (containing 1 mM IPTG) and cultured under shaking at 37° C. for 18 hours. The obtained culture was collected in an amount of 10 mL and added to 90 mL of the LBAmp medium containing 0.5% calcium 2-oxoisovaleric acid, followed by culture under shaking at 37° C. for 25 hours. Once the culture is completed, the culture was filtered and analysis was made by HPLC according to the following conditions.

Conditions for HPLC Analysis
  Column: Wakopak Wakobeads-T-132-E, ϕ7.8 mm×300 mm
  Mobile phase: 0.1% phosphoric acid
  Flow amount: 0.5 μl/min
  column temperature: 40° C.
  Detection: UV 210 nm
  Injection amount: 5 ul As a result, production of methacrylic acid and methacrylyl-CoA was not observed but the production of isobutyric acid of 14.2 mM was observed. Thus, from the in vivo reaction in E. coli, it was shown to be impossible to have synthesis of methacrylic acid or methacrylyl-CoA.

Concentration of Isobutyric Acid Produced

TABLE 40

| Name of strain | Concentration of isobutyric acid (mM) |
|---|---|
| JM109/pMMA201 | 13.5 |
| JM109/pMMA202 | 13.4 |
| JM109/pMMA203 | 13.4 |
| JM109/pMMA204 | 14.2 |

Reference Example 5: Synthesis of Methacrylic Acid from 2-Oxoisovaleric Acid Using Recombinant E. coli resting Cells in which BCKAD and ACD are Expressed According to the same method as the method described in Example 35, JM109/pMMA201 strain was cultured. From the obtained culture, the cells were collected by centrifuge (3,700×g, 10 minutes, 4° C.), washed with 10 mM sodium phosphate buffer (pH 7.0), and suspended in the same buffer solution to obtain cell suspension. By using the cell suspension, about 3 ml of the resting cell reaction solution was prepared and the reaction was performed at 30° C., 180 rpm for 24 hours.

Composition of Resting Cell Reaction Solution
  50 mM Sodium phosphate buffer solution (pH7.0)
  0.5% Calcium 2-oxoisovalerate
  OD10 Cell suspension.

Once the culture is completed, the culture was filtered and analysis was made by HPLC according to the conditions described in Reference example 4. As a result, production of methacrylic acid was not observed but production of isobutyric acid of 15.2 mM was observed. Similar to Reference example 4, it was shown to be impossible to have synthesis of methacrylic acid or methacrylyl-CoA using *E. coli* in the resting cell reaction.

Reference Example 6: Cloning of ACD Gene (acdH) from *Streptomyces coelicolor* A3 (2), Production of Expression Recombinant, Preparation of Cell Extract, Analysis of Protein Expression, and Measurement of ACD Activity According to the method described in Example 33 to 32, an expression recombinant in which acdH gene derived from *Streptomyces coelicolor* A3 (2) is added was prepared, and preparation of cell extract, analysis of protein expression, and measurement of ACD activity were performed. The results of analyzing the protein expression and the results of measuring the enzyme activity are shown in FIG. 7(C) and Table 38, respectively. Meanwhile, oligonucloetides used for PCR to produce the plasmid are as follows.

```
Oligonucleotide primer
MMA-001:
                                  (SEQ ID NO. 124)
5'-CACCATGGACCACAAGCTCTCCCCCGAAC-3'

MMA-002:
                                  (SEQ ID NO. 125)
5'-GCCCTGCAGGCTCAGCCCACCAGCCCCAAC-3'
```

Reference Example 7: Synthesis of Isobutyl Methacrylate by AAT

After removing the skin, banana flesh was sliced using a cutter to a thickness of about 1 mm, and cut again to four pieces. 2 g of the sliced banana, 2 mL of the solution containing 2 3 mM methacrylyl-CoA and 0.35 M KCl, and 5 μL of isobutyl alcohol were added in order to a 100 ml flask. After sealing, the reaction was allowed to occur at 30° C. The reaction mixture containing isobutyl methacrylate which has been produced after 1, 2 or 3 hours was collected in an amount of 150 μl from the head space of the 100 ml flask and then analyzed by GC under following conditions. The results are shown in Table 41.

TABLE 41

| Production amount of isobutyl methacrylate | |
|---|---|
| Time | Production amount of isobutyl methacrylate (mM) |
| 1 | 0.19 |
| 2 | 0.38 |
| 3 | 0.45 |

Conditions for GLC Analysis
Column: DB-WAX, 30 m×0.32 mm
Column temperature: 50° C.-5 min→5° C./min→100° C. (total 15 min)
Carrier gas: He
Inject: 200° C. splitless (sampling time 1 min)
Detect: 250° C. FID injection amount: 150 μl Meanwhile, concentration of methacrylic acid ester was calculated as follows: an aqueous solution with known concentration is prepared first, 2 mL of the aqueous solution is added to a 100 mL flask, and after incubation at 30° C. for 30 min, collection is made from the head space with the same method as above, GC analysis is made, and then a calibration curve is constructed.

Reference Example 8: Synthesis of Butyl Methacrylate by AAT

The same process as Reference example 7 was performed except that n-butyl alcohol is used instead of isobutyl alcohol. The results are shown in Table 42.

TABLE 42

| Production amount of butyl methacrylate | |
|---|---|
| Time | Production amount of butyl methacrylate (mM) |
| 2 | 0.20 |
| 5.5 | 0.30 |

Reference Example 9: Synthesis 2 of Butyl Methacrylate by AAT 2 g of the plant specimen shown in Table 43, 2 ml of the solution containing 2.3 mM methacrylyl-CoA and 0.35 M KCl, and 10 μl of n-butyl alcohol were added in order to a 100 ml flask. After sealing, the reaction was allowed to occur at 30° C. Analysis of methacrylic acid ester was performed in the same manner as Reference example 7. The results are shown in Table 43.

TABLE 43

| Production amount of butyl methacrylate | | | |
|---|---|---|---|
| Plant | Part for use | Reaction time | Production amount of butyl methacrylate (mM) |
| Strawberry | Fruit flesh • sliced to thickness of about 1 mm | 3 | 0.010 |
| Kiwi | Fruit flesh • sliced to thickness of about 1 mm | 5 | 0.012 |
| Apple | Fruit skin • sliced to thickness of about 1 mm | 5 | 0.016 |
| Melon | Fruit flesh • sliced to thickness of about 1 mm | 6 | 0.015 |
| Pear | Fruit skin • sliced to thickness of about 1 mm | 4 | 0.013 |
| Papaya | Fruit skin • sliced to thickness of about 1 mm | 4 | 0.027 |
| Avocado | Fruit skin • sliced to thickness of about 1 mm | 6 | 0.035 |
| Blueberry | Fruit skin • sliced to thickness of about 1 mm | 6 | 0.009 |
| Plum | Fruit skin • sliced to thickness of about 1 mm | 4 | 0.002 |

Reference Example 10: Synthesis of Ethyl Methacrylate by AAT 2 g of the plant specimen shown in Table 44, 2 ml of the solution containing 2 3 mM methacrylyl-CoA and 0.35 M KCl, and 6.4 ml of ethyl alcohol were added in order to a 100 ml flask. After sealing, the reaction was allowed to occur at 30° C. Analysis of methacrylic acid ester was performed in the same manner as Reference example 7. The results are shown in Table 44.

TABLE 44

| | Production amount of ethyl methacrylate | | |
|---|---|---|---|
| Plant | Part for use | Reaction time | Production amount of ethyl methacrylate (mM) |
| Apple | Fruit skin • sliced to thickness of about 1 mm | 5 | 0.110 |
| Papaya | Fruit skin • sliced to thickness of about 1 mm | 6 | 0.003 |
| Avocado | Fruit skin • sliced to thickness of about 1 mm | 6 | 0.006 |

Reference Example 11: Synthesis of Methyl Methacrylate by AAT 2 g of the plant specimen shown in Table 45, 2 ml of the solution containing 2.3 mM methacrylyl-CoA and 0.35 M KCl, and 4.4 µl of methyl alcohol were added in order to a 100 ml flask. After sealing, the reaction was allowed to occur at 30° C. Analysis of methacrylic acid ester was performed in the same manner as Reference example 7. The results are shown in Table 45.

TABLE 45

| | Production amount of methyl methacrylate | | |
|---|---|---|---|
| Plant | Part for use | Reaction time | Production amount of methyl methacrylate (mM) |
| Apple | Fruit skin • sliced to thickness of about 1 mm | 5 | 0.043 |
| Papaya | Fruit skin • sliced to thickness of about 1 mm | 6 | 0.004 |
| Avocado | Fruit skin • sliced to thickness of about 1 mm | 6 | 0.007 |

Example 45: Production of Recombinant E. coli Having Plant-Derived AAT Gene Incorporated Therein Synthesis of the plant-derived AAT gene represented by SEQ ID NOS. 77, 79 and 81 was performed by Takara Bio Inc.

Apple AAT (MpAAT1): amino acid sequence (SEQ ID NO. 76), nucleotide sequence (SEQ ID NO. 77)

Strawberry AAT (SAAT): amino acid sequence (SEQ ID NO. 78), nucleotide sequence (SEQ ID NO. 79)

Strawberry AAT (VAAT): amino acid sequence (SEQ ID NO. 80), nucleotide sequence (SEQ ID NO. 81)

Those synthetic gene fragments were inserted to the vector pMD19, and each of them was named pAAT001 to 003 (Table 46). By having those AAT001 to 003 as a template and designing an oligonucleotide such that it is in the form in which a restriction enzyme recognition site, which is easily introducible to an expression vector, is added, a DNA fragment containing the AAT gene was produced by PCR method.

```
Oligonucleotide primer
MMA-044:
                              (SEQ ID NO. 82)
5'-GTTTGCACGCCTGCCGTTCGACG-3'

MMA-045:
                              (SEQ ID NO. 83)
5'-CGGTACGCGCGGATCTTCCAGAG-3'
```

Composition of Reaction Solution
  sterilized water 22 µL
  2× PrimeSTAR (manufactured by Takara Bio Inc.) 25 µL
  Forward primer 1 µL
  Reverse primer 1 µL
  Genomic DNA 1 µL
  Total volume 50 µL Temperature Cycle
30 Cycles of the Reaction Including 98° C. for 10 Seconds, 55° C. for 15 Seconds, and 72° C. for 150 Seconds Band of the amplified product obtained was purified by QIAquick Gel Extraction Kit (QIAGEN). Each purified DNA was digested with the restriction enzyme PagI (restriction recognition site is included in the forward primer) and Sse8387I (restriction recognition site is included in the reverse primer). After performing the separation by agarose gel electrophoresis, the target band was cut out from the gel and purified. For the purification, Gel/PCR Purification Kit (manufactured by FAVORGEN) was used and elution was made using 30 µL of sterilized water.

By mixing the purified DNA (5 µL), the vector pTrc99A (1 µL) which has been digested in advance with NcoI and Sse8387I, distilled water (4 µL) and solution I (DNA Ligation Kit ver. 2 (Takara Bio Inc.)) (10 µL) and incubating them for 12 hours at 16° C., the PCR amplified product and the vector were ligated to each other.

To 200 µL of the competent cell which has been prepared in the same manner as Example 33, 10 µL of the above ligation solution was added. After keeping it at 0° C. for 30 minutes, a heat shock of 42° C. was applied for 30 seconds, and after cooling at 0° C. for 2 minutes, 1 mL of the SOC medium was added followed by culture under shaking at 37° C. for 1 hour.

After the culture, each was applied in an amount of 100 µL to the LBAmp agar medium (LB medium containing ampicillin 100 mg/l and 1.5% agar) and further cultured at 37° C. Plural colonies of the transformant which have been grown on the agar medium were cultured overnight at 37° C. on 1.5 ml LBAmp medium (LB medium containing ampicillin at 100 mg/l). After collecting the cells, the plasmid DNA was prepared by using QIAprep Spin Miniprep kit (manufactured by QIAGEN).

The nucleotide sequence of the each obtained recombinant plasmid DNA was determined by using CEQ DTCS Quick Start Kit and Fluorescence sequence CEQ 2000XL DNA Analysis (both manufactured by BECKMAN COULTER, USA), and named plasmid pAAT101 to pAAT103 (Table 46).

The AAT gene was also inserted to the pET16b vector according to the same operation, and obtained plasmids were named pAAT201 to pAAT203 (Table 46). Meanwhile, because the pET16b does not contain a Sse8387I site, pET16b added at BamHI site with a linker containing Sse8387I restriction sequence is produced in advance, and used as a vector.

By introducing the plasmid pAAT101 to pAAT103 to JM109 strain, the recombinants JM109/pAAT101 to pAAT103 were obtained. By introducing the plasmid pAAT201 to pAAT203 to BL21 (DE3) strain, the recombinant BL21 (DE3)/pAAT201 to pAAT203 were obtained.

TABLE 46

Plasmid for expressing plant-derived AAT gene

| SEQ ID NO. | Plant (gene name) | Template plasmid | Plasmid for expression | |
|---|---|---|---|---|
| | | | pTrc99A | pET16b |
| 2 | Apple (MpAAT1) | pAAT001 | pAAT101 | pAAT201 |
| 4 | Strawberry (SAAT) | pAAT002 | pAAT102 | pAAT202 |
| 6 | Strawberry (VAAT) | pAAT003 | pAAT103 | pAAT203 |

Example 46: Preparation of Cell Extract from Recombinant E. coli which AAT is Expressed (1) Culturing Recombinant E. coli Using pTrc99A as Vector The recombinant E. coli JM109/pAAT101 to pAAT103 obtained from Example 45 was inoculated to LB medium containing 1 mL of 100 µg/mL ampicillin and subjected to pre-culture at 37° C. for 7 hours. 0.1 ml of the culture was harvested and added to 100 ml of the same medium (containing 100 µg/mL ampicillin, 1 mM IPTG) and cultured under shaking at 37° C. for 15 hours. From the obtained culture, the cells were collected by centrifuge (3,700×g, 10 minutes, 4° C.), washed with 10 mM sodium phosphate buffer (pH 7.0), and suspended in the same buffer solution. As a control strain, JM109/pTrc99A was used.

(2) Culturing Recombinant E. coli Using pET16b as Vector

The recombinant E. coli BL21 (DE3)/pAAT201 to pAAT203 obtained from Example 45 was inoculated to LB medium containing 1 mL of 100 µg/mL ampicillin and subjected to pre-culture at 37° C. for 14 hours. 0.1 ml of the culture was harvested and added to 100 ml of the same medium (containing 100 µg/mL ampicillin) and cultured under shaking at 37° C. until OD at 37° C. becomes 0.3. Then, IPTG was added to have the final concentration of 1 mM followed by further culture under shaking for several hours. From the obtained culture, the cells were collected by centrifuge (3,700×g, 10 minutes, 4° C.) with 10 mM sodium phosphate buffer (pH 7.0), and suspended in the same buffer solution so as to have OD6 (630 nm). As a control strain, BL21 (DE3)/pET16b was used.

(3) Preparation of Cell Extract

A cell extract was prepared from the cell suspension obtained above. By using ultrasonic homogenizer VP-15S (manufactured by DYTEC, Japan), the cell suspension was disrupted for 1 minute under conditions including output control 4, DUTY CYCLE 40%, PULS, TIMER=B mode 10 s. Next, by performing centrifuge (10,000×g, 5 minutes, 4° C.), 1 mL of the obtained supernatant was collected (cell extract).

Example 47: Synthesis of Butyl Methacrylate by Using Cell Extract of AAT Gene Recombinant By using the cell extract which has been prepared by the method described in Example 46, the following reaction was performed. By adding 0.2 ml of the cell extract to a 10 µl-volume sample bottle (for GC) added with a septum to which 0.8 µl of a solution of methacrylyl-CoA and alcohol has been added such that the final concentration of the reaction solution includes 7 mM methacrylyl-CoA and 40.5 mM n-butanol, the reaction was started. The sample bottle added with a septum was incubated at 30° C. for 1 to 5 hours for having the reaction.

Gas in the head space of sample bottle added with a septum was analyzed in the same manner as Reference example 7. The results are shown in Table 47.

TABLE 47

Production of butyl methacrylate by using AAT gene

| Recombinant | Production amount (mM) | | |
|---|---|---|---|
| | 1 Hour | 3 Hours | 5 Hours |
| JM109/pAAT102 | 0.001 | 0.003 | 0.004 |
| JM109/pAAT103 | 0 | 0.001 | 0.002 |
| BL21(DE3)/pAAT201 | 0.003 | 0.014 | 0.026 |
| BL21(DE3)/pET16b | 0 | 0 | 0 |

Example 48: Synthesis of Methacrylic Acid Ester by Using Cell Extract of AAT Gene Recombinant By using methanol, ethanol, or n-butanol as the alcohol and the extract derived from BL21 (DE3)/pAAT201 (Apple) as the cell extract, the reaction was performed in the same manner as Example 47. The results of analyzing the product after 5 hours are shown in Table 48.

TABLE 48

Production of methacrylic acid ester by using AAT gene recombinant

| Recombinant | Production amount after 5 hours (mM) | | |
|---|---|---|---|
| | Methyl methacrylate | Ethyl methacrylate | Butyl methacrylate |
| BL21(DE3)/pAAT201 | 0.021 | 0.045 | 0.091 |

Example 49: Synthesis 2 of Methacrylic Acid Ester by Using Cell Extract of AAT Gene Recombinant By using isobutanol, phenol, benzyl alcohol or 2-ethylhexyl alcohol as the alcohol and the cell extract of BL21

(DE3)/pAAT201 (Apple) obtained from Example 46, the following reaction was performed.

By adding 0.2 ml of the cell extract to a 10 μl-volume sample bottle (for GC) added with a septum to which 0.8 ml of a solution of methacrylyl-CoA and alcohol has been added such that the final concentration of the reaction solution includes 1 mM methacrylyl-CoA and 40 mM alcohol, the reaction was started. The sample bottle added with a septum was incubated at 30° C. for 1 to 5 hours for having the reaction. When the reaction is completed, 1 mL of acetonitrile was added to the reaction solution in the sample bottled added with a septum followed by mixing well. After filtration using a syringe filter DISMIC/hole diameter 0.45 μm (manufactured by ADVANTEC), it was subjected to HPLC analysis. In Table 49, the results of analyzing the product after 5 hours are shown.

Synthesis of Methacrylic Acid Ester (Isobutyl Methacrylate, Phenyl Methacrylate, Benzyl Methacrylate, and 2-Ethylhexyl Methacrylate) by Using Cell Extract of AAT Gene Recombinant

TABLE 49

| | Production amount after 5 hours (mM) | | | |
|---|---|---|---|---|
| Recombinant | Isobutyl methacrylate | Phenyl methacrylate | Benzyl methacrylate | 2-Ethylhexyl methacrylate |
| BL21(DE3)/ pAAT201 | 0.009 | 0.001 | 0.17 | 0.31 |

Conditions for HPLC Analysis
    Apparatus: Waters 2695
    Column: Shiseido CAPCELL PAK C18 UG120 5 μm
    Mobile phase: 65% MeOH, 0.2% phosphoric acid
    Flow amount: 0.25 μl/min
    column temperature: 35° C.
    Detection: UV 210 nm
    Injection amount: 10 μL Comparative Example 1

Reaction for Synthesis of Methacrylic Acid Ester by Using Cell Extract of Yeast-Derived AAT Gene Recombinant Plasmids for expressing yeast-derived AAT gene were prepared in the same manner as Example 45 (Table 50), and after transforming *E. coli* using them, a recombinant expressing AAT was obtained.

Plasmid for Expressing Yeast-Derived AAT Gene

TABLE 50

| | | Template | Plasmid for expression | |
|---|---|---|---|---|
| SEQ ID NO. | Gene name | plasmid | pTrc99A | pET16b |
| 133 | ATF1 | pAAT005 | pAAT105 | pAAT205 |
| 135 | ATF2 | pAAT006 | pAAT106 | pAAT206 |

The cell extract was prepared in the same manner as Example 46 and the reaction for synthesizing butyl methacrylate was performed by having methacrylyl-CoA and n-butanol as a substrate in the same manner as Example 47. As a result, no production of butyl methacrylate was observed. Meanwhile, when acetyl-CoA and n-butanol are used as a substrate, production of butyl acetate was observed. In other words, the AAT derived from yeast was not observed with the ability to produce a methacrylic acid ester.

Production of Ester by Using Yeast AAT Gene Recombinant

TABLE 51

| | Production amount (mM) | | | | | |
|---|---|---|---|---|---|---|
| | Butyl methacrylate | | | Butyl acetate | | |
| Recombinant | 1 Hour | 3 Hours | 5 Hours | 30 Minutes | 1 Hour | 3 Hours |
| JM109/pAAT105 | 0 | 0 | 0 | 0.089 | 0.145 | 0.170 |
| JM109/pAAT106 | 0 | 0 | 0 | 0.104 | 0.189 | 0.290 |
| JM109/pTrc99A | 0 | 0 | 0 | 0 | 0 | 0 |

INDUSTRIAL APPLICABILITY

According to the method for producing methacrylic acid of the invention, methacrylic acid can be produced from recyclable biogenous resources (renewable raw materials) by using microbes without depending on a chemical method. According to the ACH method of the related art, a treatment of oxidizing acetone cyanhydrin by acid is required so that a large amount of waste acid is generated. Further, as separation or purification is needed for each step, it causes high energy consumption. Meanwhile, according to the method for producing methacrylic acid of the invention, methacrylic acid can be produced efficiently and simply in a single step directly from a biomass. In addition, a less load is applied in terms of safety, environment, facility, works, and cost. Further, by converting the raw materials of methacrylic acid to those derived from a biomass, it becomes also possible to reduce the carbon dioxide discharge amount to an environment.

SEQ ID NO. 82: MMA-044
SEQ ID NO. 83: MMA-045
SEQ ID NO. 84: MMA-003
SEQ ID NO. 85: MMA-004
SEQ ID NO. 88: MMA-031
SEQ ID NO. 89: MMA-032
SEQ ID NO. 92: MAA-15
SEQ ID NO. 93: MAA-16
SEQ ID NO. 94: GB-138
SEQ ID NO. 95: GB-139
SEQ ID NO. 96: GB-140
SEQ ID NO. 97: GB-141
SEQ ID NO. 98: MMA-061
SEQ ID NO. 99: MMA-062
SEQ ID NO. 100: MMA-063
SEQ ID NO. 101: MMA-064
SEQ ID NO. 102: MMA-069
SEQ ID NO. 103: MMA-070
SEQ ID NO. 104: MMA-133
SEQ ID NO. 105: MMA-131
SEQ ID NO. 106: MMA-003
SEQ ID NO. 107: MMA-004
SEQ ID NO. 108: MMA-020
SEQ ID NO. 109: MMA-006
SEQ ID NO. 110: MMA-018
SEQ ID NO. 111: MMA-008
SEQ ID NO. 112: MMA-019
SEQ ID NO. 113: MMA-010
SEQ ID NO. 114: MMA-021
SEQ ID NO. 115: MMA-022

SEQ ID NO. 116: MMA-023
SEQ ID NO. 117: MMA-024
SEQ ID NO. 118: MAA-15
SEQ ID NO. 119: MAA-16
SEQ ID NO. 120: MMA-187
SEQ ID NO. 121: MMA-140
SEQ ID NO. 122: MMA-188
SEQ ID NO. 123: MMA-189
SEQ ID NO. 124: MMA-001
SEQ ID NO. 125: MMA-002
SEQ ID NO. 126: MMA-114
SEQ ID NO. 127: MMA-109
SEQ ID NO. 128: MMA-039
SEQ ID NO. 129: MMA-040
SEQ ID NO. 130: MMA-042
SEQ ID NO. 131: MMA-041
SEQ ID NO. 132: MMA-043

The invention claimed is:

1. A method, comprising contacting or culturing one or more microbes or genetically engineered strain thereof having an ability to produce methacrylic acid with a renewable raw material which gives rise to a biomass that acts as a carbon and/or energy source, wherein said methacrylic acid, an ester of methacrylic acid, or a mixture thereof can be produced from a pathway that utilizes isobutyric acid or valine, wherein the one or more microbes can grow on about 0.1 to 1% of valine as a sole nitrogen and/or carbon source, or about 0.1 to 1% of isobutyric acid as a sole carbon source and wherein the genetically engineered strain thereof is obtained by deletion or inactivation of one or more endogenous genes selected from the group consisting of enoyl CoA hydratase gene, 3-hydroxyisobutyryl CoA hydrolase gene, and 3-hydroxyisobutyric acid dehydrogenase gene.

2. The method of claim 1, wherein the methacrylic acid, the ester of methacrylic acid, or the mixture thereof is accumulated at 0.04 ppm or more.

3. The method of claim 1, wherein the one or more microbes are microbes belonging to genus *Pseudomonas*, genus *Bacillus*, genus *Sphingobacterium*, genus *Comamonas*, genus *Brevundimonas*, genus *Sphingomonas*, genus *Ochrobactrum*, genus *Pedobacter*, genus *Paenibacillus*, genus *Achromobacter*, genus *Acinetobacter*, genus *Shewanella*, genus *Listonella*, genus *Agrobacterium*, genus *Mesorhizobium*, genus *Rhizobium*, genus *Paracoccus*, genus *Xanthobacter*, genus *Streptomyces*, genus *Geobacillus*, genus *Rhodococcus*, genus *Saccharomyces*, genus *Candida*, or genus *Aspergillus*.

4. The method of claim 1, further comprising producing a methacrylic acid ester by having an alcohol or a phenol to act on methacrylyl-CoA in the presence of an alcohol acyl transferase.

5. The production method according to claim 4, wherein the alcohol acyl transferase is derived from a plant.

* * * * *

SEQUENCE LISTING

<160> NUMBER OF SEQ ID NOS: 136

<210> SEQ ID NO 1
<211> LENGTH: 485
<212> TYPE: DNA
<213> ORGANISM: Pseudomonas sp. B25-2

<400> SEQUENCE: 1

```
attgaacgct ggcggcaggc ctaacacatg caagtcgagc ggatgagaag agcttgctct      60
tcgattcagc ggcggacggg tgagtaatgc ctaggaatct gcctggtagt gggggacaac     120
gtttcgaaag gaacgctaat accgcatacg tcctacggga gaaagcaggg gaccttcggg     180
ccttgcgcta tcagatgagc ctaggtcgga ttagctagtt ggtgaggtaa tggctcacca     240
aggcgacgat ccgtaactgg tctgagagga tgatcagtca cactggaact gagacacggt     300
ccagactcct acgggaggca gcagtgggga atattggaca atgggcgaaa gcctgatcca     360
gccatgccgc gtgtgtgaag aaggtcttcg gattgtaaag cactttaagt tgggaggaag     420
ggcagtaagt taataccttg ctgttttgac gttaccgaca gaataagcac cggctaactc     480
tgtgc                                                                  485
```

<210> SEQ ID NO 2
<211> LENGTH: 485
<212> TYPE: DNA
<213> ORGANISM: Pseudomonas sp. D22-1

<400> SEQUENCE: 2

```
attgaacgct ggcggcaggc ctaacacatg caagtcgagc ggatgacggg agcttgctcc      60
ygaattcagc ggcggacggg tgagtaatgc ctaggaatct gcctggtagt gggggacaac     120
gtctcgaaag gacgctaat accgcatacg tcctacggga gaaagcaggg gaccttcggg      180
ccttgcgcta tcagatgagc ctaggtcgga ttagctagtt ggtgaggtaa tggctcacca     240
aggcgacgat ccgtaactgg tctgagagga tgatcagtca cactggaact gagacacggt     300
ccagactcct acgggaggca gcagtgggga atattggaca atgggcgaaa gcctgatcca     360
gccatgccgc gtgtgtgaag aaggtcttcg gattgtaaag cactttaagt tgggaggaag     420
ggcattaacc taatacgtta gtgttttgac gttaccgaca gaataagcac cggctaactc     480
tgtgc                                                                  485
```

<210> SEQ ID NO 3
<211> LENGTH: 485
<212> TYPE: DNA
<213> ORGANISM: Pseudomonas sp. D43-1

<400> SEQUENCE: 3

```
attgaacgct ggcggcaggc ctaacacatg caagtcgagc ggatgaagag agcttgctct      60
ctgattcagc ggcggacggg tgagtaatgc ctaggaatct gcctggtagt gggggacaac     120
gtctcgaaag ggacgctaat accgcatacg tcctacggga gaaagcaggg gaccttcggg     180
```

```
ccttgcgcta tcagatgagc ctaggtcgga ttagctagtt ggtgaggtaa tggctcacca    240
aggcgacgat ccgtaactgg tctgagagga tgatcagtca cactggaact gagacacggt    300
ccagactcct acgggaggca gcagtgggga atattggaca atgggcgaaa gcctgatcca    360
gccatgccgc gtgtgtgaag aaggtcttcg gattgtaaag cactttaagt tgggaggaag    420
ggcagtaaat taatactttg ctgttttgac gttaccgaca gaataagcac cggctaactc    480
tgtgc                                                                485

<210> SEQ ID NO 4
<211> LENGTH: 485
<212> TYPE: DNA
<213> ORGANISM: Pseudomonas sp. D25

<400> SEQUENCE: 4
attgaacgct ggcggcaggc ctaacacatg caagtcgagc ggatgacagg agcttgctcc    60
tgaattcagc ggcggacggg tgagtaatgc ctaggaatct gcctggtagt ggggacaac    120 gtttcgaaag gaacgctaat accgcatacg tcctacggga gaaagcaggg gaccttcggg    180
ccttgcgcta tcagatgagc ctaggtcgga ttagctagtt ggtgaggtaa tggctcacca    240
aggcgacgat ccgtaactgg tctgagagga tgatcagtca cactggaact gagacacggt    300
ccagactcct acgggaggca gcagtgggga atattggaca atgggcgaaa gcctgatcca    360
gccatgccgc gtgtgtgaag aaggtcttcg gattgtaaag cactttaagt tgggaggaag    420
ggcattaacc taatacgtta gtgttttgac gttaccgaca gaataagcac cggctaactc    480
tgtgc                                                                485

<210> SEQ ID NO 5
<211> LENGTH: 485
<212> TYPE: DNA
<213> ORGANISM: Pseudomonas sp. D26

<400> SEQUENCE: 5
attgaacgct ggcggcaggc ctaacacatg caagtcgagc ggatgamrrg agcttgctcy    60
ykrattcagc ggcggacggg tgagtaatgc ctaggaatct gcctggtagt ggggacaac    120 gtttcgaaag gaacgctaat accgcatacg tcctacggga gaaagcaggg gaccttcggg    180
ccttgcgcta tcagatgagc ctaggtcgga ttagctagtt ggtgaggtaa tggctcacca    240
aggcgacgat ccgtaactgg tctgagagga tgatcagtca cactggaact gagacacggt    300
ccagactcct acgggaggca gcagtgggga atattggaca atgggcgaaa gcctgatcca    360
gccatgccgc gtgtgtgaag aaggtcttcg gattgtaaag cactttaagt tgggaggaag    420
ggcattaacc taatacgtta gtgttttgac gttaccgaca gaataagcac cggctaactc    480
tgtgc                                                                485

<210> SEQ ID NO 6
<211> LENGTH: 485
<212> TYPE: DNA
<213> ORGANISM: Pseudomonas sp. D29

<400> SEQUENCE: 6
attgaacgct ggcggcaggc ctaacacatg caagtcgagc ggatgaagag agcttgctct    60
ctgattcagc ggcggacggg tgagtaatgc ctaggaatct gcctggtagt ggggacaac    120 gtctcgaaag gaacgctaat accgcatacg tcctacggga gaaagcaggg gaccttcggg    180
ccttgcgcta tcagatgagc ctaggtcgga ttagctagtt ggtgaggtaa tggctcacca    240
```

```
aggcgacgat ccgtaactgg tctgagagga tgatcagtca cactggaact gagacacggt    300
ccagactcct acggaggca gcagtgggga atattggaca atgggcgaaa gcctgatcca     360
gccatgccgc gtgtgtgaag aaggtcttcg gattgtaaag cactttaagt tgggaggaag    420
ggttgtagat taatactctg caattttgac gttaccgaca gaataagcac cggctaactc    480
tgtgc                                                                485
```

```
<210> SEQ ID NO 7
<211> LENGTH: 485
<212> TYPE: DNA
<213> ORGANISM: Pseudomonas sp. D41-2

<400> SEQUENCE: 7
attgaacgct ggcggcaggc ctaacacatg caagtcgagc ggatgargag agcttgctct     60
ctgattcagc ggcggacggg tgagtaatgc ctaggaatct gcctggtagt ggggacaac    120 gtttcgaaag gaacgctaat accgcatacg tcctacggga gaaagcaggg gaccttcggg   180
ccttgcgcta tcagatgagc ctaggtcgga ttagctagtt ggtgaggtaa tggctcacca   240
aggcgacgat ccgtaactgg tctgagagga tgatcagtca cactgaaact gagacacggt   300
ccagactcct acgggaggca gcagtgggga atattggaca atgggcgaaa gcctgatcca    360
gccatgccgc gtgtgtgaag aaggtcttcg gattgtaaag cactttaagt tgggaggaag    420
ggttgtagat taatactctg caattttgac gttaccgaca gaataagcac cggctaactc    480
tgtgc                                                                485
```

```
<210> SEQ ID NO 8
<211> LENGTH: 500
<212> TYPE: DNA
<213> ORGANISM: Pseudomonas putida NBRC12996

<400> SEQUENCE: 8
attgaacgct ggcggcaggc ctaacacatg caagtcgagc ggatgacggg agcttgctcc     60
ttgattcagc ggcggacggg tgagtaatgc ctaggaatct gcctggtagt ggggacaac    120 gtttcgaaag gaacgctaat accgcatacg tcctacggga gaaagcaggg gaccttcggg   180
ccttgcgcta tcagatgagc ctaggtcgga ttagctagtt ggtgaggtaa tggctcacca   240
aggcgacgat ccgtaactgg tctgagagga tgatcagtca cactggaact gagacacggt   300
ccagactcct acgggaggca gcagtgggga atattggaca atgggcgaaa gcctgatcca    360
gccatgccgc gtgtgtgaag aaggtcttcg gattgtaaag cactttaagt tgggaggaag    420
ggcagtaagt taatacctg ctgttttgac gttaccgaca gaataagcac cggctaactc    480
tgtgccagca gccgcggtaa                                                500
```

```
<210> SEQ ID NO 9
<211> LENGTH: 500
<212> TYPE: DNA
<213> ORGANISM: Bacillus sp. G1

<400> SEQUENCE: 9
gatgaacgct ggcggcgtgc ctaatacatg caagtcgagc gaatggattg agagcttgct     60
ctcaagaagt tagcggcgga cgggtgagta acacgtgggt aacctgccca taagactggg    120
ataactccgg gaaaccgggg ctaataccgg ataacatttt gaacygcatg gttcgaaatt    180
gaaaggcggc ttcggctgtc acttatggat ggacccgcgt cgcattagct agttggtgag    240
```

| | |
|---|---:|
| gtaacggctc accaaggcaa cgatgcgtag ccgacctgag agggtgatcg gccacactgg | 300 |
| gactgagaca cggcccagac tcctacggga ggcagcagta gggaatcttc cgcaatggac | 360 |
| gaaagtctga cggagcaacg ccgcgtgagt gatgaaggct ttcgggtcgt aaaactctgt | 420 |
| tgttagggaa gaacaagtgc tagttgaata agctggcacc ttgacggtac ctaaccagaa | 480 |
| agccacggct aactacgtgc | 500 |

<210> SEQ ID NO 10
<211> LENGTH: 500
<212> TYPE: DNA
<213> ORGANISM: Bacillus sp. G2

<400> SEQUENCE: 10

| | |
|---|---:|
| gatgaacgct ggcggcgtgc ctaatacatg caagtcgagc gaatggattr agagcttgct | 60 |
| ctyawgaagt tagcggcgga cgggtgagta acacgtgggt aacctgccca taagactggg | 120 |
| ataactccgg gaaaccgggg ctaataccgg ataayatttt gaactgcatg gttcgaaatt | 180 |
| gaaaggcggc ttcggctgtc acttatggat ggacccgcgt cgcattagct agttggtgag | 240 |
| gtaacggctc accaaggcaa cgatgcgtag ccgacctgag agggtgatcg gccacactgg | 300 |
| gactgagaca cggcccagac tcctacggga ggcagcagta gggaatcttc cgcaatggac | 360 |
| gaaagtctga cggagcaacg ccgcgtgagt gatgaaggct ttcgggtcgt aaaactctgt | 420 |
| tgttagggaa gaacaagtgc tagttgaata agctggcacc ttgacggtac ctaaccagaa | 480 |
| agccacggct aactacgtgc | 500 |

<210> SEQ ID NO 11
<211> LENGTH: 497
<212> TYPE: DNA
<213> ORGANISM: Bacillus sp. R1

<400> SEQUENCE: 11

| | |
|---|---:|
| gacgaacgct ggcggcgtgc ctaatacatg caagtcgagc ggacagatgg gagcttgctc | 60 |
| cctgaagtca gcggcggacg ggtgagtaac acgtgggcaa cctgcctgta agactgggat | 120 |
| aactccggga aaccggggct aataccggat aattctttcc ctcacatgag ggaaagctga | 180 |
| aagatggttt cggctatcac ttacagatgg gcccgcggcg cattagctag ttggtgaggt | 240 |
| aacggctcac caaggcaacg atgcgtagcc gacctgagag ggtgatcggc cacactggga | 300 |
| ctgagacacg gcccagactc ctacgggagg cagcagtagg gaatcttccg caatggacga | 360 |
| aagtctgacg gagcaacgcc gcgtgagtga tgaaggtttt cggatcgtaa aactctgttg | 420 |
| ttagggaaga caagtrccg gagtaactgc cggtrccttg acggtaccta accagaaagc | 480 |
| cacggctaac tacgtgc | 497 |

<210> SEQ ID NO 12
<211> LENGTH: 500
<212> TYPE: DNA
<213> ORGANISM: Bacillus subtilis NBRC12210

<400> SEQUENCE: 12

| | |
|---|---:|
| gacgaacgct ggcggcgtgc ctaatacatg caagtcgagc ggacagatgg gagcttgctc | 60 |
| cctgatgtta gcggcggacg ggtgagtaac acgtgggtaa cctgcctgta agactgggat | 120 |
| aactccggga aaccggggct aataccggat ggttgtttga accgcatggt tcaaacataa | 180 |
| aaggtggctt cggctaccac ttacagatgg acccgcggcg cattagctag ttggtgaggt | 240 |
| aacggctcac caaggcaacg atgcgtagcc gacctgagag ggtgatcggc cacactggga | 300 |

```
ctgagacacg gcccagactc ctacgggagg cagcagtagg gaatcttccg caatggacga    360
aagtctgacg gagcaacgcc gcgtgagtga tgaaggtttt cggatcgtaa agctctgttg    420
ttagggaaga acaagtaccg ttcgaatagg gcggtacctt gacggtacct aaccagaaag    480
ccacggctaa ctacgtgcca                                                500
```

<210> SEQ ID NO 13
<211> LENGTH: 500
<212> TYPE: DNA
<213> ORGANISM: Bacillus badius ATCC14574
<220> FEATURE:
<221> NAME/KEY: misc_feature
<222> LOCATION: (203)..(203)
<223> OTHER INFORMATION: n is a, c, g, or t

<400> SEQUENCE: 13

```
gacgaacgct ggcggcgtgc ctaatacatg caagtcgagc ggacttgacg gaagcttgct     60
tccgttcaag ttagcggcgg acgggtgagt aacacgtggg taacctgcct gtaagactgg    120
gataactccg ggaaaccggg gctaataccg gatattcttt tcttcgcat gaagaagaat    180 ggaaaggcgg cttttagctg tcncttacag atggacccgc ggcgcattag ctagttggtg    240
aggtaacggc tcaccaaggc aacgatgcgt agccgacctg agagggtgat cggccacact    300
gggactgaga cacggcccag actcctacgg gaggcagcag tagggaatct tccgcaatgg    360
acgaaagtct gacggagcaa cgccgcgtga gtgaagaagg ttttcggatc gtaaagctct    420
gttgtcaggg aagaacaagt acggaagtaa ctgtccgtac cttgacggta cctgaccaga    480
aagccacggc taactacgtg                                                500
```

<210> SEQ ID NO 14
<211> LENGTH: 500
<212> TYPE: DNA
<213> ORGANISM: Bacillus megaterium NBRC15308

<400> SEQUENCE: 14

```
gatgaacgct ggcggcgtgc ctaatacatg caagtcgagc gaactgatta gaagcttgct     60
tctatgacgt tagcggcgga cgggtgagta acacgtgggc aacctgcctg taagactggg    120
ataacttcgg gaaaccgaag ctaataccgg ataggatctt ctccttcatg ggagatgatt    180
gaaagatggt ttcggctatc acttacagat gggcccgcgg tgcattagct agttggtgag    240
gtaacggctc accaaggcaa cgatgcatag ccgacctgag agggtgatcg ccacactgg    300 gactgagaca cggcccagac tcctacggga ggcagcagta gggaatcttc gcaatggac    360 gaaagtctga cggagcaacg ccgcgtgagt gatgaaggct ttcgggtcgt aaaactctgt    420
tgttagggaa gaacaagtac aagagtaact gcttgtacct tgacggtacc taaccagaaa    480
gccacggcta actacgtgcc                                                500
```

<210> SEQ ID NO 15
<211> LENGTH: 500
<212> TYPE: DNA
<213> ORGANISM: Bacillus simplex ATCC49097

<400> SEQUENCE: 15

```
gacgaacgct ggcggcgtgc ctaatacatg caagtcgagc gaatcgatgg gagcttgctc     60
cctgagatta gcggcggacg ggtgagtaac acgtgggcaa cctgcctata agactgggat    120
aacttcggga aaccggagct aataccggat acgttctttt ctcgcatgag agaagatgga    180
```

```
aagacggttt acgctgtcac ttatagatgg gcccgcggcg cattagctag ttggtgaggt    240
aatggctcac caaggcgacg atgcgtagcc gacctgagag ggtgatcggc cacactggga    300
ctgagacacg gcccagactc ctacgggagg cagcagtagg gaatcttccg caatggacga    360
aagtctgacg gagcaacgcc gcgtgaacga agaaggcctt cgggtcgtaa agttctgttg    420
ttagggaaga acaagtacca gagtaactgc tggtaccttg acggtaccta accagaaagc    480
cacggctaac tacgtgccag                                                500

<210> SEQ ID NO 16
<211> LENGTH: 491
<212> TYPE: DNA
<213> ORGANISM: Sphingobacterium sp. B13

<400> SEQUENCE: 16
gatgaacgct agcggcaggc ctaatacatg caagtcggac gggatccatc ggagagcttg     60
ctcgaagatg gtgagagtgg cgcacggggtg cgtaacgcgt gagcaaccta cctctatcag   120
ggggatagcc tctcgaaaga gagattaaca ccgcataata taatctaccg gcatcgttgg    180
attattaaat atttatagga tagagatggg ctcgcgtgac attagctagt tggtagggta    240
acggcytacc aaggcgacga tgtctagggg ctctgagagg agaatccccc acactggtac    300
tgagacacgg accagactcc tacgggaggc agcagtaagg aatattggtc aatgggcgga    360
agcctgaacc agccatgccg cgtgcaggat gactgcccta tgggttgtaa actgcttttg    420
tccaggaata aacctagata cgagtatcta gctgaatgta ctggaagaat aaggatcggc    480
taactccgtg c                                                         491

<210> SEQ ID NO 17
<211> LENGTH: 500
<212> TYPE: DNA
<213> ORGANISM: Comamonas terrigena NBRC13299

<400> SEQUENCE: 17
attgaacgct ggcggcatgc tttacacatg caagtcgaac ggcagcacgg acttcggtct     60
ggtggcgagt ggcgaacggg tgagtaatac atcggaacgt gcccagttgt gggggataac    120
tactcgaaag agtagctaat accgcatgag aactgaggtt gaaagcaggg gatcgcaaga    180
ccttgcgcaa ctggagcggc cgatggcaga ttaggtagtt ggtgggataa agcttacca     240 agccgacgat ctgtagctgg tctgagagga cgaccagcca cactgggact gagacacggc    300
ccagactcct acgggaggca gcagtgggga attttggaca atgggcgaaa gcctgatcca    360
gcaatgccgc gtgcaggatg aaggccttcg ggttgtaaac tgcttttgta cggaacgaaa    420
agcttcgggt taatacctg gagtcatgac ggtaccgtaa gaataagcac cggctaacta    480
cgtgccagca gccgcggtaa                                                500

<210> SEQ ID NO 18
<211> LENGTH: 500
<212> TYPE: DNA
<213> ORGANISM: Brevundimonas diminuta ATCC11568
<220> FEATURE:
<221> NAME/KEY: misc_feature
<222> LOCATION: (387)..(387)
<223> OTHER INFORMATION: n is a, c, g, or t

<400> SEQUENCE: 18
agcgaacgct ggcggcaggc ctaacacatg caagtcgaac ggaccctcg gggttagtgg     60 cggacgggtg agtaacacgt gggaacgtgc ctttaggttc ggaatagctc ctggaaacgg    120
```

```
gtggtaatgc cgaatgtgcc cttcggggga aagatttatc gcctttagag cggcccgcgt      180
ctgattagct agttggtgag gtaacggctc accaaggcga cgatcagtag ctggtctgag      240
aggatgacca gccacactgg gactgagaca cggcccagac tcctacggga ggcagcagtg      300
gggaatcttg cgcaatgggc gaaagcctga cgcagccatg ccgcgtgaat gatgaaggtc      360
ttaggattgt aaaattcttt caccggngac gataatgacg gtacccggag aagaagcccc      420
ggctaacttc gtgccagcag ccgcggtaat acgaaggggg ctagcgttgc tcggaattac      480
tgggcgtaaa gggcgcgtag                                                 500
```

<210> SEQ ID NO 19
<211> LENGTH: 500
<212> TYPE: DNA
<213> ORGANISM: Brevundimonas vesicularis ATCC11426

<400> SEQUENCE: 19

```
agcgaacgct ggcggcaggc ctaacacatg caagtcgaac gaactcttcg gagttagtgg       60
cggacgggtg agtaacacgt gggaacgtgc ctttaggttc ggaataactc agggaaactt      120
gtgctaatac cgaatgtgcc cttcggggga aagatttatc gcctttagag cggcccgcgt      180
ctgattagct agttggtgag gtaaaggctc accaaggcga cgatcagtag ctggtctgag      240
aggatgatca gccacattgg gactgagaca cggcccaaac tcctacggga ggcagcagtg      300
gggaatcttg cgcaatgggc gaaagcctga cgcagccatg ccgcgtgaat gatgaaggtc      360
ttaggattgt aaaattcttt caccggggac gataatgacg gtacccggag aagaagcccc      420
ggctaacttc gtgccagcag ccgcggtaat acgaaggggg ctagcgttgc tcggaattac      480
tgggcgtaaa gggagcgtag                                                 500
```

<210> SEQ ID NO 20
<211> LENGTH: 500
<212> TYPE: DNA
<213> ORGANISM: Brevundimonas subvibrioides NBRC16000

<400> SEQUENCE: 20

```
agcgaacgct ggcggcaggc ctaacacatg caagtcgaac ggacctctcg ggggttagtgg      60 cggacgggtg agtaacacgt gggaacgtgc cttttggttc ggaatagctc ctggaaacgg     120
gtggtaatgc cgaatgtgcc ctttggggga aagatttatc gccattagag cggcccgcgt     180
ctgattagct agttggtgag gtaaaggctc accaaggcta cgatcagtag ctggtctgag     240
aggatgacca gccacattgg gactgagaca cggcccaaac tcctacggga ggcagcagtg     300
gggaatcttg cgcaatgggc gaaagcctga cgcagccatg ccgcgtgtat gatgaaggtc     360
ttaggattgt aaaatacttt caccggtgaa gataatgact gtagccggag aagaagcccc     420
ggctaacttc gtgccagcag ccgcggtaat acgaaggggg ctagcgttgc tcggaattac     480
tgggcgtaaa gggagcgtag                                                500
```

<210> SEQ ID NO 21
<211> LENGTH: 500
<212> TYPE: DNA
<213> ORGANISM: Sphingomonas paucimobilis NBRC13935
<220> FEATURE:
<221> NAME/KEY: misc_feature
<222> LOCATION: (268)..(268)
<223> OTHER INFORMATION: n is a, c, g, or t
<400> SEQUENCE: 21

```
aacgaacgct ggcggcatgc ctaacacatg caagtcgaac gaaggcttcg gccttagtgg      60
cgcacgggtg cgtaacgcgt gggaatctgc ccttaggttc ggaataacag ctggaaacgg     120
ctgctaatac cggatgatat cgcgagatca agatttatcg cctgaggat gagcccgcgt     180 tggattaggt agttggtggg gtaaaggcct accaagccga cgatccatag ctggtctgag     240
aggatgatca gccacactgg gactgagnca cggcccagac tcctacggga ggcagcagtg     300
gggaatattg gacaatgggc gaaagcctga tccagcaatg ccgcgtgagt gatgaaggcc     360
ctagggttgt aaagctcttt tacccgggaa gataatgact gtaccgggag aataagcccc     420
ggctaactcc gtgccagcag ccgcggtaat acgagggggg ctagcgttgt tcggaattac     480
tgggcgtaaa gcgcacgtag                                                 500

<210> SEQ ID NO 22
<211> LENGTH: 500
<212> TYPE: DNA
<213> ORGANISM: Ochrobactrum sp. NBRC12951

<400> SEQUENCE: 22
aacgaacgct ggcggcaggc ttaacacatg caagtcgagc gccccgcaag gggagcggca      60
gacgggtgag taacgcgtgg gaacgtacct tttgctacgg aataactcag ggaaacttgt     120
gctaataccg tatgtgccct tcgggggaaa gatttatcgg caaaggatcg gcccgcgttg     180
gattagctag ttggtgaggt aaaggctcac caaggcgacg atccatagct ggtctgagag     240
gatgatcagc cacactggga ctgagacacg gcccagactc ctacgggagg cagcagtggg     300
gaatattgga caatgggcgc aagcctgatc agccatgccg cgtgagtga tgaaggccct     360 agggttgtaa agctctttca ccggtgaaga taatgacggt aaccggagaa gaagccccgg     420
ctaacttcgt gccagcagcc gcggtaatac gaagggggct agcgttgttc ggatttactg     480
ggcgtaaagc gcacgtaggc                                                 500

<210> SEQ ID NO 23
<211> LENGTH: 500
<212> TYPE: DNA
<213> ORGANISM: Ochrobactrum intermedium NBRC15820

<400> SEQUENCE: 23
aacgaacgct ggcggcaggc ttaacacatg caagtcgagc gccccgcaag gggagcggca      60
gacgggtgag taacgcgtgg gaacgtacca tttgctacgg aataactcag ggaaacttgt     120
gctaataccg tatgtgcccg aaagggggaaa gatttatcgg caaatgatcg gcccgcgttg     180
gattagctag ttggtggggt aaaggcctac caaggcgacg atccatagct ggtctgagag     240
gatgatcagc cacactggga ctgagacacg gcccagactc ctacgggagg cagcagtggg     300
gaatattgga caatgggcgc aagcctgatc agccatgccg cgtgagtga tgaaggccct     360 agggttgtaa agctctttca ccggtgaaga taatgacggt aaccggagaa gaagccccgg     420
ctaacttcgt gccagcagcc gcggtaatac gaagggggct agcgttgttc ggatttactg     480
ggcgtaaagc gcacgtaggc                                                 500

<210> SEQ ID NO 24
<211> LENGTH: 500
<212> TYPE: DNA
<213> ORGANISM: Ochrobactrum intermedium NBRC13694

<400> SEQUENCE: 24
aacgaacgct ggcggcaggc ttaacacatg caagtcgagc gccccgcaag gggagcggca      60
```

```
gacgggtgag taacgcgtgg gaacgtacct tttgctacgg aataactcag ggaaacttgt    120
gctaataccg tatgtgccct tcgggggaaa gatttatcgg caaaggatcg gcccgcgttg    180
gattagctag ttggtgaggt aaaggctcac caaggcgacg atccatagct ggtctgagag    240
gatgatcagc cacactggga ctgagacacg gcccagactc ctacgggagg cagcagtggg    300
gaatattgga caatgggcgc aagcctgatc cagccatgcc gcgtgagtga tgaaggccct    360
agggttgtaa agctctttca ccggtgaaga taatgacggt aaccggagaa gaagccccgg    420
ctaacttcgt gccagcagcc gcggtaatac gaagggggct agcgttgttc ggatttactg    480
ggcgtaaagc gcacgtaggc                                               500

<210> SEQ ID NO 25
<211> LENGTH: 500
<212> TYPE: DNA
<213> ORGANISM: Ochrobactrum grignonense NBRC102586

<400> SEQUENCE: 25
aacgaacgct ggcggcaggc ttaacacatg caagtcgagc gcctcgcaag aggagcggca     60
gacgggtgag taacgcgtgg gaatctacct tttgctacgg aataactcag ggaaacttgt    120
gctaataccg tatgtgccct tttggggaaa gatttatcgg caaaggatga gcccgcgttg    180
gattagctag ttggtagggt aatggcctac caaggcgacg atccatagct ggtctgagag    240
gatgatcagc cacactggga ctgagacacg gcccagactc ctacgggagg cagcagtggg    300
gaatattgga caatgggcgc aagcctgatc cagccatgcc gcgtgagtga tgaaggccct    360
agggttgtaa agctctttca ccggtgaaga taatgacggt aaccggagaa gaagccccgg    420
ctaacttcgt gccagcagcc gcggtaatac gaagggggct agcgttgttc ggatttactg    480
ggcgtaaagc gcacgtaggc                                               500

<210> SEQ ID NO 26
<211> LENGTH: 500
<212> TYPE: DNA
<213> ORGANISM: Ochrobactrum lupini NBRC102587

<400> SEQUENCE: 26
aacgaacgct ggcggcaggc ttaacacatg caagtcgagc gccccgcaag gggagcggca     60
gacgggtgag taacgcgtgg gaacgtacct tttgctacgg aataactcag ggaaacttgt    120
gctaataccg tatgtgccct tcgggggaaa gatttatcgg caaaggatcg gcccgcgttg    180
gattagctag ttggtgaggt aaaggctcac caaggcgacg atccatagct ggtctgagag    240
gatgatcagc cacactggga ctgagacacg gcccagactc ctacgggagg cagcagtggg    300
gaatattgga caatgggcgc aagcctgatc cagccatgcc gcgtgagtga tgaaggccct    360
agggttgtaa agctctttca ccggtgaaga taatgacggt aaccggagaa gaagccccgg    420
ctaacttcgt gccagcagcc gcggtaatac gaagggggct agcgttgttc ggatttactg    480
ggcgtaaagc gcacgtaggc                                               500

<210> SEQ ID NO 27
<211> LENGTH: 500
<212> TYPE: DNA
<213> ORGANISM: Pedobacter heparinus NBRC12017

<400> SEQUENCE: 27
gatgaacgct agcggcaggc ctaatacatg caagtcgaac gagattaagg ggcttgctcc     60
```

-continued

```
ttatgaaagt ggcgcacggg tgcgtaacgc gtatgcaacc taccttaatc aggggggatag    120 cccgaagaaa ttcggattaa caccgcataa aaacacagga tagcattatc caatgttcaa    180
atatttatag gattaagatg ggcatgcgtg tcattagcta gttggcgggg taacggccca    240
ccaaggcgac gatgactagg ggatctgaga ggatgacccc ccacactggt actgagacac    300
ggaccagact cctacgggag gcagcagtaa ggaatattgg tcaatggagg gaactctgaa    360
ccagccatgc cgcgtgcagg aagacagccc tctgggtcgt aaactgcttt tattcgggaa    420
taaacctact tacgtgtaag tagctgaatg taccgaagga ataaggatcg gctaactccg    480
tgccagcagc cgcggtaata                                                500
```

<210> SEQ ID NO 28
<211> LENGTH: 500
<212> TYPE: DNA
<213> ORGANISM: Paenibacillus sp. NBRC13157
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t

<400> SEQUENCE: 28

```
gacgaacgct ggcggcgtgc ctaatacatg caagtcgagc ggacttgaag agaagcttgc     60
ttctcngatn gttagcggcg gacgggtgag taacacgtag gcaacctgcc tgtaagatcg    120
ggataactac cggaaacggt agctaagacc ggataancgg tntctccgca tggngagatc    180
gtgaaacacg gagcaatctg tggcttacgg atgggcctgc ggcgcattag ctagttggtg    240
aggtaacggc tcaccaaggc gacgatgcgt agccgacctg agagggtgaa cggccacact    300
gggactgaga cacggcccag actcctacgg gaggcagcag tagggaatct tccgcaatgg    360
acgcaagtct gacggagcaa cgccgcgtga gtgatgaagg ttttcggatc gtaaagctct    420
gttgccaggg aagaacgcca aggagagtaa ctgctctttg ggtgacggta cctgagaaga    480
aagccccggc taactacgtg                                                500
```

<210> SEQ ID NO 29
<211> LENGTH: 500
<212> TYPE: DNA
<213> ORGANISM: Achromobacter denitrificans NBRC12669

<400> SEQUENCE: 29

```
attgaacgct agcgggatgc cttacacatg caagtcgaac ggcagcacgg acttcggtct     60
ggtggcgagt ggcgaacggg tgagtaatgt atcggaacgt gcccagtagc gggggataac    120
tacgcgaaag cgtagctaat accgcatacg ccctacgggg gaaagcaggg gatcgcaaga    180
ccttgcacta ttggagcggc cgatatcgga ttagctagtt ggtggggtaa cggctcacca    240
aggcgacgat ccgtagctgg tttgagagga cgaccagcca cactgggact gagacacggc    300
```

```
ccagactcct acgggaggca gcagtgggga attttggaca atgggggaaa ccctgatcca    360
gccatcccgc gtgtgcgatg aaggccttcg ggttgtaaag cacttttggc aggaaagaaa    420
cgtcgcgggt taatacccccg cggaactgac ggtacctgca gaataagcac cggctaacta   480
cgtgccagca gccgcggtaa                                                500
```

```
<210> SEQ ID NO 30
<211> LENGTH: 500
<212> TYPE: DNA
<213> ORGANISM: Acinetobacter haemolyticus ATCC17906

<400> SEQUENCE: 30
cctggctcag attgaacgct ggcggcaggc ttaacacatg caagtcgagc ggggaagggt    60
accttgctac ctaacctagc ggcggacggg tgagtaatgc ttaggaatct gcctattagt    120
gggggacaac attccgaaag gaatgctaat accgcatacg tcctacggga gaaagcaggg   180
gatcttcgga ccttgcgcta atagatgagc ctaagtcgga ttagctagtt ggtggggtaa   240
aggcctacca aggcgacgat ctgtagcggg tctgagagga tgatccgcca cactgggact   300
gagacacggc ccagactcct acgggaggca gcagtgggga atattggaca atgggcggaa    360
gcctgatcca gccatgccgc gtgtgtgaag aaggcctttt ggttgtaaag cactttaagc    420
gaggaggagg ctactctagt taatacctag agatagtgga cgttactcgc agaataagca    480
ccggctaact ctgtgccagc                                                500
```

```
<210> SEQ ID NO 31
<211> LENGTH: 500
<212> TYPE: DNA
<213> ORGANISM: Acinetobacter junii ATCC17908
<220> FEATURE:
<221> NAME/KEY: misc_feature
<222> LOCATION: (371)..(371)
<223> OTHER INFORMATION: n is a, c, g, or t

<400> SEQUENCE: 31
cctggctcag attgaacgct ggcggcaggc ttaacacatg caagtcgagc ggagatgagg    60
tgcttgcacc ttatcttagc ggcggacggg tgagtaatgc ttaggaatct gcctattagt    120
gggggacaac attccgaaag gaatgctaat accgcatacg tcctacggga gaaagcaggg   180
gatcttcgga ccttgcgcta atagatgagc ctaagtcgga ttagctagtt ggtggggtaa   240
aggcctacca aggcgacgat ctgtagcggg tctgagagga tgatccgcca cactgggact   300
gagacacggc ccagactcct acgggaggca gcagtgggga atattggaca atgggggaa    360 ccctgatcca nccatgccgc gtgtgtgaag aaggccttat ggttgtaaag cactttaagc    420
gaggaggagg ctactgagac taatactctt ggatagtgga cgttactcgc agaataagca    480
ccggctaact ctgtgccagc                                                500
```

```
<210> SEQ ID NO 32
<211> LENGTH: 500
<212> TYPE: DNA
<213> ORGANISM: Shewanella fodinae NBRC105216
<220> FEATURE:
<221> NAME/KEY: misc_feature
<222> LOCATION: (237)..(237)
<223> OTHER INFORMATION: n is a, c, g, or t

<400> SEQUENCE: 32
attgaacgct ggcggcaggc ctaacacatg caagtcgagc ggcagcgggg agtagcttgc    60
```

```
tactctgccg gcgagcggcg gacgggtgag taatgcctgg gaatttgccc attcgagggg    120
gataacagtt ggaaacgact gctaataccg catacgccct aagggggaaa gcaggggaac    180
ttaggtcctt gcgcgaatgg ataagcccag gtgggattag ctagttggtg aggtaanggc    240
tcaccaaggc gacgatctct agctggtctg agaggatgat cagccacact ggaactgaga    300
cacggtccag actcctacgg gaggcagcag tggggaatat tgcacaatgg gggaaaccct    360
gatgcagcca tgccgcgtgt gtgaagaagg ccttcgggtt gtaaagcact ttcagtcagg    420
aggaaggtgg tgtagctaat atctgcacca attgacgtta ctgacagaag aagcaccggc    480
taactccgtg ccagcagccg                                                500

<210> SEQ ID NO 33
<211> LENGTH: 500
<212> TYPE: DNA
<213> ORGANISM: Listonella anguillarum ATCC19264

<400> SEQUENCE: 33
attgaacgct ggcggcaggc ctaacacatg caagtcgagc ggcagcacag aggaacttgt    60
tccttgggtg gcgagcggcg gacgggtgag taatgcctag gaaattgccc tgatgtgggg    120
gataaccatt ggaaacgatg gctaataccg catgatgcct acgggccaaa gaggggggacc    180 ttcgggcctc tcgcgtcagg atatgcctag gtgggattag ctagttggtg aggtaatggc    240
tcaccaaggc gacgatccct agctggtctg agaggatgat cagccacact ggaactgaga    300
cacggtccag actcctacgg gaggcagcag tggggaatat tgcacaatgg gcgcaagcct    360
gatgcagcca tgccgcgtgt atgaagaagg ccttcgggtt gtaaagtact ttcagtcgtg    420
aggaaggtgg tgttgttaat agcagcatca tttgacgtta gcgacagaag aagcaccggc    480
taactccgtg ccagcagccg                                                500

<210> SEQ ID NO 34
<211> LENGTH: 500
<212> TYPE: DNA
<213> ORGANISM: Agrobacterium luteum NBRC15768T

<400> SEQUENCE: 34
aacgaacgct ggcggcatgc ttaacacatg caagtcgaac gagatcttcg gatctagtgg    60
cgcacgggtg cgtaacgcgt ggggatctac catagggtgc ggaataactc agagaaattt    120
gagctaatac cgcataatgt cttcggacca agatttatc gccctttgat gaaccgcgt    180 aggattagct tgttggtgag gtaagagctc accaaggcga cgatctttag ctggtctgag    240
aggatgatca gccacactgg gactgagaca cggcccagac tcctacggga ggcagcagtg    300
gggaatattg gacaatgggc gaaagcctga tccagcaatg ccgcgtgagt gatgaaggcc    360
ttagggttgt aaagctcttt taccagggat gataatgaca gtacctggag aataagctcc    420
ggctaactcc gtgccagcag ccgcggtaat acgagggag ctagcgttgt tcggaattac    480
tgggcgtaaa gcgcgcgtag                                                500

<210> SEQ ID NO 35
<211> LENGTH: 500
<212> TYPE: DNA
<213> ORGANISM: Mesorhizobium loti ATCC700743

<400> SEQUENCE: 35
aacgaacgct ggcggcaggc ttaacacatg caagtcgagc gcctcgcaag aggagcggca    60
gacgggtgag taacgcgtgg gaatctaccc atctctacgg aacaactccg ggaaactgga    120
```

-continued

```
gctaataccg tatacgtcct tcgggagaaa gatttatcgg agatggatga gcccgcgttg    180
gattagctag ttggtggggt aatggcctac caaggcgacg atccatagct ggtctgagag    240
gatgatcagc cacattggga ctgagacacg gcccaaactc ctacgggagg cagcagtggg    300
gaatattgga caatgggcga aagcctgatc cagccatgcc gcgtgagtga tgaaggccct    360
agggttgtaa agctctttca acggtgaaga taatgacggt aaccgtagaa gaagccccgg    420
ctaacttcgt gccagcagcc gcggtaatac gaagggggct agcgttgttc ggaattactg    480
ggcgtaaagc gcacgtaggc                                                500
```

<210> SEQ ID NO 36
<211> LENGTH: 500
<212> TYPE: DNA
<213> ORGANISM: Rhizobium leguminosarum ATCC10004

<400> SEQUENCE: 36

```
aacgaacgct ggcggcaggc ttaacacatg caagtcgagc gccccgcaag gggagcggca    60
gacgggtgag taacgcgtgg gaacgtaccc tttactacgg aataacgcag ggaaacttgt    120
gctaataccg tatgtgccct ttgggggaaa gatttatcgg taaaggatcg gcccgcgttg    180
gattagctag ttggtggggt aaaggcctac caaggcgacg atccatagct ggtctgagag    240
gatgatcagc cacattggga ctgagacacg gcccaaactc ctacgggagg cagcagtggg    300
gaatattgga caatgggcgc aagcctgatc cagccatgcc gcgtgagtga tgaaggccct    360
agggttgtaa agctctttca ccggagaaga taatgacggt atccgagaa gaagccccgg     420 ctaacttcgt gccagcagcc gcggtaatac gaagggggct agcgttgttc ggaattactg    480
ggcgtaaagc gcacgtaggc                                                500
```

<210> SEQ ID NO 37
<211> LENGTH: 500
<212> TYPE: DNA
<213> ORGANISM: Paracoccus aminophilus NBRC16710

<400> SEQUENCE: 37

```
aacgaacgct ggcggcaggc ctaacacatg caagtcgagc gcgcccttcg gggtgagcgg    60
cggacgggtg agtaacacgt gggaacatac cctttctac ggaatagcct cgggaaactg    120
agagtaatac cgtatacgcc cttcggggga aagatttatc ggagaaggat tggcccgcgt    180
tggattaggt agttggtggg gtaatggcct accaagccga cgatccatag ctggtttgag    240
aggatgatca gccacactgg gactgagaca cggcccagac tcctacggga ggcagcagtg    300
gggaatctta gacaatgggg gcaaccctga tctagccatg ccgcgtgagt gatgaaggcc    360
ttagggttgt aaagctcttt cagctggaa gataatgacg gtaccagcag aagaagcccc    420
ggctaactcc gtgccagcag ccgcggtaat acggaggggg ctagcgttgt tcggaattac    480
tgggcgtaaa gcgcacgtag                                                500
```

<210> SEQ ID NO 38
<211> LENGTH: 500
<212> TYPE: DNA
<213> ORGANISM: Xanthobacter autotrophicus ATCC35674

<400> SEQUENCE: 38

```
agcgaacgct ggcggcaggc ctaacacatg caagtcgagc gcccagcaat gggagcggca    60
gacgggtgag taacacgtgg ggatctaccc aatggtacgg aataacccag ggaaacttgg    120
```

```
actaataccg tatgtgccct tcggggggaaa gatttatcgc cattggatga acccgcgtcg    180
gattagctag ttggtgaggt aaaggctcac caaggcgacg atccgtagct ggtctgagag    240
gatgatcagc cacactggga ctgagacacg gcccagactc ctacgggagg cagcagtggg    300
gaatattgga caatgggcgc aagcctgatc cagccatgcc gcgtgtgtga tgaaggcctt    360
agggttgtaa agcactttcg ccggtgaaga taatgacggt aaccggagaa gaagcccggg    420
ctaacttcgt gccagcagcc gcggtaatac gaagggggca agcgttgctc ggaatcactg    480
ggcgtaaagc gcacgtaggc                                               500

<210> SEQ ID NO 39
<211> LENGTH: 500
<212> TYPE: DNA
<213> ORGANISM: Streptomyces griseus NBRC13350

<400> SEQUENCE: 39
acgaacgctg gcggcgtgct taacacatgc aagtcgaacg atgaagcctt tcggggtgga     60
ttagtggcga acgggtgagt aacacgtggg caatctgccc ttcactctgg gacaagccct    120
ggaaacgggg tctaataccg gataacactc tgtcccgcat gggacggggt taaaagctcc    180
ggcggtgaag gatgagcccg cggcctatca gcttgttggt ggggtaatgg cctaccaagg    240
cgacgacggg tagccggcct gagagggcga ccggccacac tgggactgag acacggccca    300
gactcctacg ggaggcagca gtggggaata ttgcacaatg ggcgaaagcc tgatgcagcg    360
acgccgcgtg agggatgacg gccttcgggt tgtaaacctc tttcagcagg gaagaagcga    420
gagtgacggt acctgcagaa gaagcgccgg ctaactacgt gccagcagcc gcggtaatac    480
gtagggcgca agcgttgtcc                                               500

<210> SEQ ID NO 40
<211> LENGTH: 500
<212> TYPE: DNA
<213> ORGANISM: Geobacillus stearothermophilus NBRC12983
<220> FEATURE:
<221> NAME/KEY: misc_feature
<222> LOCATION: (462)..(462)
<223> OTHER INFORMATION: n is a, c, g, or t

<400> SEQUENCE: 40
gacgaacgct ggcggcgtgc ctaatacatg caagtcgagc ggaccggatt ggggcttgcc     60
ttgattcggt cagcggcgga cgggtgagta acacgtgggc aacctgcccg caagaccggg    120
ataactccgg gaaaccggag ctaataccgg ataacaccga agaccgcatg gtcttcggtt    180
gaaaggcggc ctttgggctg tcacttgcgg atgggcccgc ggcgcattag ctagttggtg    240
aggtaacggc tcaccaaggc gacgatgcgt agccggcctg agagggtgac cggccacact    300
gggactgaga cacggcccag actcctacgg gaggcagcag tagggaatct tccgcaatgg    360
gcgaaagcct gacggagcga cgccgcgtga gcgaagaagg ccttcgggtc gtaaagctct    420
gttgtgaggg acgaaggagc gccgttcgaa gagggcggcg cngtgacggt acctcacgag    480
aaagccccgg ctaactacgt                                               500

<210> SEQ ID NO 41
<211> LENGTH: 1520
<212> TYPE: DNA
<213> ORGANISM: Rhodococcus erythropolis PR4

<400> SEQUENCE: 41
tcaacggaga gtttgatcct ggctcaggac gaacgctggc ggcgtgctta acacatgcaa     60
```

```
gtcgagcggt aaggcctttc ggggtacacg agcggcgaac gggtgagtaa cacgtgggtg    120
atctgccctg cacttcggga taagcctggg aaactgggtc taataccgga tatgacctca    180
ggttgcatga cttggggtgg aaagatttat cggtgcagga tgggcccgcg gcctatcagc    240
ttgttggtgg ggtaatggcc taccaaggcg acgacgggta gccgacctga gagggtgacc    300
ggccacactg ggactgagac acggcccaga ctcctacggg aggcagcagt ggggaatatt    360
gcacaatggg cgaaagcctg atgcagcgac gccgcgtgag ggatgacggc cttcgggttg    420
taaacctctt tcagcaggga cgaagcgcaa gtgacggtac ctgcagaaga agcaccggct    480
aactacgtgc cagcagccgc ggtaatacgt agggtgcaag cgttgtccgg aattactggg    540
cgtaaagagt tcgtaggcgg tttgtcgcgt cgtttgtgaa aaccagcagc tcaactgctg    600
gcttgcaggc gatacgggca gacttgagta ctgcagggga gactggaatt cctggtgtag    660
cggtgaaatg cgcagatatc aggaggaaca ccggtggcga aggcgggtct ctggcagta     720
actgacgctg aggaacgaaa gcgtgggtag cgaacaggat tagataccct ggtagtccac    780
gccgtaaacg gtgggcgcta ggtgtgggtt ccttccacgg aatccgtgcc gtagctaacg    840
cattaagcgc cccgcctggg gagtacggcc gcaaggctaa aactcaaagg aattgacggg    900
ggcccgcaca agcggcggag catgtggatt aattcgatgc aacgcgaaga accttacctg    960
ggtttgacat ataccggaaa gctgcagaga tgtggccccc cttgtggtcg gtatacaggt   1020
ggtgcatggc tgtcgtcagc tcgtgtcgtg agatgttggg ttaagtcccg caacgagcgc   1080
aaccccctatc ttatgttgcc agcacgttat ggtggggact cgtaagagac tgccggggtc   1140
aactcggagg aaggtgggga cgacgtcaag tcatcatgcc ccttatgtcc agggcttcac   1200
acatgctaca atggccagta cagagggctg cgagaccgtg aggtggagcg aatcccttaa   1260
agctggtctc agttcggatc ggggtctgca actcgacccc gtgaagtcgg agtcgctagt   1320
aatcgcagat cagcaacgct gcggtgaata cgttcccggg ccttgtacac accgcccgtc   1380
acgtcatgaa agtcggtaac acccgaagcc ggtggcttaa ccccttgtgg gagggagccg   1440
tcgaaggtgg gatcggcgat tgggacgaag tcgtaacaag gtagccgtac cggaaggtgc   1500
ggctggatca cctcctttct                                                1520
```

<210> SEQ ID NO 42
<211> LENGTH: 572
<212> TYPE: DNA
<213> ORGANISM: Saccharomyces cerevisiae NBRC1136

<400> SEQUENCE: 42

```
aaaccaaccg ggattgcctt agtaacggcg agtgaagcgg caaaagctca aatttgaaat     60
ctggtacctt cggtgcccga gttgtaattt ggagagggca actttgggc cgttccttgt    120
ctatgttcct tggaacagga cgtcatagag ggtgagaatc ccgtgtggcg aggagtgcgg    180
ttctttgtaa agtgccttcg aagagtcgag ttgtttggga atgcagctct aagtgggtgg    240
taaattccat ctaaagctaa atattggcga gagaccgata gcgaacaagt acagtgatgg    300
aaagatgaaa agaactttga aaagagagtg aaaaagtacg tgaaattgtt gaagggaag    360
ggcatttgat cagacatggt gttttgtgcc ctctgctcct tgtgggtagg ggaatctcgc    420
atttcactgg gccagcatca gttttggtgg caggataaat ccataggaat gtagcttgcc    480
tcggtaagta tttagcctg tgggaatact gccagctggg actgaggact gcgacgtaag    540
tcaaggatgc tggcataatg gttatatgcc gc                                  572
```

<210> SEQ ID NO 43
<211> LENGTH: 572
<212> TYPE: DNA
<213> ORGANISM: Saccaromyces cerevisiae NBRC2347

<400> SEQUENCE: 43

```
aaaccaaccg ggattgcctt agtaacggcg agtgaagcgg caaaagctca aatttgaaat      60
ctggtacctt cggtgcccga gttgtaattt ggagagggca actttggggc cgttccttgt     120
ctatgttcct tggaacagga cgtcatagag ggtgagaatc ccgtgtggcg aggagtgcgg     180
ttctttgtaa agtgccttcg aagagtcgag ttgtttggga atgcagctct aagtgggtgg     240
taaattccat ctaaagctaa atattggcga gagaccgata gcgaacaagt acagtgatgg     300
aaagatgaaa agaactttga aaagagagtg aaaaagtacg tgaaattgtt gaaagggaag     360
ggcatttgat cagacatggt gttttgtgcc ctctgctcct tgtgggtagg ggaatctcgc     420
atttcactgg gccagcatca gttttggtgg caggataaat ccataggaat gtagcttgcc     480
tcggtaagta ttatagcctg tgggaatact gccagctggg actgaggact gcgacgtaag     540
tcaaggatgc tggcataatg gttatatgcc gc                                   572
```

<210> SEQ ID NO 44
<211> LENGTH: 568
<212> TYPE: DNA
<213> ORGANISM: Saccharomyces paradoxus NBRC10609

<400> SEQUENCE: 44

```
aaaccaaccg ggattgcctt agtaacggcg agtgaagcgg caaaagctca aatttgaaat      60
ctggtacctt cggtgcccga gttgtaattt ggagagggca actttggggc cgttccttgt     120
ctatgttcct tggaacagga cgtcatagag ggtgagaatc ccgtgtggcg aggagtgcgg     180
ttctatgtaa agtgccttcg aagagtcgag ttgtttggga atgcagctct aagtgggtgg     240
taaattccat ctaaagctaa atattggcga gagaccgata gcgaacaagt acagtgatgg     300
aaagatgaaa agaactttga aaagagagtg aaaaagtacg tgaaattgtt gaaagggaag     360
ggcatttgat cagacatggt gttttgtgcc ctctgctcct tgtgggtagg ggaatctcgc     420
atttcactgg gccagcatca gttttggtgg caggataaat ccgtaggaat gtaacttgct     480
tcgggaagta ttatagcctg cgggaatact gccagctggg actgaggact gcgacgtaag     540
tcaaggatgc tggcataatg gttatatg                                        568
```

<210> SEQ ID NO 45
<211> LENGTH: 577
<212> TYPE: DNA
<213> ORGANISM: Candida utilis NBRC1086

<400> SEQUENCE: 45

```
aaaccaacag ggattgcctc agtaacggcg agtgaagcgg caaaagctca aatttgaaat      60
ctgaggctct cagcccccga gttgtaattt gaagatggtg ttctggcgcc ggccccctgt     120
ctacgttcct tggaacagga catcacagag ggtgagaatc ccgtctggcg gggcggcctg     180
gctccgtgta gagcgccatc gacgagtcga gttgtttggg aatgcagctc taagtgggtg     240
gtaaattcca tctaaagcta atattggcg agagaccgat agcgaacaag tacagtgatg     300
gaaagatgaa aagaactttg aaaagagagt gaaaaagtac gtgaaattgt tgaaagggaa     360
gggtattgga tcagacttgg tgctgtgcga atagcggctc ttcttgggcc gcccactcgc     420
actccaccgg gccagcatcg gtttgggcgg caagacaatg gcggggggaac gtggcactgc     480
```

```
tctcgggcag tgtgtttata gcccccgctg atgttgcctg cctagaccga ggactgcggc        540
ttctgcctag gatgctggcg taatgatcca acaccgc                                 577

<210> SEQ ID NO 46
<211> LENGTH: 569
<212> TYPE: DNA
<213> ORGANISM: Candida parapsilosis ATCC22019

<400> SEQUENCE: 46
aaaccaacag ggattgcctt agtagcggcg agtgaagcgg caaaagctca aatttgaaat         60
ctggcacttt cagtgtccga gttgtaattt gaagaaggta tctttgggtc tggctcttgt        120
ctatgtttct tggaacagaa cgtcacagag ggtgagaatc ccgtgcgatg agatgtccca        180
gacctatgta aagttccttc gaagagtcga gttgtttggg aatgcagctc taagtgggtg        240
gtaaattcca tctaaagcta aatattggcg agagaccgat agcgaacaag tacagtgatg        300
gaaagatgaa aagaactttg aaaagagagt gaaaaagtac gtgaaattgt tgaaagggaa        360
gggcttgaga tcagacttgg tattttgtat gttactctct cggggtggc ctctacagtt         420 taccgggcca gcatcagttt gagcggtagg ataagtgcaa agaaatgtgg cactgcttcg        480
gtagtgtgtt atagtctttg tcgatactgc cagcttagac tgaggactgc ggcttcggcc        540
taggatgttg gcataatgat cttaagtcg                                          569

<210> SEQ ID NO 47
<211> LENGTH: 571
<212> TYPE: DNA
<213> ORGANISM: Aspergillus niger ATCC6275

<400> SEQUENCE: 47
aaaccaaccg ggattgcctc agtaacggcg agtgaagcgg caagagctca aatttgaaag         60
ctggctcctt cggagtccgc attgtaattt gcagaggatg ctttgggtgc ggcccccgtc        120
taagtgccct ggaacgggcc gtcagagagg gtgagaatcc cgtcttgggc ggggtgtccg        180
tgcccgtgta aagctccttc gacgagtcga gttgtttggg aatgcagctc taaatgggtg        240
gtaaatttca tctaaagcta aatactggcc ggagaccgat agcgcacaag tagagtgatc        300
gaaagatgaa aagcactttg aaaagagagt taaacagcac gtgaaattgt tgaaagggaa        360
gcgcttgcga ccagactcgc ccgcggggtt cagccggcat tcgtgccggt gtacttcccc        420
gtgggcgggc cagcgtcggt ttgggcggcc ggtcaaaggc cctggaatg tagtgccctc         480 cggggcacct tatagccagg ggtgcaatgc ggccagcctg gaccgaggaa cgcgcttcgg        540
cacggacgct ggcataatgg tcgtaaacga c                                       571

<210> SEQ ID NO 48
<211> LENGTH: 556
<212> TYPE: DNA
<213> ORGANISM: Aspergillus flavus NBRC8558

<400> SEQUENCE: 48
gcggaaggat cattaccgag tgtagggttc ctagcgagcc caacctccca cccgtgttta         60 ctgtaccttag gttgcttcgg cgggcccgcc attcatggcc gccggggct ctcagccccg        120 ggcccgcgcc cgccggagac accacgaact ctgtctgatc tagtgaagtc tgagttgatt        180
gtatcgcaat cagttaaaac tttcaacaat ggatctcttg gttccggcat cgatgaagaa        240
cgcagcgaaa tgcgataact agtgtgaatt gcagaattcc gtgaatcatc gagtctttga        300
```

```
acgcacattg cgcccctgg tattccgggg ggcatgcctg tccgagcgtc attgctgccc    360
atcaagcacg gcttgtgtgt tgggtcgtcg tccctctcc gggggggacg ggccccaaag    420
gcagcggcgg caccgcgtcc gatcctcgag cgtatgggc tttgtcaccc gctctgtagg    480
cccggccggc gcttgccgaa cgcaaatcaa tcttttttcca ggttgacctc ggatcaggta    540
gggatacccg ctgaac                                                    556
```

<210> SEQ ID NO 49
<211> LENGTH: 554
<212> TYPE: DNA
<213> ORGANISM: Aspergillus oryzae NBRC4255

<400> SEQUENCE: 49

```
tgaacctgcg gaaggatcat taccgagtgt agggttccta gcgagcccaa cctcccaccc     60
gtgtttactg taccttagtt gcttcggcgg gcccgccatt catggccgcc ggggctctc    120 agccccgggc ccgcgcccgc cggagacacc acgaactctg tctgatctag tgaagtctga    180
gttgattgta tcgcaatcag ttaaaacttt caacaatgga tctcttggtt ccggcatcga    240
tgaagaacgc agcgaaatgc gataactagt gtgaattgca gaattccgtg aatcatcgag    300
tctttgaacg cacattgcgc ccctggtat tccgggggc atgcctgtcc gagcgtcatt    360
gctgcccatc aagcacggct tgtgtgttgg gtcgtcgtcc cctctccggg gggacgggc    420 cccaaaggca gcggcggcac cgcgtccgat cctcgagcgt atgggctttt gtcacccgct    480
ctgtaggccc ggccggcgct tgccgaacgc aaatcaatct tttccaggtt gacctcggat    540
caggtaggga tacc                                                      554
```

<210> SEQ ID NO 50
<211> LENGTH: 387
<212> TYPE: PRT
<213> ORGANISM: Pseudomonas aeruginosa PAO1 Acd1

<400> SEQUENCE: 50

Met Asp Phe Asp Leu Thr Glu Glu Gln Arg Leu Val Glu Ser Ala
1               5                   10                  15

Arg Ala Phe Ala Arg His Glu Leu Ala Pro Lys Ala Ala Asp Trp Asp
            20                  25                  30

Arg Asp His His Phe Pro Val Glu Val Ile Arg Ala Ala Ala Glu Gln
        35                  40                  45

Gly Tyr Leu Gly Leu Tyr Ile Ala Glu Glu Asp Gly Gly Leu Gly Leu
    50                  55                  60

Ser Arg Leu Ser Thr Ser Leu Ile Phe Glu Gln Leu Ala Ala Gly Cys
65                  70                  75                  80

Val Ala Thr Thr Ala Tyr Ile Ser Ile His Asn Met Ala Ala Trp Met
                85                  90                  95

Leu Ala Ser Phe Gly Asp Ala Ala Leu Lys Glu Ala Trp Leu Pro Gly
            100                 105                 110

Leu Ile Gly Gly Glu Ser Leu Ala Ser Tyr Cys Leu Thr Glu Pro Asp
        115                 120                 125

Ala Gly Ser Asp Ala Ala Arg Leu Arg Thr Arg Ala Arg Glu Gly
    130                 135                 140

Asp Glu Tyr Val Leu Asp Gly Ser Lys Cys Phe Ile Ser Gly Ala Gly
145                 150                 155                 160

Ser Thr Gln Val Leu Ile Val Met Ala Arg Thr Gly Glu Asp Gly Ala
                165                 170                 175

Arg Gly Ile Ser Cys Phe Leu Val Pro Ala Asp Ala Pro Gly Ile Arg
            180                 185                 190

Tyr Gly Arg Asn Glu Asp Lys Met Gly Trp Arg Ala Gln Pro Thr Arg
        195                 200                 205

Thr Ile Thr Phe Glu Gly Val Arg Ile Pro Ala Gly Asn Arg Ile Gly
    210                 215                 220

Pro Glu Gly Gln Gly Phe Val Tyr Ala Met Lys Gly Leu Asp Gly Gly
225                 230                 235                 240

Arg Leu Asn Ile Ala Ser Cys Ser Leu Gly Ala Gln Ala Ala Leu
                245                 250                 255

Glu Gln Ser Met Arg Tyr Val Glu Glu Arg Glu Gln Phe Gly Lys Pro
            260                 265                 270

Leu Ala Thr Phe Gln Ala Leu Gln Phe Lys Leu Ala Asp Met Leu Thr
        275                 280                 285

Glu Leu Thr Ala Ser Arg Gln Met Val Arg Leu Gly Ala His Arg Leu
    290                 295                 300

Asp Arg Gly Asp Ala Glu Ala Thr Leu Tyr Cys Ala Met Ala Lys Arg
305                 310                 315                 320

Phe Ala Thr Asp Arg Cys Phe Asp Val Cys Asn Glu Ala Leu Gln Leu
                325                 330                 335

His Gly Gly Tyr Gly Tyr Leu Asn Asp Tyr Pro Leu Glu Arg Trp Val
            340                 345                 350

Arg Asp Thr Arg Val His Gln Ile Leu Glu Gly Thr Asn Glu Ile Met
        355                 360                 365

Arg Val Ile Val Ala Arg Arg Leu Leu Glu Gln Gly Gly Met Leu Asp
    370                 375                 380

Arg Leu Leu
385

<210> SEQ ID NO 51
<211> LENGTH: 1164
<212> TYPE: DNA
<213> ORGANISM: Pseudomonas aeruginosa PAO1 Acd1

<400> SEQUENCE: 51
atggatttcg acctcaccga agaacaacgc ctgctggtgg agagcgcccg cgccttcgcc     60
cgccacgaac tggcgccgaa ggcggccgac tgggaccgcg accatcactt cccggtggaa    120
gtcatccgcg ccgccgccga cagggctac ctcggcctgt acatcgccga ggaagacggc    180
ggcctgggcc tgtcgcggct gtccacttcg ctgatcttcg agcaactggc cgccggctgc    240
gtggccacta ccgcctacat cagcatccac aacatggccg cctggatgct cgcctcgttc    300
ggcgacgcgg cgctgaagga ggcctggctg cccggcctga tcggcggcga gtcgctcgcc    360
tcctattgcc tgaccgagcc cgatgccggc tccgacgccg cgcgcctgcg caccgcgcc    420 cgccgcgagg cgacgaaata cgtgctggac ggcagcaagt gcttcatttc cggcgccggc    480
agcacccagg tgctgatcgt catggcgcgc accggcgagg acggcgccag gggcatctcc    540
tgcttcctgg taccggccga cgcgcccggc atccgctacg ccgcaacga ggacaagatg    600 ggctggcgcg cgcagccgac ccgcaccatc accttcgaag gcgtgcgcat ccccgccggc    660
aaccgcatcg gcccggaggg ccaaggcttc gtctatgcca tgaaaggcct cgacggcggc    720
cgcctgaaca tcgccagttg ttccctgggc gccgccagg cggcgctgga gcagtcgatg    780
cgctacgtcg aggagcgcga gcagttcggc aagccgctgg cgaccttcca ggccttgcag    840
ttcaagctcg ccgacatgct caccgaactc accgccagcc gccagatggt ccgcctcggc    900

```
gcccatcggc tggaccgcgg cgacgccgag gcgaccctgt actgcgcaat ggccaagcgc      960
ttcgccaccg accgctgctt cgatgtctgc aacgaggcct tgcaactgca cggcggctac     1020
ggctatctca cgattatcc gctggagcgc tgggtacgcg acccgcgt gcaccagatc       1080 ctcgaaggca ccaacgaaat catgcgggtg atcgtcgccc ccgcctgct ggagcagggc     1140 ggcatgctcg atcgcctgct gtga                                            1164
```

```
<210> SEQ ID NO 52
<211> LENGTH: 386
<212> TYPE: PRT
<213> ORGANISM: Rhodococcus erythropolis PR4 RE_Acd1

<400> SEQUENCE: 52

Met Phe Thr Leu Thr Asp Asp Glu Arg Ala Ile Arg Asp Thr Ala Arg
1               5                   10                  15

Asp Phe Ala Ala Glu His Leu Ala Pro Asn Ala Val Glu Trp Asp Gln
            20                  25                  30

Thr Lys His Phe Pro Val Asp Leu Arg Lys Ala Ala Ser Leu Gly
        35                  40                  45

Met Gly Gly Ile Tyr Ile Arg Glu Asp Val Gly Gly Ser Glu Leu Ser
    50                  55                  60

Arg Val Asp Ala Ala Arg Ile Phe Glu Glu Leu Ala Lys Gly Asp Pro
65                  70                  75                  80

Ser Ile Ala Ala Tyr Ile Ser Ile His Asn Met Val Thr Trp Met Ile
                85                  90                  95

Asp Gln Phe Gly Asn Asp Glu Gln Arg His Lys Trp Val Pro Gly Leu
            100                 105                 110

Cys Ser Met Asp Gln Leu Gly Ser Tyr Cys Leu Thr Glu Pro Gly Ala
        115                 120                 125

Gly Ser Asp Ala Ala Gly Leu Ser Thr Lys Ala Val Arg Asp Gly Asp
    130                 135                 140

Asp Tyr Ile Leu Asn Gly Val Lys Gln Phe Ile Ser Gly Ala Gly Thr
145                 150                 155                 160

Ser Asp Val Tyr Val Val Met Ala Arg Thr Gly Ser Ala Gly Ala Lys
                165                 170                 175

Gly Ile Ser Ala Phe Ile Val Pro Lys Asp Ser Pro Gly Leu Ser Phe
            180                 185                 190

Gly Ala Asn Glu Val Lys Met Gly Trp Asn Ala Gln Pro Thr Arg Gln
        195                 200                 205

Val Ile Phe Glu Asp Val Arg Val Pro Ala Ala Asn Met Leu Gly Glu
    210                 215                 220

Glu Gly Ser Gly Phe Arg Ile Ala Met Lys Gly Leu Asn Gly Gly Arg
225                 230                 235                 240

Leu Asn Ile Ala Ala Cys Ser Val Gly Gly Ala Gln Ala Ala Leu Glu
                245                 250                 255

Lys Ala Val Ala Tyr Leu Val Asp Arg Lys Ala Phe Gly Ser Ala Leu
            260                 265                 270

Ile Glu Ser Gln Ala Leu Gln Phe Gln Leu Ala Asp Met Arg Thr Glu
        275                 280                 285

Leu Glu Ala Ala Arg Thr Leu Leu Trp Arg Ala Ala Ala Leu Glu
    290                 295                 300

Asp Gly Ala Ser Asp Val Val Glu Leu Cys Ala Met Ala Lys Arg Phe
305                 310                 315                 320
```

Ala Thr Asp Thr Gly Phe Asp Val Ala Asn Lys Ala Leu Gln Leu His
            325                 330                 335

Gly Gly Tyr Gly Tyr Leu Ala Glu Tyr Gly Ile Glu Lys Ile Val Arg
            340                 345                 350

Asp Leu Arg Val His Gln Ile Leu Glu Gly Ser Asn Glu Ile Met Arg
        355                 360                 365

Val Val Ile Ala Arg Ser Val Val Ala Ser Gly Gln Gly Lys Gln Gly
    370                 375                 380

Ala Ala
385

<210> SEQ ID NO 53
<211> LENGTH: 1161
<212> TYPE: DNA
<213> ORGANISM: Rhodococcus erythropolis PR4 RE_Acd1

<400> SEQUENCE: 53

```
atgtttactc tgaccgatga cgagcgggcg attcgcgaca ctgcccgcga cttcgcggcc      60
gagcatctgg cgcccaacgc agtggagtgg atcagacca agcatttccc ggtggacgtc     120
ctccgtaagg cggcgtccct ggggatgggc ggtatctaca ttcgtgagga cgtgggcggc     180
agtgagctga gccgcgtcga cgctgcccgg atcttcgaag agctggccaa gggcgatccg     240
tcgatcgccg cgtacatctc catccacaac atggtcacgt ggatgatcga ccagttcggc     300
aacgacgaac agcgccacaa gtgggtcccc ggactctgct cgatggatca actgggcagc     360
tactgcctca ccgaacccgg cgctggctcc gatgctgcgg gcttgagcac caaggccgtt     420
cgtgacggcg acgactacat cctcaacggc gtcaaacagt tcatttccgg cgcaggcact     480
tccgacgtgt acgtcgtgat ggcacgcacc ggatctgccg gtgccaaggg gatctcggcg     540
ttcatcgtgc ccaaggattc gcccggactg tcgttcggtg ccaacgaggt caagatgggc     600
tggaacgcgc agcccacccg tcaggtgatc ttcgaagacg tgcgagttcc tgccgccaac     660
atgctcggtg aagagggcag cggcttccgc atcgctatga agggtctcaa cggcggccgg     720
ctgaacatcg ccgcctgctc ggtcggtggg gcccaggcag cgctggagaa ggcagtcgca     780
tatctggtgg accgcaaagc tttcggttcg gcactgatcg agtcgcaggc cctgcagttc     840
cagctcgccg acatgcgtac cgaactcgaa gcggccagga cgttgctgtg gcgcgccgct     900
gccgcactcg aagacggagc gtccgacgtc gtggagttgt gtgcgatggc caagcgcttt     960
gccaccgaca ccgggttcga cgtagccaac aaggctctcc agcttcacgg cgggtacggc    1020
tatcttgctg agtacgggat cgagaagatc gtccgcgatc ttcgggttca tcagatcctc    1080
gaaggcagca acgagatcat gagggtggtc atcgcgcgaa gcgtggtcgc atcaggtcag    1140
ggaaagcaag gagcagcatg a                                              1161
```

<210> SEQ ID NO 54
<211> LENGTH: 410
<212> TYPE: PRT
<213> ORGANISM: Pseudomonas aeruginosa PAO1 bkdA1

<400> SEQUENCE: 54

Met Ser Asp Tyr Glu Pro Leu Arg Leu His Val Pro Glu Pro Thr Gly
1               5                   10                  15

Arg Pro Gly Cys Lys Thr Asp Phe Ser Tyr Leu His Leu Ser Pro Ala
            20                  25                  30

Gly Glu Val Arg Lys Pro Pro Val Asp Val Glu Pro Ala Glu Thr Ser
        35                  40                  45

Asp Leu Ala Tyr Ser Leu Val Arg Val Leu Asp Asp Gly His Ala
    50              55                  60

Val Gly Pro Trp Asn Pro Gln Leu Ser Asn Glu Gln Leu Leu Arg Gly
 65              70                  75                  80

Met Arg Ala Met Leu Lys Thr Arg Leu Phe Asp Ala Arg Met Leu Thr
                 85                  90                  95

Ala Gln Arg Gln Lys Lys Leu Ser Phe Tyr Met Gln Cys Leu Gly Glu
            100                 105                 110

Glu Ala Ile Ala Thr Ala His Thr Leu Ala Leu Arg Asp Gly Asp Met
        115                 120                 125

Cys Phe Pro Thr Tyr Arg Gln Gln Gly Ile Leu Ile Thr Arg Glu Tyr
130                 135                 140

Pro Leu Val Asp Met Ile Cys Gln Leu Leu Ser Asn Glu Ala Asp Pro
145                 150                 155                 160

Leu Lys Gly Arg Gln Leu Pro Ile Met Tyr Ser Ser Lys Glu Ala Gly
                165                 170                 175

Phe Phe Ser Ile Ser Gly Asn Leu Ala Thr Gln Phe Ile Gln Ala Val
            180                 185                 190

Gly Trp Gly Met Ala Ser Ala Ile Lys Gly Asp Thr Arg Ile Ala Ser
        195                 200                 205

Ala Trp Ile Gly Asp Gly Ala Thr Ala Glu Ser Asp Phe His Thr Ala
210                 215                 220

Leu Thr Phe Ala His Val Tyr Arg Ala Pro Val Ile Leu Asn Val Val
225                 230                 235                 240

Asn Asn Gln Trp Ala Ile Ser Thr Phe Gln Ala Ile Ala Gly Gly Glu
                245                 250                 255

Gly Thr Thr Phe Ala Asn Arg Gly Val Gly Cys Gly Ile Ala Ser Leu
            260                 265                 270

Arg Val Asp Gly Asn Asp Phe Leu Ala Val Tyr Ala Ala Ser Glu Trp
        275                 280                 285

Ala Ala Glu Arg Ala Arg Arg Asn Leu Gly Pro Ser Leu Ile Glu Trp
290                 295                 300

Val Thr Tyr Arg Ala Gly Pro His Ser Thr Ser Asp Asp Pro Ser Lys
305                 310                 315                 320

Tyr Arg Pro Ala Asp Asp Trp Thr Asn Phe Pro Leu Gly Asp Pro Ile
                325                 330                 335

Ala Arg Leu Lys Arg His Met Ile Gly Leu Gly Ile Trp Ser Glu Glu
            340                 345                 350

Gln His Glu Ala Thr His Lys Ala Leu Glu Ala Glu Val Leu Ala Ala
        355                 360                 365

Gln Lys Gln Ala Glu Ser His Gly Thr Leu Ile Asp Gly Arg Val Pro
370                 375                 380

Ser Ala Ala Ser Met Phe Glu Asp Val Tyr Ala Glu Leu Pro Glu His
385                 390                 395                 400

Leu Arg Arg Gln Arg Gln Glu Leu Gly Val
                405                 410

<210> SEQ ID NO 55
<211> LENGTH: 1233
<212> TYPE: DNA
<213> ORGANISM: Pseudomonas aeruginosa PAO1 bkdA1

<400> SEQUENCE: 55
atgagtgatt acgagccgtt gcgtctgcat gtcccggagc ccaccgggcg tcctggctgc    60

```
aagaccgact tttcctatct gcacctgtcc cccgccggcg aggtacgcaa gccgccggtg    120
gatgtcgagc ccgccgagac cagcgacctg gcctacagcc tggtacgtgt gctcgacgac    180
gacggccacg ccgtcggtcc ctggaatccg cagctcagca acgaacaact gctgcgcggc    240
atgcgggcga tgctcaagac ccgcctgttc gacgcgcgca tgctcaccgc gcaacggcag    300
aaaaagcttt ccttctatat gcaatgcctc ggcgaggaag ccatcgccac cgcccacacc    360
ctggccctgc gcgacggcga catgtgcttt ccgacctatc gccagcaagg catcctgatc    420
acccgcgaat acccgctggt ggacatgatc tgccagcttc tctccaacga ggccgacccg    480
ctcaagggcc gccagctgcc gatcatgtac tcgagcaagg aggcaggttt cttctccatc    540
tccggcaacc tcgccaccca gttcatccag gcggtcggct ggggcatggc ctcggcgatc    600
aagggcgaca cgcgcatcgc ctcggcctgg atcggcgacg cgccaccgc cgagtcggac    660 ttccacaccg ccctcacctt cgcccatgtc taccgcgcgc cggtaatcct caacgtggtc    720
aacaaccagt gggcgatctc caccttccag gccatcgccg gcggcgaagg caccaccttc    780
gccaaccgtg gcgtgggctg cgggatcgcc tcgctgcggg tcgacggcaa tgacttcctg    840
gcggtctacg ccgcctccga gtgggccgcc gagcgcgccc ggcgcaacct cgggccgagc    900
ctgatcgaat gggtcaccta ccgcgccggc ccgcactcga cttcggacga cccgtccaag    960
taccgccccg ccgacgactg gaccaacttc ccgctgggcg acccgatcgc ccgcctgaag   1020
cggcacatga tcggcctcgg catctggtcg gaggaacagc acgaagccac ccacaaggcc   1080
ctcgaagccg aagtactggc cgcgcagaaa caggcggaga ccatggcac cctgatcgac    1140 ggccgggtgc cgagcgccgc cagcatgttc gaggacgtct atgcagaact gccggagcac   1200
ctgcgccggc aacgccagga gctcggggta tga                                1233
```

<210> SEQ ID NO 56
<211> LENGTH: 350
<212> TYPE: PRT
<213> ORGANISM: Pseudomonas aeruginosa PAO1 bkdA2

<400> SEQUENCE: 56

```
Met Asn Ala Met Asn Pro Gln His Glu Asn Ala Gln Thr Val Thr Ser
1               5                   10                  15

Met Thr Met Ile Gln Ala Leu Arg Ser Ala Met Asp Ile Met Leu Glu
            20                  25                  30

Arg Asp Asp Asp Val Val Val Phe Gly Gln Asp Val Gly Tyr Phe Gly
        35                  40                  45

Gly Val Phe Arg Cys Thr Glu Gly Leu Gln Lys Lys Tyr Gly Thr Ser
    50                  55                  60

Arg Val Phe Asp Ala Pro Ile Ser Glu Ser Gly Ile Ile Gly Ala Ala
65                  70                  75                  80

Val Gly Met Gly Ala Tyr Gly Leu Arg Pro Val Val Glu Ile Gln Phe
                85                  90                  95

Ala Asp Tyr Val Tyr Pro Ala Ser Asp Gln Leu Ile Ser Glu Ala Ala
            100                 105                 110

Arg Leu Arg Tyr Arg Ser Ala Gly Asp Phe Ile Val Pro Met Thr Val
        115                 120                 125

Arg Met Pro Cys Gly Gly Gly Ile Tyr Gly Gly Gln Thr His Ser Gln
    130                 135                 140

Ser Pro Glu Ala Met Phe Thr Gln Val Cys Gly Leu Arg Thr Val Met
145                 150                 155                 160
```

```
Pro Ser Asn Pro Tyr Asp Ala Lys Gly Leu Leu Ile Ala Cys Ile Glu
            165                 170                 175

Asn Asp Asp Pro Val Ile Phe Leu Glu Pro Lys Arg Leu Tyr Asn Gly
        180                 185                 190

Pro Phe Asp Gly His His Asp Arg Pro Val Thr Pro Trp Ser Lys His
    195                 200                 205

Pro Ala Ser Gln Val Pro Asp Gly Tyr Tyr Lys Val Pro Leu Asp Lys
210                 215                 220

Ala Ala Ile Val Arg Pro Gly Ala Ala Leu Thr Val Leu Thr Tyr Gly
225                 230                 235                 240

Thr Met Val Tyr Val Ala Gln Ala Ala Asp Glu Thr Gly Leu Asp
                245                 250                 255

Ala Glu Ile Ile Asp Leu Arg Ser Leu Trp Pro Leu Asp Leu Glu Thr
            260                 265                 270

Ile Val Ala Ser Val Lys Lys Thr Gly Arg Cys Val Ile Ala His Glu
            275                 280                 285

Ala Thr Arg Thr Cys Gly Phe Gly Ala Glu Leu Met Ser Leu Val Gln
            290                 295                 300

Glu His Cys Phe His His Leu Glu Ala Pro Ile Glu Arg Val Thr Gly
305                 310                 315                 320

Trp Asp Thr Pro Tyr Pro His Ala Gln Glu Trp Ala Tyr Phe Pro Gly
                325                 330                 335

Pro Ala Arg Val Gly Ala Ala Phe Lys Arg Val Met Glu Val
                340                 345                 350

<210> SEQ ID NO 57
<211> LENGTH: 1053
<212> TYPE: DNA
<213> ORGANISM: Pseudomonas aeruginosa PAO1 bkdA2

<400> SEQUENCE: 57
atgaatgcca tgaacccgca acacgagaac gcccagacgg tcaccagcat gaccatgatc        60
caggcgctgc gctcggcgat ggacatcatg ctcgagcgcg acgacgacgt ggtggtattc       120
ggccaggacg tcggctactt cggcggcgtg ttccgctgca ccgaaggcct gcagaagaaa       180
tacggcacct cgcgggtgtt cgatgcgccg atctccgaga gcggcatcat cggcgccgcg       240
gtcggcatgg gtgcctacgg cctgcgcccg gtggtggaga tccagttcgc cgactacgtc       300
tacccggcct ccgaccagtt gatctccgag gcggcgcgcc tgcgctatcg ctcggccggc       360
gacttcatcg tgccgatgac cgtacgcatg ccctgtggcg gcggcatcta cggcgggcaa       420
acgcacagcc agagcccgga ggcgatgttc acccaggtct gcggcctgcg cacggtgatg       480
ccgtccaacc cctacgacgc caagggcctg ctgatcgcct gcatcgagaa cgacgacccg       540
gtgatcttcc tcgagcccaa gcgcctctac aacggcccgt tcgatggcca ccacgaccgc       600
ccggtgacgc cctggtccaa gcatccggcc agccaggtgc cggacggcta ctacaaggtg       660
ccgctggaca aggcggcgat cgtccgcccc ggcgcggcgc tgaccgtgct gacctacggc       720
accatggtct acgtggccca ggccgcggcc gacgagaccg gcctggacgc cgagatcatc       780
gacctgcgca gcctctggcc gctggacctg gaaaccatcg tcgcctcggt gaagaagacc       840
ggccgctgcg tcatcgccca cgaggcgacc cgcacctgcg ggttcggcgc cgagctgatg       900
tcgctggtgc aggagcactg cttccaccac ctggaggcgc cgatcgagcg cgtcaccggt       960
tgggacaccc cctacccgca tgcccaggag tgggcgtatt tccccggccc cgcgcgcgtc      1020
ggcgcggcat tcaagcgtgt gatggaggtc tga                                   1053
```

<210> SEQ ID NO 58
<211> LENGTH: 428
<212> TYPE: PRT
<213> ORGANISM: Pseudomonas aeruginosa PAO1 bkdB

<400> SEQUENCE: 58

```
Met Gly Thr His Val Ile Lys Met Pro Asp Ile Gly Glu Gly Ile Ala
1               5                   10                  15

Glu Val Glu Leu Val Glu Trp His Val Gln Val Gly Asp Ser Val Asn
            20                  25                  30

Glu Asp Gln Val Leu Ala Glu Val Met Thr Asp Lys Ala Thr Val Glu
        35                  40                  45

Ile Pro Ser Pro Val Ala Gly Arg Ile Leu Ala Leu Gly Gly Gln Pro
    50                  55                  60

Gly Gln Val Met Ala Val Gly Gly Glu Leu Ile Arg Leu Glu Val Glu
65                  70                  75                  80

Gly Ala Gly Asn Leu Ala Glu Ser Pro Ala Ala Thr Pro Ala Ala
                85                  90                  95

Pro Val Ala Ala Thr Pro Glu Lys Pro Lys Glu Ala Pro Val Ala Ala
                100                 105                 110

Pro Lys Ala Ala Glu Ala Pro Arg Ala Leu Arg Asp Ser Glu Ala
            115                 120                 125

Pro Arg Gln Arg Gln Pro Gly Glu Arg Pro Leu Ala Ser Pro Ala
    130                 135                 140

Val Arg Gln Arg Ala Arg Asp Leu Gly Ile Glu Leu Gln Phe Val Gln
145                 150                 155                 160

Gly Ser Gly Pro Ala Gly Arg Val Leu His Glu Asp Leu Asp Ala Tyr
                165                 170                 175

Leu Thr Gln Asp Gly Ser Val Ala Arg Ser Gly Gly Ala Ala Gln Gly
            180                 185                 190

Tyr Ala Glu Arg His Asp Glu Gln Ala Val Pro Val Ile Gly Leu Arg
        195                 200                 205

Arg Lys Ile Ala Gln Lys Met Gln Asp Ala Lys Arg Arg Ile Pro His
    210                 215                 220

Phe Ser Tyr Val Glu Glu Ile Asp Val Thr Asp Leu Glu Ala Leu Arg
225                 230                 235                 240

Ala His Leu Asn Gln Lys Trp Gly Gly Gln Arg Gly Lys Leu Thr Leu
                245                 250                 255

Leu Pro Phe Leu Val Arg Ala Met Val Val Ala Leu Arg Asp Phe Pro
            260                 265                 270

Gln Leu Asn Ala Arg Tyr Asp Asp Glu Ala Glu Val Val Thr Arg Tyr
        275                 280                 285

Gly Ala Val His Val Gly Ile Ala Thr Gln Ser Asp Asn Gly Leu Met
    290                 295                 300

Val Pro Val Leu Arg His Ala Glu Ser Arg Asp Leu Trp Gly Asn Ala
305                 310                 315                 320

Ser Glu Val Ala Arg Leu Ala Glu Ala Ala Arg Ser Gly Lys Ala Gln
                325                 330                 335

Arg Gln Glu Leu Ser Gly Ser Thr Ile Thr Leu Ser Ser Leu Gly Val
            340                 345                 350

Leu Gly Gly Ile Val Ser Thr Pro Val Ile Asn His Pro Glu Val Ala
        355                 360                 365

Ile Val Gly Val Asn Arg Ile Val Glu Arg Pro Met Val Val Gly Gly
```

Asn Ile Val Val Arg Lys Met Met Asn Leu Ser Ser Phe Asp His
385             390                 395                 400

Arg Val Val Asp Gly Met Asp Ala Ala Ala Phe Ile Gln Ala Val Arg
            405                 410                 415

Gly Leu Leu Glu His Pro Ala Thr Leu Phe Leu Glu
            420                 425

<210> SEQ ID NO 59
<211> LENGTH: 1287
<212> TYPE: DNA
<213> ORGANISM: Pseudomonas aeruginosa PAO1 bkdB

<400> SEQUENCE: 59

```
atgggtaccc atgtgatcaa gatgccggac atcggggaag gcatcgccga ggtcgaactg      60
gtggagtggc atgtccaggt cggcgactcg gtcaatgaag accaggtcct cgccgaggtg     120
atgaccgaca aggccacggt ggagattccc tcgccggtgg ccggacgcat cctcgccctc     180
ggcggccagc cgggccaggt gatggcggtg gcggcgaac tgatccgcct ggaggtggaa      240
ggcgccggca acctcgccga gagtccggcc gcggcgacgc cggccgcgcc cgtcgccgcc     300
accccggaga aaccgaagga agccccggtc gcggcgccga agccgccgc cgaagcgccg      360
cgcgccttgc gcgacagcga ggcgccacgg cagcggcgcc agcccggcga acgcccgctg     420
gcctccccg cggtgcgcca gcgcgcccgc gacctgggca tcgagttgca gttcgtgcag     480
ggcagcggtc cgccggacg cgtcctccac gaggacctcg atgcctacct gacccaggat      540
ggcagcgtcg cgcgcagcgg cggcgccgcg caggggtatg ccgagcgaca cgacgaacag     600
gcggtgccgg tgatcggcct gcgtcgcaag atcgcccaga gatgcagga cgccaagcga      660
cgcatcccgc atttcagcta tgtcgaggaa atcgacgtca ccgatctgga agccctgcgc     720
gcccatctca accagaaatg gggtggccag cgcggcaagc tgaccctgct gccgttcctg     780
gtccgcgcca tggtcgtggc gctgcgcgac ttcccgcagt tgaacgcgcg ctacgacgac     840
gaggccgagg tggtcacccg ctacggcgcg gtgcacgtcg gcatcgccac ccagagcgac     900
aacggcctga tggtgccggt gctgcgccac gccgaatcgc gcgacctctg ggcaacgcc      960
agcgaagtgg cgcgcctggc cgaagccgca cgcagcggca aggcgcaacg ccaggagctg    1020
tccggctcga ccatcaccct gagcagcctc ggcgtgctcg gcgggatcgt cagcacaccg    1080
gtgatcaacc atccggaggt ggccatcgtc ggcgtcaacc gcatcgtcga gcgaccgatg    1140
gtggtcggcg caacatcgt cgtgcgcaag atgatgaacc tctcctcctc cttcgaccac    1200
cgggtggtcg acgggatgga cgcggcggcc ttcatccagg ccgtgcgcgg cctgctcgaa    1260
catcccgcca ccctgttcct ggagtaa                                        1287
```

<210> SEQ ID NO 60
<211> LENGTH: 464
<212> TYPE: PRT
<213> ORGANISM: Pseudomonas aeruginosa PAO1 lpdV

<400> SEQUENCE: 60

Met Ser Gln Ile Leu Lys Thr Ser Leu Leu Ile Val Gly Gly Gly Pro
1               5                   10                  15

Gly Gly Tyr Val Ala Ala Ile Arg Ala Gly Gln Leu Gly Ile Pro Thr
            20                  25                  30

Val Leu Val Glu Gly Ala Ala Leu Gly Gly Thr Cys Leu Asn Val Gly
        35                  40                  45

-continued

```
Cys Ile Pro Ser Lys Ala Leu Ile His Ala Ala Glu Glu Tyr Leu Lys
     50                  55                  60

Ala Arg His Tyr Ala Ser Arg Ser Ala Leu Gly Ile Gln Val Gln Ala
 65                  70                  75                  80

Pro Ser Ile Asp Ile Ala Arg Thr Val Glu Trp Lys Asp Ala Ile Val
                 85                  90                  95

Asp Arg Leu Thr Ser Gly Val Ala Ala Leu Leu Lys Lys His Gly Val
            100                 105                 110

Asp Val Val Gln Gly Trp Ala Arg Ile Leu Asp Gly Lys Ser Val Ala
        115                 120                 125

Val Glu Leu Ala Gly Gly Ser Gln Arg Ile Glu Cys Glu His Leu
130                 135                 140

Leu Leu Ala Ala Gly Ser Gln Ser Val Glu Leu Pro Ile Leu Pro Leu
145                 150                 155                 160

Gly Gly Lys Val Ile Ser Ser Thr Glu Ala Leu Ala Pro Gly Ser Leu
                165                 170                 175

Pro Lys Arg Leu Val Val Val Gly Gly Gly Tyr Ile Gly Leu Glu Leu
            180                 185                 190

Gly Thr Ala Tyr Arg Lys Leu Gly Val Glu Val Ala Val Val Glu Ala
        195                 200                 205

Gln Pro Arg Ile Leu Pro Gly Tyr Asp Glu Glu Leu Thr Lys Pro Val
210                 215                 220

Ala Gln Ala Leu Arg Arg Leu Gly Val Glu Leu Tyr Leu Gly His Ser
225                 230                 235                 240

Leu Leu Gly Pro Ser Glu Asn Gly Val Arg Val Arg Asp Gly Ala Gly
                245                 250                 255

Glu Glu Arg Glu Ile Ala Ala Asp Gln Val Leu Val Ala Val Gly Arg
            260                 265                 270

Lys Pro Arg Ser Glu Gly Trp Asn Leu Glu Ser Leu Gly Leu Asp Met
        275                 280                 285

Asn Gly Arg Ala Val Lys Val Asp Asp Gln Cys Arg Thr Ser Met Arg
290                 295                 300

Asn Val Trp Ala Ile Gly Asp Leu Ala Gly Glu Pro Met Leu Ala His
305                 310                 315                 320

Arg Ala Met Ala Gln Gly Glu Met Val Ala Glu Leu Ile Ala Gly Lys
                325                 330                 335

Arg Arg Gln Phe Ala Pro Val Ala Ile Pro Ala Val Cys Phe Thr Asp
            340                 345                 350

Pro Glu Val Val Ala Gly Leu Ser Pro Glu Gln Ala Lys Asp Ala
        355                 360                 365

Gly Leu Asp Cys Leu Val Ala Ser Phe Pro Phe Ala Ala Asn Gly Arg
370                 375                 380

Ala Met Thr Leu Glu Ala Asn Glu Gly Phe Val Arg Val Val Ala Arg
385                 390                 395                 400

Arg Asp Asn His Leu Val Val Gly Trp Gln Ala Val Gly Lys Ala Val
                405                 410                 415

Ser Glu Leu Ser Thr Ala Phe Ala Gln Ser Leu Glu Met Gly Ala Arg
            420                 425                 430

Leu Glu Asp Ile Ala Gly Thr Ile His Ala His Pro Thr Leu Gly Glu
        435                 440                 445

Ala Val Gln Glu Ala Ala Leu Arg Ala Leu Gly His Ala Leu His Ile
450                 455                 460
```

<210> SEQ ID NO 61
<211> LENGTH: 1395
<212> TYPE: DNA
<213> ORGANISM: Pseudomonas aeruginosa PAO1 lpdV

<400> SEQUENCE: 61

```
atgagccaga tcctgaagac ttccctgctg atcgtcggcg gcggtccgg cggctacgtc      60
gcggcgatcc gtgccgggca actgggcatt cccaccgtac tggtggaggg cgccgccctc    120
ggcggcacct gcctgaacgt cggctgcatc ccgtcgaagg cgctgatcca cgccgccgag    180
gaatacctca aggcccgcca ctatgccagc cggtcggcgc tgggcatcca ggtacaggcg    240
ccgagcatcg acatcgcccg caccgtggaa tggaaggacg ccatcgtcga ccgcctcacc    300
agcggcgtcg ccgcgctgct gaagaaacac ggggtcgatg tcgtccaggg ctgggcgagg    360
atcctcgacg gcaaaagcgt ggcggtcgaa ctcgccggcg gcggcagcca gcgcatcgag    420
tgcgagcacc tgctgctggc cgccggctcg cagagcgtcg agctaccgat cctgccgctg    480
ggcggcaagg tgatctcctc caccgaggcg ctggcgcccg cagcctgcc caagcgcctg    540
gtggtggtcg gcggcggcta catcggcctg gagctgggta ccgcctaccg caagctcggc    600
gtcgaggtgg cggtggtgga agcgcaacca cgcatcctgc cgggctacga cgaagaactg    660
accaagccgg tggcccaggc cttgcgcagg ctgggcgtcg agctgtacct cgggcacagc    720
ctgctgggcc cgagcgagaa cggcgtgcgg gtccgcgacg cgccggcga ggagcgcgag    780
atcgccgccg accaggtact ggtggcggtc ggccgcaagc cgcgcagcga aggctggaac    840
ctggaaagcc tgggcctgga catgaacggc cgggcggtga aggtcgacga ccagtgccgc    900
acctcgatgc gcaatgtctg ggccataggc gatctcgccg gcgagccgat gctcgcgcac    960
cgggccatgg cccagggcga gatggtcgcc gagctgatcg ccggcaagcg tcgccagttc   1020
gccccggtgg cgatccccgc ggtgtgcttc accgatccgg aagtggtggt cgccgggttg   1080
tccccggagc aggcgaagga tgccggcctg gactgcctgg tggcgagctt cccgttcgcc   1140
gccaacggtc gcgccatgac cctggaggcc aacgaaggct tcgtccgcgt ggtggcgcgt   1200
cgcgacaacc acctggtcgt cggctggcag gcggtgggca aggcggtctc ggaactgtcc   1260
acggccttcg cccagtcgct ggagatgggc gcccgcctgg aagacatcgc cggcaccatc   1320
cacgcccatc cgaccctcgg cgaagcggtc caggaagccg ccctgcgcgc gctgggacac   1380
gccctgcaca tctga                                                    1395
```

<210> SEQ ID NO 62
<211> LENGTH: 375
<212> TYPE: PRT
<213> ORGANISM: Rhodococcus erythropolis PR4

<400> SEQUENCE: 62

```
Met Thr Leu Val Glu Pro Leu Gly Glu Leu Arg Tyr Gln Lys Phe Leu
1               5                   10                  15

Pro Ala Asp Ser Ala Val Gln Tyr Leu Asp Pro Ala Gly Glu Leu Thr
                20                  25                  30

Arg Ser Glu Ala Arg Tyr Ala Lys Pro Ser Asp Asp Arg Leu Ile Glu
            35                  40                  45

Met Tyr Arg Lys Met Phe Leu Gly Arg Arg Phe Asp Gln Gln Ala Thr
        50                  55                  60

Ala Leu Thr Lys Gln Gly Arg Leu Ala Val Tyr Pro Ser Ser Arg Gly
65                  70                  75                  80
```

```
Gln Glu Ala Cys Gln Ile Ala Ala Ala Met Ser Leu Glu Pro Ser Asp
             85                  90                  95

Trp Leu Phe Pro Thr Tyr Arg Asp Ser Met Ala Leu Ala Ala Arg Gly
            100                 105                 110

Val Asp Pro Val Gln Ile Leu Ser Met Leu Ala Gly Asp Trp His Cys
        115                 120                 125

Gly Tyr Asp Pro Val Ala Leu Arg Ser Ala Pro Gln Cys Thr Pro Leu
    130                 135                 140

Ala Thr Gln Leu Leu His Ala Ala Gly Val Ala Tyr Gly Glu Ser Arg
145                 150                 155                 160

Arg Gly Leu Asn Thr Val Ala Leu Ala Leu Cys Gly Asp Gly Ala Thr
                165                 170                 175

Ser Glu Gly Asp Phe His Glu Ala Leu Asn Phe Ala Ala Val Phe Lys
            180                 185                 190

Ala Pro Val Val Phe Leu Val Gln Asn Asn Gly Phe Ala Ile Ser Val
        195                 200                 205

Pro Leu Ser Arg Gln Ser Ala Ala Pro Thr Leu Ala His Lys Gly Val
    210                 215                 220

Gly Tyr Gly Ile Gly Ser Glu Gln Val Asp Gly Asn Asp Pro Val Ala
225                 230                 235                 240

Met Met Ala Val Met Asp Glu Ala Ala Arg Phe Val Arg Ser Gly Asn
                245                 250                 255

Gly Pro Val Ile Val Glu Ala His Thr Tyr Arg Ile Asp Ala His Thr
            260                 265                 270

Asn Ala Asp Asp Ala Thr Arg Tyr Arg Asp Ser Ala Glu Val Glu Ser
        275                 280                 285

Trp Arg Gly Arg Asp Pro Leu Pro Arg Leu Glu Lys Tyr Leu Arg Ala
    290                 295                 300

His Asp Leu Ile Asp Asp Ala Phe Val Glu Ser Leu Thr Ala Glu Ala
305                 310                 315                 320

Glu Thr Glu Ala Ala Thr Leu Arg Ala Gly Met Asn Val Asp Arg Pro
                325                 330                 335

His Asp Pro Leu Asp Leu Phe Arg Tyr Val Phe Ala Glu Gln Thr Pro
            340                 345                 350

Gln Leu Arg Glu Gln Gln Ala Gln Leu Glu Thr Glu Leu Ala Ala Glu
        355                 360                 365

Ala Ala Asp Thr Gly Gly His
    370                 375

<210> SEQ ID NO 63
<211> LENGTH: 1128
<212> TYPE: DNA
<213> ORGANISM: Rhodococcus erythropolis PR4

<400> SEQUENCE: 63
gtgactcttg tcgagccctt gggggaactg cggtatcaaa agttcctgcc ggccgattcc      60
gcggtgcagt acctcgaccc tgctggagaa ctgacgcgca gcgaggcccg ctacgcaaaa     120
ccgagcgacg atcgcctgat cgagatgtat cgaaagatgt tcctgggcag acgcttcgac     180
cagcaggcga cggcgctgac caaacagggg cgcttggccg tgtatccgtc ctcgcgaggg     240
caggaggcat gccagatcgc ggcagcgatg agtctggagc gagtgactg gctcttcccc      300 acctatcggg attcgatggc gttggctgct cggggtgtcg atccggtgca gattctgagc     360
atgcttgccg gcgactggca ctgcgggtac gacccggtag cgctgcgcag tgcgccgcag     420
```

-continued

```
tgcaccccgc tggcaacgca attgctgcat gcagcggggg tggcctacgg ggagtccaga    480
cggggcctga acaccgtcgc gctggcgctc tgcggcgacg gggccaccag tgagggtgat    540
ttccacgaag cgctgaactt cgccgccgtc ttcaaggcac cggtcgtctt tctggtgcag    600
aacaacggat ttgcgatcag cgtcccgttg tcacgtcaaa gcgcagcacc gacgttggcg    660
cacaagggtg tcggctacgg gatcggcagc gagcaggtcg acggcaacga tcctgttgcg    720
atgatggccg tcatggacga ggcggcgcgc ttcgtccgca gcggaaacgg accggtgatc    780
gtcgaggcac acacctatcg catcgacgca cacaccaacg ccgacgacgc cacccgctac    840
cgcgacagcg ccgaggtgga aagctggcgc gggcgagatc cgttgccgcg tctcgaaaag    900
tatctgcgcg cacacgatct gatcgacgac gcgttcgtgg aatcactgac cgcagaggca    960
gaaaccgagg ccgccacact tcgcgccggc atgaacgtcg accgcccgca cgatccgctc   1020
gatctgttcc ggtacgtctt cgccgagcag acaccgcaat tgcgtgagca acaagcccaa   1080
ctcgaaaccg aacttgccgc cgaagccgct gacacagggg gacactga                 1128
```

<210> SEQ ID NO 64
<211> LENGTH: 334
<212> TYPE: PRT
<213> ORGANISM: Rhodococcus erythropolis PR4

<400> SEQUENCE: 64

```
Met Pro Met Leu Thr Met Ala Gln Ala Leu Asn Thr Ala Leu Arg Asp
1               5                   10                  15

Ser Leu Ala Ala Asp Asp Asn Val Val Phe Gly Glu Asp Val Gly
            20                  25                  30

Thr Leu Gly Gly Val Phe Arg Val Thr Asp Gly Leu Thr Arg Asp Phe
        35                  40                  45

Gly Asp Asp Arg Cys Phe Asp Thr Pro Leu Ala Glu Ser Gly Ile Ile
    50                  55                  60

Gly Phe Ala Ile Gly Met Thr Met Ala Gly Phe Arg Pro Val Val Glu
65                  70                  75                  80

Met Gln Phe Asp Ala Phe Ala Tyr Pro Ala Phe Glu Gln Ile Ala Ser
                85                  90                  95

His Val Ala Lys Ile Arg Asn Arg Thr Lys Gly Ala Leu Ser Ile Pro
            100                 105                 110

Ile Val Ile Arg Val Pro Phe Ala Gly Gly Ile Gly Gly Val Glu His
        115                 120                 125

His Cys Asp Ser Ser Glu Gly Tyr Tyr Ala His Thr Pro Gly Leu Lys
    130                 135                 140

Val Val Ala Pro Ser Thr Val Glu Asp Ala Tyr Ser Leu Leu Arg Ser
145                 150                 155                 160

Ala Ile Glu Asp Pro Asp Pro Val Ile Phe Leu Glu Pro Lys Lys Leu
                165                 170                 175

Tyr Phe Ser Arg Ala Asp Val Glu Leu Thr Ala Arg Glu Pro Ile Gly
            180                 185                 190

Arg Ala Val Val Arg Arg Pro Gly Arg Asp Val Thr Leu Ile Ala Tyr
        195                 200                 205

Gly Pro Ser Val Glu Val Ala Leu Lys Ser Ala Glu Ala Ala Ala
    210                 215                 220

Glu Gly Arg Asp Ile Glu Val Ile Asp Ile Arg Ser Ile Val Pro Phe
225                 230                 235                 240

Asp Asp Glu Thr Val Thr Ala Ser Val Arg Lys Thr Gly Arg Cys Ile
                245                 250                 255
```

Val Ile Gln Glu Ala Gln Gly Phe Ala Gly Val Gly Ala Glu Ile Ala
              260                 265                 270

Ala Arg Val Gln Glu Arg Cys Phe His His Leu His Ala Pro Val Leu
            275                 280                 285

Arg Val Ser Gly Phe Asp Ile Pro Tyr Pro Ala Pro Lys Leu Glu Arg
        290                 295                 300

His His Leu Pro Ser Val Asp Arg Val Leu Asp Ala Val Asp Arg Leu
305                 310                 315                 320

Gln Trp Asn Asp Ala Pro Asp Thr Arg Trp Ala Val Thr Ala
                325                 330

<210> SEQ ID NO 65
<211> LENGTH: 1005
<212> TYPE: DNA
<213> ORGANISM: Rhodococcus erythropolis PR4

<400> SEQUENCE: 65
atgcccatgc tcacgatggc tcaggccctc aacaccgcgc tacgggactc tctggctgcg      60
gacgacaacg ttgtcgtctt cggtgaggac gtcggcaccc tgggcggcgt tttccgcgtc     120
accgacggcc tcacccgcga cttcggcgac gaccgatgct tcgacactcc cctcgccgag     180
tccggcatca tcggattcgc aatcggcatg accatggctg gttttcgtcc ggtcgtggaa     240
atgcagttcg acgcgtttgc ctatccggca ttcgagcaga tcgcctccca cgtcgcaaag     300
atccgcaacc gtaccaaggg tgcactgtcg attccgatag tcatccgtgt tccttttgcc     360
ggcggtatcg gcggggtgga gcatcactgt gattccagcg agggctacta cgcacacacg     420
cccggcctga aggtcgtggc gccgtccacg gtggaagatg cgtactcact gctacgttcg     480
gcgatcgagg accccgaccc ggtgatcttc ctcgaaccca gaagctgta cttctcgcga     540 gccgatgtcg aactgaccgc acgggagccg atcgggcgcg ccgtcgtccg gcgccccggt     600
cgtgacgtga cgctcattgc ctacggtccg tccgtggagg ttgcactgaa gtccgccgag     660
gctgctgcgg ccgagggccg cgacatcgag gtgatcgaca tccggtcgat agtgccgttc     720
gacgacgaga cggtcaccgc gtcggtgcga aagaccggac gctgcatcgt catccaggaa     780
gcgcagggct tgccggtgt tggtgcggaa attgctgctc gcgtgcagga gcgatgcttc     840
caccatctcc acgctccggt gctcagggtc agcggattcg acatccccta ccccgcgccg     900
aagctcgagc gtcaccacct gcccagcgtc gaccgtgtcc tggacgccgt cgaccgtctg     960
cagtggaacg acgccccgga tacccgttgg gcggtgacgg catga                     1005

<210> SEQ ID NO 66
<211> LENGTH: 407
<212> TYPE: PRT
<213> ORGANISM: Rhodococcus erythropolis PR4

<400> SEQUENCE: 66

Met Ser Asn Gln Val Phe Met Leu Pro Asp Leu Gly Glu Gly Leu Ala
1               5                   10                  15

Glu Ala Asp Ile Ala Glu Trp His Val Lys Val Gly Asp Val Val Thr
            20                  25                  30

Ile Asp Gln Ile Val Val Glu Val Thr Ala Lys Ala Val Asp
        35                  40                  45

Val Pro Ile Pro Phe Ala Gly Thr Val Val Glu Leu His Gly Lys Asp
    50                  55                  60

Gly Asp Thr Leu Lys Val Gly Thr Pro Leu Ile Thr Val Ser Gly Gly

```
              65                  70                  75                  80
        Gly Ser Val Asp Ala Val Ser Ala Asn His Glu Arg Tyr Arg Glu
                        85                  90                  95
        Glu Glu Arg Ala Gly Ser Gly Asn Val Leu Ile Gly Tyr Gly Thr Ser
                    100                 105                 110
        Glu Asp Ala Pro Arg Arg Arg Ala Ala Pro Ser Val Arg Val
                    115                 120                 125
        Ile Ser Pro Ile Val Arg Lys Leu Ala Val Asp Asn Asp Ile Asp Leu
        130                 135                 140
        Ser Leu Leu Ser Gly Ser Gly Ala Gly Gly Val Ile Thr Arg Ala Asp
        145                 150                 155                 160
        Val Glu Ala Gly Ser Asn Ala Gly Thr Glu Thr Glu Pro Ser His Val
                        165                 170                 175
        Ser Asp Gln Arg Ile Pro Ile Lys Gly Leu Arg Lys Val Val Ala Asp
                    180                 185                 190
        Lys Leu Ser Ala Ser Arg Arg Glu Ile Pro Asp Ala Thr Thr Trp Val
                195                 200                 205
        Asp Val Asp Ala Thr Glu Leu Leu Ala Ala Arg Ala Glu Ile Asn Lys
        210                 215                 220
        Ser Leu Pro Asp Ser Asp Lys Ile Ser Leu Met Ala Leu Leu Ala Arg
        225                 230                 235                 240
        Leu Thr Ile Ala Ala Leu Gly Gln Tyr Pro Glu Leu Asn Ser Ser Val
                        245                 250                 255
        Asp Thr Ala Arg Gly Glu Ile Val Arg His Ala Arg Ile His Leu Gly
                    260                 265                 270
        Ile Ala Ala Gln Thr Pro Lys Gly Leu Met Val Pro Val Ile Arg Asn
                275                 280                 285
        Ala Asp Ala Leu Ser Thr Val Glu Leu Ala Gln Ala Leu Arg Val Thr
        290                 295                 300
        Thr Asp Leu Ala Arg Asp Gly Lys Leu Glu Pro Ala Arg Leu Thr Gly
        305                 310                 315                 320
        Gly Thr Phe Thr Leu Asn Asn Tyr Gly Val Phe Gly Val Asp Gly Ser
                        325                 330                 335
        Thr Pro Ile Ile Asn His Pro Glu Ala Ala Ile Leu Gly Ile Gly Arg
                    340                 345                 350
        Ile Ile Asp Lys Pro Trp Val Val Asn Gly Glu Leu Thr Val Arg Lys
                355                 360                 365
        Val Thr Gln Ile Ser Leu Ser Phe Asp His Arg Val Cys Asp Gly Gly
                370                 375                 380
        Glu Ala Gly Gly Phe Leu Arg Leu Phe Gly Asp Tyr Ile Glu Asn Pro
        385                 390                 395                 400
        Ile Arg Val Leu Gly Arg Leu
                        405

<210> SEQ ID NO 67
<211> LENGTH: 1224
<212> TYPE: DNA
<213> ORGANISM: Rhodococcus erythropolis PR4

<400> SEQUENCE: 67
atgagcaatc aggtattcat gctccccgat ctgggtgaag gtctggccga ggccgatatc    60
gcggagtggc acgtcaaggt cggcgacgtg gtcaccatcg atcagatcgt cgtcgaggtc   120
gagaccgcga agctgctgtg gacgtgcct atcccgttcg ccgggaccgt cgtcgaatta   180
```

-continued

| | |
|---|---|
| catggcaagg acggcgacac cttgaaggtg gcacgccgt tgatcactgt gagtggtggc | 240 |
| ggcagtgtcg acgcggtcgt ttcggccaac cacgagcgtt accgtgaaga ggaacgcgcg | 300 |
| ggttcgggca acgtcctgat cggctacggc accagcgagg atgcaccgag acgccgtcgc | 360 |
| agagctgctc cgtcggtacg cgtgatctca ccaatcgttc gtaagctggc tgtcgacaac | 420 |
| gatatcgacc tctccttgct ctccggatcc ggtgccggcg gggtgataac gcgcgctgac | 480 |
| gtcgaggccg ggtcgaacgc cggcacggaa acggaaccgt cgcacgtgag cgaccaacgg | 540 |
| atcccgatca aggggcttcg caaggtggtg ccgacaagc tgtccgccag ccgccgcgag | 600 |
| attcccgacg caacaacctg ggtcgacgtc gacgccaccg aactgttggc ggcgcgagcc | 660 |
| gagatcaaca agtcactgcc cgattccgac aagatcagcc tgatggcgct cctggctcgg | 720 |
| ctgaccatcg cggcgttggg gcagtacccc gaactgaact cgtcggtcga tactgctcga | 780 |
| ggcgagatcg ttcgacacgc ccgcatccac ctgggaatcg ccgcacagac accgaaggga | 840 |
| ttgatggtgc cggtcattcg aaatgcggat gccctgagca ccgtcgaact cgcacaagca | 900 |
| cttcgggtga ccaccgacct tgcgcgcgac ggcaaactcg aacccgcccg cctgaccggc | 960 |
| ggcacgttca cgctcaacaa ctacggggta ttcggggttg acggatcgac tccgatcatc | 1020 |
| aatcaccccg aggcggcaat tctggggatc gggcgcatca tcgacaagcc gtgggtggtg | 1080 |
| aacggcgagt tgaccgtccg taaggtcact cagatctcgt tgagcttcga ccaccgcgtc | 1140 |
| tgtgacggag gcgaagccgg cggattcctg aggctgttcg gtgactacat cgagaacccg | 1200 |
| atccgcgtcc tgggaaggct ctga | 1224 |

<210> SEQ ID NO 68
<211> LENGTH: 459
<212> TYPE: PRT
<213> ORGANISM: Rhodococcus erythropolis PR4

<400> SEQUENCE: 68

Met Thr Thr Ala Glu Pro His Ser Asp Val Val Ile Leu Gly Gly Gly
1               5                   10                  15

Ser Gly Gly Tyr Ala Cys Ala Ile Arg Ala Ala Gln Leu Gly Leu Ser
                20                  25                  30

Val Thr Leu Ile Glu Ala Asp Lys Val Gly Gly Thr Cys Leu His Arg
            35                  40                  45

Gly Cys Ile Pro Thr Lys Ala Leu Leu His Ser Ala Glu Val Ala Asp
        50                  55                  60

Ser Ala Arg Thr Ser Glu Gln Phe Gly Val Arg Ala Ser Phe Asp Gly
65                  70                  75                  80

Ile Asp Ile Ala Gln Val His Asp Tyr Lys Asn Gly Thr Val Glu Arg
                85                  90                  95

Leu Tyr Ser Gly Leu Gln Gly Leu Leu Ala Gln His Lys Ile Thr Ile
            100                 105                 110

Val Asn Gly Tyr Gly Thr Tyr Val Gly Gly Arg Ser Ile Asp Val Asp
        115                 120                 125

Gly Thr Arg Tyr Thr Gly Thr Ser Leu Val Leu Ala Thr Gly Ser Tyr
    130                 135                 140

Pro Arg Glu Leu Pro Gly Ile Glu Leu Gly Arg Arg Ile Leu Thr Ser
145                 150                 155                 160

Asp Gln Ala Leu Glu Leu Asp Arg Val Pro Thr Ser Ala Thr Val Leu
                165                 170                 175

Gly Gly Gly Val Ile Gly Val Glu Phe Ala Ser Ile Trp Arg Ser Phe
            180                 185                 190

```
Gly Ala Glu Val Thr Ile Val Glu Ala Leu Pro Arg Leu Ile Ala Ala
        195                 200                 205

Glu Asp Pro Trp Ser Ser Lys Gln Leu Glu Arg Ala Tyr Arg Lys Arg
    210                 215                 220

Gly Ile Val Cys Lys Thr Asp Thr Lys Ile Val Ser Ala Lys Glu Ala
225                 230                 235                 240

Ala Asp Ser Val Arg Val Glu Leu Gly Asp Gly Thr Ile Phe Asp Thr
                245                 250                 255

Glu Leu Leu Leu Val Ala Val Gly Arg Gly Pro Arg Thr Asp Gly Asn
            260                 265                 270

Gly Phe Glu Glu Asn Gly Ile Ser Leu Asp Lys Gly Phe Val Val Thr
        275                 280                 285

Asp Glu Arg Leu Arg Thr Ser Val Asp Gly Val Tyr Ala Val Gly Asp
    290                 295                 300

Ile Val Pro Gly Leu Ala Leu Ala His Arg Gly Phe Gln Gln Gly Ile
305                 310                 315                 320

Phe Val Ala Glu Gln Ile Ala Gly Lys Asp Pro Ile Pro Val Ala Glu
                325                 330                 335

His Leu Ile Pro Arg Val Thr Tyr Ser His Pro Glu Val Ala Ser Val
            340                 345                 350

Gly Leu Gly Glu Glu Ala Ala Arg Thr Gln Tyr Gly Asp Ile Ser Thr
        355                 360                 365

Val Val Tyr Asp Leu Ser Gly Asn Gly Lys Ser Gln Ile Leu Arg Thr
    370                 375                 380

Thr Gly Gly Ile Lys Val Ile Arg Ser Gly Thr Arg Gly Pro Val Ile
385                 390                 395                 400

Gly Val His Leu Val Gly Asp Arg Val Gly Glu Leu Ile Gly Glu Ala
                405                 410                 415

Gln Leu Ala Val Ala Trp Glu Ala Leu Pro Asp Glu Val Gly Arg Phe
            420                 425                 430

Ile His Ala His Pro Ser Gln Asn Glu Ala Leu Gly Glu Ala Met Leu
        435                 440                 445

Ala Leu Ala Gly Thr Pro Leu His Ala His Ser
    450                 455

<210> SEQ ID NO 69
<211> LENGTH: 1380
<212> TYPE: DNA
<213> ORGANISM: Rhodococcus erythropolis PR4

<400> SEQUENCE: 69
atgacaactg cagaacccca cagcgacgtc gtgatcctcg gtggaggatc gggcggctat      60
gcctgcgcca tccgcgccgc ccaactcgga ttgtcggtca cgctgatcga ggcggacaag     120
gtcggcggaa cgtgtctgca ccgcggatgc atcccgacca aggcgctgct gcattccgcc     180
gaggtcgccg actcagcacg caccagtgag caattcggag tccgggcatc ttttgacggc     240
atcgacatcg cgcaggtgca cgactacaag aacggaacag tcgagcggct gtacagcggt     300
ctgcaaggtt tgttggcgca acacaagatc actattgtca acggttacgg aacgtacgtc     360
ggtgggcgaa gcatcgacgt cgacggaacc cgctataccg aacatcact cgttctggcc     420 accggttcgt atccgcggga actgcccggc atagaactcg ccgccggat cctcaccagt     480 gaccaggcgc tcgaactcga ccgggtgccc accagcgcga cagtgctcgg tgccggtgtc     540
atcggcgtcg agttcgcgag catctggcgc tcgttcggcg ccgaagtcac gatcgtcgag     600
```

```
gcactcccac gactgatcgc cgccgaggac ccgtggtcgt cgaagcagct ggagcgggcc    660
taccggaaac gcggaatcgt ctgtaagaca gacacaaaga tcgtttccgc gaaagaagca    720
gccgattcgg tccgcgtcga actaggcgac ggaacgatat tcgataccga actactgttg    780
gtcgccgtcg gccgcggacc ccgcacggac ggtaacggtt tcgaagaaaa cggaatcagc    840
ctcgacaagg gttttgtcgt taccgacgaa cgcctccgta cgtccgtgga cggtgtgtac    900
gcggtcggcg acatcgtgcc cggtcttgcg ttggcgcacc gaggtttcca acaaggaatc    960
tttgtggctg aacagatcgc cgggaaggat ccgataccgg tcgccgaaca cttgattcct   1020
cgcgtgacgt actcacatcc cgaagttgcg tcagtcggac tcggcgaaga ggcggcgcgc   1080
acgcagtacg gcgacatctc caccgtcgtc tacgacctgt cgggtaacgg caagagtcag   1140
atcctgcgaa ccaccggggg aatcaaagtg attcgcagcg gaaccagagg tcccgtcatc   1200
ggcgtccacc tggtaggcga ccgggttggt gaactgatcg gtgaggcgca gttggccgtt   1260
gcctgggaag cacttcccga tgaagtgggg cgtttcatcc acgcgcaccc cagccagaac   1320
gaggcgttgg gcgaggccat gctcgcactc gcgggaacac cactgcacgc gcacagctga   1380
```

<210> SEQ ID NO 70
<211> LENGTH: 362
<212> TYPE: PRT
<213> ORGANISM: Rhodococcus erythropolis PR4

<400> SEQUENCE: 70

```
Met Ile Asp Asn Leu Asp Tyr Pro Val Gln Leu Ile Gln Pro Asn Gly
1               5                   10                  15

Ala Arg Val Cys Arg Pro Glu Phe Asp Arg Leu Ile Thr Asp Ile Gly
            20                  25                  30

Pro Asp Glu Leu Leu Ser Leu Tyr Arg Asp Leu Val Val Ser Arg Arg
        35                  40                  45

Ile Asp Thr Glu Ala Val Ala Leu Gln Arg Gln Gly Glu Ile Gly Leu
    50                  55                  60

Trp Ala Pro Met Leu Gly Gln Glu Ala Ala Gln Val Gly Ser Ala Arg
65                  70                  75                  80

Ala Leu Ala Pro Asp Asp Phe Ala Phe Thr Ser Tyr Arg Glu His Ala
                85                  90                  95

Val Ala Tyr Cys Arg Gly Val Pro Pro Glu Leu Leu Thr Thr Met Trp
            100                 105                 110

Arg Gly Ile Ser His Ser Gly Trp Asp Pro Glu Gln Val Asn Val Thr
        115                 120                 125

Asn Pro Ala Ile Val Val Gly Ser Gln Gly Leu His Ala Thr Gly Tyr
    130                 135                 140

Ala Leu Gly Ala His Leu Asp Gly Ala Glu Ile Ala Thr Ile Ala Tyr
145                 150                 155                 160

Phe Gly Asp Gly Ala Thr Ser Gln Gly Asp Ile Ala Glu Ala Met Gly
                165                 170                 175

Phe Ala Ala Ser Phe Arg Val Gly Val Val Phe Phe Cys Gln Asn Asn
            180                 185                 190

Gln Trp Ala Ile Ser Glu Pro Val Ser Leu Gln Ser Arg Thr Pro Ile
        195                 200                 205

Ser His Arg Ala Ile Gly Tyr Gly Ile Pro Ala Ile Arg Val Asp Gly
    210                 215                 220

Asn Asp Val Leu Ala Val Leu Ala Val Thr Arg Ser Ala Leu Asn Arg
225                 230                 235                 240
```

```
Ala Arg Glu Gly Ser Gly Pro Thr Phe Ile Glu Ala Ile Thr Cys Arg
                245                 250                 255

Met Gly Pro His Thr Thr Ser Asp Asp Pro Ser Arg Tyr Arg Ala Asp
            260                 265                 270

Thr Asp Met Ser Glu Trp Arg Ser Arg Asp Pro Leu Glu Arg Met Arg
        275                 280                 285

Leu Phe Leu Gly Arg Arg Asp Leu Leu Gly Glu Asn Glu Leu Ser Thr
    290                 295                 300

Ile Ala Ala Ala Ala Asp Asp Val Ala Ala Gly Leu Arg Arg Ala Thr
305                 310                 315                 320

Ile Ala Leu Ala Asp Pro Pro Pro Ser Ala Leu Phe Asp His Val Tyr
                325                 330                 335

Ala Glu Ala His Pro Leu Ile Asp Val Glu Arg Glu Glu His Arg Ala
            340                 345                 350

Tyr Leu Arg Ser Met Glu Gly Ala Ser Ser
        355                 360
```

<210> SEQ ID NO 71
<211> LENGTH: 1089
<212> TYPE: DNA
<213> ORGANISM: Rhodococcus erythropolis PR4

<400> SEQUENCE: 71

```
atgatcgaca acctcgatta tccggtccaa ctcatccaac cgaacggcgc acgagtgtgc      60
cgtcccgaat tcgaccgtct gataacagac atcgggcctg acgaactgct gtcgttgtat     120
cgcgatctcg tcgtgagtcg ccgaatcgac accgaagctg ttgccctgca gcgtcaaggc     180
gaaataggtt tgtgggctcc gatgctgggc aagaagccg cccaggtcgg ttccgcgaga      240
gcgctcgccc cagacgactt cgcgttcacc agctaccgcg aacacgccgt cgcgtactgc     300
cggggagttc cccccgaatt gctgaccacc atgtggcgag gaatctccca ttccggttgg     360
gatccagaac aagtcaacgt caccaatccg gcgatcgtcg tcggctccca agggctgcac     420
gccaccggat acgcactcgg cgcacacctg gacggcgccg agatcgcaac gatcgcgtac     480
ttcggcgacg gcgccacaag tcagggcgac atcgccgagg cgatgggatt tgccgccagt     540
ttccgtgtcg gcgttgtctt cttctgccag aacaaccagt gggccatcag tgaaccggta     600
tccctccagt cacgcacgcc catctcacat cgggcgatcg gttacggcat ccccgcgatc     660
cgcgtcgacg gcaacgacgt cctcgccgtt ctcgcagtca cgcgctcggc gctcaatcgc     720
gcacgcgaag gcagcggccc gacgttcatc gaggcgatca cctgccgaat gggcccgcac     780
acgacgtccg acgatccgag caggtaccgc gccgatacgg acatgtcgga gtggagaagc     840
cgcgatccgc tcgagcgaat gcgtctgttc ctcggccgtc gcgatcttct cggagaaaac     900
gaactcagca ccatcgcggc ggcggccgac gacgtcgcag ctggactgcg acgcgcgacc     960
atcgcgctcg ccgatccacc cccgtcagcg ctcttcgatc acgtctacgc cgaggcacac    1020
ccactgatcg acgttgaacg cgaagagcat cgcgcgtatc tccgcagcat ggaagggggct   1080
tcgtcatga                                                            1089
```

<210> SEQ ID NO 72
<211> LENGTH: 326
<212> TYPE: PRT
<213> ORGANISM: Rhodococcus erythropolis PR4

<400> SEQUENCE: 72

```
Met Thr Val Met Asn Leu Val Thr Ala Leu Asn Thr Gly Leu Arg Arg
1               5                   10                  15

Ala Leu Glu Asp Asp Arg Arg Val Val Ile Met Gly Glu Asp Val Gly
            20                  25                  30

Arg Leu Gly Gly Val Phe Arg Val Thr Asp Ala Leu Gln Lys Asp Phe
        35                  40                  45

Gly Asp Thr Arg Val Ile Asp Met Pro Leu Ala Glu Ser Gly Ile Val
    50                  55                  60

Gly Thr Ala Phe Gly Leu Ala Leu Arg Gly Tyr Arg Pro Val Cys Glu
65                  70                  75                  80

Ile Gln Phe Asp Gly Phe Val Tyr Pro Ala Phe Asp Gln Ile Val Ser
                85                  90                  95

Gln Val Ala Lys Ile His Tyr Arg Thr Arg Gly Thr Ala Ser Ala Pro
            100                 105                 110

Leu Thr Ile Arg Ile Pro Ser Gly Gly Ile Gly Ala Val Glu His
        115                 120                 125

His Ser Glu Ser Pro Glu Ala Tyr Phe Ala His Thr Ala Gly Leu Arg
    130                 135                 140

Val Val Tyr Pro Ser Asn Pro Ile Asp Gly Phe His Met Ile Arg Gln
145                 150                 155                 160

Ser Ile Ala Ala Asp Asp Pro Val Ile Phe Leu Glu Pro Lys Arg Arg
                165                 170                 175

Tyr Trp Asp Thr Ala Asp Val Asn Thr Asp Ala Ala Pro Glu Leu Pro
            180                 185                 190

Leu His Arg Ala Arg Val Ala Arg Pro Gly Asp Ala Thr Val Val
        195                 200                 205

Ala Tyr Gly Ser Met Val Ala Thr Ala Leu Asp Ala Ala Arg Ile Ala
    210                 215                 220

Glu Glu Glu Glu Gly His Asp Leu Glu Val Val Asp Leu Arg Ser Leu
225                 230                 235                 240

Ser Pro Ile Asp Phe Asp Thr Ile Glu Ala Ser Val Asn Lys Thr Gly
                245                 250                 255

Arg Leu Val Val Val His Glu Ala Pro Ser Phe Leu Gly Val Gly Ala
            260                 265                 270

Glu Ile Ala Ala His Val Ala Glu His Cys Phe Tyr Gln Leu Glu Ser
        275                 280                 285

Pro Val Leu Arg Val Thr Gly Phe Asp Ile Pro Tyr Pro Pro Ala Lys
    290                 295                 300

Leu Glu Arg Phe His Leu Pro Asp Ala Asp Arg Ile Leu Ala Ala Leu
305                 310                 315                 320

Asp Arg Thr Leu Ala Ala
                325
```

<210> SEQ ID NO 73
<211> LENGTH: 981
<212> TYPE: DNA
<213> ORGANISM: Rhodococcus erythropolis PR4

<400> SEQUENCE: 73

```
atgaccgtca tgaatctggt gaccgcgctc aacaccggcc ttcgacgcgc actcgaagac    60
gatcgtcgcg ttgtcatcat gggagaggac gtgggccgtc tcggcggtgt attccgggtt   120
accgacgccc tgcagaagga cttcggcgat actcgggtga tcgacatgcc cctcgccgaa   180
tcagggatcg tgggaacagc tttcggtctt gccttgcgcg atatcggcc tgtctgcgaa    240
```

```
attcagttcg acgggtttgt ctacccggct ttcgatcaga tcgtctcgca ggtggccaag    300
atccactacc gcacccgagg cactgcctct gcgccactga cgattcggat tcccagtggc    360
ggcggaatcg gtgcggtgga acatcattcg gagtcgccgg aagcgtactt cgctcacact    420
gcgggactgc gggtggtgta cccgagcaat ccgatcgacg gttttcacat gatccgccaa    480
tccattgcgg ccgacgaccc ggtgatattc ctcgaaccca aacggcgcta ctgggatacc    540
gccgacgtga ataccgatgc cgcgcctgag cttccgctcc accgtgcccg cgtcgctcgc    600
cctggagacg acgcgacagt agttgcgtac ggatccatgg tcgccaccgc gctcgacgcc    660
gcgcggatcg ccgaagaaga agaaggccac gatctggagg tcgtggatct gcgttcactc    720
tcccccatcg acttcgacac gatcgaggcg tcggtgaaca agacaggacg gctggtcgtc    780
gtccacgagg cgccgagttt tctcggcgtc ggcgccgaaa tcgcagcaca cgtcgcggaa    840
cactgcttct atcagctcga gtcaccggtc ctgcgggtca ccggattcga catcccctac    900
ccgcccgcca agctcgagcg atttcacctt ccggacgccg accggatcct cgcagcactc    960
gaccggacgc tggcagcatg a                                              981
```

<210> SEQ ID NO 74
<211> LENGTH: 411
<212> TYPE: PRT
<213> ORGANISM: Rhodococcus erythropolis PR4

<400> SEQUENCE: 74

```
Met Ser Thr Gly His Glu Phe Arg Leu Pro Asp Leu Gly Glu Gly Leu
1               5                   10                  15

Thr Ser Ala Asp Leu Val Glu Trp Thr Val Gly Val Gly Asp Thr Val
            20                  25                  30

Glu Leu Asn Gln Val Leu Ala Gln Val Glu Thr Ala Lys Ala Leu Val
        35                  40                  45

Glu Leu Pro Ser Pro Tyr Val Gly Val Arg Glu Leu Leu Val Glu
    50                  55                  60

Pro Gly Ser Thr Val Pro Val Gly Thr Pro Ile Ile Arg Ile Glu Glu
65                  70                  75                  80

Pro Ala Asp Ser Pro Ser Pro Asp Ser Gln Ser Pro Ser Val Leu
            85                  90                  95

Val Gly Tyr Gly Pro Ala Ala Glu Arg Pro Ser Arg Arg Asn Arg
        100                 105                 110

Val Thr Pro His Ser Gln Thr Ala Ala Ser Thr Glu Arg Arg Pro Ala
    115                 120                 125

Thr Pro Ser Ala Arg Arg Ala Ala Arg Glu Ala Gly Ile Asp Leu Ser
130                 135                 140

Glu Ile Thr Gly Ser Gly Phe Asp Gly Ala Val Thr Ala Ala Asp Val
145                 150                 155                 160

Ala Asp Ala Leu Arg Val Lys Ala Ala Ser Asn Glu Ala Pro Arg Pro
                165                 170                 175

Ala Gly Ser Gly Met Gln Lys Gln Pro Val Ser Ser Gly Met Arg Lys
            180                 185                 190

Gln Met Ala Ser Ala Met Val Ala Ser Thr Arg Ala Pro Gln Ala Ser
        195                 200                 205

Val Phe Leu Thr Ala Asp Val Thr Pro Ser Met Glu Leu Leu Gly Arg
    210                 215                 220

Leu Arg Pro Ser Asp Ala Phe Thr Gly Leu Ser Leu Thr Pro Leu Thr
225                 230                 235                 240
```

```
Leu Ala Ala Lys Ala Leu Val Thr Ala Ile Ser Ser His Pro Met Val
                245                 250                 255

Asn Ala His Trp Asp Glu Ala Arg Gly Asp Ala Val Ile Asp Asp His
        260                 265                 270

Val Asn Leu Gly Ile Ala Val Ala Ser Glu Arg Gly Leu Ser Val Pro
            275                 280                 285

Asn Ile Lys Ser Ala Glu Thr Leu Ser Leu Val Gln Leu Ala Arg Ala
        290                 295                 300

Val Thr Glu Leu Thr Val Ala Ala Arg Ala Gly Val Thr Asp Val His
305                 310                 315                 320

His Leu Thr Gly Gly Thr Val Thr Ile Thr Asn Val Gly Val Phe Gly
                325                 330                 335

Val Asp Gly Gly Ile Pro Leu Leu Asn Pro Gly Glu Ala Val Ile Leu
            340                 345                 350

Cys Leu Gly Thr Val Ser Glu Arg Pro Trp Val Ile Glu Arg Lys Ile
        355                 360                 365

Glu Ala Arg Ser Val Ala Thr Leu Thr Leu Thr Phe Asp His Arg Ile
        370                 375                 380

Leu Asp Gly Glu Gln Ala Ala Arg Phe Leu Ser Phe Val Ala Gln Met
385                 390                 395                 400

Leu Ala Asp Pro Asp Leu Leu Leu Ser His Leu
                405                 410

<210> SEQ ID NO 75
<211> LENGTH: 1236
<212> TYPE: DNA
<213> ORGANISM: Rhodococcus erythropolis PR4

<400> SEQUENCE: 75
atgagtacag ggcacgaatt ccggttgccg gatctcggcg agggcctgac gtccgccgat    60
ctggtcgagt ggacggtcgg cgtcggcgac acggtggaac tcaatcaagt tctcgcccag   120
gtagagacag ccaaggctct cgtcgaactg ccgtcgccct acgtcggcgt tgtcagagaa   180
ctcctcgtcg aacctggctc taccgtcccg gtcggcactc cgatcatccg tatcgaggag   240
cctgcagatt caccgtctcc aagtgattca cagtctccga gcgtgcttgt cggatacgga   300
cccgcggccg agagaccgag ccgacgacgg aaccgggtta cgccacactc gcaaaccgcg   360
gcgagtaccg agcgtcggcc cgcaacaccc tcggcgcggc gcgcggcccg cgaagccggc   420
atcgatctga gcgaaatcac cggaagtgga ttcgacggtg ccgtcacggc agcggacgtc   480
gcagacgcgc ttcgcgtgaa ggccgcgtcg aatgaagctc gcggccggc cggatccggt    540 atgcagaaac agccggtctc gtccggcatg cggaaacaga tggcgtcggc gatggtcgcc   600
agtacccgtg cccctcaggc cagcgtcttc ctcaccgccg atgtcacgcc ttcgatggaa   660
ctactcggca ggctccgtcc ctcggacgca ttcaccggac tttctctcac tccgctgact   720
ctcgcggcca aggccttggt tacgcgcgatc tcgtcgcacc cgatggtgaa cgcgcattgg   780
gacgaggccc gcggcgacgc cgtcatcgac gatcacgtga atctcggcat cgccgtcgcc   840
tccgaacgtg gactgtccgt gcccaacatc aaaagcgccg agacgctgag cctggtccaa   900
cttgcacgcg cggtgaccga actgaccgtc gctgcccgcg cggagtgac cgatgtccat    960 cacctgaccg gtggcaccgt cacgatcacc aatgtcggag tcttcggcgt cgacgggggc  1020
attccgctcc tcaatccggg agaagccgtc atcctttgcc tggcacagt gagcgagcgt  1080 ccctgggtaa ttgagcgcaa gatcgaagcg cggagcgtcg cgacactgac gttgacgttc  1140
```

```
gaccaccgga tactcgatgg tgagcaggcc gcgagattcc tctcatttgt cgcacagatg    1200
ctcgcggacc cggacctgtt gctgtctcac ctgtaa                              1236
```

<210> SEQ ID NO 76
<211> LENGTH: 455
<212> TYPE: PRT
<213> ORGANISM: Malus x domestica(MpAAT1)

<400> SEQUENCE: 76

```
Met Lys Ser Phe Ser Val Leu Gln Val Lys Arg Leu Gln Pro Glu Leu
1               5                   10                  15

Ile Thr Pro Ala Lys Ser Thr Pro Gln Glu Thr Lys Phe Leu Ser Asp
            20                  25                  30

Ile Asp Asp Gln Glu Ser Leu Arg Val Gln Ile Pro Ile Ile Met Cys
        35                  40                  45

Tyr Lys Asp Asn Pro Ser Leu Asn Lys Asn Arg Asn Pro Val Lys Ala
    50                  55                  60

Ile Arg Glu Ala Leu Ser Arg Ala Leu Val Tyr Tyr Tyr Pro Leu Ala
65                  70                  75                  80

Gly Arg Leu Arg Glu Gly Pro Asn Arg Lys Leu Val Val Asp Cys Asn
                85                  90                  95

Gly Glu Gly Ile Leu Phe Val Glu Ala Ser Ala Asp Val Thr Leu Glu
            100                 105                 110

Gln Leu Gly Asp Lys Ile Leu Pro Pro Cys Pro Leu Leu Glu Glu Phe
        115                 120                 125

Leu Tyr Asn Phe Pro Gly Ser Asp Gly Ile Ile Asp Cys Pro Leu Leu
    130                 135                 140

Leu Ile Gln Val Thr Cys Leu Thr Cys Gly Gly Phe Ile Leu Ala Leu
145                 150                 155                 160

Arg Leu Asn His Thr Met Cys Asp Ala Ala Gly Leu Leu Leu Phe Leu
                165                 170                 175

Thr Ala Ile Ala Glu Met Ala Arg Gly Ala His Ala Pro Ser Ile Leu
            180                 185                 190

Pro Val Trp Glu Arg Glu Leu Leu Phe Ala Arg Asp Pro Pro Arg Ile
        195                 200                 205

Thr Cys Ala His His Glu Tyr Glu Asp Val Ile Gly His Ser Asp Gly
    210                 215                 220

Ser Tyr Ala Ser Ser Asn Gln Ser Asn Met Val Gln Arg Ser Phe Tyr
225                 230                 235                 240

Phe Gly Ala Lys Glu Met Arg Val Leu Arg Lys Gln Ile Pro Pro His
                245                 250                 255

Leu Ile Ser Thr Cys Ser Thr Phe Asp Leu Ile Thr Ala Cys Leu Trp
            260                 265                 270

Lys Cys Arg Thr Leu Ala Leu Asn Ile Asn Pro Lys Glu Ala Val Arg
        275                 280                 285

Val Ser Cys Ile Val Asn Ala Arg Gly Lys His Asn Asn Val Arg Leu
    290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Gln Tyr Ser Ser Thr Gly
```

```
              355                 360                 365
Ser Tyr Leu Ile Val Ser Asp Asn Thr Arg Val Gly Phe Gly Asp Val
    370                 375                 380

Asn Phe Gly Trp Gly Gln Pro Val Phe Ala Gly Pro Val Lys Ala Leu
385                 390                 395                 400

Asp Leu Ile Ser Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
            420                 425                 430

Gln Glu Leu Glu Arg Ile Thr Gln Glu Pro Lys Glu Asp Ile Cys Asn
        435                 440                 445

Asn Leu Arg Ser Thr Ser Gln
    450                 455

<210> SEQ ID NO 77
<211> LENGTH: 1368
<212> TYPE: DNA
<213> ORGANISM: Malus x domestica(MpAAT1)

<400> SEQUENCE: 77
atgaaatcat tctcagtact tcaggtgaaa cgattgcaac cggaacttat aactccggca      60
aagtcaacgc ctcaagaaac aaagtttctc tcagatattg acgaccaaga aagcttgaga     120
gttcagattc caatcataat gtgttacaaa gacaaccctt cacttaataa aaatcgtaat     180
cccgttaagg caattaggga agccttaagt agagcattag tgtattacta ccccttagct     240
ggaaggctta gggaagggcc taatagaaag ctcgtggtcg attgcaatgg tgaaggtatc     300
ttgttcgttg aggcttctgc tgatgtcaca cttgagcaac taggagacaa aattctaccc     360
ccttgtccac ttttagagga gttcttatat aattttccag ctctgatgg aattattgat      420
tgtcctttgc tgctgattca ggtgacctgt cttacatgtg aggtttcat acttgcattg      480
cgcctaaacc acacaatgtg tgatgcagct ggattgctct tgttcctgac cgccatcgcg     540
gagatggcaa gaggcgcaca tgcaccatct attctaccag tgtgggagag agagctcttg     600
ttcgctcgag atccaccaag aattacatgt gctcatcacg aatatgaaga cgtgattggt     660
cattctgatg gctcatacgc atccagtaac cagtcaaaca tggttcaacg atctttctac     720
tttggtgcca aggagatgag agtccttcga aaacagattc cacccccacct aatttccact     780
tgctccacat ttgacttgat cacagcttgt ttgtggaaat gtcgcactct tgcacttaac     840
attaatccaa aagaggctgt tcgagtttca tgcattgtca atgcacgagg aaagcacaac     900
aatgtacgtc ttcccttggg atactatggc aatgcatttg catttccagc tgcaatttcg     960
aaggctgaac ctctatgcaa aaatccactg ggatatgctt tggagttggt gaagaaggct    1020
aaagctacca tgaatgaaga atacttaaga tcagtggcag atcttttggt actaagaggg    1080
cgacctcaat attcatcgac aggaagttat ttaatagttt ctgataatac gcgtgtaggt    1140
tttggagatg tcaattttgg atggggacag ccggtatttg ctggacccgt caaggccttg    1200
gatttgatta gcttctacgt tcaacacaaa acaacacag aggatggaat attggtacca    1260
atgtgtttgc catcctcggc catggagaga tttcagcagg aactagagag gattactcag    1320
gaacctaagg aggatatatg taacaacctt agatcaacta gtcaatga               1368

<210> SEQ ID NO 78
<211> LENGTH: 452
<212> TYPE: PRT
<213> ORGANISM: Fragaria x ananassa(SAAT)
```

```
<400> SEQUENCE: 78

Met Asn Lys Ile Glu Val Ser Ile Asn Ser Lys His Thr Ile Lys Pro
1               5                   10                  15

Ser Thr Ser Thr Pro Leu Gln Pro Tyr Lys Leu Thr Leu Leu Asp
            20                  25                  30

Gln Leu Thr Pro Pro Ala Tyr Val Pro Ile Val Phe Tyr Pro Ile
        35                  40                  45

Thr Asp His Asp Phe Asn Leu Pro Gln Thr Leu Ala Asp Leu Arg Gln
50                  55                  60

Ala Leu Ser Glu Thr Leu Thr Leu Tyr Tyr Pro Leu Ser Gly Arg Val
65                  70                  75                  80

Lys Asn Asn Leu Tyr Ile Asp Asp Phe Glu Glu Gly Val Pro Tyr Leu
                85                  90                  95

Glu Ala Arg Val Asn Cys Asp Met Thr Asp Phe Leu Arg Leu Arg Lys
            100                 105                 110

Ile Glu Cys Leu Asn Glu Phe Val Pro Ile Lys Pro Phe Ser Met Glu
        115                 120                 125

Ala Ile Ser Asp Glu Arg Tyr Pro Leu Leu Gly Val Gln Val Asn Val
130                 135                 140

Phe Asp Ser Gly Ile Ala Ile Gly Val Ser Val Ser His Lys Leu Ile
145                 150                 155                 160

Asp Gly Gly Thr Ala Asp Cys Phe Leu Lys Ser Trp Gly Ala Val Phe
                165                 170                 175

Arg Gly Cys Arg Glu Asn Ile Ile His Pro Ser Leu Ser Glu Ala Ala
            180                 185                 190

Leu Leu Phe Pro Pro Arg Asp Asp Leu Pro Glu Lys Tyr Val Asp Gln
        195                 200                 205

Met Glu Ala Leu Trp Phe Ala Gly Lys Lys Val Ala Thr Arg Arg Phe
210                 215                 220

Val Phe Gly Val Lys Ala Ile Ser Ser Ile Gln Asp Glu Ala Lys Ser
225                 230                 235                 240

Glu Ser Val Pro Lys Pro Ser Arg Val His Ala Val Thr Gly Phe Leu
                245                 250                 255

Trp Lys His Leu Ile Ala Ala Ser Arg Ala Leu Thr Ser Gly Thr Thr
            260                 265                 270

Ser Thr Arg Leu Ser Ile Ala Ala Gln Ala Val Asn Leu Arg Thr Arg
        275                 280                 285

Met Asn Met Glu Thr Val Leu Asp Asn Ala Thr Gly Asn Leu Phe Trp
290                 295                 300

Trp Ala Gln Ala Ile Leu Glu Leu Ser His Thr Thr Pro Glu Ile Ser
305                 310                 315                 320

Asp Leu Lys Leu Cys Asp Leu Val Asn Leu Leu Asn Gly Ser Val Lys
                325                 330                 335

Gln Cys Asn Gly Asp Tyr Phe Gly Thr Phe Lys Gly Lys Glu Gly Tyr
            340                 345                 350

Gly Arg Met Cys Glu Tyr Leu Asp Phe Gln Arg Thr Met Ser Ser Met
        355                 360                 365

Glu Pro Ala Pro Asp Ile Tyr Leu Phe Ser Ser Trp Thr Asn Phe Phe
370                 375                 380

Asn Pro Leu Asp Phe Gly Trp Gly Arg Thr Ser Trp Ile Gly Val Ala
385                 390                 395                 400

Gly Lys Ile Glu Ser Ala Ser Cys Lys Phe Ile Ile Leu Val Pro Thr
```

405                 410                 415
Gln Cys Gly Ser Gly Ile Glu Ala Trp Val Asn Leu Glu Glu Glu Lys
            420                 425                 430

Met Ala Met Leu Glu Gln Asp Pro His Phe Leu Ala Leu Ala Ser Pro
        435                 440                 445

Lys Thr Leu Ile
        450

<210> SEQ ID NO 79
<211> LENGTH: 1359
<212> TYPE: DNA
<213> ORGANISM: Fragaria x ananassa(SAAT)

<400> SEQUENCE: 79

```
atgaacaaaa ttgaggtcag tataaattcc aaacacacca tcaaaccatc aacttcctct      60
acaccacttc agccttacaa gcttaccctc ctggaccagc tcactcctcc ggcgtatgtc     120
cccatcgtgt tcttctaccc cattactgac catgacttca tcttcctca aaccctagct      180
gacttaagac aagccctttc ggagactctc actttgtact atccactctc tggaagggtc     240
aaaaacaacc tatacatcga tgattttgaa aaggtgtcc catacttga ggctcgagtg      300
aattgtgaca tgactgattt tctaaggctt cggaaaatcg agtgccttaa tgagtttgtt     360
ccaataaaac catttagtat ggaagcaata tctgatgagc gttacccctt gcttggagtt     420
caagtcaacg ttttcgattc tggaatagca atcggtgtct ccgtctctca aagctcatc     480
gatggaggaa cggcagactg ttttctcaag tcctggggtg ctgttttcg agggtgtcgt     540
gaaaatatca tacatcctag tctctctgaa gcagcattgc ttttcccacc gagagatgac     600
ttgcctgaaa agtatgtcga tcagatggaa gcgttatggt ttgccggaaa aaaagttgct     660
acaaggagat ttgtatttgg tgtgaaagcc atatcttcaa ttcaagatga agcgaagagc     720
gagtccgtgc ccaagccatc acgagttcat gccgtcactg ttttctctg aaacatcta    780
atcgctgctt ctcgggcact aacatcaggt actacttcaa caagactttc tatagcggcc     840
caggcagtga acttaagaac acggatgaac atggagacag tgttggataa tgccactgga     900
aacttgttct ggtgggcaca ggccatacta gagctaagtc atacaacacc agagatcagt     960
gatcttaagc tgtgtgactt ggttaacttg ctcaatggat ctgtcaaaca atgtaacggt    1020
gattactttg agactttcaa gggtaaagag ggatatggaa gaatgtgcga gtatctagat    1080
tttcagagga ctatgagttc tatggaacca gcaccggata tttatttatt ctcgagctgg    1140
actaattttt tcaacccact tgattttgga tggggagga catcatggat tggagttgca    1200
ggaaaaattg aatctgcaag ttgcaagttc ataatattag ttccaacaca atgcggttct    1260
ggaattgaag cgtgggtgaa tctagaagaa gagaaaatgg ctatgctaga caagatccc    1320
cattttctag cgttagcatc tccaaagacc ttaatttaa                          1359
```

<210> SEQ ID NO 80
<211> LENGTH: 455
<212> TYPE: PRT
<213> ORGANISM: Fragaria vesca(VAAT)

<400> SEQUENCE: 80

Met Asn Lys Ile Glu Val Ser Ile Ile Ser Lys His Thr Ile Lys Pro
 1               5                  10                  15

Ser Thr Ser Ser Ser Pro Leu Gln Pro Tyr Lys Leu Thr Leu Leu Asp
            20                  25                  30

-continued

```
Gln Leu Thr Pro Pro Ser Tyr Val Pro Met Val Phe Phe Tyr Pro Ile
         35                  40                  45

Thr Gly Pro Ala Val Phe Asn Leu Gln Thr Leu Ala Asp Leu Arg His
 50                  55                  60

Ala Leu Ser Glu Thr Leu Thr Leu Tyr Tyr Pro Leu Ser Gly Arg Val
 65                  70                  75                  80

Lys Asn Asn Leu Tyr Ile Asp Asp Phe Glu Glu Gly Val Pro Tyr Leu
                 85                  90                  95

Glu Ala Arg Val Asn Cys Asp Met Asn Asp Phe Leu Arg Leu Pro Lys
            100                 105                 110

Ile Glu Cys Leu Asn Glu Phe Val Pro Ile Lys Pro Phe Ser Met Glu
        115                 120                 125

Ala Ile Ser Asp Glu Arg Tyr Pro Leu Leu Gly Val Gln Val Asn Ile
    130                 135                 140

Phe Asn Ser Gly Ile Ala Ile Gly Val Ser Val Ser His Lys Leu Ile
145                 150                 155                 160

Asp Gly Arg Thr Ser Asp Cys Phe Leu Lys Ser Trp Cys Ala Val Phe
                165                 170                 175

Arg Gly Ser Arg Asp Lys Ile Ile His Pro Asn Leu Ser Gln Ala Ala
            180                 185                 190

Leu Leu Phe Pro Pro Arg Asp Asp Leu Pro Glu Lys Tyr Ala Arg Gln
        195                 200                 205

Met Glu Gly Leu Trp Phe Val Gly Lys Lys Val Ala Thr Arg Arg Phe
    210                 215                 220

Val Phe Gly Ala Lys Ala Ile Ser Val Ile Gln Asp Glu Ala Lys Ser
225                 230                 235                 240

Glu Ser Val Pro Lys Pro Ser Arg Val Gln Ala Val Thr Ser Phe Leu
                245                 250                 255

Trp Lys His Leu Ile Ala Thr Ser Arg Ala Leu Thr Ser Gly Thr Thr
            260                 265                 270

Ser Thr Arg Leu Ser Ile Ala Thr Gln Val Val Asn Ile Arg Ser Arg
        275                 280                 285

Arg Asn Met Glu Thr Val Trp Asp Asn Ala Ile Gly Asn Leu Ile Trp
    290                 295                 300

Phe Ala Pro Ala Ile Leu Glu Leu Ser His Thr Thr Leu Glu Ile Ser
305                 310                 315                 320

Asp Leu Lys Leu Cys Asp Leu Val Asn Leu Leu Asn Gly Ser Val Lys
                325                 330                 335

Gln Cys Asn Gly Asp Tyr Phe Gly Thr Phe Met Gly Lys Glu Gly Tyr
            340                 345                 350

Gly Ser Met Cys Glu Tyr Leu Asp Phe Gln Arg Thr Met Ser Ser Met
        355                 360                 365

Glu Pro Ala Pro Glu Ile Tyr Leu Phe Thr Ser Trp Thr Asn Phe Phe
    370                 375                 380

Asn Gln Leu Asp Phe Gly Trp Gly Arg Thr Ser Trp Ile Gly Val Ala
385                 390                 395                 400

Gly Lys Ile Glu Ser Ala Phe Cys Asn Leu Thr Thr Leu Val Pro Thr
                405                 410                 415

Pro Cys Asp Thr Gly Ile Glu Ala Trp Val Asn Leu Glu Glu Glu Lys
            420                 425                 430

Met Ala Met Leu Glu Gln Asp Pro Gln Phe Leu Ala Leu Ala Ser Pro
        435                 440                 445

Lys Thr Leu Ile Ser Arg Tyr
```

<210> SEQ ID NO 81
<211> LENGTH: 1368
<212> TYPE: DNA
<213> ORGANISM: Fragaria vesca(VAAT)

<400> SEQUENCE: 81

| | | | | | |
|---|---|---|---|---|---|
| atgaacaaaa | ttgaggtcag | tataatttcc | aaacacacca | tcaaaccatc | aacttcctct | 60 |
| tcaccacttc | agccttacaa | gcttaccctg | ctcgaccagc | tcactcctcc | atcgtatgtc | 120 |
| cccatggtat | tcttctaccc | cattactggc | cctgcagtct | tcaatcttca | aaccctagct | 180 |
| gacttaagac | atgcccttc | cgagactctc | actttgtact | atccactctc | tggaagggtc | 240 |
| aaaaacaacc | tatacatcga | tgattttgaa | gagggtgtcc | cataccttga | ggctcgagtg | 300 |
| aactgtgaca | tgaatgattt | tctaaggctt | ccgaaaatcg | agtgcctaaa | tgagtttgtt | 360 |
| ccaataaaac | catttagtat | ggaagcaata | tctgatgagc | gttaccctt | gctcggagtt | 420 |
| caagttaaca | ttttcaactc | cggaatagca | atcggggtct | ccgtctctca | caagctcatc | 480 |
| gatggaagaa | cttcagactg | ttttctcaag | tcgtggtgtg | ctgttttcg | tggttctcgt | 540 |
| gacaaaatca | tacatcctaa | tctctctcaa | gcagcattgc | ttttcccacc | aagagatgac | 600 |
| ttgcctgaaa | agtatgcccg | tcagatggaa | gggttatggt | ttgtcggaaa | aaaagttgct | 660 |
| acaaggagat | ttgtatttgg | tgcgaaagcc | atatctgtaa | ttcaagatga | agcaaagagc | 720 |
| gagtccgtgc | ccaagccatc | acgagttcag | gctgtcacta | gttttctctg | gaaacatcta | 780 |
| atcgctactt | ctcgggcact | aacatcaggt | actacttcaa | caagactttc | tatagcaacc | 840 |
| caggtagtga | acataagatc | acggaggaac | atggagacag | tgtgggataa | tgccattgga | 900 |
| aacttgatat | ggttcgctcc | ggccatacta | gagctaagtc | atacaacact | agagatcagt | 960 |
| gatcttaagc | tgtgtgactt | ggttaacttg | ctcaatggat | ctgtcaaaca | atgtaacggt | 1020 |
| gattactttg | agactttcat | gggtaaagag | ggatatggaa | gcatgtgcga | gtatctagat | 1080 |
| tttcagagga | ctatgagttc | tatggaacca | gcaccagaga | tttatttatt | cacgagctgg | 1140 |
| actaattttt | tcaaccaact | tgattttgga | tggggagga | catcatggat | tggagttgca | 1200 |
| ggaaaaattg | aatctgcatt | ttgcaatctc | acaacattag | ttccaacacc | atgcgatact | 1260 |
| ggaattgaag | cgtgggtgaa | tctagaagaa | gaaaaaatgg | ctatgctaga | acaagatccc | 1320 |
| cagtttctag | cactagcatc | tccaaagacg | ctaattcaa | gatattga | | 1368 |

<210> SEQ ID NO 82
<211> LENGTH: 23
<212> TYPE: DNA
<213> ORGANISM: Artificial Sequence
<220> FEATURE:
<223> OTHER INFORMATION: MMA-044

<400> SEQUENCE: 82
gtttgcacgc ctgccgttcg acg                                              23

<210> SEQ ID NO 83
<211> LENGTH: 23
<212> TYPE: DNA
<213> ORGANISM: Artificial Sequence
<220> FEATURE:
<223> OTHER INFORMATION: MMA-045

<400> SEQUENCE: 83
cggtacgcgc ggatcttcca gag                                              23

<210> SEQ ID NO 84
<211> LENGTH: 30
<212> TYPE: DNA
<213> ORGANISM: Artificial Sequence
<220> FEATURE:
<223> OTHER INFORMATION: MMA-003

<400> SEQUENCE: 84
gacccatgga tttcgacctc accgaagaac                                           30

<210> SEQ ID NO 85
<211> LENGTH: 31
<212> TYPE: DNA
<213> ORGANISM: Artificial Sequence
<220> FEATURE:
<223> OTHER INFORMATION: MMA-004

<400> SEQUENCE: 85
gccctgcagg atgcgatggt tcgcggcgtt c                                         31

<210> SEQ ID NO 86
<211> LENGTH: 387
<212> TYPE: PRT
<213> ORGANISM: Pseudomonas aeruginosa PAO1(acd1)

<400> SEQUENCE: 86

```
Met Asp Phe Asp Leu Thr Glu Glu Gln Arg Leu Leu Val Glu Ser Ala
1               5                   10                  15

Arg Ala Phe Ala Arg His Glu Leu Ala Pro Lys Ala Ala Asp Trp Asp
            20                  25                  30

Arg Asp His His Phe Pro Val Glu Val Ile Arg Ala Ala Ala Glu Gln
        35                  40                  45

Gly Tyr Leu Gly Leu Tyr Ile Ala Glu Glu Asp Gly Gly Leu Gly Leu
    50                  55                  60

Ser Arg Leu Ser Thr Ser Leu Ile Phe Glu Gln Leu Ala Ala Gly Cys
65                  70                  75                  80

Val Ala Thr Thr Ala Tyr Ile Ser Ile His Asn Met Ala Ala Trp Met
                85                  90                  95

Leu Ala Ser Phe Gly Asp Ala Ala Leu Lys Glu Ala Trp Leu Pro Gly
            100                 105                 110

Leu Ile Gly Gly Glu Ser Leu Ala Ser Tyr Cys Leu Thr Glu Pro Asp
        115                 120                 125

Ala Gly Ser Asp Ala Ala Arg Leu Arg Thr Arg Ala Arg Arg Glu Gly
    130                 135                 140

Asp Glu Tyr Val Leu Asp Gly Ser Lys Cys Phe Ile Ser Gly Ala Gly
145                 150                 155                 160

Ser Thr Gln Val Leu Ile Val Met Ala Arg Thr Gly Glu Asp Gly Ala
                165                 170                 175

Arg Gly Ile Ser Cys Phe Leu Val Pro Ala Asp Ala Pro Gly Ile Arg
            180                 185                 190

Tyr Gly Arg Asn Glu Asp Lys Met Gly Trp Arg Ala Gln Pro Thr Arg
        195                 200                 205

Thr Ile Thr Phe Glu Gly Val Arg Ile Pro Ala Gly Asn Arg Ile Gly
    210                 215                 220

Pro Glu Gly Gln Gly Phe Val Tyr Ala Met Lys Gly Leu Asp Gly Gly
225                 230                 235                 240

Arg Leu Asn Ile Ala Ser Cys Ser Leu Gly Ala Ala Gln Ala Ala Leu
```

```
                    245                 250                 255
        Glu Gln Ser Met Arg Tyr Val Glu Glu Arg Glu Gln Phe Gly Lys Pro
                260                 265                 270

Leu Ala Thr Phe Gln Ala Leu Gln Phe Lys Leu Ala Asp Met Leu Thr
                275                 280                 285

Glu Leu Thr Ala Ser Arg Gln Met Val Arg Leu Gly Ala His Arg Leu
                290                 295                 300

Asp Arg Gly Asp Ala Glu Ala Thr Leu Tyr Cys Ala Met Ala Lys Arg
        305                 310                 315                 320

Phe Ala Thr Asp Arg Cys Phe Asp Val Cys Asn Glu Ala Leu Gln Leu
                        325                 330                 335

His Gly Gly Tyr Gly Tyr Leu Asn Asp Tyr Pro Leu Glu Arg Trp Val
                    340                 345                 350

Arg Asp Thr Arg Val His Gln Ile Leu Glu Gly Thr Asn Glu Ile Met
                    355                 360                 365

Arg Val Ile Val Ala Arg Arg Leu Leu Glu Gln Gly Gly Met Leu Asp
                370                 375                 380

Arg Leu Leu
        385

<210> SEQ ID NO 87
<211> LENGTH: 1164
<212> TYPE: DNA
<213> ORGANISM: Pseudomonas aeruginosa PAO1(acd1)

<400> SEQUENCE: 87
atggatttcg acctcaccga agaacaacgc ctgctggtgg agagcgcccg cgccttcgcc      60
cgccacgaac tggcgccgaa ggcggccgac tgggaccgcg accatcactt cccggtggaa     120
gtcatccgcg ccgccgccga cagggctac ctcggcctgt acatcgccga ggaagacggc     180
ggcctgggcc tgtcgcggct gtccacttcg ctgatcttcg agcaactggc cgccggctgc     240
gtggccacta ccgcctacat cagcatccac aacatggccg cctggatgct cgcctcgttc     300
ggcgacgcgg cgctgaagga ggcctggctg cccggcctga tcggcggcga gtcgctcgcc     360
tcctattgcc tgaccgagcc cgatgccggc tccgacgccg cgcgcctgcg cacccgcgcc     420
cgccgcgagg gcgacgaata cgtgctggac ggcagcaagt gcttcatttc cggcgccggc     480
agcacccagg tgctgatcgt catggcgcgc accggcgagg acggcgccag ggcatctcc     540 tgcttcctgg taccggccga cgcgcccggc atccgctacg ccgcaacga ggacaagatg     600 ggctggcgcg cgcagccgac ccgcaccatc accttcgaag gcgtgcgcat ccccgccggc     660
aaccgcatcg gcccggaggg ccaaggcttc gtctatgcca tgaaaggcct cgacggcggc     720
cgcctgaaca tcgccagttg ttccctgggc gccgcccagg cggcgctgga gcagtcgatg     780
cgctacgtcg aggagcgcga gcagttcggc aagccgctgg cgaccttcca ggccttgcag     840
ttcaagctcg ccgacatgct caccgaactc accgccagcc gccagatggt ccgcctcggc     900
gcccatcggc tggaccgcgg cgacgccgag gcgaccctgt actgcgcaat ggccaagcgc     960
ttcgccaccg accgctgctt cgatgtctgc aacgaggcct tgcaactgca cggcggctac    1020
ggctatctca acgattatcc gctggagcgc tgggtacgcg acacccgcgt gcaccagatc    1080
ctcgaaggca ccaacgaaat catgcgggtg atcgtcgccc gccgcctgct ggagcagggc    1140
ggcatgctcg atcgcctgct gtga                                           1164

<210> SEQ ID NO 88
```

-continued

<211> LENGTH: 31
<212> TYPE: DNA
<213> ORGANISM: Artificial Sequence
<220> FEATURE:
<223> OTHER INFORMATION: MMA-031

<400> SEQUENCE: 88
ggtcatgacc gacttcaaca ccatcatcct c        31

<210> SEQ ID NO 89
<211> LENGTH: 34
<212> TYPE: DNA
<213> ORGANISM: Artificial Sequence
<220> FEATURE:
<223> OTHER INFORMATION: MMA-032

<400> SEQUENCE: 89
ggcctgcagg ttcagctgtt cgaaagttca gcgc        34

<210> SEQ ID NO 90
<211> LENGTH: 258
<212> TYPE: PRT
<213> ORGANISM: Rhodococcus erythropolis PR4(RE_echA)

<400> SEQUENCE: 90

```
Met Thr Asp Phe Asn Thr Ile Ile Leu Glu Arg Lys Gly Arg Val Gly
1               5                   10                  15

Val Ile Thr Leu Asn Arg Pro Lys Ala Leu Asn Ala Leu Asn Ser Glu
            20                  25                  30

Leu Met Asn Glu Val Val Ala Ala Val Ala Asp Leu Glu Ala Asp Asn
        35                  40                  45

Gly Ile Gly Ala Ile Leu Ile Thr Gly Ser Glu Arg Ala Phe Ala Ala
    50                  55                  60

Gly Ala Asp Ile Lys Glu Met Gln Ser Lys Thr Tyr Met Asp Ala Tyr
65                  70                  75                  80

Val Glu Asp Phe Phe Thr Pro Trp Asp Arg Val Ala Ala Ala Arg Lys
                85                  90                  95

Pro Leu Ile Ala Ala Val Ser Gly Tyr Ala Leu Gly Gly Gly Cys Glu
            100                 105                 110

Leu Ala Met Leu Cys Asp Phe Ile Ile Ala Ser Asp Thr Ala Lys Phe
        115                 120                 125

Gly Gln Pro Glu Ile Lys Leu Gly Val Ile Pro Gly Ile Gly Gly Ser
    130                 135                 140

Gln Arg Leu Thr Arg Ala Val Gly Lys Ala Lys Ala Met Glu Leu Cys
145                 150                 155                 160

Leu Thr Gly Arg Asn Met Asp Ala Glu Glu Ala Glu Arg Ala Gly Leu
                165                 170                 175

Val Ala Arg Ile Val Pro Ala Ala Asp Leu Leu Asp Asp Ala Leu Lys
            180                 185                 190

Thr Ala Thr Thr Ile Ala Glu Met Ser Leu Pro Ile Ala Met Met Ala
        195                 200                 205

Lys Glu Ala Val Asn Arg Ser Phe Glu Thr Thr Leu Ala Glu Gly Val
    210                 215                 220

Arg Phe Glu Arg Arg Val Phe His Ser Thr Phe Ala Thr Glu Asp Gln
225                 230                 235                 240

Lys Glu Gly Met Thr Ala Phe Val Glu Lys Arg Ser Ala Glu Phe Lys
                245                 250                 255

His Arg
```

<210> SEQ ID NO 91
<211> LENGTH: 777
<212> TYPE: DNA
<213> ORGANISM: Rhodococcus erythropolis PR4(RE_echA)

<400> SEQUENCE: 91

```
gtgaccgact tcaacaccat catcctcgag cgtaagggtc gcgtcggcgt catcacgctc      60
aaccgcccga aggctctcaa cgccctgaac tccgagctga tgaacgaggt cgtcgccgcg     120
gttgccgacc tcgaagcgga caacggcatc ggagccatcc tgatcaccgg ttccgagcgc     180
gccttcgccg ccggcgccga catcaaggaa atgcagtcca agacgtacat ggacgcatac     240
gtcgaagatt tcttcacccc gtgggaccgc gtcgcagccg ctcgtaagcc gctgatcgcc     300
gccgtctccg gtacgcgct cggtggtggc tgcgaactgg cgatgctctg cgatttcatc     360
atcgcttcgg ataccgcgaa gttcggccag cccgagatca agctcggtgt cattccgggt     420
atcggtggct cacagcgcct acgcgcgcc gtgggtaagg ccaaggccat ggagctgtgc     480
ctgaccggcc gcaacatgga cgcagaagag gccgagcgcg caggcctggt tgcccggatc     540
gttccggccg ccgatctgct cgacgacgca ttgaagaccg caaccaccat cgccgagatg     600
tcgctgccca tcgcgatgat ggccaaggaa gcggtcaacc gttccttcga gaccacactc     660
gccgagggcg tccgcttcga gcgtcgggtg ttccactcga ccttcgcgac ggaggatcag     720
aaggaaggca tgaccgcgtt cgtggagaag cggtccgccg agttcaagca ccgctga       777
```

<210> SEQ ID NO 92
<211> LENGTH: 26
<212> TYPE: DNA
<213> ORGANISM: Artificial Sequence
<220> FEATURE:
<223> OTHER INFORMATION: MAA-15

<400> SEQUENCE: 92
ggcctgtcat gagtgattac gagccg      26

<210> SEQ ID NO 93
<211> LENGTH: 32
<212> TYPE: DNA
<213> ORGANISM: Artificial Sequence
<220> FEATURE:
<223> OTHER INFORMATION: MAA-16

<400> SEQUENCE: 93
cggccctgca ggttcgcggg aatcagatgt gc      32

<210> SEQ ID NO 94
<211> LENGTH: 33
<212> TYPE: DNA
<213> ORGANISM: Artificial Sequence
<220> FEATURE:
<223> OTHER INFORMATION: GB-138

<400> SEQUENCE: 94
ggcctgcagg taccgatcat caccatcggt gtc      33

<210> SEQ ID NO 95
<211> LENGTH: 28
<212> TYPE: DNA
<213> ORGANISM: Artificial Sequence
<220> FEATURE:
<223> OTHER INFORMATION: GB-139

```
<400> SEQUENCE: 95
ggtctagact gagcagtgtt ccaatgcg                                          28

<210> SEQ ID NO 96
<211> LENGTH: 31
<212> TYPE: DNA
<213> ORGANISM: Artificial Sequence
<220> FEATURE:
<223> OTHER INFORMATION: GB-140

<400> SEQUENCE: 96
gaggaaatgg tcacagggcg agaataggtt g                                      31

<210> SEQ ID NO 97
<211> LENGTH: 29
<212> TYPE: DNA
<213> ORGANISM: Artificial Sequence
<220> FEATURE:
<223> OTHER INFORMATION: GB-141

<400> SEQUENCE: 97
gccctgtgac catttcctca ttgtgctgg                                         29

<210> SEQ ID NO 98
<211> LENGTH: 35
<212> TYPE: DNA
<213> ORGANISM: Artificial Sequence
<220> FEATURE:
<223> OTHER INFORMATION: MMA-061

<400> SEQUENCE: 98
cgactctaga ggatcgctca gtacatctac gagac                                  35

<210> SEQ ID NO 99
<211> LENGTH: 30
<212> TYPE: DNA
<213> ORGANISM: Artificial Sequence
<220> FEATURE:
<223> OTHER INFORMATION: MMA-062

<400> SEQUENCE: 99
agtgtgagga aagtgttccg atcagttcat                                        30

<210> SEQ ID NO 100
<211> LENGTH: 30
<212> TYPE: DNA
<213> ORGANISM: Artificial Sequence
<220> FEATURE:
<223> OTHER INFORMATION: MMA-063

<400> SEQUENCE: 100
cactttcctc acactcgtcg agagtatgag                                        30

<210> SEQ ID NO 101
<211> LENGTH: 35
<212> TYPE: DNA
<213> ORGANISM: Artificial Sequence
<220> FEATURE:
<223> OTHER INFORMATION: MMA-064

<400> SEQUENCE: 101
cggtacccgg ggatcagcgc gacgaacaac gagac                                  35
```

<210> SEQ ID NO 102
<211> LENGTH: 22
<212> TYPE: DNA
<213> ORGANISM: Artificial Sequence
<220> FEATURE:
<223> OTHER INFORMATION: MMA-069

<400> SEQUENCE: 102
gcgcatctac aaggaagaga tc                                              22

<210> SEQ ID NO 103
<211> LENGTH: 20
<212> TYPE: DNA
<213> ORGANISM: Artificial Sequence
<220> FEATURE:
<223> OTHER INFORMATION: MMA-070

<400> SEQUENCE: 103
gcgacgctca tcgagatctc                                                 20

<210> SEQ ID NO 104
<211> LENGTH: 36
<212> TYPE: DNA
<213> ORGANISM: Artificial Sequence
<220> FEATURE:
<223> OTHER INFORMATION: MMA-133

<400> SEQUENCE: 104
tgacctgcag gtgcactccg ctgcgacatg tatcga                               36

<210> SEQ ID NO 105
<211> LENGTH: 45
<212> TYPE: DNA
<213> ORGANISM: Artificial Sequence
<220> FEATURE:
<223> OTHER INFORMATION: MMA-131

<400> SEQUENCE: 105
actctagcct gcaggtcatt gactagttga tctaaggttg ttaca                     45

<210> SEQ ID NO 106
<211> LENGTH: 30
<212> TYPE: DNA
<213> ORGANISM: Artificial Sequence
<220> FEATURE:
<223> OTHER INFORMATION: MMA-003

<400> SEQUENCE: 106
gacccatgga tttcgacctc accgaagaac                                      30

<210> SEQ ID NO 107
<211> LENGTH: 31
<212> TYPE: DNA
<213> ORGANISM: Artificial Sequence
<220> FEATURE:
<223> OTHER INFORMATION: MMA-004

<400> SEQUENCE: 107
gccctgcagg atgcgatggt tcgcggcgtt c                                    31

<210> SEQ ID NO 108
<211> LENGTH: 31
<212> TYPE: DNA
<213> ORGANISM: Artificial Sequence
<220> FEATURE:
<223> OTHER INFORMATION: MMA-020

<400> SEQUENCE: 108
ggacatgttt cgtgatccgg aaaccctgaa c                                31

<210> SEQ ID NO 109
<211> LENGTH: 32
<212> TYPE: DNA
<213> ORGANISM: Artificial Sequence
<220> FEATURE:
<223> OTHER INFORMATION: MMA-006

<400> SEQUENCE: 109
ggcctgcagg cgaaggatcg acgctagccc tg                               32

<210> SEQ ID NO 110
<211> LENGTH: 31
<212> TYPE: DNA
<213> ORGANISM: Artificial Sequence
<220> FEATURE:
<223> OTHER INFORMATION: MMA-018

<400> SEQUENCE: 110
ggacatgttt ccctgcgaag aagagatcca g                                31

<210> SEQ ID NO 111
<211> LENGTH: 30
<212> TYPE: DNA
<213> ORGANISM: Artificial Sequence
<220> FEATURE:
<223> OTHER INFORMATION: MMA-008

<400> SEQUENCE: 111
ggcctgcagg cgccgttgcg gaaacgacgg                                  30

<210> SEQ ID NO 112
<211> LENGTH: 30
<212> TYPE: DNA
<213> ORGANISM: Artificial Sequence
<220> FEATURE:
<223> OTHER INFORMATION: MMA-019

<400> SEQUENCE: 112
ggccatggta ccgagaaccc tgttcagctc                                  30

<210> SEQ ID NO 113
<211> LENGTH: 30
<212> TYPE: DNA
<213> ORGANISM: Artificial Sequence
<220> FEATURE:
<223> OTHER INFORMATION: MMA-010

<400> SEQUENCE: 113
ggcctgcagg ctggacgagg aggtgctcgc                                  30

<210> SEQ ID NO 114
<211> LENGTH: 30
<212> TYPE: DNA
<213> ORGANISM: Artificial Sequence
<220> FEATURE:
<223> OTHER INFORMATION: MMA-021

<400> SEQUENCE: 114
ggacatgttt actctgaccg atgacgagcg                                  30

```
<210> SEQ ID NO 115
<211> LENGTH: 33
<212> TYPE: DNA
<213> ORGANISM: Artificial Sequence
<220> FEATURE:
<223> OTHER INFORMATION: MMA-022

<400> SEQUENCE: 115
ggcctgcagg ccgtcacgct tttcgatcaa tac                              33

<210> SEQ ID NO 116
<211> LENGTH: 30
<212> TYPE: DNA
<213> ORGANISM: Artificial Sequence
<220> FEATURE:
<223> OTHER INFORMATION: MMA-023

<400> SEQUENCE: 116
ccacatgtcc gattaccttg ccaccggagc                                  30

<210> SEQ ID NO 117
<211> LENGTH: 33
<212> TYPE: DNA
<213> ORGANISM: Artificial Sequence
<220> FEATURE:
<223> OTHER INFORMATION: MMA-024

<400> SEQUENCE: 117
ggcctgcagg atcttcttgg ggttcgtcac aac                              33

<210> SEQ ID NO 118
<211> LENGTH: 26
<212> TYPE: DNA
<213> ORGANISM: Artificial Sequence
<220> FEATURE:
<223> OTHER INFORMATION: MAA-15

<400> SEQUENCE: 118
ggcctgtcat gagtgattac gagccg                                      26

<210> SEQ ID NO 119
<211> LENGTH: 32
<212> TYPE: DNA
<213> ORGANISM: Artificial Sequence
<220> FEATURE:
<223> OTHER INFORMATION: MAA-16

<400> SEQUENCE: 119
cggccctgca ggttcgcggg aatcagatgt gc                               32

<210> SEQ ID NO 120
<211> LENGTH: 25
<212> TYPE: DNA
<213> ORGANISM: Artificial Sequence
<220> FEATURE:
<223> OTHER INFORMATION: MMA-187

<400> SEQUENCE: 120
ggtcatgact cttgtcgagc ccttg                                       25

<210> SEQ ID NO 121
<211> LENGTH: 30
<212> TYPE: DNA
<213> ORGANISM: Artificial Sequence
<220> FEATURE:
<223> OTHER INFORMATION: MMA-140
```

<400> SEQUENCE: 121
gacctgcagg tcctcttctg gtcatggttc                                      30

<210> SEQ ID NO 122
<211> LENGTH: 32
<212> TYPE: DNA
<213> ORGANISM: Artificial Sequence
<220> FEATURE:
<223> OTHER INFORMATION: MMA-188

<400> SEQUENCE: 122
aggaaacaga ccatgatcga caacctcgat ta                                   32

<210> SEQ ID NO 123
<211> LENGTH: 37
<212> TYPE: DNA
<213> ORGANISM: Artificial Sequence
<220> FEATURE:
<223> OTHER INFORMATION: MMA-189

<400> SEQUENCE: 123
cttgcatgcc tgcaggctca ctcgttcctt tttacag                              37

<210> SEQ ID NO 124
<211> LENGTH: 29
<212> TYPE: DNA
<213> ORGANISM: Artificial Sequence
<220> FEATURE:
<223> OTHER INFORMATION: MMA-001

<400> SEQUENCE: 124
caccatggac cacaagctct cccccgaac                                       29

<210> SEQ ID NO 125
<211> LENGTH: 30
<212> TYPE: DNA
<213> ORGANISM: Artificial Sequence
<220> FEATURE:
<223> OTHER INFORMATION: MMA-002

<400> SEQUENCE: 125
gccctgcagg ctcagcccac cagccccaac                                      30

<210> SEQ ID NO 126
<211> LENGTH: 34
<212> TYPE: DNA
<213> ORGANISM: Artificial Sequence
<220> FEATURE:
<223> OTHER INFORMATION: MMA-114

<400> SEQUENCE: 126
ggtctagaat gtttactctg accgatgacg agcg                                 34

<210> SEQ ID NO 127
<211> LENGTH: 32
<212> TYPE: DNA
<213> ORGANISM: Artificial Sequence
<220> FEATURE:
<223> OTHER INFORMATION: MMA-109

<400> SEQUENCE: 127
ggtctagaat gaaatcattc tcagtacttc ag                                   32

```
<210> SEQ ID NO 128
<211> LENGTH: 37
<212> TYPE: DNA
<213> ORGANISM: Artificial Sequence
<220> FEATURE:
<223> OTHER INFORMATION: MMA-039

<400> SEQUENCE: 128
tagagtcgac ctgcacgaga tctcgatccc gcgaaat                              37

<210> SEQ ID NO 129
<211> LENGTH: 38
<212> TYPE: DNA
<213> ORGANISM: Artificial Sequence
<220> FEATURE:
<223> OTHER INFORMATION: MMA-040

<400> SEQUENCE: 129
gcttgcatgc ctgcacagca gccaactcag cttcctttt                            38

<210> SEQ ID NO 130
<211> LENGTH: 37
<212> TYPE: DNA
<213> ORGANISM: Artificial Sequence
<220> FEATURE:
<223> OTHER INFORMATION: MMA-042

<400> SEQUENCE: 130
tagagtcgac ctgcacctct agaaataatt ttgttta                              37

<210> SEQ ID NO 131
<211> LENGTH: 37
<212> TYPE: DNA
<213> ORGANISM: Artificial Sequence
<220> FEATURE:
<223> OTHER INFORMATION: MMA-041

<400> SEQUENCE: 131
ccatcgcatc ctgcacgaga tctcgatccc gcgaaat                              37

<210> SEQ ID NO 132
<211> LENGTH: 37
<212> TYPE: DNA
<213> ORGANISM: Artificial Sequence
<220> FEATURE:
<223> OTHER INFORMATION: MMA-043

<400> SEQUENCE: 132
ccatcgcatc ctgcacctct agaaataatt ttgttta                              37

<210> SEQ ID NO 133
<211> LENGTH: 1578
<212> TYPE: DNA
<213> ORGANISM: Saccharomyces cerevisiae

<400> SEQUENCE: 133
atgaatgaaa tcgatgagaa aaatcaggcc cccgtgcaac aagaatgcct gaaagagatg      60
attcagaatg ggcatgctcg gcgtatggga tctgttgaag atctgtatgt tgctctcaac     120
agacaaaact tatatcgaaa cttctgcaca tatggagaat tgagtgatta ctgtactagg     180
gatcagctca cattagcttt gagggaaatc tgcctgaaaa atccaactct tttacatatt     240
gttctaccaa caagatggcc aaatcatgaa aattattatc gcagttccga atactattca     300
cggccacatc cagtgcatga ttatatttca gtattacaag aattgaaact gagtggtgtg     360
```

```
gttctcaatg aacaacctga gtacagtgca gtaatgaagc aaatattaga agaattcaaa    420
aatagtaagg gttcctatac tgcaaaaatt tttaaactta ctaccacttt gactattcct    480
tactttggac caacaggacc gagttggcgg ctaatttgtc ttccagaaga gcacacagaa    540
aagtggaaaa aatttatctt tgtatctaat cattgcatgt ctgatggtcg gtcttcgatc    600
cacttttttc atgatttaag agacgaatta aataatatta aaactccacc aaaaaaatta    660
gattacattt tcaagtacga ggaggattac caattattga ggaaacttcc agaaccgatc    720
gaaaaggtga tagactttag accaccgtac ttgtttattc cgaagtcact tctttcgggt    780
ttcatctaca atcatttgag atttcttca aaaggtgtct gtatgagaat ggatgatgtg     840
gaaaaaaccg atgatgttgt caccgagatc atcaatattt caccaacaga atttcaagcg    900
attaaagcaa atattaaatc aaatatccaa ggtaagtgta ctatcactcc gttttacat     960 gtttgttggt ttgtatctct tcataaatgg ggtaaatttt tcaaaccatt gaacttcgaa   1020
tggcttacgg atattttat ccccgcagat tgccgctcac aactaccaga tgatgatgaa    1080
atgagacaga tgtacagata tggcgctaac gttggattta ttgacttcac ccctggata   1140 agcgaatttg acatgaatga taacaaagaa aattttttggc cacttattga gcactaccat   1200
gaagtaattt cggaagcttt aagaaataaa agcatctcc atggcttagg gttcaatata    1260
caaggcttcg ttcaaaaata tgtgaacatt gacaaggtaa tgtgcgatcg tgccatcggg   1320
aaaagacgcg gaggtacatt gttaagcaat gtaggtctgt ttaatcagtt agaggagccc   1380
gatgccaaat attctatatg cgatttggca tttggccaat tcaaggatc ctggcaccaa    1440 gcatttttcct tgggtgtttg ttcgactaat gtaaggggga tgaatattgt tgttgcttca   1500
acaaagaatg ttgttggtag tcaagaatct ctcgaagagc tttgctccat ttacaaagct   1560
ctccttttag gcccttag                                                 1578
```

<210> SEQ ID NO 134
<211> LENGTH: 525
<212> TYPE: PRT
<213> ORGANISM: Saccharomyces cerevisiae

<400> SEQUENCE: 134

```
Met Asn Glu Ile Asp Glu Lys Asn Gln Ala Pro Val Gln Gln Glu Cys
1               5                   10                  15

Leu Lys Glu Met Ile Gln Asn Gly His Ala Arg Arg Met Gly Ser Val
            20                  25                  30

Glu Asp Leu Tyr Val Ala Leu Asn Arg Gln Asn Leu Tyr Arg Asn Phe
        35                  40                  45

Cys Thr Tyr Gly Glu Leu Ser Asp Tyr Cys Thr Arg Asp Gln Leu Thr
    50                  55                  60

Leu Ala Leu Arg Glu Ile Cys Leu Lys Asn Pro Thr Leu Leu His Ile
65                  70                  75                  80

Val Leu Pro Thr Arg Trp Pro Asn His Glu Asn Tyr Tyr Arg Ser Ser
                85                  90                  95

Glu Tyr Tyr Ser Arg Pro His Pro Val His Asp Tyr Ile Ser Val Leu
            100                 105                 110

Gln Glu Leu Lys Leu Ser Gly Val Val Leu Asn Glu Gln Pro Glu Tyr
        115                 120                 125

Ser Ala Val Met Lys Gln Ile Leu Glu Glu Phe Lys Asn Ser Lys Gly
    130                 135                 140

Ser Tyr Thr Ala Lys Ile Phe Lys Leu Thr Thr Thr Leu Thr Ile Pro
145                 150                 155                 160
```

```
Tyr Phe Gly Pro Thr Gly Pro Ser Trp Arg Leu Ile Cys Leu Pro Glu
                165                 170                 175

Glu His Thr Glu Lys Trp Lys Lys Phe Ile Phe Val Ser Asn His Cys
            180                 185                 190

Met Ser Asp Gly Arg Ser Ile His Phe His Asp Leu Arg Asp
        195                 200                 205

Glu Leu Asn Asn Ile Lys Thr Pro Pro Lys Lys Leu Asp Tyr Ile Phe
    210                 215                 220

Lys Tyr Glu Glu Asp Tyr Gln Leu Leu Arg Lys Leu Pro Glu Pro Ile
225                 230                 235                 240

Glu Lys Val Ile Asp Phe Arg Pro Pro Tyr Leu Phe Ile Pro Lys Ser
                245                 250                 255

Leu Leu Ser Gly Phe Ile Tyr Asn His Leu Arg Phe Ser Ser Lys Gly
                260                 265                 270

Val Cys Met Arg Met Asp Asp Val Glu Lys Thr Asp Val Val Thr
            275                 280                 285

Glu Ile Ile Asn Ile Ser Pro Thr Glu Phe Gln Ala Ile Lys Ala Asn
    290                 295                 300

Ile Lys Ser Asn Ile Gln Gly Lys Cys Thr Ile Thr Pro Phe Leu His
305                 310                 315                 320

Val Cys Trp Phe Val Ser Leu His Lys Trp Gly Lys Phe Phe Lys Pro
                325                 330                 335

Leu Asn Phe Glu Trp Leu Thr Asp Ile Phe Ile Pro Ala Asp Cys Arg
                340                 345                 350

Ser Gln Leu Pro Asp Asp Asp Glu Met Arg Gln Met Tyr Arg Tyr Gly
            355                 360                 365

Ala Asn Val Gly Phe Ile Asp Phe Thr Pro Trp Ile Ser Glu Phe Asp
    370                 375                 380

Met Asn Asp Asn Lys Glu Asn Phe Trp Pro Leu Ile Glu His Tyr His
385                 390                 395                 400

Glu Val Ile Ser Glu Ala Leu Arg Asn Lys Lys His Leu His Gly Leu
                405                 410                 415

Gly Phe Asn Ile Gln Gly Phe Val Gln Lys Tyr Val Asn Ile Asp Lys
                420                 425                 430

Val Met Cys Asp Arg Ala Ile Gly Lys Arg Gly Gly Thr Leu Leu
            435                 440                 445

Ser Asn Val Gly Leu Phe Asn Gln Leu Glu Glu Pro Asp Ala Lys Tyr
    450                 455                 460

Ser Ile Cys Asp Leu Ala Phe Gln Phe Gln Gly Ser Trp His Gln
465                 470                 475                 480

Ala Phe Ser Leu Gly Val Cys Ser Thr Asn Val Lys Gly Met Asn Ile
                485                 490                 495

Val Val Ala Ser Thr Lys Asn Val Gly Ser Gln Glu Ser Leu Glu
            500                 505                 510

Glu Leu Cys Ser Ile Tyr Lys Ala Leu Leu Leu Gly Pro
    515                 520                 525

<210> SEQ ID NO 135
<211> LENGTH: 1608
<212> TYPE: DNA
<213> ORGANISM: Saccharomyces cerevisiae
```

<400> SEQUENCE: 135

```
atggaagata tagaaggata cgaaccacat atcactcaag agttgataga ccgtggccat        60
gcaagacgta tgggccactt ggaaaactac tttgctgttt tgagtaggca gaaaatgtac       120
tcgaatttta ctgtttacgc ggaattgaat aaaggtgtta ataagagaca actaatgctt       180
gtcttgaaag tattacttca aaaatactca actcttgcgc atacaatcat tcctaagcat       240
tatcctcatc atgaagcgta ctactctagc gaagagtacc ttagtaaacc ttttccacag       300
catgatttca taaggtgat ttctcatctt gaattcgatg acttgattat gaataatcaa        360
ccagaataca gagaagtcat ggagaaaatc tcagaacagt tcaaaaagga tgatttcaaa       420
gtcaccaata ggttaatcga attgattagc cctgtaatca tacctctggg taatccgaag       480
aggcctaatt ggagattgat ttgtttacca ggtaaggata ctgatgggtt tgaaacgtgg       540
aaaaacttcg tttatgtcac taaccactgc ggctccgacg gtgtcagtgg atcgaatttt       600
ttcaaagatt tagctctact cttttgtaaa atcgaagaaa aagggtttga ttatgatgaa       660
gagttcatcg aagatcaagt catcattgac tatgatcgag actacactga aatttctaaa       720
ttgccaaaac cgattacgga tcgtattgac tacaagccag cattgacttc attacccaaa       780
ttcttttttaa caaccttcat ttatgaacat tgtaatttta aaacctccag cgaatctaca       840
cttacagcta gatatagccc ctctagtaat gctaatgcta gttacaatta cttgttgcat       900
ttcagtacta agcaagtaga acaaatcaga gctcagatca agaaaaatgt tcacgatggg       960
tgcaccctaa caccctttca tcaagcgtgc tttcttgtag ccctgtatag actggataag      1020
ctgttcacaa aatctcttct cgagtatggg ttcgatgtgg ctattccaag caacgcaaga      1080
aggttttttac caaacgatga agagttaaga gattcttata aatacggctc caacgttgga      1140
ggttcgcatt acgcctatct aatctcctca ttcgacattc ccgaaggtga caatgacaag      1200
ttttggagtc ttgtcgaata ctactatgac cgcttttttag aatcgtacga caacggtgac      1260
cacttgattg gtctgggggt cctacaactt gattttatcg ttgaaaacaa gaatatagac      1320
agccttcttg ccaactctta tttgcaccag caaagaggcg gtgcaatcat cagtaataca      1380
ggacttgtct cgcaagatac gaccaagccg tactacgttc gggatttaat cttctcgcag      1440
tctgcaggcg ccttgagatt tgcgttcggc ctaaacgttt gctccacaaa cgtgaatggt      1500
atgaacatgg acatgagcgt ggttcagggc actctacggg atcgtggcga atgggaatcg      1560
ttctgcaagc tcttctacca aaccatcggc gaatttgcgt cgctttaa                   1608
```

<210> SEQ ID NO 136
<211> LENGTH: 535
<212> TYPE: PRT
<213> ORGANISM: Saccharomyces cerevisiae

<400> SEQUENCE: 136

```
Met Glu Asp Ile Glu Gly Tyr Glu Pro His Ile Thr Gln Glu Leu Ile
1               5                   10                  15

Asp Arg Gly His Ala Arg Arg Met Gly His Leu Glu Asn Tyr Phe Ala
            20                  25                  30

Val Leu Ser Arg Gln Lys Met Tyr Ser Asn Phe Thr Val Tyr Ala Glu
        35                  40                  45

Leu Asn Lys Gly Val Asn Lys Arg Gln Leu Met Leu Val Leu Lys Val
    50                  55                  60

Leu Leu Gln Lys Tyr Ser Thr Leu Ala His Thr Ile Ile Pro Lys His
65                  70                  75                  80
```

```
Tyr Pro His His Glu Ala Tyr Tyr Ser Ser Glu Glu Tyr Leu Ser Lys
            85                  90                  95
Pro Phe Pro Gln His Asp Phe Ile Lys Val Ile Ser His Leu Glu Phe
        100                 105                 110
Asp Asp Leu Ile Met Asn Asn Gln Pro Glu Tyr Arg Glu Val Met Glu
        115                 120                 125
Lys Ile Ser Glu Gln Phe Lys Lys Asp Asp Phe Lys Val Thr Asn Arg
    130                 135                 140
Leu Ile Glu Leu Ile Ser Pro Val Ile Ile Pro Leu Gly Asn Pro Lys
145                 150                 155                 160
Arg Pro Asn Trp Arg Leu Ile Cys Leu Pro Gly Lys Asp Thr Asp Gly
                165                 170                 175
Phe Glu Thr Trp Lys Asn Phe Val Tyr Val Thr Asn His Cys Gly Ser
            180                 185                 190
Asp Gly Val Ser Gly Ser Asn Phe Phe Lys Asp Leu Ala Leu Leu Phe
        195                 200                 205
Cys Lys Ile Glu Glu Lys Gly Phe Asp Tyr Asp Glu Glu Phe Ile Glu
    210                 215                 220
Asp Gln Val Ile Ile Asp Tyr Asp Arg Asp Tyr Thr Glu Ile Ser Lys
225                 230                 235                 240
Leu Pro Lys Pro Ile Thr Asp Arg Ile Asp Tyr Lys Pro Ala Leu Thr
                245                 250                 255
Ser Leu Pro Lys Phe Phe Leu Thr Thr Phe Ile Tyr Glu His Cys Asn
            260                 265                 270
Phe Lys Thr Ser Ser Glu Ser Thr Leu Thr Ala Arg Tyr Ser Pro Ser
        275                 280                 285
Ser Asn Ala Asn Ala Ser Tyr Asn Tyr Leu Leu His Phe Ser Thr Lys
        290                 295                 300
Gln Val Glu Gln Ile Arg Ala Gln Ile Lys Lys Asn Val His Asp Gly
305                 310                 315                 320
Cys Thr Leu Thr Pro Phe Ile Gln Ala Cys Phe Leu Val Ala Leu Tyr
                325                 330                 335
Arg Leu Asp Lys Leu Phe Thr Lys Ser Leu Leu Glu Tyr Gly Phe Asp
            340                 345                 350
Val Ala Ile Pro Ser Asn Ala Arg Arg Phe Leu Pro Asn Asp Glu Glu
        355                 360                 365
Leu Arg Asp Ser Tyr Lys Tyr Gly Ser Asn Val Gly Gly Ser His Tyr
    370                 375                 380
Ala Tyr Leu Ile Ser Ser Phe Asp Ile Pro Glu Gly Asp Asn Asp Lys
385                 390                 395                 400
Phe Trp Ser Leu Val Glu Tyr Tyr Tyr Asp Arg Phe Leu Glu Ser Tyr
                405                 410                 415
Asp Asn Gly Asp His Leu Ile Gly Leu Gly Val Leu Gln Leu Asp Phe
            420                 425                 430
Ile Val Glu Asn Lys Asn Ile Asp Ser Leu Leu Ala Asn Ser Tyr Leu
        435                 440                 445
His Gln Gln Arg Gly Gly Ala Ile Ile Ser Asn Thr Gly Leu Val Ser
    450                 455                 460
Gln Asp Thr Thr Lys Pro Tyr Tyr Val Arg Asp Leu Ile Phe Ser Gln
465                 470                 475                 480
Ser Ala Gly Ala Leu Arg Phe Ala Phe Gly Leu Asn Val Cys Ser Thr
                485                 490                 495
```

-continued

```
Asn Val Asn Gly Met Asn Met Asp Met Ser Val Val Gln Gly Thr Leu
        500             505             510

Arg Asp Arg Gly Glu Trp Glu Ser Phe Cys Lys Leu Phe Tyr Gln Thr
        515             520             525

Ile Gly Glu Phe Ala Ser Leu
    530             535
```